United States Patent
Amberg et al.

(10) Patent No.: US 9,296,697 B2
(45) Date of Patent: Mar. 29, 2016

(54) HETARYL-SUBSTITUTED GUANIDINE COMPOUNDS AND USE THEREOF AS BINDING PARTNERS FOR 5-HT$_5$-RECEPTORS

(75) Inventors: Wilhelm Amberg, Mannheim (DE); Astrid Netz, Mannheim (DE); Andreas Kling, Mannheim (DE); Michael Ochse, Bad Durkheim (DE); Udo Lange, Berlin (DE); Charles W. Hutchins, Green Oaks, IL (US); Francisco Javier Garcia-Ladona, Kandel (DE); Wolfgang Wernet, Neustadt (DE); Alfred Hahn, Mannheim (DE)

(73) Assignees: Abbott Laboratories, Abbott Park, IL (US); AbbVie Deutschland GmbH & Co. KG, Wiesbaden (DE)

( * ) Notice: Subject to any disclaimer, the term of this patent is extended or adjusted under 35 U.S.C. 154(b) by 1529 days.

(21) Appl. No.: 11/990,937

(22) PCT Filed: Aug. 23, 2006

(86) PCT No.: PCT/EP2006/008279
§ 371 (c)(1),
(2), (4) Date: Feb. 23, 2010

(87) PCT Pub. No.: WO2007/022964
PCT Pub. Date: Mar. 1, 2007

(65) Prior Publication Data
US 2010/0184787 A1 Jul. 22, 2010

Related U.S. Application Data

(60) Provisional application No. 60/710,804, filed on Aug. 24, 2005.

(30) Foreign Application Priority Data

Feb. 9, 2006 (DE) .......................... 10 2006 005 915

(51) Int. Cl.

| | | |
|---|---|---|
| C07D 213/75 | (2006.01) |
| C07D 213/84 | (2006.01) |
| C07D 213/85 | (2006.01) |
| C07D 215/38 | (2006.01) |
| C07D 217/22 | (2006.01) |
| C07D 239/42 | (2006.01) |
| C07D 409/04 | (2006.01) |
| A61K 31/44 | (2006.01) |
| A61K 31/47 | (2006.01) |
| A61K 31/505 | (2006.01) |

(52) U.S. Cl.
CPC .............. *C07D 213/75* (2013.01); *A61K 31/44* (2013.01); *A61K 31/47* (2013.01); *A61K 31/505* (2013.01); *C07D 213/84* (2013.01); *C07D 213/85* (2013.01); *C07D 215/38* (2013.01); *C07D 217/22* (2013.01); *C07D 239/42* (2013.01); *C07D 409/04* (2013.01)

(58) Field of Classification Search
CPC .. C07D 409/04; C07D 215/38; C07D 213/75; C07D 213/84; C07D 213/85; C07D 217/22; C07D 239/42; A61K 31/44; A61K 31/47; A61K 31/505
See application file for complete search history.

(56) References Cited

U.S. PATENT DOCUMENTS

| | | |
|---|---|---|
| 2,537,384 A | 1/1951 | Waghorne |
| 3,574,744 A | 4/1971 | Krapcho et al. |
| 4,057,636 A | 11/1977 | Petersen |
| 4,293,549 A | 10/1981 | Rachlin et al. |
| 4,405,644 A | 9/1983 | Kabbe et al. |

(Continued)

FOREIGN PATENT DOCUMENTS

| | | |
|---|---|---|
| CA | 1 221 699 | 5/1987 |
| CA | 2 359 360 | 7/2000 |

(Continued)

OTHER PUBLICATIONS

Kennet G.A., 5-HT Receptors and Their Ligands; Serotonin Receptors and Their Function, TOCRIS Review (http://www.tocris.com/serotonin.htm), May 1997.
Peroutka S.J., 1994, Molecular Biology of Serotonin (5-HT) Receptors, Synapse 18, 241-260.
Nelson, D.L., Current Drug Targets—CNS & Neurological Disorders 2004, , Issue 1, 53-58.
Erlander et al., Proc. Natl. Acad. Sci. USA, "Two Members of a Distinct Subfamily of 5-Hydroxytryptamine Receptors Differentially Expressed in Rat Brain", vol. 90. pp. 3452-3456 (1993).

(Continued)

*Primary Examiner* — Samantha Shterengarts
(74) *Attorney, Agent, or Firm* — Lisa V. Mueller; Michael Best & Friedrich LLP

(57) ABSTRACT

The invention relates to the hetaryl-substituted guanidine compounds of general formula (I), enantiomeres, diastereomeres and/or tautomeres thereof, in addition to the pharmaceutically acceptable salts thereof and the prodrugs of the known compounds. The invention also relates to the use of said hetaryl-substituted guanidine compounds as binding partners for 5-HT5-receptors for treating and/or for the prophylaxis of illnesses which are modulated by a 5-HT5-receptor activity, in particular, for treating and/or for the prophylaxis of neurodegenerative and neuropsychiatric disorders, and signs, symptoms and dysfunctions associated with said disorders.

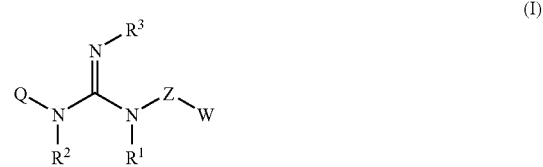

(I)

22 Claims, No Drawings

(56) References Cited

U.S. PATENT DOCUMENTS

| | | | |
|---|---|---|---|
| 4,743,294 A | | 5/1988 | Diehr et al. |
| 4,797,484 A | | 1/1989 | Moriya et al. |
| 4,880,932 A | * | 11/1989 | Moriya et al. ............... 544/320 |
| 5,403,861 A | | 4/1995 | Goldin et al. |
| 5,567,722 A | | 10/1996 | Humphrey et al. |
| 5,668,157 A | | 9/1997 | Humphrey et al. |
| 5,741,661 A | | 4/1998 | Goldin et al. |
| 5,942,544 A | | 8/1999 | Maduskuie, Jr. et al. |
| 6,020,357 A | | 2/2000 | Pinto et al. |
| 6,187,797 B1 | | 2/2001 | Pruitt et al. |
| 6,420,367 B1 | | 7/2002 | Ueda et al. |
| 6,583,162 B1 | | 6/2003 | Dickinson et al. |
| 6,750,221 B1 | | 6/2004 | Garcia-Ladona et al. |
| 2002/0028836 A1 | | 3/2002 | Altenbach et al. |
| 2003/0073747 A1 | | 4/2003 | Gross et al. |
| 2004/0167181 A1 | | 8/2004 | Solow-Cordero et al. |
| 2005/0171195 A1 | | 8/2005 | Carroll et al. |
| 2007/0299074 A1 | | 12/2007 | Netz et al. |

FOREIGN PATENT DOCUMENTS

| | | | |
|---|---|---|---|
| DE | | 3233380 | 7/1920 |
| DE | | 25 57 438 | 12/1975 |
| DE | | 28 47 792 | 5/1979 |
| DE | | 3334455 | 9/1984 |
| DE | | 3517842 | 3/1986 |
| DE | | 10 2004 008 141 | 9/2005 |
| EP | | 0 022 958 | 7/1980 |
| EP | | 0 121 082 | 10/1984 |
| EP | | 0 173 321 | 3/1986 |
| EP | | 0 224 078 | 6/1987 |
| EP | | 0 401 010 | 12/1990 |
| EP | | 1 044 967 | 10/2000 |
| EP | | 1 203 766 | 5/2002 |
| EP | | 1 270 551 | 1/2003 |
| FR | | 2609603 | 7/1988 |
| GB | | 2105331 | 3/1983 |
| JP | | 08-30184 | 8/1996 |
| WO | WO 88/00583 | | 1/1988 |
| WO | WO 89/06530 | | 7/1989 |
| WO | WO 90/14067 | | 11/1990 |
| WO | WO 91/18868 | | 12/1991 |
| WO | WO 92/02513 | | 2/1992 |
| WO | WO 92/14697 | | 9/1992 |
| WO | WO 93/12788 | | 7/1993 |
| WO | WO 93/15055 | | 8/1993 |
| WO | WO 94/04499 | | 3/1994 |
| WO | WO 94/04500 | | 3/1994 |
| WO | WO 94/06770 | | 3/1994 |
| WO | WO 94/26715 | | 11/1994 |
| WO | WO 9426715 | * | 11/1994 ............... 546/200 |
| WO | WO 94/29280 | | 12/1994 |
| WO | WO 95/00505 | | 1/1995 |
| WO | WO 95/06034 | | 3/1995 |
| WO | WO 95/20579 | | 8/1995 |
| WO | WO 97/36861 | | 10/1997 |
| WO | WO 98/24782 | | 6/1998 |
| WO | WO 98/54146 | | 12/1998 |
| WO | WO 99/20599 | | 4/1999 |
| WO | WO 00/04014 | | 1/2000 |
| WO | WO 00/41472 | | 7/2000 |
| WO | WO 00/41696 | | 7/2000 |
| WO | WO 00/61559 | | 10/2000 |
| WO | WO 00/61561 | | 10/2000 |
| WO | WO 00/67746 | | 11/2000 |
| WO | WO 00/76508 | | 12/2000 |
| WO | WO 01/09096 | | 2/2001 |
| WO | WO 01/78717 | | 10/2001 |
| WO | WO 02/16318 | | 2/2002 |
| WO | WO 02/18327 | | 3/2002 |
| WO | WO 02/22581 | | 3/2002 |
| WO | WO 02/24681 | | 3/2002 |
| WO | WO 02/30881 | | 4/2002 |
| WO | WO 02/42265 | | 5/2002 |
| WO | WO 02/088323 | | 11/2002 |
| WO | WO 03/011872 | | 2/2003 |
| WO | WO 03/097601 | | 11/2003 |
| WO | WO 2004/037166 | | 5/2004 |
| WO | WO 2004/037789 | | 5/2004 |
| WO | WO 2004/044046 | | 5/2004 |
| WO | WO 2004/058709 | | 7/2004 |
| WO | WO 2004/058736 | | 7/2004 |
| WO | WO 2004/096771 | | 11/2004 |
| WO | WO 2005/083754 | | 9/2005 |
| WO | WO 2005/095345 | | 10/2005 |
| WO | WO 2006/007532 | | 1/2006 |
| WO | WO 2006/021805 | | 3/2006 |

OTHER PUBLICATIONS

Oliver et al., Brain Research, "Localization of 5-ht5A Receptor-Like Immunoreactivity in the Rat Brain", 867 (2000) pp. 131-142.

Pasqualetti et al., Molecular Brain Research, "Distribution of the 5-HT5A Serotonin Receptor mRNA in the Human Brain", 56 (1998), pp. 1-8.

Diener, H. C. et al., Arzneimitteltherapie, "Behandlung der Migraneattacke und Migraneprophylaxe Empfehlungen der Deutschen Migrane—und Kopfschmerzgesellschaft". 15:387-394 (1997).

Jefferson et al., Bioorganic & Medicinal Chemistry Letters, "Biaryl Guanidine Inhibitors of In Vitro HCV-IRES Activity", 14 (2004) pp. 5139-5143.

Aquino et al., Bioorganic & Medicinal Chemistry, "Synthesis and Structure Activity Relationship of Guanidines as NPY Y5 Antagonists", 12 (2004), pp. 2691-2708.

Tanaka et al., Chem, Pharm, Bull., "Studies on Anti-platelet Agents. IV. A Series of Substituted 4,5-Bis(4-methoxyphenyl)pyrimidines as Novel Anti-platelet Agents", 42(9), (1994), pp. 1828-1834.

Shuto et al., Agric. Biol. Chem. "Cytotoxicity-Structure Relationship of Guanidinopyrimidines", 43 (4), (1979), pp. 861-862.

Shuto et al., Agric. Biol. Chem. "Electronic Structure and Biological Activity of Guanidinopyrimidines", 43 (11), (1979), pp. 2245-2248.

Furukawa et al., Chem. Pharm. Bull. "Reaction of Biguanides and Related Compounds. I. Reaction of Biguanides with β-Diketone", 19(11) (1971), pp. 2284-2288.

Lange et al., The Journal of Biological Chemistry "The Stereoenantiomers of a Pinacidil Analog Open or Close Cloned ATP-sensitive K+ Channels", vol. 277 No. 43, Oct. 25, 2002, pp. 40196-40205.

Clark et al., Methods Find. Exp. Clin. Pharmacol. "K+ Channel Blockers: Natriuretic Potency Correlates to Vascular ATP-Sensitive K+ Channel Blockade", (1999), 21(1), pp. 25-30.

Khan et al., The Journal of Pharmacol. Ex. Therapeutics, "Pharmacological Characterization of Novel Cyanoguanidines as Vascular $K_{ATP}$ Channel Blockers", (1997), 283(3), pp. 1207-1213.

Shouping et al., Journal of China Pharmaceutical University "QSAR Study on Hypotensive Activity of Analogues of Pinacidil", (1997) 28(1), pp. 1-4.

Barvian et al., Pergamon Tetrahedron Letters, "PII: S0040-4039(97)01598-0, Preparation of N, N'-Bis(aryl)guanidines from Electron Deficient Amines Via Masked Carbodiimides", vol. 38, No. 39, (1997), pp. 6799-6802.

Quintela et al., Bioorganic & Medicinal Chemistry, "Synthesis and Antihistaminic Activity of 2-guanidino-3-cyanopyridines and pyrido[2,3-d]pyrimidines", vol. 5. No. 8 (1997), pp. 1543-1553.

Shouping et al., Journal of China Pharmaceutical University, "Synthesis and Hypotensive Activity of Some Thiourea/Cyanoguanidine Analogues of Pinacidil", 26(4), (1995), pp. 193-198.

Jianyong et al., Journal of China Pharmaceutical University, "Synthesis of Potassium Channel Opener Pinacidil and Its Analogues", 24(4), (1993), pp. 202-204.

Steinberg et al., Journal of Cardivascular Pharmacology, "The Relation Between Vascular Relaxant and Cardiac Electrophysiological Effects of Pinacidil", 12(Suppl. 2), (1988), pp. S30-S40.

Smallwood et al., Journal of Cardiovascular Pharmacology, "Cardiac Electrophysiological Effects of Pinacidil and Related Pyridycyanoguanidines: Relationship to Antihypertensive Activity", 12(1), (1988), pp. 102-109.

(56) References Cited

OTHER PUBLICATIONS

Hansen et et al., Synthetic Communications, "Synthesis of N-Alkyl-N'-Cyano-N-4-Pyridyl-Guanidines from 4-Pyridyldithiocarbamic Acid Via N-Alkyl-N-4-Pyridylthioureas, or Via 4-Pyridylcyaniminothiocarbamic Acid", 14(13), (1984), pp. 1275-1283.

Tanaka et al., Agric. Biol. Chem., "Fungicidal Activities of 1,1-Diisopropyl-2-(3-pyridyl)-3-p-ethoxy-phenylguanidine and Its Analogs", 42(4), (1978), pp. 803-807.

Petersen et al., Journal of Medicinal Chemistry, "Synthesis and Hypotensive Activity of N-Alkyl-N'''-cyano-N''pyridylguanidines", 21(8), (1978), pp. 773-781.

Tanaka et al., Agric. Biol. Chem., "Structure Modifications of S-n-Butyl S'-p-tert-Butylbenzyl N-3-Pyridyldithiocarbonimidate (S-1358, Denmert®) and Fungicidal Activities", 41(10), (1977), pp. 1953-1959.

Plassat et al., The EMBO Journal, "The Mouse 5HT5 Receptor Reveals a Remarkable Heterogeneity Within the 5HT1D Receptor Family", 1992 vol. 11 No. 13, pp. 4779-4786.

Carson et al., Glia, "The 5-HT5A Serotonin Receptor is Expressed Predominantly by Astrocytes in Which it InhibitscAMP Accumulation of Reactive Astrocytes", 1996, pp. 317-326.

Pfaffenrath, MMW Seminar, "Triptane Gegen Migraneattacken", 1998, pp. 625-626.

Heinisch et al., J. Heterocyclic Chem., "Diazine-Derived Guanidines, Isothioureas, and Isoureas: Synthesis and Attempts of Configurational Assignment", Jul.-Aug. 2002, vol. 39, pp. 695-702.

Moriguchi et al., J. Med. Chem. "Adaptive Least-Squares Method Applied to Structure-Activity Correlation of Hypotensive N-Alkyl-"-cyano-N"-pyridylguanidines", 1980, vol. 23, No. 1, pp. 20-26.

\* cited by examiner

HETARYL-SUBSTITUTED GUANIDINE COMPOUNDS AND USE THEREOF AS BINDING PARTNERS FOR 5-HT$_5$-RECEPTORS

CROSS-REFERENCE TO RELATED APPLICATION(S)

This is a U.S. national stage entry of International Patent Application No. PCT/EP2006/008279, filed on Aug. 23, 2006, which claims priority to German Patent Application No. 10 2006 005 915.8, filed on Feb. 9, 2006, and U.S. Provisional patent application No. 60/710,804, filed on Aug. 24, 2005.

FIELD OF THE INVENTION

The present invention relates to novel hetaryl-substituted guanidine compounds and the use of hetaryl-substituted guanidine compounds as binding partners for 5-HT$_5$ receptors for the treatment and/or prevention of diseases which are modulated by 5-HT$_5$ receptor activity, in particular for the treatment and/or prevention of neurodegenerative and neuropsychiatric disorders and the signs, symptoms, and dysfunctions associated with said disorders.

BACKGROUND OF THE INVENTION

At least seven different receptor classes mediate the physiological activities attributed to the participation of the neurotransmitter serotonin (5-hydroxytryptamine or 5-HT for short). These receptor classes are designated as 5-HT$_1$, 5-HT$_2$, 5-HT$_3$, 5-HT$_4$, 5-HT$_5$, 5-HT$_6$, and 5-HT$_7$ according to an internationally recognized classification system. Most of these classes include further distinguishable receptor subtypes; thus, the 5-HT$_1$ class includes receptors which in turn may be divided into at least five subclasses, designated 5-HT$_{1A}$, 5-HT$_{1B}$, 5-HT$_{1C}$, 5-HT$_{1D}$, and 5-HT$_{1E}$ (Boess, Martin; Neuropharmacology 33:275-317 (1994)).

The properties, function, and pharmacology of these receptor subtypes have been summarized, for example, by: (a) Kennet G. A., "Serotonin Receptors and Their Function," TOCRIS Review (http://www.tocris.com/serotonin.htm), published May 1997; and (b) Peroutka, S. J., 1994, "Molecular Biology of Serotonin (5-HT) Receptors," Synapse 18, 241-260 and Current Drug Targets—CNS & Neurological Disorders 2004, 3, Issue 1.

The 5-HT$_5$ class was first described by Plassat et al., The EMBO Journal, Vol. 11, No. 13, PP. 4779-4786 (1992). A distinction is made between 5-HT$_{5A}$ and 5-HT$_{5B}$ receptors (Erlander et al., Proc. Natl. Acad. Sci. USA 90:3452-3456 (1993)). Although only slight sequence homologies exist between 5-HT$_5$ receptors and other 5-HT receptors, the pharmacological profiles of these receptors are markedly different.

5-HT$_5$ receptors may be localized in the olfactory bulb, hippocampus, cortex, cerebral ventricles, corpus callosum, and cerebellum using molecular biological techniques. Immunohistochemical methods have shown that 5-HT$_5$ receptors of neurons are expressed in various regions of the brain (Oliver et al., Brain Res. 2000, 867, 131-142; Pasqualetti et al., Mol. Brain Res. 1998, 56, 1-8). On the one hand, these 5-HT$_5$ receptors may directly or indirectly modulate important functions of the brain, and on the other hand may also participate in mechanisms involved in neuropathological, neurodegenerative, and neuropsychiatric diseases. 5-HT$_5$ receptors have also been localized in astrocytes (Carson et al., GLIA 17:317-326 (1996)). Astrocytes are in direct contact with the basal membrane of brain capillaries of the blood-brain barrier; an abnormal astrocyte-endothelium structure is accompanied by a loss of the blood-brain barrier. The exact function of astrocytes is not understood. Astrocytes appear to perform transport tasks and connective functions. Reactive astrocytes have been observed in conjunction with reactive gliosis for a number of pathological brain changes and neuropsychiatric diseases. Such astrocytes alter their morphology as the result of brain injuries. The protein expression pattern changes, and growth factors are produced. In vitro tests of cultivated astrocytes have shown 5-HT$_5$ receptor-mediated responses. For this reason it is suspected that 5-HT$_5$ receptors are involved in healing processes of the brain subsequent to disorders, but on the other hand it cannot be ruled out that they also contribute to the origin or even proliferation of damage.

Neuropathological conditions currently affect a large percentage of the population, and the number of patients is continually on the rise due to the increasing numbers of older persons.

Neuropathological conditions such as cerebral ischemia, stroke, epilepsy, and attacks in general, chronic schizophrenia, other psychotic conditions, depression, anxiety, bipolar disorders, dementia, in particular Alzheimer's dementia, demyelinating diseases, in particular multiple sclerosis, and brain tumors result in damage to the brain and the associated neuronal deficiencies. Therapeutic treatments of the described neurodegenerative and neuropathological disorders have heretofore focused on various membrane receptors, with the objective of compensating for deficits in neurotransmission processes. It has been possible to achieve neuroprotective effects by use of various serotonergic compounds in animal models for neuropathological conditions such as ischemia, stroke, and excitotoxicity, and in some cases beneficial effects have also been observed for mood disorders such as depression or anxiety. Named here as examples are 5-HT$_{1A}$ agonists such as buspirone, or the compound 8-hydroxy-2-(di-n-propylamino)tetraline (8-OH-DPAT) which is characterized as a selective 5-HT$_{1A}$ receptor ligand. However, these active substances alleviate the described neurological deficits to only a limited extent, and there is currently no effective therapy for these conditions.

Another neuropathological condition which affects large numbers of people is migraine. In most cases migraine is manifested by recurring headaches, which affect an estimated 8 million persons, namely, 3-5% of all children, 7% of all men, and 14% of all women. Although a genetic predisposition is popularly reported, the causes appear to be multifaceted (Diener H. C. et al., Arzneimitteltherapie 15:387-394 (1997)). There are two dominant hypotheses: The long-known blood vessel theory proposes that the cause is a dilation process of the internal and external cerebral vascular system. The neurogenic theory is based on a release of vasoactive neurotransmitters, primarily neuropeptides such as substance P and neurokinin, from axons of the vascular system due to stimulation of ganglia which innervate specific brain tissue, resulting in inflammatory reactions and pain.

There is currently no causal therapy for treatment of migraine. Two different treatment methods are presently in use: first, a prophylactic therapy for prevention of recurring migraine attacks, and second, symptomatic therapy for suppression of acute symptoms during attacks. Migraine-specific active substances such as Sanmigran®, Nocerton®, Deseril®, and Vidora®, as well as active substances customarily used for other indications, such as beta blockers, antiemetic active substances such as Sibelium®, antidepressive agents such as Laroxyl®, or antiepileptic active substances such as Depakin® are administered for preventative treatment. Administered within the scope of acute therapy are analgesics such as aspirin, paracetamol, or Optalidon®, nonsteroidal anti-inflammatory agents such as Cebutid®, Voltaren®, Brufen®, Ponstyl®, Profenid®, Apranx®, and Naprosin® for pain and inflammation, ergot alkaloids such as ergotamine and dihydroergotamine, which may trigger vasoconstriction, or substances of the triptan family, such as sumatriptan, Naramig®, and AscoTop® with a high affinity for 5-$HT_{1D}$ receptors. The latter substances act as agonists and inhibit vasodilation.

However, the referenced active substances are not optimally suited for treatment of migraine. Nonopioid analgesics frequently have side effects. Due to the powerful peripheral vasoconstriction, the complex action mechanism of ergot alkaloids results in side effects such as hypertonia and gangrene. Compounds of the triptan family are likewise not fully satisfactory (Pfaffenrath V. Münch. Med. Wschr. 625-626 (1998).

5-$HT_5$ receptors show a high affinity for various antidepressants and antipsychotic agents. Previous studies indicate that 5-$HT_5$ receptors play a role in the following disease profiles:

Psychosis, depression, chronic schizophrenia, other psychotic conditions, anxiety, bipolar disorders, dementia, in particular Alzheimer's dementia, demyelinating diseases, in particular multiple sclerosis, and ischemia, stroke, and migraine.

The use of 5-$HT_5$ receptor ligands for the general treatment of migraine and other cerebrovascular diseases is described in WO 00/041472, and for the treatment of neurodegenerative and neuropsychiatric diseases, in WO 00/041696.

Therefore, there is a need for substances which effect modulation of 5-$HT_{5A}$ receptor activity.

PRIOR ART

The use of 5-$HT_5$ receptor ligands for the general treatment of migraine and other cerebrovascular diseases is described in WO 00041472, and for the treatment of neurodegenerative and neuropsychiatric diseases, in WO 00/041696 and WO 04096771.

WO 2002018327 A2 describes the synthesis of guanidinobenzamides as melanocortin-4 receptor antagonists (MC-4R), which are used in the treatment of diseases such as obesity and type II diabetes.

WO 9426715 A1 describes the preparation of N-pyridyl-N'-aryl-guanidines and analogs such as pyrimidines and pyrazines as gastric acid secretion inhibitors.

WO 2004037166 A2 provides a general description of the synthesis of guanidinoazines as antiviral agents, with the primary focus on the 4,6-dimethyl-, 4,6-dimethoxy-, and 4-methoxy-6-methyl-substituted N-(pyrimidin-2-yl)-N'-(2-phenylethyl)guanidines and N'-[2-(1H-indole-3-yl)ethyl] guanidines.

WO 2000004014 A1 describes the synthesis of pyrimidine derivatives as antitumor therapeutic agents, with the focus on N-[5-(hetaryloxymethyl)pyrimidin-4-yl]guanidine or N-{5-[(hetarylthio)methyl]pyrimidin-4-yl}guanidine.

WO 9202513 A1 describes the synthesis of diphenylazines and their use as antithrombotic vasodilators, antihypertensive agents, and anti-inflammatory agents.

DE 3334455 A1 describes sulfonyl-substituted guanidine derivatives which are substituted, for example, with the N-(4,6-dimethylpyrimidin-2-yl) radical and used as a herbicide.

The same applies for DE 3517842 A1 and EP 173321 A1, which describe sulfonylguanidinopyrimidine derivatives, the method for preparing same, and their use as herbicides.

US 20040167181 A1 relates to N,N',N"-trisubstituted guanidine derivatives of a general formula, whereby none of the exemplary embodiments bears a guanidine unit; instead, the focus is on amides and ureas.

Similarly, in WO 9736861 A1, titled "Meta-substituted phenylensulfonamide derivatives," the focus is on amides and ureas. The guanidine compounds of a general formula contained therein bear a benzyl radical in the meta position with respect to an optionally substituted N-{3-[(3-oxopropyl)sulfonyl]phenyl}sulfonamide or N-{3-[(3-oxopropyl)sulfonyl] phenyl}amide radical.

JP 0830184 A1 describes "Squalene epoxidase activity inhibitors," wherein the 2-pyridyl guanidine compounds are substituted with a phenyl side chain only in the meta and para positions with respect to the linkage point.

WO 9506034 A1 describes compounds such as substituted N-(2-phenylethyl)-N'-pyridin-2-yl ureas and several guanidines, and methods for inhibition of HIV and other related viruses.

Patent applications WO 0067746 A1, EP 1203766 A2, and WO 2004044046 A2 describe carboxylic acid derivatives which inhibit the binding of integrins to their receptors. The compounds represent urea derivatives on which pyridinones and pyrimidones may be substituted.

WO 2003011872 A1 describes "Platelet ADP receptor inhibitors" in which the N-hetaryl radical linked to the guanidine is [substituted] with an amide, alkoxy radical, or also more complex radicals, for example from the group comprising isoquinoline-1,3(2H,4H)-dione-2-yl, 3,4-dihydroisoquinoline-1(2H)-one-2-yl, 1,4-dihydroisoquinoline-3(2H)-one-2-yl, 1H-1,4-benzodiazepine-3,5(2H,4H)-dione-4-yl, and 1H-indene-1-one-2-yl. The exemplary embodiments relate primarily to substituted N-(anilinocarbonyl)thiophene-2-sulfonamides, N-[anilino(imino)methyl]thiophene-2-sulfonamides, and N-[anilino(methoxyimino)methyl]- or N-[anilino(cyanoimino)methyl]- or N-[anilino(H-imino)methyl]- or N-[anilino(methylimino)methyl]thiophene-2-sulfonamides, i.e., generally from the group of N-hetaryl-N'-sulfonylaryl-substituted ureas or N"-cyano, N"-methyl, N'-methoxy, or N"—H-guanidines.

WO 2004037789 A2 describes methylene urea derivatives as RAF kinase inhibitors. The exemplary embodiments relate exclusively to N-aryl/hetaryl-N'-methylenearyl/hetaryl-substituted urea derivatives, which in particular with respect to the urea in the N'-methylenearyl/hetaryl unit are characterized by the special substitution pattern such as meta- or para-substituted oxy-bridged aryl/hetaryl substituents.

International Patent application WO 0109096 A2 describes generally substituted N-methylene-(1-isoindoline)- and N-methylene-(1-isoquinoline)-substituted guanidines used as potassium channel blockers.

European Patent application EP 1270551 A1 describes urea derivatives having antiproteolytic activity for the treatment and prevention of thromboembolic diseases and restenoses. The structures upon which this application is based comprise para-substituted amidine units or also the cyclic variants such as 3-{2H-[1,2,4]oxadiazole-5-one}. N-6-nicotinamidie, N-5-pyridine-2-carboxamididine, N-6-pyridazine-3-carboxamidine, N-4-benzamidine urea/thiourea/guanidine derivatives may be produced, whereby the exemplary embodiments relate to benzamidine urea derivatives.

International Patent application WO 9824782 A2 describes substituted pyrimidine compounds and their use for the prevention and treatment of diseases which are mediated by TNF-alpha, IL-1 b, IL-6, and/or IL-8, and other conditions such as inflammation, pain, and diabetes. The exemplary embodiments relate primarily to 4,5-biaryl or 4-hetaryl-5-aryl-substituted pyrimidines, which in turn may be linked in the 2-position to 2,6-dichlorobenzyl, 2-(2-chlorophenyl) ethylamino, 2-(4-fluorophenyl)ethylamino, 3-phenylpropylamino, 3-imidazolylpropylamino, piperazinyl, or other nitrogen-containing radicals.

U.S. Pat. No. 5,942,544 A, U.S. Pat. No. 6,187,797 B1, and U.S. Pat. No. 6,020,357 A describe novel alpha-branched anilines, toluenes, and analogs, phenylisoxazoles, and nitrogen-containing heteroaromatic compounds as factor XA inhibitors.

International Patent application WO 2004058736 A1 describes CCR8 inhibitors which are primarily N-substituted N-(4-sulfamoylnaphthalene-1-yl)-2-methylbenzamides.

EP 1044967 describes 2-pyridinylguanidines as urokinase inhibitors which are not further substituted in the additional N',N''-position on the guanidine.

International Patent application WO 9315055 A1 describes pyridine derivatives, their synthesis, and use as pharmaceuticals. The exemplary embodiments relate to substituted N-(3-benzyloxypyridin-2-yl)-N'-phenyl-guanidine.

U.S. Pat. No. 5,403,861 A and WO 9214697 A1 describe substituted guanidines and their derivatives as modulators for the release of neurotransmitters. Also disclosed is a novel methodology in which such neurotransmitter release modulators are used for the treatment and prevention of pathophysiological conditions characterized by the release of excess levels of the neurotransmitters. The claim relates to N,N',N'',N'''-tetrasubstituted hydrazinedicardicarboximidamides [sic; hydrazinedicarboximidamides]. In addition, some of the preferred structures bear adamantyl or acenaphthalene radicals on the guanidine.

U.S. Pat. No. 5,741,661 likewise describes neurotransmitter release modulators comprising substituted guanidines, N''-aminoguanidines, and N,N',N'',N'''-tetrasubstituted hydrazinedicarboximiamides. Named as examples are applications for nerve cell death, Alzheimer's and Huntington's diseases, anxiety, dementia, and arteriosclerosis.

International Patent applications WO 9118868 A1, WO 9014067 A2, and WO 8800583 describe N,N'-disubstituted guanidines which have a high binding rate to the sigma receptor and inhibit same. Said guanidines are used in the treatment or prevention of psychoses, depression, hypertension, or anxieties in mammals. The preferred structures contain N,N'-disubstituted guanidines substituted with adamantyl, norbornyl, and various substituted phenyl radicals.

International Patent application WO 0222581 A1 describes nitrogen-containing compounds, their high affinity for glycine transport inhibitors, and their use for treatment of neurological conditions such as schizophrenia, dementia, epilepsy, muscle spasms, mood disorders, learning disabilities, neurodegenerative diseases, and pain. The exemplary embodiments reference thiourea derivatives having an N'-substituted (2E)-N-{1-[(aminocarbonothioyl)amino]-2,2,2-trichlorethyl}-3-phenylacrylamide or N-{1-[(aminocarbonothioyl)amino]-2,2,2-trichloroethyl}-2,2-alkylamide unit on the thiourea as a repeating structural element.

WO 0230881 A1 describes the synthesis of (hetero)arylsulfonyl-guanidines used for treatment of pain, epilepsy, migraine, and other conditions.

The following literature citations are known with regard to the N-substituted pyrimidine derivatives:

In the literature citation titled "*Biaryl guanidine inhibitors of in vitro HCV-IRES activity*," E. A. Jefferson, *Bioorg. Med. Chem. Lett.* 2004, 14(20), 5139-5143, a structure-activity relationship is established in a high-throughput screening, resulting in small active molecules such as N-(4,6-dimethylpyrimidin-2-yl)-N'-phenethylguanidines.

The literature citation titled "*Synthesis and structure activity relationship of guanidines as NPY Y5 antagonists*," C. J. Aquino, *Bioorg. Med. Chem.* 2004, 12(10), 2691-2708 describes bis-heteroaryl-guanidines, for example N-(4-methylpyrimidin-2-yl)-N'-phenylguanidines substituted in the 6-position with respect to the pyrimidine, and tertiary guanidines such as N-methyl-N'-(4-methyl-6-phenethylaminopyrimidin-2-yl)-N''-(4-trifluoromethylphenyl)guanidine.

The literature citation titled "*Diazine-derived guanidines, isothioureas, and isoureas: Synthesis and attempts of configurational assignment*," G. Heinisch, *J. Het. Chem.* 2002, 39(4), 695-702 describes a novel synthetic approach and the spectroscopic structural elucidation for N'-pyrimid-2-yl-, N'-pyrazin-2-yl-, and N'-pyridazin-3-yl-substituted N-tert-butyl guanidines, 1-tert-butyl isothioureas, and 1-tert-butyl isoureas.

The literature citation titled "*Studies on anti-platelet agents. IV. A series of 2-substituted 4,5-bis(4-methoxyphenyl) pyrimidines as novel anti-platelet agents*," A. Tanaka, *Chem. Pharm. Bulletin* 1994, 42(9), 1828-34 describes the synthesis and structure-activity relationship of a series of 2-substituted 4,5-bis(4-methoxyphenyl)pyrimidines as novel cyclooxygenase (CO) inhibitors.

The following three literature citations are part of a series of publications of the Shuto et al. work group, which calculated the electronic structure of various guanidinopyrimidines using the extended Hückel method, described the syntheses of novel compounds, and investigated the cytotoxicity and the antifungal and antiviral activity of this structural class: "*Studies on biologically active guanidinopyrimidines. Electronic structure and biological activity of guanidinopyrimidines*" in Y. Shuto, *Agric. Biol. Chem.* 1979, 43(11), 2245-8; "*Studies on biologically active guanidinopyrimidines. Part III. Cytotoxicity-structure relationship of guanidinopyrimidines*," Y. Shuto, *Agric. Biol. Chem.* 1979, 43(4), 861-2, and "*Studies on biologically active guanidinopyrimidines. Part II. Effect of guanidinopyrimidines on phytopathogens*" in Y. Shuto, J. Fac. Agric., *Kyushu Univ.* 1979, 23(3-4), 125-32.

The literature citation titled "*Antimalarial drugs. 35. Synthesis and antimalarial effects of 1-(3,4-dichlorophenyl)-3-[4-[(1-ethyl-3-piperidyl)amino]-6-methyl-2-pyrimidinyl] guanidine and related substances*," E. F. Elslager, *J. Med. Chem.* 1974, 17(1), 75-100 describes the syntheses of 121 compounds of the 1-aryl-3-{4-[(mono- and dialkylamino)alkyl]amino]-6-methyl-2-pyrimidinyl}guanidines by condensation of 1-(4-chloro-6-methyl-2-pyrimidinyl)-3-arylguanidines with suitable polyamines. Ninety of these compounds show curative activity against *Plasmodium berghei*. Structure-activity relationships are likewise discussed.

The literature citation titled "*Reaction of biguanides and related compounds. I. Reaction of biguanides with β-diketone*," M. Furukawa, *Chem. Pharm. Bulletin* 1971, 19(11), 2284-8 describes the reaction of aryl and alkyl biguanides with acetylacetone to produce the corresponding 4,6-dimethyl-2-alkyl or -arylguanidinopyrimidines. In addition, the differing reactivities of the aryl and alkyl biguanides with respect to benzoylacetone are compared, which in the first case result in 6-arylamino-4-amino-2-phenyl-2-(6'-arylamino-4'-amino-2'-methyl-1',2'-dihydro-s-triazinyl-2'-methyl)-1,2-dihydro-s-triazines, and in the second case result in the corresponding 6-methyl-4-phenyl-2-alkylguanidinopyrimidines.

The following patent applications describe exclusively N,N',N''-trisubstituted guanidine derivatives in which one of the substituents directly linked to the guanidines bears a cyano group.

Applications WO 0061561 A1 and WO 2000061559 A1 describe the preparation of N-substituted cyanoguanidines as antitumor agents.

Cyanoguanidines as cell proliferation inhibitors are also described in WO 9854146 A1.

Applications WO 0242265 A2 and WO 2003097601 A1 describe cyanoguanidines, in particular substituted N-{1-[(carboxy)methyl]pyridinium-N'-cyanoguanidine derivatives, which are suitable as prodrugs for human and veterinary treatment of proliferative diseases such as cancer.

Applications WO 200061561 A1 and WO 200061559 A1 describe novel substituted cyanoguanidine derivatives for treatment as antitumor agents or treatment of tumors, for example leukemia, melanomas, or cancer of the lungs, colon, ovary, cervix, kidney, prostate, breast, or central nervous system.

WO 9520579 A1 describes the synthesis of pyridinylcyanoguanidines, WO 9404500 A1 describes the synthesis of pyridylcyanoguanidines, U.S. Pat. No. 5,567,722 A describes the synthesis of N-(3-pyridyl)-N''-cyanoguanidines, WO 9404499 A1 describes the synthesis of N-phenyl(cyclo)alkyl-N'-3-pyridylcyanoguanidines, and in each case the use as potassium channel blockers is described.

U.S. Pat. No. 5,668,157 A also describes cyanoguanidines as potassium channel blockers, their use for treatment of cardiovascular diseases and as diuretic agents, and syntheses thereof.

WO 9404500 A1 and WO 9404499 A1 describe cyanoguanidines and WO 9429280 A1 describes pyrimidinecyanoguanidines, likewise as potassium channel blockers.

DE 2557438 A1 describes N-substituted N''-cyano-N'-pyridyl-guanidine derivatives, and DE 3233380 A1 describes substituted pyridylcyanoguanidine compounds, whose effect as antihypertensive agents has been demonstrated.

WO 0216318 A1 claims various hetaryl-substituted thioureas, ureas, and cyanoguanidines, with the focus on novel thiourea derivatives and the pharmaceutical compositions thereof.

WO 8906530 A1, titled "New topical preparation for treatment of alopecia," describes various linked pyridylcyanoguanidines.

EP 0022958 A1 describes urea derivatives for use [in the treatment] of lipometabolic disorders, whereby instead of thioureas and ureas, cyanamide analogs are claimed.

The following applications describe exclusively N,N',N''-trisubstituted guanidine derivatives in which one of the substituents directly linked to the guanidine bears an alkoxy, hydroxy, amino, alkyl, cycloalkyl, or sulfonyl group.

Application WO 0076508 A1 describes IL-8 receptor antagonists used for the treatment of diseases caused by chemokines.

U.S. Pat. No. 4,880,932 A (guanidinopyrimidines), U.S. Pat. No. 797,484 A ((sulfonyl-guanidine)pyrimidines), and U.S. Pat. No. 4,743,294 A (N'-(substituted-1,3,5-triazinyl)-N''-amino-N''-(substituted benzenesulfonyl) guanidines) describe the synthesis and use thereof as herbicides and plant growth regulators.

FR 2609603 A1 describes guanidinoacetic acid and ethanamidinoacetic acid derivatives as sweeteners.

WO 0178717 A1 describes N-hydroxyguanidines for pharmacotherapy for vascular dysfunction associated with deficient nitric oxide bioactivity.

US 20030073747 describes amino acid-substituted N-hydroxyguanidines which reverse or prevent premature arteriosclerotic aging of the blood vessels.

WO 9500505 A1 relates to various N-amino acid-N',N''-disubstituted guanidine derivatives, thiourea derivatives, and amidine derivatives of a general formula, whereby the exemplary embodiments relate to N-amino acid-substituted thioureas used as NO synthase inhibitors.

DE 2847792 A1 describes N'-alkyl- and N'-cycloalkyl-substituted N-4-quinolylguanidine.

DE 351784 2 A1 and EP173321 A1 describe sulfonylguanidinopyrimidine derivatives.

WO 2002088323 A2 describes hydrazinecarboximidamides which activate gene transfer.

The following comprehensive literature overview lists all literature citations and corresponding titles relating to N-hetaryl-substituted N''-cyanoguanidines and N''-alkylguanidines:

"*The stereoenantiomers of a pinacidil analog open or close cloned ATP-sensitive K+ channels,*" U. Lange, *J. Biol. Chem.* 2002, 277(43), 40196-40205, and "*K+ channel blockers: natriuretic potency correlates to vascular ATP-sensitive K+ channel blockade,*" M. A. Clark, *Methods Find. Exp. Clin. Pharmacol.* 1999, 21(1), 25-30.

"*Pharmacological characterization of novel cyanoguanidines as vascular KATP channel blockers,*" S. A. Khan, *J. Pharmacol. Exp. Therapeutics* 1997, 283(3), 1207-1213.

"*QSAR study on hypotensive activity of analogs of pinacidil,*" S. Liu, *Zhongguo Yaoke Daxue Xuebao* 1997, 28(1), 1-4.

"*Preparation of N,N'-bis(aryl)guanidines from electron deficient amines via masked carbodiimides,*" M. R. Barvian, *Tetrahedron Lett.* 1997, 38(39), 6799-6802.

"*Synthesis and antihistaminic activity of 2-guanidino-3-cyanopyridines and pyrido[2,3-d]pyrimidines,*" J. M. Quintela, *Bioorg. Med. Chem.* 1997, 5(8), 1543-1553.

"*Synthesis and hypotensive activity of some thiourea/cyanoguanidine analogs of pinacidil,*" S. Liu, *Zhongguo Yaoke Daxue Xuebao* 1995, 26(4), 193-8. "*Synthesis of potassium channel opener pinacidil and its analogs,*" J. Chen, *Zhongguo Yaoke Daxue Xuebao* 1993, 24(4), 202-4.

"*The relation between vascular relaxant and cardiac electrophysiological effects of pinacidil,*" M. Steinberg, *J. Cardiovascular Pharmacol.* 1988, 12 (Suppl. 2), 30-40.

"*Cardiac electrophysiological effects of pinacidil and related pyridylcyanoguanidines: relationship to antihypertensive activity,*" J. K. Smallwood, *J. Cardiovascular Pharmacol.* 1988, 12(1), 102-9.

"*Synthesis of N-alkyl-N'-cyano-N''-4-pyridyl-guanidines from 4-pyridyldithiocarbamic acid via N-alkyl-N'-4-pyridylthioureas or via 4-pyridylcyaniminothiocarbamic acid,*" E. T. Hansen, *Synthetic Commun.* 1984, 14(13), 1275-83.

"*Adaptive least-squares method applied to structure-activity correlation of hypotensive N-alkyl-N''-cyano-N'-pyridyl-guanidines,*" I. Moriguchi, *J. Med. Chem.* 1980, 23(1), 20-6.

"*Fungicidal activities of 1,1-diisopropyl-2-(3-pyridyl-3-p-ethoxyphenyl-guanidine and its analogs,*" S. Tanaka, *Agric. Biol. Chem.* 1978, 42(4), 803-7.

"Synthesis and hypotensive activity of N-alkyl-N''-cyano-N'-pyridyl-guanidines," H. J. Petersen, *J. Med. Chem.* 1978, 21(8), 773-81.

"Structure-activity study of S-1358 and its derivatives. Part II. Structure modifications of S-n-butyl S'-p-tert-butylbenzyl N-3-pyridyldithiocarbonimidate (S-1358, Denmert) and fungicidal activities," Tanaka, *Agricultural and Biological Chemistry* 1977, 41(10), 1953-9.

WO 2005/095345 (PCT/US2005/009710) describes 2-pyridyl- and 2-pyrimidylguanidine derivatives and their use as inhibitors of viral replication.

WO 94/06770 (PCT/DK93/00291) describes N-cyanoguanidine compounds and their use as serotonin antagonists with affinity for the 5-HT$_2$ receptor, whereby the guanidine group in each case bears only one additional N substituent per NH$_2$ group, the substituent of the one NH$_2$ group being an optionally substituted pyridine ring, and the substituent of the other NH$_2$ group being a C$_1$-C$_8$ alkylene-X-phenyl radical, where X stands for —O—, —S(O)$_n$ where n=0, 1, or 2, and —NR$_1$— where R$_1$=H or C$_1$-C$_4$ alkyl, and the phenyl ring may be substituted with the radical R, where R stands for C$_1$-C$_4$ alkyl or alkoxy, hydroxy, halogen, trifluoromethyl, cyano, carboxamide, sulfamoyl, or nitro.

WO 2002/24681 (PCT/US01/29175) describes 1,4-pyrazineguanidine derivatives and their use as inhibitors of tyrosine kinase activity, the pyrazine ring being substituted with a heteroaryl or biheteroaryl group.

US 2002/028836 (Abbott) describes guanidine derivatives and their use as potassium channel openers.

WO 2006/007532 (PCT/US2005/023346) describes 2-substituted heteroaryl compounds and their use as interleukin IL-12 modulators.

WO 2005/086754 (PCT/US2005/007316) describes dicationic compounds for treatment of trichomoniasis infections.

WO 2004/058709 (PCT/US2003/041360) describes guanidine derivatives as chemokine receptor (CCR8) inhibitors.

WO 2006/021805 (PCT/GB2005/003352) describes diarylsulfones as 5-HT$_{2A}$ antagonists.

WO 93/12788 (PCT/US92/10254) describes pyridylguanidine compounds for treatment of erectile dysfunction.

EP 0401010 B1 describes pyranylcyanoguanidine derivatives and their use as cardiovascular agents.

U.S. Pat. No. 3,574,744 describes guanidine alkyl derivatives of substituted anilides having antiserotonin and antibacterial activity for treatment of asthma and bronchial diseases.

U.S. Pat. No. 2,537,834 describes substituted guanidinylmelamines for use as flame retardants.

US 2005/0171195 A1 describes N-cyanoguanidine derivatives as P2X7 antagonists for treatment of neuropathic pain.

SUMMARY OF THE INVENTION

According to a first object of the present invention, the objective is to provide compounds which allow the treatment and/or prevention of neuropathological, neuropsychiatric, and neurodegenerative disorders with sufficient efficacy and low incidence of side effects.

According to a further object of the present invention, the objective is to provide compounds which modulate 5-HT$_{5A}$ receptor activity for the treatment and/or prevention of diseases which may be treated by modulation of 5-HT$_{5A}$ receptor activity.

Surprisingly, it has been found that substances of general formula I act as ligands of the 5-HT$_5$ receptor, thus allowing treatment of the associated medical conditions described above as well as the accompanying symptoms and dysfunctions.

According to one aspect of the present invention, at least one guanidine compound of general formula I

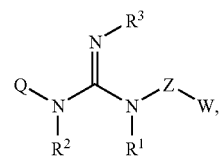

the corresponding enantiomeric, diastereomeric, and/or tautomeric forms thereof, and/or pharmaceutically acceptable salts thereof, and/or the corresponding active substance precursors ("prodrugs") thereof,
are prepared, wherein the stated radicals have the following definitions:

R$^1$, R$^2$ in each case independently stand for:
hydrogen, OH, CN,
or
in each case optionally substituted C$_1$-C$_6$ alkyl, O—C$_1$-C$_6$ alkyl, C$_1$-C$_6$ alkylene-O—C$_1$-C$_6$ alkyl, C$_3$-C$_7$ cycloalkyl, O—C$_3$-C$_7$ cycloalkyl, aryl, hetaryl, C$_1$-C$_4$ alkylene-aryl, C$_1$-C$_4$ alkylene-hetaryl, O-aryl, O—C$_1$-C$_4$ alkylene-aryl, O-hetaryl, O—C$_1$-C$_4$ alkylene-hetaryl, CO—C$_1$-C$_6$ alkyl, CO-aryl, CO-hetaryl, CO—C$_1$-C$_4$ alkylene-aryl, CO—C$_1$-C$_4$ alkylene-hetaryl, CO—O—C$_1$-C$_6$ alkyl, CO—O-aryl, CO—O-hetaryl, CO—O—C$_1$-C$_4$ alkylene-aryl, SO$_2$—C$_1$-C$_6$ alkyl, SO$_2$-aryl, SO$_2$-hetaryl, SO$_2$—C$_1$-C$_4$ alkylene-aryl, OCO—C$_1$-C$_6$ alkyl, OCO-aryl, OCO-hetaryl, OCO—C$_1$-C$_4$ alkylene-aryl, OCO—C$_1$-C$_4$ alkylene-hetaryl, SO$_2$—C$_1$-C$_6$ alkyl, SO$_2$-aryl, SO$_2$-hetaryl, or SO$_2$—C$_1$-C$_4$ alkylene-aryl, R$^3$ is hydrogen
or
in each case optionally substituted C$_1$-C$_6$ alkyl, O—C$_1$-C$_6$ alkyl, C$_1$-C$_6$ alkylene-O—C$_1$-C$_6$ alkyl, C$_3$-C$_7$ cycloalkyl, O—C$_3$-C$_7$ cycloalkyl, aryl, hetaryl, C$_1$-C$_4$ alkylene-aryl, C$_1$-C$_4$ alkylene-hetaryl, O-aryl, O—C$_1$-C$_4$ alkylene-aryl, O-hetaryl, O—C$_1$-C$_4$ alkylene-hetaryl, CO—C$_1$-C$_6$ alkyl, CO-aryl, CO-hetaryl, CO—C$_1$-C$_4$ alkylene-aryl, CO—C$_1$-C$_4$ alkylene-hetaryl, CO—O—C$_1$-C$_6$ alkyl, CO—O-aryl, CO—O-hetaryl, CO—O—C$_1$-C$_4$ alkylene-aryl, SO$_2$—C$_1$-C$_6$ alkyl, SO$_2$-aryl, SO$_2$-hetaryl, SO$_2$—C$_1$-C$_4$ alkylene-aryl, OCO—C$_1$-C$_6$ alkyl, OCO-aryl, OCO-hetaryl, OCO—C$_1$-C$_4$ alkylene-aryl, OCO—C$_1$-C$_4$ alkylene-hetaryl, SO$_2$—C$_1$-C$_6$ alkyl, SO$_2$-aryl, SO$_2$-hetaryl, or SO$_2$—C$_1$-C$_4$ alkylene-aryl,
or
in each case two radicals selected from the group comprising R$^1$, R$^2$, or R$^3$, independently from the remaining radical R$^1$, R$^2$, or R$^3$, together with the nitrogen atom to which they are bonded form a 5- to 7-membered optionally substituted, saturated or unsaturated heterocycle which may contain one, two, or three further heteroatoms, which may be different or the same, selected from the group comprising C, O, N, and S, wherein optionally two radicals substituted on this heterocycle together with the ring atom to which they are bonded may form a 3- to 7-membered optionally substituted, anellated, saturated, unsaturated, or aromatic carbocycle or heterocycle, wherein the heterocycle may contain one, two, or three heteroatoms, which may be different or the same, comprising O, N, and S, and wherein the cyclic compound formed may optionally be substituted, and/or a further 3- to 7-membered, optionally substituted cyclic compound may be condensed thereon;

Z is a radical of general formula Z1

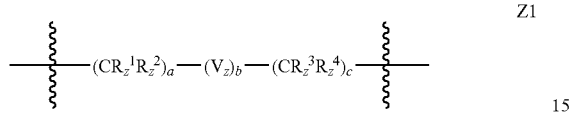

Z1 having the indices
a=0, 1, 2, 3, or 4
b=0 or 1
c=0, 1, 2, 3, or 4
wherein the sum of a, b, and c is equal to 1, 2, 3, 4, or 5,
$R_Z^1$, $R_Z^2$, $R_Z^3$, $R_Z^4$ in each case independently stand for:
hydrogen, halogen, OH,
or
in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_3$-$C_7$ cycloalkyl, aryl, $C_1$-$C_4$ alkylene-aryl, hetaryl, or $C_1$-$C_4$ alkylene-hetaryl,
or
two radicals $R_Z^1$ and $R_Z^2$ or $R_Z^3$ and $R_Z^4$ independently in each case, together with the C atom to which they are bonded, form a 3- to 7-membered, optionally substituted, saturated or unsaturated carbocycle or heterocycle which may contain one, two, or three heteroatoms, which may be the same or different, selected from the group comprising O, N, and/or S;

$V_Z$ is —CO—, —CO—$NR_Z^5$—, —$NR_Z^5$—CO—, —O—, —S—, —SO—, —$SO_2$—, —$SO_2$—$NR_Z^5$—, $NR_Z^5$—$SO_2$—, —CS—, —CS—$NR_Z^5$—, —$NR_Z^5$—CS—, —CS—O—, —O—CS—, —CO—O—, O—CO—, ethynylene, —C(=$CR_Z^6R_Z^7$)—, —$CR_Z^6$=$CR_Z^7$—, —$NR_Z^5$—CO—$NR_Z^{5*}$—, —O—CO—$NR_Z^5$—, —$NR_Z^5$—;
wherein
$R_Z^5$, $R_Z^{5*}$ independently, and in each case independently of their respective occurrence, stand for:
hydrogen, or
in each case optionally substituted $C_1$-$C_6$ alkyl, $C_1$-$C_4$ alkylene-O—$C_1$-$C_6$ alkyl, $C_2$-$C_6$ alkenyl, $C_2$-$C_{12}$ alkynyl, CO—$C_1$-$C_6$ alkyl, CO—O—$C_1$-$C_6$ alkyl, $SO_2$—$C_1$-$C_6$ alkyl, $C_3$-$C_7$ cycloalkyl, aryl, $C_1$-$C_4$ alkylene-aryl, CO—O—$C_1$-$C_4$ alkylene-aryl, CO—$C_1$-$C_4$ alkylene-aryl, CO-aryl, $SO_2$-aryl, hetaryl, CO-hetaryl, or $SO_2$—$C_1$-$C_4$ alkylene-aryl;
$R_Z^6$, $R_Z^7$ independently, and in each case independently of their respective occurrence, stand for:
hydrogen, OH, or
in each case optionally substituted $C_1$-$C_6$ alkyl, $C_1$-$C_6$ alkoxy, $C_2$-$C_6$ alkenyl, $C_2$-$C_6$ alkynyl, $C_1$-$C_4$ alkylene-$C_3$-$C_7$ cycloalkyl, $C_3$-$C_7$ cycloalkyl, aryl, $C_1$-$C_4$ alkylene-aryl, hetaryl, or $C_1$-$C_4$ alkylene-hetaryl;

W is a radical of general formula W1, W2, or W3

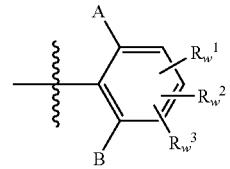

W1

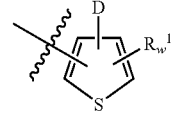

W2

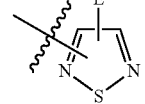

W3 wherein
A is $NO_2$, $NH_2$, OH, CN, $CF_3$, $OCF_3$, $CHF_2$, $CH_2F$, $OCHF_2$, $OCH_2F$, COOH, O—$CH_2$—COOH, halogen, SH, O—$C_1$-$C_6$ alkyl, S—$C_1$-$C_6$ alkyl, or
in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, $C_1$-$C_4$ alkylene-hetaryl, heterocycloalkyl, or
$R_A^1$, O—$R_A^1$, CO—$R_A^1$, S—$R_A^1$, SO—$R_A^1$, CO—O—$R_A^1$, $NR_A^4$—CO—O—$R_A^1$, O—$CH_2$—COO—$R_A^1$, $NR_A^2R_A^3$, $CONH_2$, $SO_2NH_2$, $NR_A^4$—CO—$R_A^1$, $SO_2$—$R_A$, $NR_A^4$—$SO_2$—$R_A^1$, $SO_2$—$NR_A^2R_A^3$, CO—$NR_A^2R_A^3$, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$, or $C_1$-$C_4$ alkylene-O—$R_A^1$;
wherein
$R_A^1$ independently of its respective occurrence stands for:
in each case optionally substituted $C_1$-$C_6$ alkyl, $C_1$-$C_6$ alkylene-O—$C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_2$-$C_6$ alkenylene-aryl, or in each case optionally substituted $C_1$-$C_4$ alkylene-hetaryl, —CO—$C_1$-$C_6$ alkyl, —CO—O—$C_1$-$C_6$ alkyl, —CO-aryl, —CO-hetaryl, —CO—O-aryl, —CO—O-hetaryl, —CO—$C_3$-$C_7$ cycloalkyl, —CO—O—$C_3$-$C_7$ cycloalkyl, —CO-heterocycloalkyl, —CO—O-heterocycloalkyl, $C_1$-$C_4$ alkylene-$NR_A^2R_A^3$, $C_1$-$C_4$ alkylene-$CONR_A^2R_A^3$, $C_1$-$C_4$ alkylene-$SO_2$—$NR_A^2R_A^3$, $C_1$-$C_6$ alkylene-O—$R_A^2$;
$R_A^2$ independently of its respective occurrence stands for:
hydrogen, OH, CN, or
in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$R_A^3$ independently of its respective occurrence stands for:
in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_4$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;
or the radicals $R_A^2$ and $R_A^3$ together with the nitrogen atom to which they are bonded form a 3- to 7-membered optionally substituted, saturated or aromatic heterocycle which may contain one, two, or three further heteroatoms, which may be different or the same, selected from the group comprising O, N, and S, wherein optionally two radicals substituted on this heterocycle together with the ring atom to which they are bonded may form a 3- to 7-membered optionally substituted, anellated, saturated, unsaturated, or aromatic carbocycle or heterocycle, wherein the heterocycle may contain one, two, or three heteroatoms, which may be different or the same, selected from the group comprising O, N, and S, and wherein the cyclic compound formed may optionally be substituted, $R_A^4$ independently of its respective occurrence stands for:
hydrogen, or
in each case optionally substituted $C_1$-$C_6$ alkyl, $C_1$-$C_6$ alkylene-O—$C_1$-$C_6$ alkyl, $C_2$-$C_6$ alkenyl, $C_2$-$C_{12}$ alkynyl, CO—$C_1$-$C_6$ alkyl, CO—O—$C_1$-$C_6$ alkyl, $SO_2$—$C_1$-$C_6$ alkyl, $C_3$-$C_7$ cycloalkyl, aryl, $C_1$-$C_4$ alkylene-aryl, CO—O-arylalkyl, CO—$C_1$-$C_4$ alkylene-aryl, CO-aryl, $SO_2$-aryl, hetaryl, CO-hetaryl or $SO_2$—$C_1$-$C_4$ alkylene-aryl;

B is a radical that is
hydrogen, or in each case optionally substituted aryl or hetaryl, or, independently of radical A, has the same meaning as for radical A,
or
two radicals selected from the group comprising A, B, $R_w^1$, $R_w^2$, and $R_w^3$ independently in each case, together with the C atom to which they are bonded, form a 3- to 7-membered, optionally substituted, saturated, unsaturated, or aromatic carbocycle or a 3- to 7-membered, optionally substituted, saturated, unsaturated, or aromatic heterocycle which may contain one, two, or three further heteroatoms, which may be different or the same, selected from the group comprising O, N, and S, and two radicals substituted on this carbocycle or heterocycle together with the ring atom to which they are bonded may optionally form a further 3- to 7-membered, optionally substituted, annelated, saturated, unsaturated, or aromatic carbocycle or heterocycle, wherein the heterocycle may contain one, two, or three heteroatoms, which may be different or the same, selected from the group comprising O, N, and S, and the cyclic compound thus formed may optionally be substituted;

$R_w^1$, $R_w^2$, $R_w^3$ in each case independently stand for:
hydrogen, $NO_2$, $NH_2$, OH, CN, $CF_3$, $OCF_3$, $CHF_2$, $CH_2F$, $OCHF_2$, $OCH_2F$, COOH, O—$CH_2$—COOH, halogen, SH, O—$C_1$-$C_6$ alkyl, S—$C_1$-$C_6$ alkyl, or
in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_6$ alkylene-$C_3$-$C_7$ cycloalkyl, $C_1$-$C_6$ alkylene-heterocycloalkyl, $C_1$-$C_6$ alkylene-aryl, $C_1$-$C_6$ alkylene-hetaryl, heterocycloalkyl, or in each case optionally substituted $R_A^1$, O—$R_A^1$, CO—$R_A^1$, S—$R_A^1$, SO—$R_A^1$, CO—O—$R_A^1$, $NR_A^4$—CO—O—$R_A^1$, O—$CH_2$—COO—$R_A^1$, $NR_A^2R_A^3$, $CONH_2$, $SO_2NH_2$, $NR_A^4$—CO—$R_A^1$, $SO_2$—$R_A^1$, $NR_A^4$—$SO_2$—$R_A^1$, $SO_2$—$NR_A^2R_A^3$, CO—$NR_A^2R_A^3$, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$, or $C_1$-$C_4$ alkylene-O—$R_A^1$; wherein $R_A^1$, $R_A^2$, $R_A^3$, and $R_A^4$ independently, and in each case independently of their respective occurrence and independently of their respective meaning for radical A, may have the meanings given for radical A;

D independently of radical A stands for a radical having the same meanings defined for radical A;

E is hydrogen or, independently of radical A, stands for a radical having the same meanings defined for radical A;

Q: is an at least 6-membered hetaryl radical of general formula Q

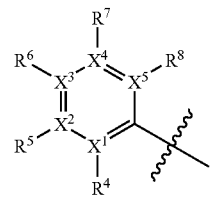

wherein
$X^1$: is C or N,
$X^2$: is C or N,
$X^3$: is C or N,
$X^4$: is C or N,
$X^5$: is C or N,
wherein one, two, or three radicals selected from the group comprising the radicals $X^1$, $X^2$, $X^3$, $X^4$, and $X^5$ are simultaneously N, and the associated binding partner selected from the group comprising $R^4$, $R^5$, $R^6$, $R^7$, and $R^8$ then stands for a free electron pair.

$R^4$, $R^5$, $R^6$, $R^7$, and $R^8$ in each case independently stand for a radical selected from groups 1.), 2.), 3.), 4.), 5.), 6.), and 7.), which may be the same or different, wherein groups 1.) through 7.) have the meanings given below:

1.) Hydrogen, halogen, CN, $CF_3$, $CHF_2$, $CH_2F$, $OCF_3$, $OCH_2F$, $OCHF_2$, $NH_2$, $NO_2$, COOH, O—$CH_2$—COOH, or
in each case optionally substituted $C_1$-$C_{10}$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, $C_1$-$C_6$ alkylene-O—$C_1$-$C_6$ alkyl, $C_1$-$C_6$ alkylene-O-aryl, COO—$C_1$-$C_4$ alkyl, $C_1$-$C_4$ alkylene-COO—$C_1$-$C_4$ alkyl, or in each case optionally substituted O—$R_Q^4$, S—$R_Q^4$, $NR_Q^6R_Q^7$, CO—$OR_Q^5$, CO—$R_Q^5$, SO—$R_Q^5$, $NR_Q^7$—CO—O—$R_Q^5$, O—$CH_2$—COO—$R_Q^5$, $NR_Q^7$—CO—$R_Q^5$, $SO_2$—$R_Q^5$, $NR_Q^7$—$SO_2$—$R_Q^5$, $SO_2NH_2$, $CONH_2$, $SO_2$—$NR_Q^6R_Q^7$, or CO—$NR_Q^6R_Q^7$; wherein $R_Q^4$, $R_Q^5$, $R_Q^6$, and $R_Q^7$ independently, and independently of their respective occurrence, are defined as below;

2.) In each case optionally substituted phenyl, 1-naphthyl, or 2-naphthyl may be substituted with one, two, or three radicals selected from the group comprising $R_Q^1$, $R_Q^2$, and $R_Q^3$, wherein $R_Q^1$, $R_Q^2$, and $R_Q^3$ in each case independently stand for a substituent, which may be the same or different, selected from the following group:

Hydrogen, $NO_2$, $NH_2$, OH, CN, $CF_3$, $CHF_2$, $CH_2F$, $OCF_3$, $OCHF_2$, $OCH_2F$, COOH, $O-CH_2-COON$, SH, halogen, or in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted $O-R_Q^4$, $S-R_Q^4$, $NR_Q^6R_Q^7$, $CO-OR_Q^5$, $NR_Q^7-CO-O-R_Q^5$, $O-CH_2-COO-R_Q^5$, $NR_Q^7-CO-R_Q^5$, $SO_2-R_Q^5$, $NR_Q^7-SO_2-R_Q^5$, $SO_2NH_2$, $CONH_2$, $SO_2-NR_Q^6R_Q^7$, or $CO-NR_Q^6R_Q^7$, or in each case two radicals selected from the group comprising $R_Q^1$, $R_Q^2$, and $R_Q^3$ together with the atom to which they are bonded form a 3- to 7-membered, optionally substituted, saturated, or unsaturated carbocycle or a 3- to 7-membered, optionally substituted, saturated, unsaturated, or aromatic heterocycle which may contain up to three further heteroatoms, which may be different or the same, selected from the group comprising O, N, and S, wherein two radicals substituted on this carbocycle or heterocycle together may optionally form a 3- to 7-membered, optionally substituted, annelated, saturated, unsaturated, or aromatic carbocycle or heterocycle, wherein the heterocycle may contain one, two, or three heteroatoms, which may be different or the same, selected from the group comprising O, N, and S, and the cyclic compound thus formed may optionally be substituted, and/or a further 3- to 7-membered, optionally substituted cyclic compound may be condensed thereon; wherein the substituents below have the following meanings:

$R_Q^4$ independently of its respective occurrence in each case stands for hydrogen, or in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, heterocycloalkyl, aryl, or hetaryl;

$R_Q^5$ independently of its respective occurrence in each case stands for hydrogen, or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, or $C_1$-$C_6$ alkylene-O-$C_1$-$C_6$ alkyl;

$RQ^6$ independently of its respective occurrence stands for hydrogen, OH, CN, or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O-$C_1$-$C_6$ alkyl, CO-$C_1$-$C_6$ alkyl, $C_1$-$C_4$ alkylene-aryl, $C_1$-$C_4$ alkylene-hetaryl, CO-aryl, CO-hetaryl, $CO-C_1$-$C_4$ alkylene-aryl, $CO-C_1$-$C_4$ alkylene-hetaryl, $CO-O-C_1$-$C_6$ alkyl, CO-O-aryl, $CO-O-C_1$-$C_4$ alkylene-aryl, CO-O-hetaryl, $CO-O-C_1$-$C_4$ alkylene-hetaryl, $SO_2-C_1$-$C_6$ alkyl, $SO_2$-aryl, $SO_2$-hetaryl, $SO_2-C_1$-$C_4$ alkylene-aryl, or $SO_2-C_1$-$C_4$ alkylene-hetaryl;

$RQ^7$ independently of its respective occurrence stands for hydrogen, or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $CO-C_1$-$C_6$ alkyl, CO-aryl, CO-hetaryl, $CO-C_1$-$C_4$ alkylene-aryl, $CO-C_1$-$C_4$ alkylene-hetaryl, $CO-O-C_1$-$C_6$ alkyl, CO-O-aryl, $CO-O-C_1$-$C_4$-alkylene-aryl, CO-O-hetaryl, $CO-O-C_1$-$C_4$ alkylene-hetaryl, $SO_2-C_1$-$C_6$ alkyl, $SO_2$-aryl, $SO_2$-hetaryl, $SO_2-C_1$-$C_4$ alkylene-aryl, or $SO_2-C_1$-$C_4$ alkylene-hetaryl;

or both radicals $R_Q^6$ and $R_Q^7$ together with the nitrogen atom to which they are bonded form a 3- to 7-membered, optionally substituted, saturated or aromatic heterocycle which may contain one, two, or three further heteroatoms, which may be different or the same, selected from the group comprising O, N, and S, and optionally two radicals substituted on this heterocycle together with the atom to which they are respectively bonded may form a 3- to 7-membered, annelated, saturated, unsaturated, or aromatic carbocycle or heterocycle, wherein the heterocycle may contain one, two, or three heteroatoms, which may be different or the same, selected from the group comprising O, N, and S, and the cyclic compound thus formed may optionally be substituted, and/or a further 3- to 7-membered, optionally substituted cyclic compound may be condensed thereon;

3.) A 5- or 6-membered hetaryl radical which is unsubstituted, or optionally singly or doubly substituted the same or differently, selected from the group comprising:

2-furyl, 3-furyl, 2-pyrrolyl, 3-pyrrolyl, 2-thienyl, 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 1-pyrazolyl, 3-pyrazolyl, 4-pyrazolyl, 5-pyrazolyl, 3-isothiazolyl, 4-isothiazolyl, 5-isothiazolyl, 1-imidazolyl, 2-imidazolyl, 4-imidazolyl, 5-imidazolyl, 3-pyridazinyl, 4-pyridazinyl, 5-pyridazinyl, 6-pyridazinyl, 2-pyrazinyl, 3-pyrazinyl, 3-isoxazolyl, 4-isoxazolyl, 5-isoxazolyl, and thiadiazolyl, oxadiazolyl, or triazinyl in each case bonded to one of the available free C—H or N—H bonds on $X^1$, $X^2$, $X^3$, $X^4$, and/or $X^5$, or their annelated derivatives indazolyl, indolyl, benzothiophenyl, benzofuranyl, indolinyl, benzimidazolyl, benzthiazolyl, benzoxazolyl, quinolinyl, and isoquinolinyl;

4.) In each case two of the following radicals (1) $R^4$ and $R^5$ for the case $X^1$=C and $X^2$=C, (2) $R^5$ and $R^6$ for the case $X^2$=C and $X^3$=C, (3) $R^6$ and $R^7$ for the case $X^3$=C and $X^4$=C, or (4) $R^7$ and $R^8$ for the case $X^4$=C and $X^5$=C, together with the C atom to which they are bonded, form a 4- to 7-membered, optionally substituted, saturated or unsaturated or aromatic carbocycle, or a 5- or 6-membered, optionally substituted, saturated or unsaturated or aromatic heterocycle which may contain one, two, or three further heteroatoms, which may be different or the same, selected from the group comprising O, N, and S, and which may optionally be singly or doubly substituted, wherein optionally two radicals substituted on this carbocycle or heterocycle together with the atom to which they are respectively bonded may form a 3- to 7-membered, optionally substituted, annelated, saturated, unsaturated, or aromatic carbocycle or heterocycle, wherein the heterocycle may contain one, two, or three heteroatoms, which may be different or the same, selected from the group comprising O, N, and S, and the carbocycle or heterocycle thus formed may optionally be substituted;

5.) A $C_5$-$C_{18}$ bi- or tricyclic saturated hydrocarbon radical which in each case is optionally substituted;

6.) In each case optionally substituted $C_1$-$C_8$ alkyl-$NH_2$, $C_1$-$C_8$ alkyl-$NR_Q^6R_Q^7$, $C_1$-$C_8$ alkyl-CO—$NR_Q^6R_Q^7$, $C_1$-$C_8$ alkyl-$SO_2NR_Q^6R_Q^7$, $C_1$-$C_8$ alkyl-CO—$NH_2$, $C_1$-$C_8$ alkyl-$SO_2NH_2$;

7.) A 4- to 7-membered mono- or bicyclic, optionally substituted, saturated or unsaturated heterocycle which may contain one or two heteroatoms, which may be different or the same, selected from the group comprising O, N, and/or S, wherein this cyclic compound may optionally be substituted, namely, substituted the same or differently 1, 2, 3, 4, or 5 times, and for the case that the heterocycle contains an N atom, this N atom may be substituted with an $R_Q^8$ radical, wherein $R_Q^8$ independently from $R_Q^6$ may have a meaning as defined for $R_Q^6$.

Each of the above-referenced definitions of a variable may be [combined] with any given number of the above-referenced definitions of the remaining variables. This applies in particular for the combination of preferred definitions of a variable with any given or preferred definitions of the remaining variables.

According to one preferred embodiment of the present invention, at least one guanidine compound of general formula I

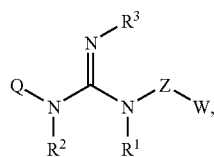

the corresponding enantiomeric, diastereomeric, and/or tautomeric forms thereof, and/or pharmaceutically acceptable salts thereof, and/or the corresponding active substance precursors ("prodrugs") thereof, are prepared, wherein the stated radicals have the following definitions:

$R^1$, $R^2$ in each case independently stand for:
hydrogen, OH, CN,
or
in each case optionally substituted $C_1$-$C_6$ alkyl, O—$C_1$-$C_6$ alkyl, $C_1$-$C_6$ alkylene-O—$C_1$-$C_6$ alkyl, $C_3$-$C_7$ cycloalkyl, O—$C_3$-$C_7$ cycloalkyl, aryl, hetaryl, $C_1$-$C_4$ alkylene-aryl, $C_1$-$C_4$ alkylene-hetaryl, O-aryl, O—$C_1$-$C_4$ alkylene-aryl, O-hetaryl, O—$C_1$-$C_4$ alkylene-hetaryl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O-hetaryl, CO—O—$C_1$-$C_4$ alkylene-aryl, $SO_2$—$C_1$-$C_6$ alkyl, $SO_2$-aryl, $SO_2$-hetaryl, $SO_2$—$C_1$-$C_4$ alkylene-aryl, OCO—$C_1$-$C_6$ alkyl, OCO-aryl, OCO-hetaryl, OCO—$C_1$-$C_4$ alkylene-aryl, OCO—$C_1$-$C_4$ alkylene-hetaryl, $SO_2$—$C_1$-$C_6$ alkyl, $SO_2$-aryl, $SO_2$-hetaryl, or $SO_2$—$C_1$-$C_4$ alkylene-aryl, $R^3$ is hydrogen
or
in each case optionally substituted $C_1$-$C_6$ alkyl, O—$C_1$-$C_6$ alkyl, $C_1$-$C_6$ alkylene-O—$C_1$-$C_6$ alkyl, $C_3$-$C_7$ cycloalkyl, O—$C_3$-$C_7$ cycloalkyl, aryl, hetaryl, $C_1$-$C_4$ alkylene-aryl, $C_1$-$C_4$ alkylene-hetaryl, O-aryl, O—$C_1$-$C_4$ alkylene-aryl, O-hetaryl, O—$C_1$-$C_4$ alkylene-hetaryl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O-hetaryl, CO—O—$C_1$-$C_4$ alkylene-aryl, $SO_2$—$C_1$-$C_6$ alkyl, $SO_2$-aryl, $SO_2$-hetaryl, $SO_2$—$C_1$-$C_4$ alkylene-aryl, OCO—$C_1$-$C_6$ alkyl, OCO-aryl, OCO-hetaryl, OCO—$C_1$-$C_4$ alkylene-aryl, OCO—$C_1$-$C_4$ alkylene-hetaryl, $SO_2$—$C_1$-$C_6$ alkyl, $SO_2$-aryl, $SO_2$-hetaryl, or $SO_2$—$C_1$-$C_4$ alkylene-aryl,
or
in each case two radicals selected from the group comprising $R^1$, $R^2$, and $R^3$, independently from the remaining radical $R^1$, $R^2$, or $R^3$, together with the nitrogen atom to which they are bonded form a 5- to 7-membered, optionally substituted, saturated or unsaturated heterocycle which may contain one, two, or three further heteroatoms, which may be different or the same, selected from the group comprising C, O, N, and S, wherein optionally two radicals substituted on this heterocycle together with the ring atom to which they are bonded may form a 3- to 7-membered, optionally substituted, annelated, saturated, unsaturated, or aromatic carbocycle or heterocycle, wherein the heterocycle may contain one, two, or three heteroatoms, which may be different or the same, selected from the group comprising O, N, and S, and wherein the cyclic compound formed may optionally be substituted, and/or a further 3- to 7-membered, optionally substituted cyclic compound may be condensed thereon;

Z is a radical of general formula Z1

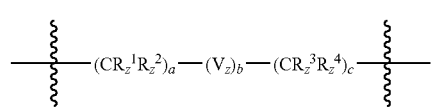

having the indices
a=0, 1, 2, 3, or 4
b=0 or 1
c=0, 1, 2, 3, or 4
wherein the sum of a, b, and c is equal to 1, 2, 3, 4, or 5;
$R_z^1$, $R_z^2$, $R_z^3$, $R_z^4$ in each case independently stand for:
hydrogen, halogen, OH,
or
in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_3$-$C_7$ cycloalkyl, aryl, $C_1$-$C_4$ alkylene-aryl, hetaryl or $C_1$-$C_4$ alkylene-hetaryl,
or
two radicals $R_z^1$ and $R_z^2$ or $R_z^3$ and $R_z^4$, independently in each case, together with the C atom to which they are bonded form a 3- to 7-membered, optionally substituted, saturated or unsaturated carbocycle or heterocycle which may contain one, two, or three heteroatoms which may be the same or different, selected from the group comprising O, N, and/or S;

Vz is —CO—, —CO—$NR_z^5$—, —$NR_z^5$—CO—, —O—, —S—, —SO—, —$SO_2$—, —$SO_2$—$NR_z^5$—, $NR_z^5$—$SO_2$—, —CS—, —CS—$NR_z^5$—, —$NR_z^5$—CS—, —CS—O—, —O—CS—, —CO—O—, O—CO—, ethynylene, —C(=$CR_z^6R_z^7$)—, —$CR_z^6$=$CR_z^7$—, —$NR_z^5$—CO—$NR_z^5$*—, —O—CO—$NR_z^5$—, —$NR_z^5$—;

wherein $R_Z^5$, $R_Z^{5*}$ independently, and in each case independently of their respective occurrence, stand for:
hydrogen, or
in each case optionally substituted $C_1$-$C_6$ alkyl, $C_1$-$C_4$ alkylene-O—$C_1$-$C_6$ alkyl, $C_2$-$C_6$ alkenyl, $C_2$-$C_{12}$ alkynyl, CO—$C_1$-$C_6$ alkyl, CO—O—$C_1$-$C_6$ alkyl, $SO_2$—$C_1$-$C_6$ alkyl, $C_3$-$C_7$ cycloalkyl, aryl, $C_1$-$C_4$ alkylene-aryl, CO—O—$C_1$-$C_4$ alkylene-aryl, CO—$C_1$-$C_4$ alkylene-aryl, CO-aryl, $SO_2$-aryl, hetaryl, CO-hetaryl or $SO_2$—$C_1$-$C_4$ alkylene-aryl;

$R_Z^6$, $R_Z^7$ independently, and in each case independently of their respective occurrence, stand for:
hydrogen, OH, or
in each case optionally substituted $C_1$-$C_6$ alkyl, $C_1$-$C_6$ alkoxy, $C_2$-$C_6$ alkenyl, $C_2$-$C_6$ alkynyl, $C_1$-$C_4$ alkylene-$C_3$-$C_7$ cycloalkyl, $C_3$-$C_7$ cycloalkyl, aryl, $C_1$-$C_4$ alkylene-aryl, hetaryl, or $C_1$-$C_4$ alkylene-hetaryl;

W is a radical of general formula W1, W2, or W3

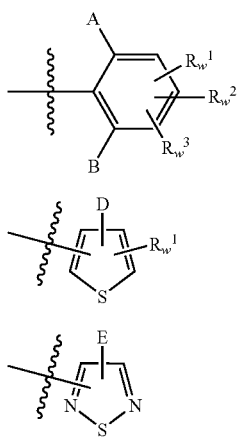

wherein

A is $NO_2$, $NH_2$, OH, CN, $CF_3$, $OCF_3$, $CHF_2$, $CH_2F$, $OCHF_2$, $OCH_2F$, COOH, O—$CH_2$—COOH, halogen, SH, O—$C_1$-$C_6$ alkyl, S—$C_1$-$C_6$ alkyl, or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, $C_1$-$C_4$ alkylene-hetaryl, heterocycloalkyl, or
$R_A^1$, O—$R_A^1$, CO—$R_A^1$, S—$R_A^1$, SO—$R_A^1$, CO—O—$R_A^1$, $NR_A^4$—CO—O—$R_A^1$, O—$CH_2$—COO—$R_A^1$, $NR_A^2R_A^3$, $CONH_2$, $SO_2NH_2$, $NR_A^4$—CO—$R_A^1$, $SO_2$—$R_A^1$, $NR_A^4$—$SO_2$—$R_A^1$, $SO_2$—$NR_A^2R_A^3$, CO—$NR_A^2R_A^3$, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$, or $C_1$-$C_4$ alkylene-O—$R_A^1$;

wherein $R_A^1$ independently of its respective occurrence stands for:
in each case optionally substituted $C_1$-$C_6$ alkyl, $C_1$-$C_6$ alkylene-O—$C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_2$-$C_6$ alkenylene-aryl, or in each case optionally substituted $C_1$-$C_4$ alkylene-hetaryl, —CO—$C_1$-$C_6$ alkyl, —CO—O—$C_1$-$C_6$ alkyl, —CO-aryl, —CO-hetaryl, —CO—O-aryl, —CO—O-hetaryl, —CO—$C_3$-$C_7$ cycloalkyl, —CO—O—$C_3$-$C_7$ cycloalkyl, —CO-heterocycloalkyl, —CO—O-heterocycloalkyl, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$, $C_1$-$C_6$ alkylene-O—$R_A^2$;

$R_A^2$ independently of its respective occurrence stands for:
hydrogen, OH, CN, or
in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$R_A^3$ independently of its respective occurrence stands for:
in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_4$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

or the radicals $R_A^2$ and $R_A^3$ together with the nitrogen atom to which they are bonded form a 3- to 7-membered, optionally substituted, saturated or aromatic heterocycle which may contain one, two, or three further heteroatoms, which may be different or the same, selected from the group comprising O, N, and S, wherein optionally two radicals substituted on this heterocycle together with the ring atom to which they are bonded may form a 3- to 7-membered, optionally substituted, annelated, saturated, unsaturated, or aromatic carbocycle or heterocycle, wherein the heterocycle may contain one, two, or three heteroatoms, which may be different or the same, selected from the group comprising O, N, and S, wherein the cyclic compound thus formed may optionally be substituted;

$R_A^4$ independently of its respective occurrence stands for:
hydrogen, or
in each case optionally substituted $C_1$-$C_6$ alkyl, $C_1$-$C_6$ alkylene-O—$C_1$-$C_6$ alkyl, $C_2$-$C_6$ alkenyl, $C_2$-$C_{12}$ alkynyl, CO—$C_1$-$C_6$ alkyl, CO—O—$C_1$-$C_6$ alkyl, $SO_2$—$C_1$-$C_6$ alkyl, $C_3$-$C_7$ cycloalkyl, aryl, $C_1$-$C_4$ alkylene-aryl, CO—O-arylalkyl, CO—$C_1$-$C_4$ alkylene-aryl, CO-aryl, $SO_2$-aryl, hetaryl, CO-hetaryl, or $SO_2$—$C_1$-$C_4$ alkylene-aryl;

B is a radical that is
hydrogen, or in each case optionally substituted aryl or hetaryl, or, independently of radical A, has the same meaning as for radical A,
or
two radicals selected from the group comprising A, B, $R_w^1$, $R_w^2$, and $R_w^3$, independently in each case, together with the C atom to which they are bonded form a 3- to 7-membered, optionally substituted, saturated, unsaturated, or aromatic carbocycle, or a 3- to 7-membered, optionally substituted, saturated, unsaturated, or aromatic heterocycle which may contain one, two, or three further heteroatoms, which may be different or the same, selected from the group comprising O, N, and S; wherein optionally two radicals substituted on this carbocycle or heterocycle together with the ring atom to which they are bonded may form a further 3- to 7-membered, optionally substituted, annelated, saturated, unsaturated, or aromatic carbocycle or heterocycle, wherein the heterocycle may contain one, two, or three heteroatoms, which may be different or the same, selected from the group comprising O, N, and S, and wherein the cyclic compound thus formed may optionally be substituted;

$R_w^1$, $R_w^2$, $R_w^3$ in each case independently stand for:

hydrogen, $NO_2$, $NH_2$, OH, CN, $CF_3$, $OCF_3$, $CHF_2$, $CH_2F$, $OCHF_2$, $OCH_2F$, COOH, $O-CH_2-COOH$, halogen, SH, $O-C_1-C_6$ alkyl, $S-C_1-C_6$ alkyl, or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_6$ alkylene-$C_3$-$C_7$ cycloalkyl, $C_1$-$C_6$ alkylene-heterocycloalkyl, $C_1$-$C_6$ alkylene-aryl, $C_1$-$C_6$ alkylene-hetaryl, heterocycloalkyl, or in each case optionally substituted $R_A^1$, $O-R_A^1$, $CO-R_A^1$, $S-R_A^1$, $SO-R_A^1$, $CO-O-R_A^1$, $NR_A^4-CO-O-R_A^1$, $O-CH_2-COO-R_A^1$, $NR_A^2R_A^3$, $CONH_2$, $SO_2NH_2$, $NR_A^4-CO-R_A^1$, $SO_2R_A^1$, $NR_A^4-SO_2-R_A^1$, $SO_2-NR_A^2R_A^3$, $CO-NR_A^2R_A^3$, $C_1$-$C_4$ alkylene-$NR_A^2R_A^3$, $C_1$-$C_4$ alkylene-$CO-NR_A^2R_A^3$, $C_1$-$C_4$ alkylene-$SO_2-NR_A^2R_A^3$, or $C_1$-$C_4$ alkylene-$O-R_A^1$; wherein $R_A^1$, $R_A^2$, $R_A^3$, and $R_A^4$ in each case independently, and in each case independently of their respective occurrence and independently of their respective meaning for radical A, may have the meanings given for radical A;

D independently of radical A stands for a radical having the same meanings defined for radical A;

E is hydrogen or, independently of radical A, stands for a radical having the same meanings defined for radical A;

Q is an at least 6-membered hetaryl radical of general formula Q

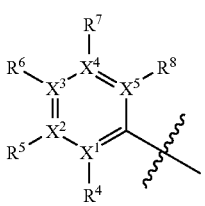

wherein $X^1$: is C or N,
$X^2$: is C or N,
$X^3$: is C or N,
$X^4$: is C or N,
$X^5$: is C or N, wherein one, two, or three radicals selected from the group comprising the radicals $X^1$, $X^2$, $X^3$, $X^4$, and $X^5$ simultaneously stand for N, and the associated binding partner selected from the group comprising $R^4$, $R^5$, $R^6$, $R^7$, and $R^8$ then stands for a free electron pair.

$R^4$, $R^5$, $R^6$, $R^7$, and $R^8$ in each case independently stand for a radical selected from groups 1.), 2.), 3.), 4.), 5.), 6.), and 7.), which may be the same or different, wherein groups 1.) through 7.) have the meanings given below:

1.) Hydrogen, halogen, CN, $CF_3$, $CHF_2$, $CH_2F$, $OCF_3$, $OCH_2F$, $OCHF_2$, $NH_2$, $NO_2$, COOH, $O-CH_2-COOH$, or in each case optionally substituted $C_1$-$C_{10}$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, $C_1$-$C_6$ alkylene-$O-C_1-C_6$ alkyl, $C_1$-$C_6$ alkylene-O-aryl, $COO-C_1-C_4$ alkyl, $C_1$-$C_4$ alkylene-$COO-C_1-C_4$ alkyl, or in each case optionally substituted $O-R_Q^4$, $S-R_Q^4$, $NR_Q^6R_Q^7$, $CO-OR_Q^5$, $CO-R_Q^5$, $SO-R_Q^5$, $NR_Q^7-CO-O-R_Q^6$, $O-CH_2-COO-R_Q^5$, $NR_Q^7-CO-R_Q^5$, $SO_2-R_Q^5$, $NR_Q^7-SO_2-R_Q^5$, $SO_2NH_2$, $CONH_2$, $SO_2-NR_Q^6R_Q^7$, or $CO-NR_Q^6R_Q^7$; and $R_Q^4$, $R_Q^5$, $R_Q^6$, and $R_Q^7$ independently, and independently of their respective occurrence, are defined as below;

2.) In each case optionally substituted phenyl, 1-naphthyl, or 2-naphthyl may be substituted with one, two, or three radicals selected from the group comprising $R_Q^1$, $R_Q^2$, and $R_Q^3$, wherein $R_Q^1$, $R_Q^2$, and $R_Q^3$ in each case independently stand for a substituent, which may be the same or different, selected from the following group:

Hydrogen, $NO_2$, $NH_2$, OH, CN, $CF_3$, $CHF_2$, $CH_2F$, $OCF_3$, $OCHF_2$, $OCH_2F$, COOH, $O-CH_2-COOH$, SH, halogen, or in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted $O-R_Q^4$, $S-R_Q^4$, $NR_Q^6R_Q^7$, $CO-OR_Q^5$, $NR_Q^7-CO-O-R_Q^5$, $O-CH_2-COO-R_Q^5$, $NR_Q^7-CO-R_Q^5$, $SO_2-R_Q^5$, $NR_Q^7-SO_2-R_Q^5$, $SO_2NH_2$, $CONH_2$, $SO_2-NR_Q^6R_Q^7$, or $CO-NR_Q^6R_Q^7$, or in each case two radicals selected from the group comprising $R_Q^1$, $R_Q^2$, and $R_Q^3$ together with the C atom to which they are bonded form a 3- to 7-membered, optionally substituted, saturated or unsaturated carbocycle or a 3- to 7-membered, optionally substituted, saturated, unsaturated, or aromatic heterocycle which may contain up to three further heteroatoms, which may be different or the same, selected from the group comprising O, N, and S, wherein two radicals substituted on this carbocycle or heterocycle together with the ring atom to which they are bonded may optionally form a 3- to 7-membered, optionally substituted, annelated, saturated, unsaturated, or aromatic carbocycle or heterocycle, wherein the heterocycle may contain one, two, or three heteroatoms, which may be different or the same, selected from the group comprising O, N, and S, and the cyclic compound thus formed may optionally be substituted, and/or a further 3- to 7-membered, optionally substituted cyclic compound may be condensed thereon; wherein the substituents below have the following meanings:

$R_Q^4$ independently of its respective occurrence in each case stands for hydrogen, or in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, heterocycloalkyl, aryl, or hetaryl;

$R_Q^5$ independently of its respective occurrence in each case stands for hydrogen, or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, or $C_1$-$C_6$ alkylene-O—$C_1$-$C_6$ alkyl;

$RQ^6$ independently of its respective occurrence stands for hydrogen, OH, CN, or
  in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, $C_1$-$C_4$ alkylene-aryl, $C_1$-$C_4$ alkylene-hetaryl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$RQ^7$ independently of its respective occurrence stands for hydrogen, or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$-alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

or both radicals $R_Q^6$ and $R_Q^7$ together with the nitrogen atom to which they are bonded form a 3- to 7-membered, optionally substituted, saturated or aromatic heterocycle which may contain one, two, or three further heteroatoms, which may be different or the same, selected from the group comprising O, N, and S, and optionally two radicals substituted on this heterocycle together with the ring atom to which they are bonded may form a 3- to 7-membered, annelated, saturated, unsaturated, or aromatic carbocycle or heterocycle, wherein the heterocycle may contain one, two, or three heteroatoms, which may be different or the same, selected from the group comprising O, N, and S, and the cyclic compound thus formed may optionally be substituted, and/or a further 3- to 7-membered, optionally substituted cyclic compound may be condensed thereon;

3.) A 5- or 6-membered hetaryl radical which is unsubstituted, or optionally singly or doubly substituted the same or differently, selected from the group comprising:

2-furyl, 3-furyl, 2-pyrrolyl, 3-pyrrolyl, 2-thienyl, 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, and thiadiazolyl, oxadiazolyl, or triazinyl in each case bonded to one of the available free C—H or N—H bonds on $X^1$, $X^2$, $X^3$, $X^4$, and/or $X^5$, or their annelated derivatives indazolyl, indolyl, benzothiophenyl, benzofuranyl, indolinyl, benzimidazolyl, benzthiazolyl, benzoxazolyl, quinolinyl, and isoquinolinyl;

4.) In each case two of the following radicals (1) $R^4$ and $R^5$ for the case $X^1$=C and $X^2$=C, (2) $R^5$ and $R^6$ for the case $X^2$=C and $X^3$=C, (3) $R^6$ and $R^7$ for the case $X^3$=C and $X^4$=C, or (4) $R^7$ and $R^8$ for the case $X^4$=C and $X^5$=C, together with the C atom to which they are bonded, form a 4- to 7-membered, optionally substituted, saturated or unsaturated or aromatic carbocycle, or a 5- or 6-membered, optionally substituted, saturated or unsaturated or aromatic heterocycle which may contain one, two, or three further heteroatoms, which may be different or the same, selected from the group comprising O, N, and S, and which may optionally be singly or doubly substituted, wherein optionally two radicals substituted on this carbocycle or heterocycle together with the ring atom to which they are bonded may form a 3- to 7-membered, optionally substituted, annelated, saturated, unsaturated, or aromatic carbocycle or heterocycle, wherein the heterocycle may contain one, two, or three heteroatoms, which may be different or the same, selected from the group comprising O, N, and S, and the carbocycle or heterocycle thus formed may optionally be substituted;

5.) A $C_5$-$C_{18}$ bi- or tricyclic saturated hydrocarbon radical which in each case is optionally substituted;

6.) In each case optionally substituted $C_1$-$C_8$ alkyl-$NH_2$, $C_1$-$C_8$ alkyl-$NR_Q^6R_Q^7$, $C_1$-$C_8$ alkyl-CO—$NR_Q^6R_Q^7$, $C_1$-$C_8$ alkyl-$SO_2NR_Q^6R_Q^7$, $C_1$-$C_8$ alkyl-CO—$NH_2$, $C_1$-$C_8$ alkyl-$SO_2NH_2$;

7.) A 4- to 7-membered mono- or bicyclic, saturated or unsaturated heterocycle which may contain one or two heteroatoms, which may be different or the same, selected from the group comprising O, N, and/or S, wherein this cyclic compound may likewise be substituted, namely, substituted 1, 2, 3, 4, or 5 times, and for the case that the heterocycle contains an N atom, this N atom may be substituted with an $R_Q^8$ radical, wherein $R_Q^8$ independently from $R_Q^6$ may have a meaning as defined for $R_Q^6$, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_W^1$, $R_W^2$, $R_W^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$ have the meanings given above, subject to one, two, three, four, five, six, seven, eight, nine, ten, eleven, twelve, or thirteen of the conditions independently selected from the group comprising the following conditions (i) through (xiii):

(i) preferably with the condition that when W=W1, none of the radicals $R_W^1$, $R_W^2$, or $R_W^3$ stands for a CO—NH-phenyl-(meta-$SO_2$NH-RADICAL) or $SO_2$—NH-phenyl-(meta-$SO_2$NH-RADICAL) group bonded to Z in the meta position with respect to the linkage point, where RADICAL=—CH($R^1_{RADICAL}$)—$CH_2$—$COR_{RADICAL}$, with $R_{RADICAL}$=$X_{RADICAL}$—$R^3_{RADICAL}$ wherein $X_{RADICAL}$=O, S, $NR^4_{RADICAL}$, in which $R^3_{RADICAL}$ and $R^4_{RADICAL}$ are independently selected from H, alkyl, alkenyl, alkynyl, haloalkyl, aryl, arylalkyl, sugars, steroids, and in the case of the free acid, pharmaceutically acceptable salts thereof, with $R^1_{RADICAL}$ being selected from the group comprising H, alkyl, alkenyl, alkynyl, aryl, and aryl [sic], which may optionally be substituted with one or more substituents selected from the group comprising halogen, haloalkyl, hydroxy, alkoxy, aryloxy, aralkoxy, amino, aminoalkyl, carboxy, cyano, and nitro;

(ii) and/or preferably with the condition that when Q=pyridyl, where (1) $X^1$=N and $R^4$=a free electron pair, or (2) $X^5$=N and $R^8$=a free electron pair, or (3) $X^2$=N and $R^5$=free electron pair, or (4) $X^4$=N and $R^7$=a free electron pair, then $R^6$ does not stand for a —CO—$NR_Q^6R_Q^7$ radical;

(iii) and/or preferably with the condition that when Q=pyrimidyl, where (1) $X^1$=N and $X^5$=N, or (2) $X^1$=N and $X^3$=N, or (3) $X^3$=N and $X^5$=N, then none of the substituents $R^4$, $R^5$, $R^6$, $R^7$, or $R^8$ stands for the aryl or hetaryl radicals;

(iv) and/or preferably with the condition that [when] $R^1$, $R^2$, $R^3$, W, and Z have the meanings given above, then Q does not stand for (1) Q=pyrimidyl, where $X^1$=N and $X^5$=N, or (2) Q=triazinyl, where $X^3$=N, $X^1$=N, and $X^5$=N;

(v) and/or preferably with the conditions (A) and (B), condition (A) being that when (A1) Q=pyridyl, pyrimidyl, or pyrazinyl where in each case $X^1$=N and $R^4$=a free electron pair, or (A2) Q=pyridyl, pyrimidyl, or pyrazinyl where in each case $X^5$=N and $R^8$=a free electron pair, then in case (A1) or (A2), where Q=pyrimidyl or pyrazinyl, the radicals $R^5$ and/or $R^7$ in each case do not stand for —$CH_2$-aryl, —CH(alkyl)aryl, or —CH(alkyl)hetaryl, and in case (A1) or (A2), where Q=pyridyl, in each case none of the radicals $R^4$, $R^5$, $R^7$, or $R^8$ stands for a —$CH_2$-aryl, —CH($C_1$-$C_6$ alkyl)aryl, or —CH($C_1$-$C_6$ alkyl)hetaryl radical, simultaneously with condition (B) that when W=W1, then (B1) none of the radicals $R_w^1$, $R_w^2$, or $R_w^3$ stands for an F-, CN-, Cl-, Me-, or OMe-radical substituted in the para position with respect to the linkage point Z, or (B2) for the case that radical A stands for a Cl radical substituted in the ortho position with respect to the linkage point Z, then the radicals B, $R_w^1$, $R_w^2$, and $R_w^3$ do not simultaneously stand for hydrogen;

(vi) and/or preferably with the exception of the compound N-[3-benzylpyrid-2-yl]-N'-(2-chlorobenzyl)guanidine;

(vii) and/or preferably with the following conditions (1) through (3), which apply for Z when W=W1:
(1) when c=0 and b=0, then a is not 2,
(2) when a=0 and b=0, then c is not 2, and
(3) when b=0, then the sum a+c is not equal to 2.

(viii) and/or preferably with the condition that when the following apply for radical Q: (i) [when] $X^1$ and $X^4$ in each case stand for N, then none of the remaining radicals $R^5$, $R^6$, and $R^8$ stand for a radical from group 3.), or (ii) [when] $X^2$ and $X^5$ in each case stand for N, then none of the remaining radicals $R^4$, $R^6$, and $R^7$ stand for a radical from group 3.).

(ix) and/or preferably with the condition that when a=1 applies for the radical Z, then group $V_Z$ does not stand for the $NR_Z^5$—CO— radical, where $R_Z^5$=hydrogen;

(x) and/or optionally, preferably with the condition that when a=1 applies for the radical Z, then group $V_Z$ does not stand for the $NR_Z^5$—CO— radical;

(xi) and/or preferably with the condition that when Z stands for the radical Z1, with a=1 and b=c=0, or with b=1 and a=b=0, or with c=1 and $V_Z$=—CO— and a=b=0, and W stands for the radical W1, then the radicals A, B, $R_w^1$, $R_w^2$, and $R_w^3$ are selected such that none stand for the $SO_2$—$NR_A^2R_A^3$ group, where $R_A^2$=H and $R_A^3$=substituted or unsubstituted phenyl, benzyl, phenethyl, or a substituted or unsubstituted nonaromatic ring; and the others in each case stand for H;

(xii) and/or preferably with the condition that when $X^1$=N or $X^1$ and $X^5$ in each case stand for N, then B, $R_w^1$, $R_w^2$, and $R_w^3$ do not simultaneously stand for a radical selected from the group comprising the radicals $C_3$-$C_6$ alkyl, $C_3$-$C_6$ alkenyl, $C_3$-$C_6$ alkynyl, or hetaryl, defined as a stable 5- to 7-membered monocyclic aromatic ring containing 1 to 3, preferably 1 to 2, heteroatoms selected from N, O, and S, wherein the remaining ring atoms are carbon, or a stable bi- or tricyclic system having at least one 5- to 7-membered aromatic ring containing 1 to 3, preferably 1 to 2, heteroatoms selected from N, O, and S, wherein the remaining ring atoms are carbon; and a carbocyclic group defined as an optionally substituted 3- to 8-membered saturated, partially unsaturated, or aromatic ring cyclic compound containing only carbon atoms as ring atoms, or an optionally substituted 6- to 11-membered saturated, partially unsaturated, or aromatic bicyclic ring system containing only carbon atoms as ring atoms;

(xiii) and/or preferably with the condition that when Q=Q1, Q2, Q4, or Q5, then $R^6$ does not stand for a —CO—$NR_Q^6R_Q^7$ radical;

particularly preferably subject to one, two, three, four, five, or six of the conditions independently selected from the group comprising the following conditions (viii) through (xiii):

(in the expression "condition of being subject to one, several, or all of conditions (i) through (xiii)" below, reference is made to the preceding statements concerning conditions (i) through (xiii), and in the expression "condition of being subject to one, several, or all of conditions (viii) through (xiii)" below, reference is made to the preceding statements concerning conditions (viii) through (xiii).

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:

$R^1$, $R^2$ independently stand for:
hydrogen, OH, CN, in each case optionally substituted $C_1$-$C_4$ alkyl, $OC_1$-$C_4$ alkyl, $C_1$-$C_4$ alkylene-O—$C_1$-$C_4$ alkyl, aryl, benzyl, CO—$C_1$-$C_4$ alkyl, CO-aryl, CO—$C_1$-$C_4$ alkylene-aryl, OCO—$C_1$-$C_4$ alkyl, OCO-aryl, or OCO—$C_1$-$C_4$ alkylene-hetaryl; and $R^3$ is hydrogen, in each case optionally substituted $C_1$-$C_4$ alkyl, $OC_1$-$C_4$ alkyl, $C_1$-$C_4$ alkylene-O—$C_1$-$C_4$ alkyl, aryl, benzyl, CO—$C_1$-$C_4$ alkyl, CO-aryl, CO—$C_1$-$C_4$ alkylene-aryl, OCO—$C_1$-$C_4$ alkyl, OCO-aryl, or OCO—$C_1$-$C_4$ alkylene-hetaryl.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:
$R^3$: is hydrogen;
$R^1$, $R^2$: in each case independently stand for:
hydrogen, OH, CN, in each case optionally substituted $C_1$-$C_4$ alkyl, $C_1$-$C_4$ alkylene-O—$C_1$-$C_4$ alkyl, aryl, benzyl, CO—$C_1$-$C_4$ alkyl, CO-aryl, CO—$C_1$-$C_4$ alkylene-aryl, OCO—$C_1$-$C_4$ alkyl, OCO-aryl, or OCO—$C_1$-$C_4$ alkylene-hetaryl.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:
W:
is a radical of general formula W1a

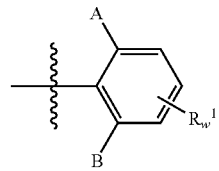

[wherein]
A:
is OH, CN, $CF_3$, $OCF_3$, $CHF_2$, $CH_2F$, $OCHF_2$, $OCH_2F$, halogen, O—$C_1$-$C_6$ alkyl, S—$C_1$-$C_6$ alkyl, in each case optionally substituted $C_1$-$C_6$ alkyl, $C_2$-$C_6$ alkenyl, O—$R_A^1$, S—$R_A^1$, $NR_A^4$—CO—O—$R_A^1$, O—$CH_2$—COO—$R_A$, $NR_A^2R_A^3$, $NR_A^4$—CO—$R_A^1$, or $NR_A^4$—$SO_2$—$R_A^1$, $SO_2$—$NR_A^2R_A^3$ or CO—$NR_A^2R_A^3$;
wherein
$R_A^1$: independently of its respective occurrence stands for:
in each case optionally substituted $C_1$-$C_6$ alkyl, $C_3$-$C_7$ cycloalkyl, aryl, or hetaryl;
$R_A^2$ independently of its respective occurrence stands for:
hydrogen, or
in each case optionally substituted $C_1$-$C_6$ alkyl, phenyl, benzyl, phenethyl, CO—$C_1$-$C_6$ alkyl, CO-aryl, $SO_2$—$C_1$-$C_6$ alkyl, $SO_2$-aryl, $SO_2$-hetaryl, or $SO_2$—$C_1$-$C_4$ alkylene-aryl;
$R_A^3$ independently of its respective occurrence stands for:
in each case optionally substituted $C_1$-$C_6$ alkyl, phenyl, benzyl, phenethyl, CO—$C_1$-$C_6$ alkyl, CO-aryl, $SO_2$—$C_1$-$C_6$ alkyl, $SO_2$-aryl, $SO_2$-hetaryl, or $SO_2$—$C_1$-$C_4$ alkylene-aryl;
or the radicals $R_A^2$ and $R_A^3$ together with the nitrogen atom to which they are bonded form an optionally substituted 5- or 6-membered saturated or unsaturated ring which may contain one or two heteroatoms, which may be the same or different, selected from the group comprising O and N, wherein optionally two radicals substituted on this heterocycle together with the ring atom to which they are bonded may form a 3- to 7-membered, optionally substituted, annelated, saturated, unsaturated, or aromatic carbocycle or heterocycle, wherein the heterocycle may contain one, two, or three heteroatoms, which may be different or the same, selected from the group comprising O, N, and S, wherein the cyclic compound thus formed may optionally be substituted;
$R_A^4$ independently of its respective occurrence stands for:
hydrogen, or in each case optionally substituted $C_1$-$C_6$ alkyl,
B:
is hydrogen, or in each case optionally substituted aryl or hetaryl, or independently of radical A stands for a radical selected from the radicals defined as for radical A;
$R_w^1$:
is hydrogen, $NO_2$, $NH_2$, OH, CN, $CF_3$, $OCF_3$, $CHF_2$, $CH_2F$, $OCHF_2$, $OCH_2F$, COOH, O—$CH_2$—COOH, halogen, SH, O—$C_1$-$C_6$ alkyl, S—$C_1$-$C_6$ alkyl, or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_6$ alkylene-$C_3$-$C_7$ cycloalkyl, $C_1$-$C_6$ alkylene-heterocycloalkyl, $C_1$-$C_6$ alkylene-aryl, $C_1$-$C_6$ alkylene-hetaryl, heterocycloalkyl, or in each case optionally substituted $R_A^1$, O—$R_A^1$, CO—$R_A^1$, S—$R_A^1$, SO—$R_A^1$, CO—O—$R_A^1$, $NR_A^4$—CO—O—$R_A^1$, O—$CH_2$—COO—$R_A^1$, $NR_A^2R_A^3$, $CONH_2$, $SO_2NH_2$, $NR_A^4$—CO—$R_A^1$, $SO_2$—$R_A^1$, $NR_A^4$—$SO_2$—$R_A^1$, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$, or $C_1$-$C_4$ alkylene-O—$R_A^1$; wherein $R_A^1$, $R_A^2$, $R_A^3$, and $R_A^4$ in each case independently, and independently of their respective occurrence, may have the meanings given for the radicals $R_A^1$, $R_A^2$ and $R_A^3$.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, characterized in that the radicals $R^1$, $R^2$, $R^3$, $R^4$, $R^5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:

Z is a radical of general formula Z1

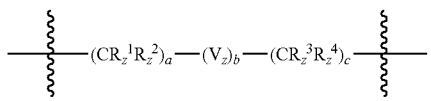

Z1 having the indices a=0, 1, or 2
b=0 or 1
c=0, 1, or 2
wherein the sum of a, b, and c is equal to 1, 2, or 3;
wherein
$R_Z^1$, $R_Z^2$, $R_Z^3$, $R_Z^4$ independently stand for:
hydrogen, halogen, OH, or optionally substituted $C_1$-$C_6$ alkyl, $V_Z$:
is —CO—, —CO—$NR_Z^5$—, or —$NR_Z^5$—CO—;

$R_Z^5$ independently of its respective occurrence stands for:
hydrogen or in each case optionally substituted $C_1$-$C_3$ alkyl;

and/or preferably with the following conditions (1) through (3), which apply for Z when W=W1:

(1) when c=0 and b=0, then a is not 2,
(2) when a=0 and b=0, then c is not 2, and
(3) when b=0, then the sum a+c is not equal to 2.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, characterized in that the radicals $R^1$, $R^2$, $R^3$, $R^4$, $R^5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:

Q is a radical according to one of the general formulas Q1, Q2, Q3, Q4, or Q5:

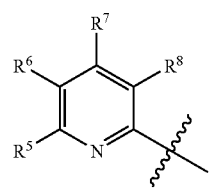

Q1

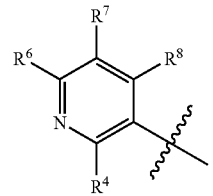

Q2

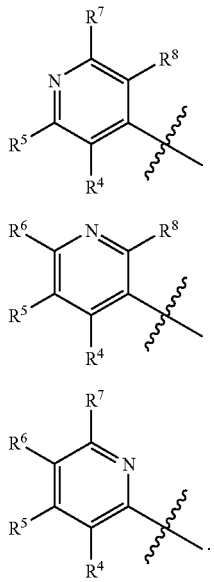

wherein $R^4$, $R^5$, $R^6$, $R^7$, and $R^8$ in each case independently stand for a radical selected from the following groups 1.), 2.), 3.), 4.), 5.), 6.), and 7.), which may be different or the same:

1.) Hydrogen, halogen, CN, $CF_3$, $CHF_2$, $CH_2F$, $OCF_3$, $OCH_2F$, $OCHF_2$, $NH_2$, or in each case optionally substituted $C_1$-$C_{10}$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, $C_1$-$C_6$ alkylene-O—$C_1$-$C_6$ alkyl, $C_1$-$C_6$ alkylene-O-aryl, COO—$C_1$-$C_4$ alkyl, $C_1$-$C_4$ alkylene-COO—$C_1$-$C_4$ alkyl, or in each case optionally substituted O—$R_Q^4$, S—$R_Q^4$, $NR_Q^6R_Q^7$, CO—$OR_Q^5$, $NR_Q^7$—CO—O—$R_Q^5$, O—$CH_2$—COO—$R_Q^5$, $NR_Q^7$—CO—$R_Q^5$, $SO_2$—$R_Q^5$, $NR_Q^7$—$SO_2$—$R_Q^5$, $SO_2NH_2$, $CONH_2$, $SO_2$—$NR_Q^6R_Q^7$, or CO—$NR_Q^6R_Q^7$; wherein $R_Q^4$, $R_Q^5$, $R_Q^6$, and $R_Q^7$ independently, and independently of their respective occurrence, are defined as below;

2.) In each case optionally substituted phenyl, 1-naphthyl, or 2-naphthyl, which in each case may be substituted with one, two, or three radicals selected from the group comprising $R_Q^1$, $R_Q^2$, and $R_Q^3$, wherein $R_Q^1$, $R_Q^2$, and $R_Q^3$ in each case independently stand for a substituent, which may be the same or different, selected from the following group:

Hydrogen, CN, $CF_3$, $CHF_2$, $OCF_3$, $OCHF_2$, O—$CH_2$—COOH, or halogen, or in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted O—$R_Q^4$, S—$R_Q^4$, $NR_Q^6R_Q^7$, CO—$OR_Q^5$, $NR_Q^7$—CO—O—$R_Q^5$, $NR_Q^7$-CO—$R_Q^5$, $SO_2$—$R_Q^5$, $NR_Q^7$—$SO_2$—$R_Q^5$, $SO_2NH_2$, $CONH_2$, $SO_2$—$NR_Q^6R_Q^7$, or CO—$NR_Q^6R_Q^7$, or in each case two radicals selected from the group comprising $R_Q^1$, $R_Q^2$, and $R_Q^3$ together with the atom to which they are bonded form a 3- to 7-membered, optionally substituted, saturated, or unsaturated carbocycle or a 3- to 7-membered, optionally substituted, saturated, unsaturated, or aromatic heterocycle which may contain one, two, or three further heteroatoms, which may be different or the same, selected from the group comprising O, N, and S;

$R_Q^4$ independently of its respective occurrence stands for: in each case optionally substituted $C_1$-$C_4$ alkylene-$C_3$-$C_7$ cycloalkyl, $C_1$-$C_4$ alkylene-heterocycloalkyl, heterocycloalkyl, aryl, or hetaryl, or $C_1$-$C_6$ alkyl which is optionally substituted with one, two, three, or more substituents, which may be the same or different, in each case independently selected from the group comprising halogen, $NO_2$, $NH_2$, OH, CN, $CF_3$, $CHF_2$, $OCF_3$, $OCHF_2$, optionally substituted NH—($C_1$-$C_6$ alkyl), and optionally substituted NH—($C_1$-$C_6$ alkyl)$_2$, $R_Q^5$ independently of its respective occurrence stands for: in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, or $C_1$-$C_6$ alkylene-O—$C_1$-$C_6$ alkyl;

$R_Q^6$ independently of its respective occurrence stands for: hydrogen, OH, CN, or in each case optionally substituted $C_1$-$C_6$ alkyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, $C_1$-$C_4$ alkylene-aryl, $C_1$-$C_4$ alkylene-hetaryl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$R_Q^7$ independently of its respective occurrence stands for: hydrogen or optionally substituted $C_1$-$C_6$ alkyl;

or both radicals $R_Q^6$ and $R_Q^7$ together with the nitrogen atom to which they are bonded form a 3- to 7-membered, optionally substituted, saturated or aromatic heterocycle which may contain one, two, or three further heteroatoms, which may be different or the same, selected from the group comprising O, N, and S;

3.) Is a 5- or 6-membered hetaryl radical, unsubstituted or optionally singly or doubly substituted the same or differently, selected from the group comprising:

2-thienyl, 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-Isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl, or triazinyl, or their annelated derivatives indazolyl, indolyl, benzothiophenyl, benzofuranyl, benzimidazolyl, benzthiazolyl, benzoxazolyl, quinolinyl and isoquinolinyl, wherein the substituents are preferably selected from the group comprising hydrogen, halogen, $NO_2$, $NH_2$, OH, CN, CF3, $OCF_3$, $CHF_2$, O—$CHF_2$, or in each case optionally substituted $C_1$-$C_6$ alkyl, O—$C_1$-$C_6$ alkyl, NH—($C_1$-$C_6$ alkyl), N($C_1$-$C_6$ alkyl)$_2$, NHCO—$C_1$-$C_4$ alkyl, $NHSO_2$—$C_1$-$C_4$ alkyl, and $SO_2$—$C_1$-$C_4$ alkyl;

4.) Two adjacent radicals selected from the group comprising the radicals $R^4$, $R^5$, $R^6$, $R^7$, and $R^8$ as follows:
for case (1) $R^4$ and $R^5$ in Q3, Q4, or Q5, for case (2) $R^5$ and $R^6$ in Q1, Q4, or Q5, for case (3) $R^6$ and $R^7$ in Q1, Q2, or Q5, and for case (4) $R^7$ and $R^8$ in Q1, Q2, or Q3, and the radicals selected according to cases (1) through (4) together with the ring atom to which they are bonded form a 4- to 7-membered, optionally substituted, saturated, unsaturated, or aromatic carbocycle or a 5- or 6-membered, optionally substituted, saturated or unsaturated or aromatic heterocycle which may contain one, two, or three further heteroatoms, which may be the same or different, selected from the group comprising O, N, and S, and may optionally be substituted singly or doubly the same or differently, wherein optionally two radicals substituted on this carbocycle or heterocycle together with the ring atom to which they are bonded may form a 3- to 7-membered, optionally substituted annelated, saturated, unsaturated, or aromatic carbocycle or heterocycle, wherein the heterocycle may contain one, two, or three heteroatoms, which may be the same or different, selected from the group comprising O, N, and S, and wherein the cyclic compound thus formed may optionally be substituted;

5.) An optionally substituted $C_5$-$C_{10}$ bi- or tricyclic saturated hydrocarbon radical;

6.) In each case optionally substituted $C_1$-$C_8$ alkyl-$NH_2$, $C_1$-$C_8$ alkyl-$NR_Q^6R_Q^7$, $C_1$-$C_8$ alkyl-CO—$NR_Q^6R_Q^7$, $C_1$-$C_8$ alkyl-$SO_2NR_Q^6R_Q^7$, or $C_1$-$C_8$ alkyl-$SO_2NH_2$, wherein $R_Q^6$ and $R_Q^7$ independently, and independently of their respective occurrence, may be defined as above;

7.) A 5- to 6-membered optionally substituted monocyclic heterocycle which is completely or partially saturated, selected from the following group:

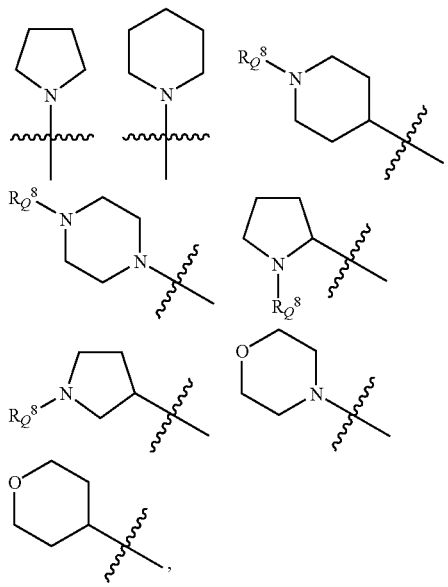

wherein for the case that the heterocycle contains an N atom, this N atom may be substituted with an $RQ^8$ radical, wherein $R_Q^8$ independently from $R_Q^6$ may have a meaning as defined for $R_Q^6$.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, characterized in that the radicals $R^1$, $R^2$, $R^3$, $R^4$, $R^5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:

$R^3$: is hydrogen;
$R^1$, $R^2$: independently stand for:
  hydrogen, OH, CN, in each case optionally substituted $C_1$-$C_4$ alkyl, $C_1$-$C_4$ alkylene-O—$C_1$-$C_4$ alkyl, aryl, benzyl, CO—$C_1$-$C_4$ alkyl, CO-aryl, CO—$C_1$-$C_4$ alkylene-aryl, OCO—$C_1$-$C_4$ alkyl, OCO-aryl, or OCO—$C_1$-$C_4$ alkylene-hetaryl;
W:
  is a radical of general formula W1a

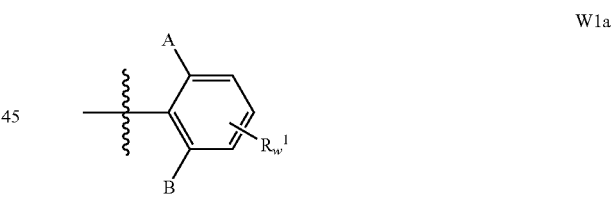

wherein
A:
  is OH, CN, $CF_3$, $OCF_3$, $CHF_2$, $CH_2F$, $OCHF_2$, $OCH_2F$, halogen, O—$C_1$-$C_6$ alkyl, S—$C_1$-$C_6$ alkyl, in each case optionally substituted $C_1$-$C_6$ alkyl, $C_2$-$C_6$ alkenyl, O—$R_A^1$, S—$R_A^1$, $NR_A^4$—CO—O—$R_A^1$, O—$CH_2$—COO—$R_A$, $NR_A^2R_A^3$, $NR_A^4$—CO—$R_A^1$, or $NR_A^4$—$SO_2$—$R_A^1$, $SO_2$—$NR_A^2R_A^3$, or CO—$NR_A^2R_A^3$;
$R_A^1$: independently of its respective occurrence stands for:
  in each case optionally substituted $C_1$-$C_6$ alkyl, $C_3$-$C_7$ cycloalkyl, aryl, or hetaryl;
$R_A^2$ independently of its respective occurrence stands for:
  hydrogen, or
  in each case optionally substituted $C_1$-$C_6$ alkyl, phenyl, benzyl, phenethyl, CO—$C_1$-$C_6$ alkyl, CO-aryl, $SO_2$—$C_1$-$C_6$ alkyl, $SO_2$-aryl, $SO_2$-hetaryl, or $SO_2$—$C_1$-$C_4$ alkylene-aryl;

$R_A{}^3$ independently of its respective occurrence stands for:
  in each case optionally substituted $C_1$-$C_6$ alkyl, phenyl, benzyl, phenethyl, CO—$C_1$-$C_6$ alkyl, CO-aryl, $SO_2$—$C_1$-$C_6$ alkyl, $SO_2$-aryl, $SO_2$-hetaryl, or $SO_2$—$C_1$-$C_4$ alkylene-aryl;
  or the radicals $R_A{}^2$ and $R_A{}^3$ together with the nitrogen atom to which they are bonded form an optionally substituted 5- or 6-membered saturated or unsaturated ring which may contain one or two heteroatoms, which may be the same or different, selected from the group comprising O and N, wherein optionally two radicals substituted on this heterocycle together with the ring atom to which they are bonded may form a 3- to 7-membered, optionally substituted, annelated, saturated, unsaturated, or aromatic carbocycle or heterocycle, wherein the heterocycle may contain one, two, or three heteroatoms, which may be different or the same, selected from the group comprising O, N, and S, wherein the cyclic compound thus formed may optionally be substituted;

$R_A{}^4$ independently of its respective occurrence stands for:
  hydrogen or optionally substituted $C_1$-$C_6$ alkyl;

B:
  is hydrogen, or in each case optionally substituted aryl or hetaryl, or independently of radical A stands for a radical selected from the radicals defined as for radical A;

$R_w{}^1$:
  is hydrogen, $NO_2$, $NH_2$, OH, CN, $CF_3$, $OCF_3$, $CHF_2$, $CH_2F$, $OCHF_2$, $OCH_2F$, COOH, O—$CH_2$—COOH, halogen, SH, O—$C_1$-$C_6$ alkyl, S—$C_1$-$C_6$ alkyl, or
  in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_6$ alkylene-$C_3$-$C_7$ cycloalkyl, $C_1$-$C_6$ alkylene-heterocycloalkyl, $C_1$-$C_6$ alkylene-aryl, $C_1$-$C_6$ alkylene-hetaryl, heterocycloalkyl, or in each case optionally substituted $R_A{}^1$, O—$R_A{}^1$, CO—$R_A{}^1$, S—$R_A{}^1$, SO—$R_A{}^1$, CO—O—$R_A{}^1$, $NR_A{}^4$—CO—O—$R_A{}^1$, O—$CH_2$—COO—$R_A{}^1$, $NR_A{}^2R_A{}^3$, $CONH_2$, $SO_2NH_2$, $NR_A{}^4$—CO—$R_A{}^1$, $SO_2$—$R_A{}^1$, $NR_A{}^4$—$SO_2$—$R_A{}^1$, $C_1$-$C_4$ alkylene-$NR_A{}^2R_A{}^3$, $C_1$-$C_4$ alkylene-CO—$NR_A{}^2R_A{}^3$, $C_1$-$C_4$ alkylene-$SO_2$—$NR_A{}^2R_A{}^3$, or $C_1$-$C_4$ alkylene-O—$R_A{}^1$; wherein $R_A{}^1$, $R_A{}^2$, $R_A{}^3$, and $R_A{}^4$ in each case independently, and independently of their respective occurrence, may have the meanings given for the radicals $R_A{}^1$, $R_A{}^2$, $R_A{}^3$, and $R_A{}^4$;

Z is a radical of general formula Z1

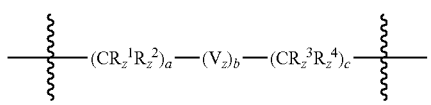

having the indices
  a=0, 1, or 2
  b=0 or 1
  c=0, 1, or 2
  wherein the sum of a, b, and c is equal to 1, 2, or 3;
wherein
$R_Z{}^1$, $R_Z{}^2$, $R_Z{}^3$, $R_Z{}^4$ independently stand for:
  hydrogen, halogen, OH, or optionally substituted $C_1$-$C_6$ alkyl;

$V_Z$:
  is —CO—, —CO—$NR_Z{}^5$—, or —$NR_Z{}^5$—CO—;

$R_Z{}^5$ independently of its respective occurrence stands for:
  hydrogen or in each case optionally substituted $C_1$-$C_3$ alkyl;

Q is a radical according to one of the general formulas Q1, Q2, Q3, Q4, or Q5:

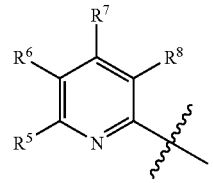

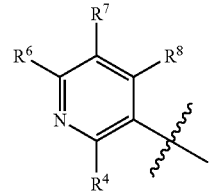

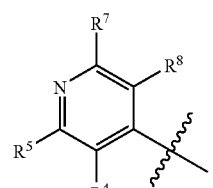

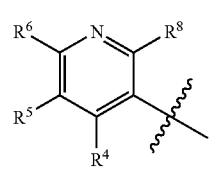

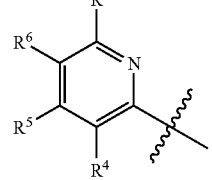

wherein $R^4$, $R^5$, $R^6$, $R^7$, and $R^8$ in each case independently stand for a radical selected from the following groups 1.), 2.), 3.), 4.), 5.), 6.), and 7.), which may be the same or different:

1.) Hydrogen, halogen, CN, $CF_3$, $CHF_2$, $CH_2F$, $OCF_3$, $OCH_2F$, $OCHF_2$, $NH_2$, or
  in each case optionally substituted $C_1$-$C_{10}$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, $C_1$-$C_6$ alkylene-O—$C_1$-$C_6$ alkyl, $C_1$-$C_6$ alkylene-O-aryl, COO—$C_1$-$C_4$ alkyl, $C_1$-$C_4$ alkylene-COO—$C_1$-$C_4$ alkyl, or in each case optionally substituted O—$R_Q{}^4$, S—$R_Q{}^4$, $NR_Q{}^6R_Q{}^7$, CO—$OR_Q{}^5$, $NR_Q{}^7$—CO—O—$R_Q{}^5$, O—$CH_2$—COO—$R_Q{}^5$, $NR_Q{}^7$—CO—$R_Q{}^5$, $SO_2$—$R_Q{}^5$, $NR_Q{}^7$—$SO_2$—$R_Q{}^5$, $SO_2NH_2$, $CONH_2$, $SO_2$—$NR_Q{}^6R_Q{}^7$, or CO—$NR_Q{}^6R_Q{}^7$; wherein $R_Q{}^4$, $R_Q{}^5$, $R_Q{}^6$, and $R_Q{}^7$ independently, and independently of their respective occurrence, are defined as below;

2.) In each case optionally substituted phenyl, 1-naphthyl, or 2-naphthyl, which in each case may be substituted with one, two, or three radicals selected from the group comprising $R_Q^1$, $R_Q^2$, and $R_Q^3$, wherein $R_Q^1$, $R_Q^2$, and $R_Q^3$ in each case independently stand for a substituent, which may be the same or different, selected from the following group:

Hydrogen, CN, $CF_3$, $CHF_2$, $OCF_3$, $OCHF_2$, O—$CH_2$—COOH, halogen, or in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted O—$R_Q^4$, S—$R_Q^4$, $NR_Q^6R_Q^7$, CO—$OR_Q^5$, $NR_Q^7$—CO—O—$R_Q^5$, $NR_Q^7$—CO—$R_Q^5$, $SO_2$—$R_Q^5$, $NR_Q^7$—$SO_2$—$R_Q^5$, $SO_2NH_2$, $CONH_2$, $SO_2$—$NR_Q^6R_Q^7$, or CO—$NR_Q^6R_Q^7$, or in each case two radicals selected from the group comprising $R_Q^1$, $R_Q^2$, and $R_Q^3$ together with the ring atom to which they are bonded form a 3- to 7-membered, optionally substituted, saturated, or unsaturated carbocycle or a 3- to 7-membered, optionally substituted, saturated, unsaturated, or aromatic heterocycle which may contain one, two, or three further heteroatoms, which may be different or the same, selected from the group comprising O, N, and S;

$R_Q^4$ independently of its respective occurrence stands for: in each case optionally substituted $C_1$-$C_4$ alkylene-$C_3$-$C_7$ cycloalkyl, $C_1$-$C_4$ alkylene-heterocycloalkyl, heterocycloalkyl, aryl, or hetaryl, or $C_1$-$C_6$ alkyl which is optionally substituted with a substituent selected from the group comprising halogen, $NO_2$, $NH_2$, OH, CN, $CF_3$, $CHF_2$, $OCF_3$, $OCHF_2$, NH—($C_1$-$C_6$ alkyl), or NH—($C_1$-$C_6$ alkyl)$_2$;

$R_Q^5$ independently of its respective occurrence stands for: in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, or $C_1$-$C_6$ alkylene-O—$C_1$-$C_6$ alkyl;

$R_Q^6$ independently of its respective occurrence stands for: hydrogen, OH, CN, or in each case optionally substituted $C_1$-$C_6$ alkyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, $C_1$-$C_4$ alkylene-aryl, $C_1$-$C_4$ alkylene-hetaryl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$R_Q^7$ independently of its respective occurrence stands for: hydrogen or optionally substituted $C_1$-$C_6$ alkyl; or both radicals $R_Q^6$ and $R_Q^7$ together with the nitrogen atom to which they are bonded form a 3- to 7-membered, optionally substituted, saturated or aromatic heterocycle which may contain one, two, or three further heteroatoms, which may be different or the same, selected from the group comprising O, N, and S;

3.) Is a 5- or 6-membered hetaryl radical, unsubstituted or optionally singly or doubly substituted the same or differently, selected from the group comprising:

2-thienyl, 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-Isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl, or triazinyl or their annelated derivatives indazolyl, indolyl, benzothiophenyl, benzofuranyl, benzimidazolyl, benzthiazolyl, benzoxazolyl, quinolinyl and isoquinolinyl, wherein the substituents are preferably selected from the group comprising hydrogen, halogen, $NO_2$, $NH_2$, OH, CN, CF3, $OCF_3$, $CHF_2$, O—$CHF_2$, or in each case optionally substituted $C_1$-$C_6$ alkyl, O—$C_1$-$C_6$ alkyl, NH—($C_1$-$C_6$ alkyl), N($C_1$-$C_6$ alkyl)$_2$, NHCO—$C_1$-$C_4$ alkyl, $NHSO_2$—$C_1$-$C_4$ alkyl, and $SO_2$—$C_1$-$C_4$ alkyl;

4.) Two adjacent radicals selected from the group comprising the radicals $R^4$, $R^5$, $R^6$, $R^7$, and $R^8$ as follows:

for case (1) $R^4$ and $R^5$ in Q3, Q4, or Q5, for case (2) $R^5$ and $R^6$ in Q1, Q4, or Q5, for case (3) $R^6$ and $R^7$ in Q1, Q2, or Q5, and for case (4) $R^7$ and $R^8$ in Q1, Q2, or Q3, and the radicals selected according to cases (1) through (4) together with the atom to which they are bonded form a 4- to 7-membered, optionally substituted, saturated, unsaturated, or aromatic carbocycle or a 5- or 6-membered, optionally substituted, saturated, or unsaturated or aromatic heterocycle which may contain one, two, or three further heteroatoms, which may be different or the same, selected from the group comprising O, N, and S, and may optionally be substituted singly or doubly the same or differently, wherein optionally two radicals substituted on this carbocycle or heterocycle together with the ring atom to which they are bonded may form a 3- to 7-membered, optionally substituted annelated, saturated, unsaturated or aromatic carbocycle or heterocycle, wherein the heterocycle may contain one, two, or three heteroatoms, which may be different or the same, selected from the group comprising O, N, and S, and wherein the cyclic compound thus formed may optionally be substituted;

5.) A $C_5$-$C_{10}$ bi- or tricyclic saturated hydrocarbon radical optionally substituted in each case;

6.) In each case optionally substituted $C_1$-$C_8$ alkyl-$NH_2$, $C_1$-$C_8$ alkyl-$NR_Q^6R_Q^7$, $C_1$-$C_8$ alkyl-CO—$NR_Q^6R_Q^7$, $C_1$-$C_8$ alkyl-$SO_2NR_Q^8R_Q^7$, or $C_1$-$C_8$ alkyl-$SO_2NH_2$, wherein $R_Q^6$ and $R_Q^7$ independently, and independently of their occurrence, may be defined as above;

7.) A 5- to 6-membered optionally substituted monocyclic heterocycle which is completely or partially saturated, selected from the following group:

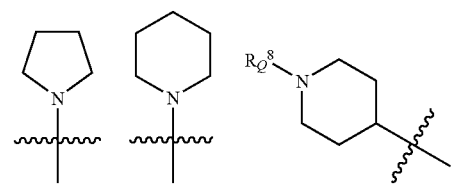

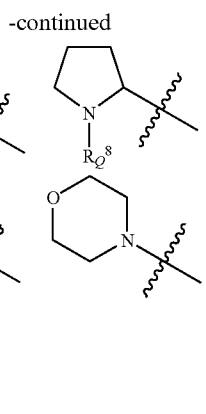

wherein for the case that the heterocycle contains an N atom, this N atom may be substituted with an $R_Q^8$ radical, wherein $R_Q^8$ independently from $R_Q^6$ may have a meaning as defined for $R_Q^6$.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, characterized in that the radicals $R^1$, $R^2$, $R^3$, $R^4$, $R^5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:

$R^1$, $R^2$, $R^3$: are hydrogen in each case.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, the corresponding enantiomeric, diastereomeric, and/or tautomeric forms thereof, and/or pharmaceutically acceptable salts thereof, and/or the corresponding active substance precursors ("prodrugs") thereof, are prepared, characterized in that the radicals $R^1$, $R^2$, $R^3$, $R^4$, $R^5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:

W:
is a radical of general formula W1a:

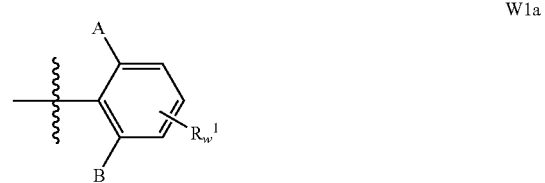

W1a

A:
is OH, CN, $CF_3$, $OCF_3$, $CHF_2$, $OCHF_2$, F, Cl, Br, or in each case optionally substituted $C_1$-$C_4$ alkyl, O—$C_1$-$C_4$ alkyl, S—$C_1$-$C_4$ alkyl, $NR_A^2 R_A^3$, $NR_A^4$—CO—$R_A^1$, or $NR_A^4$—$SO_2$—$R_A^1$;

$R_A^1$: independently of its respective occurrence stands for: in each case optionally substituted $C_1$-$C_4$ alkyl;

$R_A^2$: independently of its respective occurrence stands for: hydrogen, or
in each case optionally substituted $C_1$-$C_4$ alkyl, $SO_2$-aryl, or $SO_2$-hetaryl;

$R_A^3$: independently of its respective occurrence stands for: in each case optionally substituted $C_1$-$C_4$ alkyl, $SO_2$-aryl, or $SO_2$-hetaryl;

$R_A^4$: independently of its respective occurrence stands for: hydrogen or optionally substituted $C_1$-$C_4$ alkyl;

B:
is hydrogen, optionally substituted phenyl, or independently of radical A stands for a radical selected from the radicals defined as for radical A;

$R_w^1$:
is hydrogen, F, Cl, Br, CN, $CF_3$, O—$CF_3$, or
in each case optionally substituted $C_1$-$C_4$ alkyl, O—$C_1$-$C_4$ alkyl, $NR_A^2 R_A^3$, $NR_A^4$—CO—$R_A^1$, or $NR_A^4$—$SO_2$—$R_A^1$, wherein $R_A^1$, $R_A^2$, $R_A^3$, and $R_A^4$ independently, and independently of their respective occurrence, may have the meanings given above or defined in one of claims 1 through 9.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_z^1$, $R_z^2$, $R_z^3$, $R_z^4$, $R_z^5$, $R_z^{5*}$, $R_z^6$, $R_z^7$, $V_z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, characterized in that the radicals $R^1$, $R^2$, $R^3$, $R^4$, $R^5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:

Z:
is a radical of general formula Z1

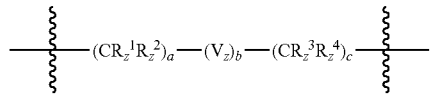

having the indices
a=1
b=0
c=0;
$R_z^1$, $R_z^2$ independently stand for:
hydrogen, halogen, OH, or optionally substituted $C_1$-$C_4$ alkyl.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_z^1$, $R_z^2$, $R_z^3$, $R_z^4$, $R_z^5$, $R_z^{5*}$, $R_z^6$, $R_z^7$, $V_z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, characterized in that the radicals $R^1$, $R^2$, $R^3$, $R^4$, $R^5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:

Q is a radical of general formula Q1, Q2, or Q3

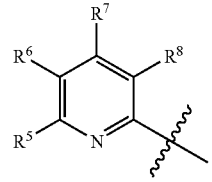

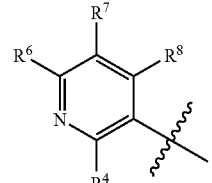

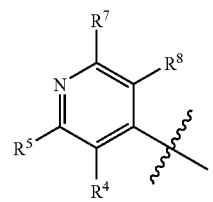

wherein $R^4$, $R^5$, $R^6$, $R^7$, and $R^8$ in each case independently stand for a radical selected from the following groups 1.), 2.), 3.), 4.), 5.), 6.), and 7.), which may be the same or different:

1.) Hydrogen, F, Cl, Br, I, CN, $CF_3$, $CHF_2$, $OCF_3$, $OCHF_2$, $NH_2$, or in each case optionally substituted $C_1$-$C_{10}$ alkyl, $C_3$-$C_7$ cycloalkyl, or $C_1$-$C_6$ alkylene-$C_3$-$C_7$ cycloalkyl, or in each case optionally substituted
O—$R_Q^4$, $NR_Q^6R_Q^7$, $NR_Q^7$—CO—O—$R_Q^5$, $NR_Q^7$—CO—$R_Q^5$, $SO_2$—$R_Q^5$, $NR_Q^7$—$SO_2$—$R_Q^5$, $SO_2NH_2$, or $SO_2$—$NR_Q^6R_Q^7$, and $R_Q^4$, $R_Q^5$, $R_Q^6$, and $R_Q^7$ independently, and independently of their respective occurrence, are defined as below;

2.) In each case optionally substituted phenyl, 1-naphthyl, or 2-naphthyl, which in each case may be substituted with one, two, or three radicals selected from the group comprising $R_Q^1$, $R_Q^2$, and $R_Q^3$, wherein
$R_Q^1$, $R_Q^2$, and $R_Q^3$ in each case independently stand for a substituent, which may be the same or different, selected from the following group:
Hydrogen, CN, $CF_3$, $CHF_2$, $OCF_3$, $OCHF_2$, O—$CH_2$—COOH, halogen, or
in each case optionally substituted aryl, hetaryl, heterocycloalkyl, $C_1$-$C_6$ alkyl, $C_3$-$C_7$ cycloalkyl, O—$R_Q^4$, $NR_Q{}^6R_Q{}^7$, $NR_Q{}^7$—$SO_2$—$R_Q{}^5$, $SO_2NH_2$, $CONH_2$, $SO_2$—$NR_Q{}^6R_Q{}^7$, or $CO$—$NR_Q{}^6R_Q{}^7$, or in each case two radicals selected from the group comprising $R_Q{}^1$, $R_Q{}^2$, and $R_Q{}^3$ together with the C atom to which they are bonded form a 3- to 7-membered, optionally substituted, saturated, or unsaturated carbocycle, or a 3- to 7-membered, optionally substituted, saturated, or unsaturated aromatic heterocycle which may contain one, two, or three further heteroatoms, which may be different or the same, selected from the group comprising O, N, and S;

$R_Q{}^4$ independently of its respective occurrence stands for: in each case optionally substituted aryl or hetaryl, or $C_1$-$C_6$ alkyl, which may optionally be substituted singly or doubly, the same or differently, with one, two, or three substituents, which may be the same or different, selected from the group comprising halogen, CN, $CF_3$, $CHF_2$, $OCF_3$, $OCHF_2$, NH—($C_1$-$C_6$ alkyl), and N($C_1$-$C_6$ alkyl)$_2$;

$R_Q{}^5$ independently of its respective occurrence stands for: in each case optionally substituted $C_1$-$C_6$ alkyl, aryl, or hetaryl;

$R_Q{}^6$ independently of its respective occurrence stands for: hydrogen, or in each case optionally substituted $C_1$-$C_6$ alkyl, aryl, hetaryl, $C_1$-$C_4$ alkylene-aryl, $C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$R_Q{}^7$ independently of its respective occurrence stands for: hydrogen or optionally substituted $C_1$-$C_6$ alkyl; or both radicals $R_Q{}^6$ and $R_Q{}^7$ together with the nitrogen atom to which they are bonded form a 3- to 7-membered, optionally substituted, saturated or aromatic heterocycle which may contain one, two, or three further heteroatoms, which may be different or the same, selected from the group comprising O, N, and S;

3.) A 5- or 6-membered hetaryl radical which is unsubstituted, or optionally singly or doubly substituted the same or differently, selected from the group comprising:
2-thienyl, 3-thienyl, 2-pyridyl, 3-pyridyl, 4-pyridyl, 2-thiazolyl, 4-thiazolyl, 5-thiazolyl, 2-pyrimidyl, 4-pyrimidyl, 5-pyrimidyl, 6-pyrimidyl, wherein the substituents are preferably selected from the group comprising hydrogen, halogen, CN, $CF_3$, $OCF_3$, $C_1$-$C_6$ alkyl, O—$C_1$-$C_6$ alkyl, NH—($C_1$-$C_6$ alkyl), N($C_1$-$C_6$alkyl)$_2$, NHCO—$C_1$-$C_4$ alkyl, NHSO$_2$—$C_1$-$C_4$ alkyl, and SO$_2$—$C_1$-$C_4$ alkyl;

4.) Two adjacent radicals selected from the group comprising the radicals $R^4$, $R^5$, $R^6$, $R^7$, and $R^8$ in cases (1) through (4), i.e., for
case (1) $R^4$ and $R^5$ in Q3; for case (2) $R^5$ and $R^6$ in Q1; for case (3) $R^6$ and $R^7$ in Q1 or Q2; and for case (4) $R^7$ and $R^8$ in Q1, Q2, or Q3,
in each case together with the ring atom to which they are bonded form an optionally substituted 6-membered, aromatic cyclic compound, preferably a quinolinyl or isoquinolinyl cyclic compound optionally substituted in each case, which optionally may be singly or doubly substituted the same or differently;

5.) Optionally substituted adamantyl;

6.) In each case optionally substituted $C_1$-$C_4$ alkyl-NH$_2$, $C_1$-$C_4$ alkyl-NR$_Q{}^6$R$_Q{}^7$, $C_1$-$C_4$ alkyl-CO—NR$_Q{}^6$R$_Q{}^7$, $C_1$-$C_4$ alkyl-SO$_2$NR$_Q{}^6$R$_Q{}^7$, $C_1$-$C_4$ alkyl-SO$_2$NH$_2$, wherein $R_Q{}^6$ and $R_Q{}^7$ independently, and independently of their respective occurrence, may have a meaning as defined above;

7.) An optionally substituted 6-membered monocyclic heterocycle selected from the following group:

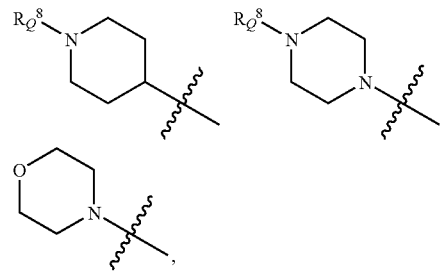

wherein for the case that the heterocycle contains an N atom, this N atom may be substituted with an $R_Q{}^8$ radical, wherein $R_Q{}^8$ independently from $R_Q{}^6$ may have a meaning as defined for $R_Q{}^6$.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z{}^1$, $R_Z{}^2$, $R_Z{}^3$, $R_Z{}^4$, $R_Z{}^5$, $R_Z{}^{5*}$, $R_Z{}^6$, $R_Z{}^7$, $V_Z$, W, W1, W2, W3, A, $R_A{}^1$, $R_A{}^2$, $R_A{}^3$, $R_A{}^4$, B, $R_w{}^1$, $R_w{}^2$, $R_w{}^3$, D, E, Q, $X^1$, $X^2$, $X^3$, $X^4$, $X^5$, $R_Q{}^1$, $R_Q{}^2$, $R_Q{}^3$, $R_Q{}^4$, $R_Q{}^5$, $R_Q{}^6$, $R_Q{}^7$, and $R_Q{}^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, the corresponding enantiomeric, diastereomeric, and/or tautomeric forms thereof, and/or pharmaceutically acceptable salts thereof, and/or the corresponding active substance precursors ("prodrugs") thereof, are prepared, characterized in that the radicals $R^1$, $R^2$, $R^3$, $R^4$, $R^5$, $R^6$, $R^7$, $R^8$, W, A, $R_A{}^1$, $R_A{}^2$, $R_A{}^3$, $R_A{}^4$, B, $R_w{}^1$, $R_w{}^2$, $R_w{}^3$, D, E, Q, $X_1$, $X_2$, $X_3$, $X_4$, $X_5$, $R_Q{}^1$, $R_Q{}^2$, $R_Q{}^3$, $R_Q{}^4$, $R_Q{}^5$, $R_Q{}^6$, $R_Q{}^7$, and $R_Q{}^8$, unless described otherwise below, have the same meaning as defined above, and the radicals below have the following definitions:

$R^1$, $R^2$, $R^3$: in each case stand for hydrogen;
W:
  is a radical of general formula W1a

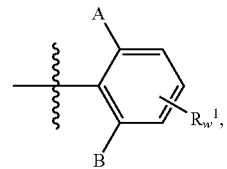

wherein

A:
is OH, CN, CF$_3$, OCF$_3$, CHF$_2$, OCHF$_2$, F, Cl, Br, or
in each case optionally substituted C$_1$-C$_4$ alkyl, O—C$_1$-C$_4$ alkyl, S—C$_1$-C$_4$ alkyl, NR$_A^2$R$_A^3$, NR$_A^4$—CO—R$_A^1$, or NR$_A^4$—SO$_2$—R$_A^1$;

R$_A^1$: independently of its respective occurrence stands for:
in each case optionally substituted C$_1$-C$_4$ alkyl;

R$_A^2$: independently of its respective occurrence stands for:
hydrogen, or
in each case optionally substituted C$_1$-C$_4$ alkyl, SO$_2$-aryl, or SO$_2$-hetaryl;

R$_A^3$: independently of its respective occurrence stands for:
in each case optionally substituted C$_1$-C$_4$ alkyl, SO$_2$-aryl, or SO$_2$-hetaryl;

R$_A^4$: independently of its respective occurrence stands for:
hydrogen or optionally substituted C$_1$-C$_4$ alkyl;

B:
is hydrogen, optionally substituted phenyl, or independently of radical A stands for a radical selected from the radicals defined as for radical A;

R$_w^1$:
is hydrogen, F, Cl, Br, CN, CF$_3$, O—CF$_3$, or
in each case optionally substituted C$_1$-C$_4$ alkyl, O—C$_1$-C$_4$ alkyl, NR$_A^2$R$_A^3$, NR$_A^4$—CO—R$_A^1$, or NR$_A^4$—SO$_2$—R$_A^1$, wherein R$_A^1$, R$_A^2$, R$_A^3$, and R$_A^4$ in each case independently, and independently of their respective occurrence, in each case may have the meanings given above for the radicals R$_A^1$, R$_A^2$, R$_A^3$, and R$_A^4$;

Z:
is a radical of general formula Z1

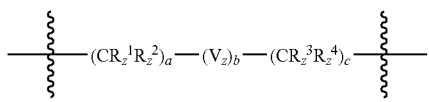

having the indices
a=1
b=0
c=0;

R$_z^1$, R$_z^2$ independently stand for:
hydrogen, halogen, OH, or optionally substituted C$_1$-C$_4$ alkyl;

Q is a radical of general formula Q1, Q2, or Q3

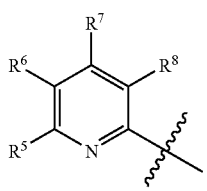

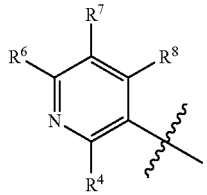

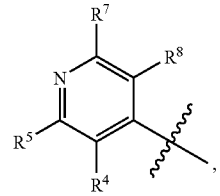

wherein R$^4$, R$^5$, R$^6$, R$^7$, and R$^8$ in each case independently stand for a radical selected from the following groups 1.), 2.), 3.), 4.), 5.), 6.), and 7.), which may be the same or different:

1.) Hydrogen, F, Cl, Br, I, CN, CF$_3$, CHF$_2$, OCF$_3$, OCHF$_2$, NH$_2$, or in each case optionally substituted C$_1$-C$_{10}$ alkyl, C$_3$-C$_7$ cycloalkyl, or C$_1$-C$_6$ alkylene-C$_3$-C$_7$ cycloalkyl, or in each case optionally substituted
R$_Q^4$, O—R$_Q^4$, NR$_Q^6$R$_Q^7$, NR$_Q^7$—CO—O—R$_Q^5$, NR$_Q^7$—CO—R$_Q^5$, SO$_2$—R$_Q^5$, R$_Q^7$—SO$_2$—R$_Q^5$, SO$_2$NH$_2$, or SO$_2$—NR$_Q^6$R$_Q^7$, wherein R$_Q^4$, R$_Q^5$, R$_Q^6$, and R$_Q^7$ independently, and independently of their respective occurrence, are defined as below;

2.) In each case optionally substituted phenyl, 1-naphthyl, or 2-naphthyl which may be substituted with one, two, or three radicals, which may be the same or different, independently selected from the group comprising R$_Q^1$, R$_Q^2$, and R$_Q^3$, wherein
R$_Q^1$, R$_Q^2$, and R$_Q^3$ in each case independently stand for a substituent, which may be the same or different, from the following group:
Hydrogen, CN, CF$_3$, CHF$_2$, OCF$_3$, OCHF$_2$, O—CH$_2$—COOH, halogen, or
in each case optionally substituted aryl, hetaryl, heterocycloalkyl, C$_1$-C$_6$ alkyl, C$_3$-C$_7$ cycloalkyl, O—R$_Q^4$, NR$_Q^6$R$_Q^7$, NR$_Q^7$—CO—R$_Q^5$, NR$_Q^7$—SO$_2$—R$_Q^5$, SO$_2$NH$_2$, CONH$_2$, SO$_2$—NR$_Q^6$R$_Q^7$, or CO—NR$_Q^6$R$_Q^7$, or
in each case two of the radicals from R$_Q^1$, R$_Q^2$, or R$_Q^3$ together with the C atom to which they are bonded form a 3- to 7-membered, optionally substituted, saturated or unsaturated carbocycle, or a 3- to 7-membered, optionally substituted, saturated or unsaturated aromatic heterocycle which may contain one, two, or three further heteroatoms, which may be different or the same, selected from the group comprising O, N, and S;

R$_Q^4$ independently of its respective occurrence stands for: in each case optionally substituted aryl or hetaryl, or C$_1$-C$_6$ alkyl, which may optionally be substituted singly or doubly, the same or differently, with a substituent selected from the group comprising halogen, CN, CF$_3$, CHF$_2$, OCF$_3$, OCHF$_2$, NH—(C$_1$-C$_6$ alkyl), and N(C$_1$-C$_6$ alkyl)$_2$;

R$_Q^5$ independently of its respective occurrence stands for: in each case optionally substituted C$_1$-C$_6$ alkyl, aryl, or hetaryl;

R$_Q^6$ independently of its respective occurrence stands for: hydrogen, or in each case optionally substituted C$_1$-C$_6$ alkyl, aryl, hetaryl, C$_1$-C$_4$ alkylene-aryl, C$_1$-C$_4$ alkylene-hetaryl, SO$_2$—C$_1$-C$_6$ alkyl, SO$_2$-aryl, SO$_2$-hetaryl, SO$_2$—C$_1$-C$_4$ alkylene-aryl, or SO$_2$—C$_1$-C$_4$ alkylene-hetaryl;

R$_Q^7$ independently of its respective occurrence stands for: hydrogen or optionally substituted C$_1$-C$_6$ alkyl;

or both radicals $R_Q^6$ and $R_Q^7$ together with the nitrogen atom to which they are bonded form a 3- to 7-membered, optionally substituted, saturated or aromatic heterocycle which may contain one, two, or three further heteroatoms, which may be different or the same, selected from the group comprising O, N, and S;

3.) A 5- or 6-membered hetaryl radical which is unsubstituted, or optionally singly or doubly substituted the same or differently, selected from the group comprising:
2-thienyl, 3-thienyl, 2-pyridyl, 3-pyridyl, 4-pyridyl, 2-thiazolyl, 4-thiazolyl, 5-thiazolyl, 2-pyrimidyl, 4-pyrimidyl, 5-pyrimidyl, 6-pyrimidyl, wherein the substituents are preferably selected from the group comprising hydrogen, halogen, CN, $CF_3$, $OCF_3$, or in each case optionally substituted $C_1$-$C_6$ alkyl, O—$C_1$-$C_6$ alkyl, NH—($C_1$-$C_6$ alkyl), N($C_1$-$C_6$ alkyl)$_2$, NHCO—$C_1$-$C_4$ alkyl, NHSO$_2$—$C_1$-$C_4$ alkyl, and SO$_2$—$C_1$-$C_4$ alkyl;

4.) Two adjacent radicals selected from the group comprising the radicals $R^4$, $R^5$, $R^6$, $R^7$, and $R^8$ in cases (1) through (4), i.e., for case (1) $R^4$ and $R^5$ in Q3; for case (2) $R^5$ and $R^6$ in Q1; for case (3) $R^6$ and $R^7$ in Q1 or Q2; and for case (4) $R^7$ and $R^8$ in Q1, Q2, or Q3,
in each case together with the ring atom to which they are bonded form an optionally substituted 6-membered, aromatic cyclic compound, preferably a quinolinyl or isoquinolinyl cyclic compound optionally substituted in each case, which optionally may be singly or doubly substituted the same or differently;

5.) Optionally substituted adamantyl;

6.) In each case optionally substituted $C_1$-$C_4$ alkyl-NH$_2$, $C_1$-$C_4$ alkyl-NR$_Q^6$R$_Q^7$, $C_1$-$C_4$ alkyl-CO—NR$_Q^6$R$_Q^7$, $C_1$-$C_4$ alkyl-SO$_2$NR$_Q^6$R$_Q^7$, $C_1$-$C_4$ alkyl-SO$_2$NH$_2$, wherein $R_Q^6$ and $R_Q^7$ independently, and independently of their respective occurrence, may have a meaning as defined above;

7.) An optionally substituted 6-membered monocyclic heterocycle selected from the following group:

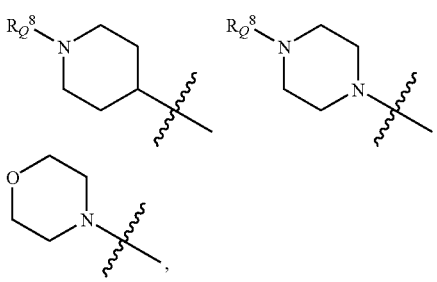

wherein for the case that the heterocycle contains an N atom, this N atom may be substituted with an $R_Q^8$ radical, wherein $R_Q^8$ independently from $R_Q^6$ may have a meaning as defined for $R_Q^6$.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, characterized in that the radicals $R^1$, $R^2$, $R^3$, $R^4$, $R_5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:
A: is $OCF_3$, $OCHF_2$, $OCH_3$, O-ethyl, O-propyl, or O-isopropyl.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:
$R^1$, $R^2$, $R^3$: in each case stand for hydrogen.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, characterized in that the radicals $R^1$, $R^2$, $R^3$, $R^4$, $R^5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:

Q: is a radical of general formula Q1

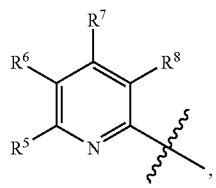

wherein $R^5$, $R^6$, $R^7$, and $R^8$ independently have each of, or one of, the meanings given above.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, characterized in that the radicals $R^1$, $R^2$, $R^3$, $R^4$, $R^5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:

Q stands for a radical Q1

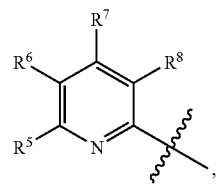

wherein the radicals $R^5$, $R^6$, $R^7$ are independently selected from the group comprising H, CN, $CH_3$, halogen, or in each case optionally substituted $C_1$-$C_6$ alkyl, O—$C_1$-$C_6$ alkyl, aryl, hetaryl, $C_1$-$C_4$ alkylene-aryl, $C_1$-$C_4$-hetaryl, and preferably stand for H, CN, halogen, halogenated $C_1$-$C_6$ alkyl, halogenated O—$C_1$-$C_6$ alkyl, and $R^6$ stands for H, CN, $CH_3$, or halogen.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, characterized in that the radicals $R^1$, $R^2$, $R^3$, $R^4$, $R^5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:

Z stands for —$CH_2$—.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, characterized in that the radicals $R^1$, $R^2$, $R^3$, $R^4$, $R^5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:

A: is $OCF_3$, $OCHF_2$, $OCH_3$, or O-ethyl,
optionally preferably with the condition that when $X^1$=N or $X^1$ and $X^5$=N in each case, then B, $R_w^1$, $R_w^2$, and $R_w^3$ do not simultaneously stand for a radical selected from the group comprising the radicals $C_3$-$C_6$ alkyl, $C_3$-$C_6$ alkenyl, $C_3$-$C_6$ alkynyl, hetaryl, and a carboxylic acid group.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, characterized in that the radicals $R^1$, $R^2$, $R^3$, $R^4$, $R^5$, $R^6$, $R^7$, $R^8$, W, A, $R_A^1$, $R_A^2$, $R_A^3$, $R_A^4$, B, $R_w^1$, $R_w^2$, $R_w^3$, D, E, Q, $X_1$, $X_2$, $X_3$, $X_4$, $X_5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:

Z stands for —$CH_2$—.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, are prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, with the condition of being subject to one, several, or all of conditions (i) through (xiii), particularly preferably with the condition of being subject to one, several, or all of conditions (viii) through (xiii).

Further preferred embodiments of at least one compound according to the invention corresponding to general formula I are described in greater detail in one of claims 2 through 20.

According to a further aspect of the invention, at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, are provided for use as a pharmaceutical.

According to a further aspect of the invention, a pharmaceutical composition containing at least one guanidine compound of general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, and optionally at least one pharmaceutically acceptable carrier and/or diluent, is prepared, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above.

According to a further aspect of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, is provided for the treatment and/or prevention of, or for producing a medicament for the treatment and/or prevention of, at least one disease which may be treated and/or prophylactically prevented by modulation of the 5-$HT_5$ receptor activity in a patient requiring such treatment and/or prevention.

According to a further aspect of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, is provided for the treatment and/or prevention of, or for producing a medicament for the treatment and/or prevention of, at least one disease which may be treated and/or prophylactically prevented by modulation of the 5-$HT_5$ receptor activity, with a simultaneous binding affinity for the 5-$HT_{5A}$ receptor less than or equal to 10 μM (Ki), preferably less than or equal to 300 nM (Ki), particularly preferably less than or equal to 100 nM, the Ki value in each case being determined according to a suitable test system, in a patient requiring such treatment and/or prevention.

According to a further aspect of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, is provided for the treatment and/or prevention of, or for producing a medicament for the treatment and/or prevention of, at least one disease selected from the group comprising neuropathological, neuropsychiatric, and neurodegenerative disorders; neuropathological, neuropsychiatric, and neurodegenerative symptoms; and neuropathological, neuropsychiatric, and neurodegenerative dysfunctions, in a patient requiring such treatment and/or prevention.

According to a further aspect of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, is provided for the treatment and/or prevention of, or for producing a medicament for the treatment and/or prevention of, migraine and brain damage in a patient requiring such treatment and/or prevention.

According to a further aspect of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R_6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, is provided for the treatment and/or prevention of, or for producing a medicament for the treatment and/or prevention of, at least one neuropathological, neuropsychiatric, and/or neurodegenerative disease selected from the group comprising cerebral ischemia, stroke, epilepsy, and attacks in general, psychoses, schizophrenia, autism, OCD syndrome, cognitive disorders, attention disorders, depression, bipolar and/or unipolar depression, anxiety, dementia, senile dementia, Alzheimer's dementia, demyelinating diseases, multiple sclerosis, and brain tumors in a patient requiring such treatment and/or prevention.

According to a further aspect of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, is provided for the treatment and/or prevention of, or for producing a medicament for the treatment and/or prevention of, at least one disease selected from the group comprising cerebrovascular disorders, pain, pain-related disorders, dependency, drug-related disorders, amnesia, alcohol abuse, drug abuse, circadian rhythm disorders, and Cushing's syndrome in a patient requiring such treatment and/or prevention.

According to a further aspect of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{6*}$, $R_Z^6$, $R_Z^7$, $V_Z$, W, W1, W2, W3, A, $R_A^1$, $R_A^2$, $R_A^3$, $R_A^4$, B, $R_w^1$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, is provided, characterized in that the treatment and/or prevention is based on modulation of the 5-$HT_{5A}$ receptor activity in the patient.

Modulation of 5-$HT_{5A}$ receptor activity is preferably based on antagonization of 5-$HT_{5A}$ receptors by substances selected from the group comprising antagonists, partial antagonists, and inverse agonists, in each case relative to the activity of the 5-$HT_{5A}$ receptor.

According to a further aspect of the invention, the use of at least one guanidine compound according to general formula (i) as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, is provided, characterized in that the treatment and/or prevention is based on a binding affinity for the 5-$HT_{5A}$ receptor that is less than or equal to 10 μM (Ki), determined according to a suitable test model.

According to a further aspect of the invention, the use of at least one guanidine compound according to general formula (i) as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, is provided, characterized in that the treatment and/or prevention is based on a binding affinity for the 5-$HT_{5A}$ receptor that is less than or equal to 300 nM (Ki), determined according to a suitable test model.

According to a further aspect of the invention, the use of at least one guanidine compound according to general formula (i) as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{6*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, is provided, characterized in that the treatment and/or prevention is based on a binding affinity for the 5-$HT_{5A}$ receptor that is less than or equal to 100 nM (Ki), determined according to a suitable test model.

According to a further aspect of the invention, the use of at least one guanidine compound according to general formula I,

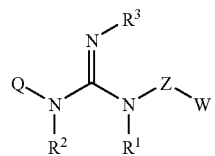

I and/or the corresponding enantiomeric, diastereomeric, and/or tautomeric forms thereof, and/or pharmaceutically acceptable salts thereof, and/or the corresponding active substance precursors ("prodrugs") thereof,
wherein the stated radicals have the following definitions:
$R^1$, $R^2$ in each case independently stand for:
hydrogen, OH, CN,
or
in each case optionally substituted $C_1$-$C_6$ alkyl, O—$C_1$-$C_6$ alkyl, $C_1$-$C_6$ alkylene-O—$C_1$-$C_6$ alkyl, $C_3$-$C_7$ cycloalkyl, O—$C_3$-$C_7$ cycloalkyl, aryl, hetaryl, $C_1$-$C_4$ alkylene-aryl, $C_1$-$C_4$ alkylene-hetaryl, O-aryl, O—$C_1$-$C_4$ alkylene-aryl, O-hetaryl, O—$C_1$-$C_4$ alkylene-hetaryl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O-hetaryl, CO—O—$C_1$-$C_4$ alkylene-aryl, $SO_2$—$C_1$-$C_6$ alkyl, $SO_2$-aryl, $SO_2$-hetaryl, $SO_2$—$C_1$-$C_4$ alkylene-aryl, OCO—$C_1$-$C_6$ alkyl, OCO-aryl, OCO-hetaryl, OCO—$C_1$-$C_4$ alkylene-aryl, OCO—$C_1$-$C_4$ alkylene-hetaryl, $SO_2$—$C_1$-$C_6$ alkyl, $SO_2$-aryl, $SO_2$-hetaryl, or $SO_2$—$C_1$-$C_4$ alkylene-aryl;
$R^3$ is hydrogen
or
in each case optionally substituted $C_1$-$C_6$ alkyl, O—$C_1$-$C_6$ alkyl, $C_1$-$C_6$ alkylene-O—$C_1$-$C_6$ alkyl, $C_3$-$C_7$ cycloalkyl, O—$C_3$-$C_7$ cycloalkyl, aryl, hetaryl, $C_1$-$C_4$ alkylene-aryl, $C_1$-$C_4$ alkylene-hetaryl, O-aryl, O—$C_1$-$C_4$ alkylene-aryl, O-hetaryl, O—$C_1$-$C_4$ alkylene-hetaryl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O-hetaryl, CO—O—$C_1$-$C_4$ alkylene-aryl, $SO_2$—$C_1$-$C_6$ alkyl, $SO_2$-aryl, $SO_2$-hetaryl, $SO_2$—$C_1$-$C_4$ alkylene-aryl, OCO—$C_1$-$C_6$ alkyl, OCO-aryl, OCO-hetaryl, OCO—$C_1$-$C_4$ alkylene-aryl, OCO—$C_1$-$C_4$ alkylene-hetaryl, $SO_2$—$C_1$-$C_6$ alkyl, $SO_2$-aryl, $SO_2$-hetaryl, or $SO_2$—$C_1$-$C_4$ alkylene-aryl,
or
in each case two radicals selected from the group comprising $R^1$, $R^2$, and $R^3$, independently of the remaining radical $R^1$, $R^2$, or $R^3$, together with the nitrogen atom to which they are bonded form a 5- to 7-membered, optionally substituted, saturated or unsaturated heterocycle which may contain one, two, or three further heteroatoms, which may be different or the same, selected from the group comprising C, O, N, and S, wherein optionally two radicals substituted on this heterocycle together with the ring atom to which they are bonded may form a 3- to 7-membered, optionally substituted annelated, saturated, unsaturated, or aromatic carbocycle or heterocycle, wherein the heterocycle may contain one, two, or three heteroatoms, which may be different or the same, selected from the group comprising O, N, and S, and wherein the cyclic compound that is formed may optionally be substituted, and/or a further 3- to 7-membered, optionally substituted cyclic compound may be condensed thereon;

Z is a radical of general formula Z1

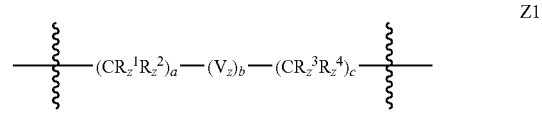

Z1 having the indices
a=0, 1, 2, 3, or 4
b=0 or 1
c=0, 1, 2, 3, or 4
wherein the sum of a, b, and c is equal to 1, 2, 3, 4, or 5;
$R_Z^1$, $R_Z^2$, $R_Z^3$, $R_Z^4$ in each case independently stand for:
hydrogen, halogen, OH,
or
in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_3$-$C_7$ cycloalkyl, aryl, $C_1$-$C_4$ alkylene-aryl, hetaryl, or $C_1$-$C_4$ alkylene-hetaryl,
or
two radicals $R_Z^1$ and $R_Z^2$ or $R_Z^3$ and $R_Z^4$, independently in each case, together with the C atom to which they are bonded form a 3- to 7-membered, optionally substituted, saturated or unsaturated carbocycle or heterocycle which may contain one, two, or three heteroatoms, which may be the same or different, selected from the group comprising O, N, or S;
$V_Z$ is —CO—, —CO—$NR_Z^5$—, —$NR_Z^5$—CO—, —O—, —S—, —SO—, —$SO_2$—, —$SO_2$—$NR_Z^5$—, $NR_Z^5$—$SO_2$—, —CS—, —CS—$NR_Z^5$—, —$NR_Z^5$—CS—, —CS—O—, —O—CS—, —CO—O—, O—CO—, ethynylene, —C(=CR$_Z^6$R$_Z^7$)—, —CR$_Z^6$=CR$_Z^7$—, —NR$_Z^5$—CO—NR$_Z^5$*—, O—CO—NR$_Z^5$—, or —NR$_Z^5$—;

wherein

R$_Z^5$, R$_Z^5$* in each case independently, and independently of their respective occurrence, stand for:
hydrogen, or
in each case optionally substituted C$_1$-C$_6$ alkyl, C$_1$-C$_4$ alkylene-O—C$_1$-C$_6$ alkyl, C$_2$-C$_6$ alkenyl, C$_2$-C$_{12}$ alkynyl, CO—C$_1$-C$_6$ alkyl, CO—O—C$_1$-C$_6$ alkyl, SO$_2$—C$_1$-C$_6$ alkyl, C$_3$-C$_7$ cycloalkyl, aryl, C$_1$-C$_4$ alkylene-aryl, CO—O—C$_1$-C$_4$ alkylene-aryl, CO—C$_1$-C$_4$ alkylene-aryl, CO-aryl, SO$_2$-aryl, hetaryl, CO-hetaryl, or SO$_2$—C$_1$-C$_4$ alkylene-aryl;

R$_Z^6$, R$_Z^7$ in each case independently, and independently of their respective occurrence, stand for:
hydrogen, OH, or
in each case optionally substituted C$_1$-C$_6$ alkyl, C$_1$-C$_6$ alkoxy, C$_2$-C$_6$ alkenyl, C$_2$-C$_6$ alkynyl, C$_1$-C$_4$ alkylene-C$_3$-C$_7$ cycloalkyl, C$_3$-C$_7$ cycloalkyl, aryl, C$_1$-C$_4$ alkylene-aryl, hetaryl or C$_1$-C$_4$ alkylene-hetaryl;

W is a radical of general formula W1, W2, or W3

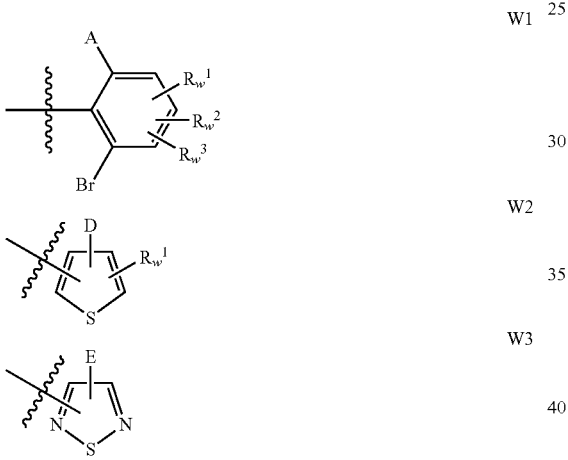

wherein

A is NO$_2$, NH$_2$, OH, CN, CF$_3$, OCF$_3$, CHF$_2$, CH$_2$F, OCHF$_2$, OCH$_2$F, COOH, —CH$_2$—COOH, halogen, SH, O—C$_1$-C$_6$ alkyl, S—C$_1$-C$_6$ alkyl, or in each case optionally substituted C$_1$-C$_6$ alkyl, C$_2$-C$_6$ alkenyl, C$_2$-C$_6$ alkynyl, C$_3$-C$_7$ cycloalkyl, C$_1$-C$_4$ alkylene-C$_3$-C$_7$ cycloalkyl, C$_1$-C$_4$ alkylene-heterocycloalkyl, C$_1$-C$_4$ alkylene-aryl, C$_1$-C$_4$ alkylene-hetaryl, heterocycloalkyl, or in each case optionally substituted R$_A^1$, O—R$_A^1$, CO—R$_A^1$, S—R$_A^1$, SO—R$_A^1$, CO—O—R$_A^1$, NR$_A^4$—CO—O—R$_A^1$, O—CH$_2$—COO—R$_A^1$, NR$_A^2$R$_A^3$, CONH$_2$, SO$_2$NH$_2$, NR$_A^4$—CO—R$_A^1$, SO$_2$—R$_A^1$, NR$_A^4$—SO$_2$—R$_A^1$, SO$_2$—NR$_A^2$R$_A^3$, CO—NR$_A^2$R$_A^3$, C$_1$-C$_4$ alkylene-NR$_A^2$R$_A^3$, C$_1$-C$_4$ alkylene-CO—NR$_A^2$R$_A^3$, C$_1$-C$_4$ alkylene-SO$_2$—NR$_A^2$R$_A^3$, or C$_1$-C$_4$ alkylene-O—R$_A^1$;

wherein

R$_A^1$ independently of its respective occurrence stands for:
in each case optionally substituted C$_1$-C$_6$ alkyl, C$_1$-C$_6$ alkylene-O—C$_1$-C$_6$ alkyl, C$_2$-C$_6$ alkenyl, C$_2$-C$_6$ alkynyl, C$_3$-C$_7$ cycloalkyl, C$_1$-C$_4$ alkylene-C$_3$-C$_7$ cycloalkyl, C$_1$-C$_4$ alkylene-heterocycloalkyl, aryl, hetaryl, heterocycloalkyl, C$_1$-C$_4$ alkylene-aryl, C$_2$-C$_6$ alkenylene-aryl or C$_1$-C$_4$ alkylene-hetaryl, —CO—C$_1$-C$_6$ alkyl, —CO—O—C$_1$-C$_6$ alkyl, —CO-aryl, —CO-hetaryl, —CO—O-aryl, —CO—O-hetaryl, —CO—C$_3$-C$_7$ cycloalkyl, —CO—O—C$_3$-C$_7$ cycloalkyl, —CO-heterocycloalkyl, —CO—O-heterocycloalkyl, C$_1$-C$_4$ alkylene-NR$_A^2$R$_A^3$, C$_1$-C$_4$ alkylene-CO—NR$_A^2$R$_A^3$, C$_1$-C$_4$ alkylene-SO$_2$—NR$_A^2$R$_A^3$, or C$_1$-C$_6$ alkylene-O—R$_A^2$;

R$_A^2$ independently of its respective occurrence stands for:
hydrogen, OH, CN, or
in each case optionally substituted C$_1$-C$_6$ alkyl, C$_2$-C$_6$ alkenyl, C$_2$-C$_6$ alkynyl, C$_1$-C$_4$ alkylene-C$_3$-C$_7$ cycloalkyl, C$_1$-C$_4$ alkylene-heterocycloalkyl, aryl, hetaryl, heterocycloalkyl, C$_1$-C$_4$ alkylene-aryl, C$_1$-C$_4$ alkylene-hetaryl, C$_1$-C$_6$ alkylene-O—C$_1$-C$_6$ alkyl, CO—C$_1$-C$_6$ alkyl, CO-aryl, CO-hetaryl, CO—C$_1$-C$_4$ alkylene-aryl, CO—C$_1$-C$_4$ alkylene-hetaryl, CO—O—C$_1$-C$_6$ alkyl, CO—O-aryl, CO—O—C$_1$-C$_4$ alkylene-aryl, CO—O-hetaryl, CO—O—C$_1$-C$_4$ alkylene-hetaryl, SO$_2$—C$_1$-C$_6$ alkyl, SO$_2$-aryl, SO$_2$-hetaryl, SO$_2$—C$_1$-C$_4$ alkylene-aryl, or SO$_2$—C$_1$-C$_4$ alkylene-hetaryl;

R$_A^3$ independently of its respective occurrence stands for:
in each case optionally substituted C$_1$-C$_6$ alkyl, C$_2$-C$_6$ alkenyl, C$_2$-C$_6$ alkynyl, C$_1$-C$_4$ alkylene-C$_3$-C$_7$ cycloalkyl, C$_1$-C$_4$ alkylene-heterocycloalkyl, aryl, hetaryl, heterocycloalkyl, C$_1$-C$_4$ alkylene-aryl, C$_1$-C$_4$ alkylene-hetaryl, C$_1$-C$_4$ alkylene-O—C$_1$-C$_6$ alkyl, CO—C$_1$-C$_6$ alkyl, CO-aryl, CO-hetaryl, CO—C$_1$-C$_4$ alkylene-aryl, CO—C$_1$-C$_4$ alkylene-hetaryl, CO—O—C$_1$-C$_6$ alkyl, CO—O-aryl, CO—O—C$_1$-C$_4$ alkylene-aryl, CO—O-hetaryl, CO—O—C$_1$-C$_4$ alkylene-hetaryl, SO$_2$—C$_1$-C$_6$ alkyl, SO$_2$-aryl, SO$_2$-hetaryl, SO$_2$—C$_1$-C$_4$ alkylene-aryl, or SO$_2$—C$_1$-C$_4$ alkylene-hetaryl;

or the radicals R$_A^2$ and R$_A^3$ together with the nitrogen atom to which they are bonded form a 3- to 7-membered, optionally substituted, saturated or aromatic heterocycle which may contain one, two, or three further heteroatoms, which may be different or the same, selected from the group comprising O, N, and S, wherein optionally two radicals substituted on this heterocycle together with the ring atom to which they are bonded may form a 3- to 7-membered, optionally substituted, annelated, saturated, unsaturated, or aromatic carbocycle or heterocycle, wherein the heterocycle may contain one, two, or three heteroatoms, which may be different or the same, selected from the group comprising O, N, and S, wherein the cyclic compound thus formed may optionally be substituted;

R$_A^4$ independently of its respective occurrence stands for:
hydrogen, or
in each case optionally substituted C$_1$-C$_6$ alkyl, C$_1$-C$_6$ alkylene-O—C$_1$-C$_6$ alkyl, C$_2$-C$_6$ alkenyl, C$_2$-C$_{12}$ alkynyl, CO—C$_1$-C$_6$ alkyl, CO—O—C$_1$-C$_6$ alkyl, SO$_2$—C$_1$-C$_6$ alkyl, C$_3$-C$_7$ cycloalkyl, aryl, C$_1$-C$_4$ alkylene-aryl, CO—O-arylalkyl, CO—C$_1$-C$_4$ alkylene-aryl, CO-aryl, SO$_2$-aryl, hetaryl, CO-hetaryl, or SO$_2$—C$_1$-C$_4$ alkylene-aryl;

B is a radical that is
hydrogen, or in each case optionally substituted aryl or hetaryl, or, independently of radical A, has the same meaning as for radical A,
or
in each case two radicals independently selected from the group comprising A, B, R$_w^1$, R$_w^2$, and R$_w^3$ together with the C atom to which they are bonded form a 3- to 7-membered, optionally substituted, saturated, unsaturated, or aromatic carbocycle or a 3- to 7-membered, optionally substituted, saturated, unsaturated, or aromatic heterocycle which may contain one, two, or three further heteroatoms, which may be different or the same, selected from the group comprising O, N, and S; wherein two radicals substituted on this carbocycle or heterocycle together with the ring atom to which they are bonded may optionally form a further 3- to 7-membered, optionally substituted, annelated, saturated, unsaturated, or aromatic carbocycle or heterocycle, wherein the heterocycle may contain one, two, or three heteroatoms, which may be different or the same, selected from the group comprising O, N, and S, and wherein the cyclic compound thus formed may optionally be substituted;

$R_w^1$, $R_w^2$, $R_w^3$ in each case independently stand for:
  hydrogen, $NO_2$, $NH_2$, OH, CN, $CF_3$, $OCF_3$, $CHF_2$, $CH_2F$, $OCHF_2$, $OCH_2F$, COOH, O—$CH_2$—COOH, halogen, SH, O—$C_1$-$C_6$ alkyl, S—$C_1$-$C_6$ alkyl, or
  in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_6$ alkylene-$C_3$-$C_7$ cycloalkyl, $C_1$-$C_6$ alkylene-heterocycloalkyl, $C_1$-$C_6$ alkylene-aryl, $C_1$-$C_6$ alkylene-hetaryl, heterocycloalkyl, or in each case optionally substituted
  $R_A^1$, O—$R_A^1$, CO—$R_A^1$, S—$R_A^1$, SO—$R_A^1$, CO—O—$R_A^1$, $NR_A^4$—CO—O—$R_A^1$, O—$CH_2$—COO—$R_A^1$, $NR_A^2R_A^3$, $CONH_2$, $SO_2NH_2$, $NR_A^4$—CO—$R_A^1$, $SO_2$—$R_A$, $NR_A^4$—$SO_2$—$R_A^1$, $SO_2$—$NR_A^2R_A^3$, CO—$NR_A^2R_A^3$, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$, or $C_1$-$C_4$ alkylene-O—$R_A^1$; wherein $R_A^1$, $R_A^2$, $R_A^3$, and $R_A^4$ in each case independently, and in each case independently of their respective occurrence and independently of their respective meaning for radical A, may have the meanings given for radical A;

D independently of radical A is a radical which may have the same meaning as defined for radical A;

E is hydrogen or, independently of radical A, a radical which may have the same meaning as defined for radical A;

Q is at least a 6-membered hetaryl radical of general formula Q

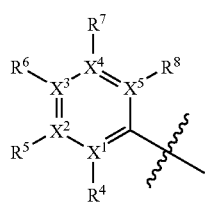

Q wherein
$X^1$: is C or N,
$X^2$: is C or N,
$X^3$: is C or N,
$X^4$: is C or N,
$X^5$: is C or N,
wherein one, two, or three radicals selected from the group comprising the radicals $X^1$, $X^2$, $X^3$, $X^4$, and $X^5$ simultaneously stand for N, and the associated binding partner selected from the group comprising $R^4$, $R^5$, $R^6$, $R^7$, and $R^8$ then stands for a free electron pair.

$R^4$, $R^5$, $R^6$, $R^7$, and $R^8$ in each case independently stand for a radical selected from the following groups 1.), 2.), 3.), 4.), 5.), 6.), and 7.), which may be the same or different:

1.) Hydrogen, halogen, CN, $CF_3$, $CHF_2$, $CH_2F$, $OCF_3$, $OCH_2F$, $OCHF_2$, $NH_2$, $NO_2$, COOH, O—$CH_2$—COOH, or in each case optionally substituted $C_1$-$C_{10}$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, $C_1$-$C_6$ alkylene-O—$C_1$-$C_6$ alkyl, $C_1$-$C_6$ alkylene-O-aryl, COO—$C_1$-$C_4$ alkyl, or $C_1$-$C_4$ alkylene-COO—$C_1$-$C_4$ alkyl, or in each case optionally substituted O—$R_Q^4$, S—$R_Q^4$, $NR_Q^6R_Q^7$, CO—$OR_Q^5$, CO—$R_Q^5$, SO—$R_Q^5$, $NR_Q^7$—CO—O—$R_Q^5$, O—$CH_2$—COO—$R_Q^5$, $NR_Q^7$—CO—$R_Q^5$, $SO_2$—$R_Q^5$, $NR_Q^7$—$SO_2$—$R_Q^5$, $SO_2NH_2$, $CONH_2$, $SO_2$—$NR_Q^6R_Q^7$, or CO—$NR_Q^6R_Q^7$; wherein $R_Q^4$, $R_Q^5$, $R_Q^6$, and $R_Q^7$ independently, and independently of their respective occurrence, are defined as below;

2.) In each case optionally substituted phenyl, 1-naphthyl, or 2-naphthyl which may be substituted with one, two, or three radicals independently selected from the group comprising $R_Q^1$, $R_Q^2$, and $R_Q^3$, wherein
  $R_Q^1$, $R_Q^2$, and $R_Q^3$ in each case independently stand for a substituent from the following group:
  Hydrogen, $NO_2$, $NH_2$, OH, CN, $CF_3$, $CHF_2$, $CH_2F$, $OCF_3$, $OCHF_2$, $OCH_2F$, COOH, O—$CH_2$—COOH, SH, halogen, or
  in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted
  O—$R_Q^4$, S—$R_Q^4$, $NR_Q^6R_Q^7$, CO—$OR_Q^5$, $NR_Q^7$—CO—O—$R_Q^5$, O—$CH_2$—COO—$R_Q^5$, $NR_Q^7$—CO—$R_Q^5$, $SO_2$—$R_Q^5$, $NR_Q^7$—$SO_2$—$R_Q^5$, $SO_2NH_2$, $CONH_2$, $SO_2$—$NR_Q^6R_Q^7$, or CO—$NR_Q^6R_Q^7$, or
  two radicals selected in each case from the group comprising $R_Q^1$, $R_Q^2$, and $R_Q^3$ together with the atom to which they are bonded form a 3- to 7-membered, optionally substituted, saturated, or unsaturated carbocycle or a 3- to 7-membered, optionally substituted, saturated, unsaturated aromatic heterocycle which may contain one, two, or three further heteroatoms, which may be different or the same, selected from the group comprising O, N, and S, wherein two radicals substituted on this carbocycle or heterocycle together with the ring atom to which they are bonded may optionally form a 3- to 7-membered, optionally substituted, annelated, saturated, unsaturated, or aromatic carbocycle or heterocycle, wherein the heterocycle may contain one, two, or three heteroatoms, which may be different or the same, selected from the group comprising O, N, and S, and the cyclic compound thus formed may optionally be substituted, or a further 3- to 7-membered, optionally substituted cyclic compound may be condensed thereon; wherein the substituents below have the following meanings:
  $R_Q^4$ independently of its respective occurrence stands for: hydrogen in each case, or in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, heterocycloalkyl, aryl, or hetaryl;

$R_Q^5$ independently of its respective occurrence stands for: hydrogen in each case, or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, or $C_1$-$C_6$ alkylene-O—$C_1$-$C_6$ alkyl;

$R_Q^6$ independently of its respective occurrence stands for: hydrogen, OH, CN, or
  in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, $C_1$-$C_4$ alkylene-aryl, $C_1$-$C_4$ alkylene-hetaryl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$R_Q^7$ independently of its respective occurrence stands for: hydrogen or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl,
  CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

or both radicals $R_Q^6$ and $R_Q^7$ together with the nitrogen atom to which they are bonded form a 3- to 7-membered, optionally substituted, saturated or aromatic heterocycle which may contain one, two, or three further heteroatoms, which may be different or the same, selected from the group comprising O, N, and S, and two radicals substituted on this heterocycle together with the ring atom to which they are bonded may optionally form a 3- to 7-membered, annelated, saturated, unsaturated, or aromatic carbocycle or heterocycle, wherein the heterocycle may contain one, two, or three heteroatoms, which may be different or the same, selected from the group comprising O, N, and S, and the cyclic compound thus formed may optionally be substituted, and/or a further 3- to 7-membered, optionally substituted cyclic compound may be condensed thereon;

3.) A 5- or 6-membered hetaryl radical which is unsubstituted, or optionally singly or doubly substituted the same or differently, selected from the group comprising:
  2-furyl, 3-furyl, 2-pyrrolyl, 3-pyrrolyl, 2-thienyl; 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl, or triazinyl, or their annelated derivatives indazolyl, indolyl, benzothiophenyl, benzofuranyl, indolinyl, benzimidazolyl, benzthiazolyl, benzoxazolyl, quinolinyl, and isoquinolinyl;

4.) In each case two of the following radicals (1) $R^4$ and $R^5$ for the case $X^1$=C and $X^2$=C, (2) $R^5$ and $R^6$ for the case $X^2$=C and $X^3$=C, (3) $R^6$ and $R^7$ for the case $X^3$=C and $X^4$=C, or (4) $R^7$ and $R^8$ for the case $X^4$=C and $X^5$=C, together form a 4- to 7-membered, optionally substituted, saturated, unsaturated, or aromatic carbocycle, or a 5- or 6-membered optionally substituted, saturated, unsaturated, or aromatic heterocycle which may contain one, two, or three further heteroatoms, which may be different or the same, selected from the group comprising O, N, and S, and which may optionally be singly or doubly substituted, wherein two radicals substituted on this carbocycle or heterocycle together with the ring atom to which they are bonded may optionally form a 3- to 7-membered, optionally substituted, annelated, saturated, unsaturated, or aromatic carbocycle or heterocycle, wherein the heterocycle may contain one, two, or three heteroatoms, which may be different or the same, selected from the group comprising O, N, and S, and the carbocycle or heterocycle thus formed may optionally be substituted;

5.) An optionally substituted $C_5$-$C_{18}$-bi- or tricyclic saturated hydrocarbon radical;

6.) In each case optionally substituted $C_1$-$C_8$ alkyl-$NH_2$, $C_1$-$C_8$ alkyl-$NR_Q^6R_Q^7$, $C_1$-$C_8$ alkyl-CO—$NR_Q^6R_Q^7$, $C_1$-$C_8$ alkyl-$SO_2NR_Q^6R_Q^7$, $C_1$-$C_8$ alkyl-CO—$NH_2$, or $C_1$-$C_8$ alkyl-$SO_2NH_2$;

7.) A 4- to 7-membered mono- or bicyclic saturated or unsaturated heterocycle which may contain one or two heteroatoms, which may be different or the same, selected from the group O, N, and/or S, wherein this cyclic compound may likewise be substituted 1, 2, 3, 4, or 5 times, and wherein for the case that the heterocycle contains an N atom, this N atom may be substituted with an $R_Q^8$ radical, wherein $R_Q^8$ independently from $R_Q^6$ may have a meaning as defined for $R_Q^6$;

is provided for the treatment and/or prevention of, or for producing a medicament for the treatment and/or prevention of, CNS diseases or CNS-related diseases, and/or diseases which may be treated and/or prophylactically prevented by modulation of 5-$HT_5$ receptor activity in a patient requiring such treatment and/or prevention.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further preferred embodiment of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R^6$, $R^7$, $R^8$, Z, a, b, C, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, is provided for the treatment and/or prevention of, or for producing a medicament for the treatment and/or prevention of, CNS diseases or CNS-related diseases, and/or diseases which may be treated and/or prophylactically prevented by modulation of 5-$HT_5$ receptor activity in a patient requiring such treatment and/or prevention, with the condition of being subject to one, several, or all of conditions (i) through (xiii), particularly preferably with the condition of being subject to one, several, or all of conditions (viii) through (xiii).

According to a further preferred embodiment of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, is provided for the treatment and/or prevention of, or for producing a medicament for the treatment and/or prevention of, CNS diseases or CNS-related diseases, and/or diseases which may be treated and/or prophylactically prevented by modulation of 5-HT$_5$ receptor activity in a patient requiring such treatment and/or prevention, with the condition that when a=1 for the radical Z, then the group $V_Z$ does not stand for the $NR_Z^5$—CO— radical.

Each of the above-referenced definitions of a variable may be [combined] with any given number of the above-referenced definitions of the remaining variables. This applies in particular for the combination of preferred definitions of a variable with any given or preferred definitions of the remaining variables.

According to one preferred embodiment of the invention, the use of at least one guanidine compound according to general formula I,

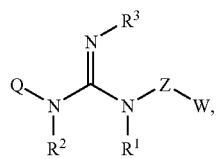

I and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, and the radicals below have the following definitions:

W: is a radical of general formula W1a:

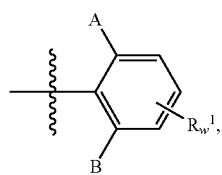

W1a wherein A, B, and $R_w^1$ in each case are defined as above, or in one of Claims 1 through 16 and 29.

Z: is a radical of general formula Z1:

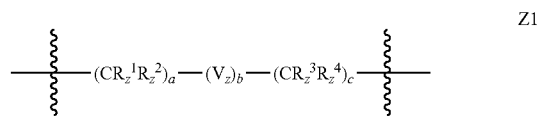

Z1 having the indices
a=0, 1, or 2
b=0 or 1
c=0, 1, or 2,
wherein the sum of a, b, and c is equal to 1, 2, or 3;
$Rz^1$, $Rz^2$, $Rz^3$, $Rz^4$ independently stand for:
  hydrogen, halogen, OH, or optionally substituted $C_1$-$C_6$ alkyl;
$V_Z$: —CO—, —CO—$NR_Z^5$—, —$NR_Z^5$—CO—, —S—, or —O—;
$R_Z^5$ independently stand for:
  hydrogen or in each case optionally substituted $C_1$-$C_6$ alkyl;
  is provided for the treatment and/or prevention of, or for producing a medicament for the treatment and/or prevention of, CNS diseases or CNS-related diseases, and/or diseases which may be treated and/or prophylactically prevented by modulation of 5-HT$_5$ receptor activity in a patient requiring such treatment and/or prevention.

Each of the above-referenced definitions of a variable may be [combined] with any given number of the above-referenced definitions of the remaining variables. This applies in particular for the combination of preferred definitions of a variable with any given or preferred definitions of the remaining variables.

According to one preferred embodiment of the invention, the use of at least one guanidine compound according to general formula (I) as respectively stated above, and/or the corresponding enantiomeric, diastereomeric, and/or tautomeric forms thereof, and/or pharmaceutically acceptable salts thereof, and/or the corresponding active substance precursors ("prodrugs") thereof is provided, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, characterized in that the CNS disease or CNS-related disease is a disease selected from the group comprising neuropathological, neuropsychiatric, and neurodegenerative disorders; neuropathological, neuropsychiatric, and neurodegenerative symptoms; and neuropathological, neuropsychiatric, and neurodegenerative dysfunctions.

Each of the above-referenced definitions of a variable may be [combined] with any given number of the above-referenced definitions of the remaining variables. This applies in particular for the combination of preferred definitions of a variable with any given or preferred definitions of the remaining variables.

According to one preferred embodiment of the invention, the use of at least one guanidine compound according to general formula (I) as respectively stated above, and/or the corresponding enantiomeric, diastereomeric, and/or tautomeric forms thereof, and/or pharmaceutically acceptable salts thereof, and/or the corresponding active substance precursors ("prodrugs") thereof is provided, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, characterized in that the CNS disease, CNS-related disease, or neuropathological, neuropsychiatric, and/or neurodegenerative disorders, symptoms, and/or dysfunctions are migraine and/or brain damage.

Each of the above-referenced definitions of a variable may be [combined] with any given number of the above-referenced definitions of the remaining variables. This applies in particular for the combination of preferred definitions of a variable with any given or preferred definitions of the remaining variables.

According to one preferred embodiment of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof is provided, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, characterized in that the CNS disease or CNS-related disease and/or or the neuropathological, neuropsychiatric, and/or neurodegenerative disorders, symptoms, and/or dysfunctions are selected from the group comprising cerebral ischemia, stroke, epilepsy, and attacks in general, psychoses, schizophrenia, autism, OCD syndrome, cognitive disorders, attention disorders, depression, bipolar and/or unipolar depression, anxiety, dementia, senile dementia, Alzheimer's dementia, demyelinating diseases, multiple sclerosis, and brain tumors.

Each of the above-referenced definitions of a variable may be [combined] with any given number of the above-referenced definitions of the remaining variables. This applies in particular for the combination of preferred definitions of a variable with any given or preferred definitions of the remaining variables.

According to one preferred embodiment of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof is provided, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, characterized in that the CNS disease or CNS-related disease and/or or the neuropathological, neuropsychiatric, and/or neurodegenerative disorders, symptoms, and/or dysfunctions are selected from the group comprising cerebrovascular disorders, pain, pain-related disorders, dependency, drug-related disorders, amnesia, alcohol abuse, drug abuse, circadian rhythm disorders, and Cushing's syndrome.

Each of the above-referenced definitions of a variable may be [combined] with any given number of the above-referenced definitions of the remaining variables. This applies in particular for the combination of preferred definitions of a variable with any given or preferred definitions of the remaining variables.

According to one preferred embodiment of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof is provided, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, characterized in that the treatment and/or prevention is based on a binding affinity for the $5\text{-HT}_{5A}$ receptor that is less than or equal to 10 μM (Ki), determined according to a suitable test model.

Each of the above-referenced definitions of a variable may be [combined] with any given number of the above-referenced definitions of the remaining variables. This applies in particular for the combination of preferred definitions of a variable with any given or preferred definitions of the remaining variables.

According to one preferred embodiment of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof is provided, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, characterized in that the treatment and/or prevention is based on a binding affinity for the $5\text{-HT}_{5A}$ receptor that is less than or equal to 300 nM (Ki), determined according to a suitable test model.

Each of the above-referenced definitions of a variable may be [combined] with any given number of the above-referenced definitions of the remaining variables. This applies in particular for the combination of preferred definitions of a variable with any given or preferred definitions of the remaining variables.

According to one preferred embodiment of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof is provided, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, characterized in that the treatment and/or prevention is based on a binding affinity for the $5\text{-HT}_{5A}$ receptor that is less than or equal to 100 nM (Ki), determined according to a suitable test model.

Each of the above-referenced definitions of a variable may be [combined] with any given number of the above-referenced definitions of the remaining variables. This applies in particular for the combination of preferred definitions of a variable with any given or preferred definitions of the remaining variables.

According to one preferred embodiment of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof is provided, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, characterized in that the treatment and/or prevention is based on modulation of the 5-$HT_5$ receptor activity and also is based on a binding affinity for the 5-$HT_{5A}$ receptor that is less than or equal to 10 μM (Ki), preferably less than or equal to 300 nM (Ki), particularly preferably less than or equal to 100 nM (Ki), in each case determined according to a suitable test model, in the subject requiring such treatment and/or prevention.

Each of the above-referenced definitions of a variable may be [combined] with any given number of the above-referenced definitions of the remaining variables. This applies in particular for the combination of preferred definitions of a variable with any given or preferred definitions of the remaining variables.

According to a further aspect of the invention, the use of at least one guanidine compound according to general formula I as respectively stated above, and/or the corresponding enantiomeric, diastereomeric, and/or tautomeric forms thereof, and/or pharmaceutically acceptable salts thereof, and/or the corresponding active substance precursors ("prodrugs") thereof, wherein the radicals $R^1$, $R^2$, $R^3$, $R^4$, $R^5$, $R^6$, $R^7$, $R^8$, Z, a, b, c, $R_Z^1$, $R_Z^2$, $R_Z^3$, $R_Z^4$, $R_Z^5$, $R_Z^{5*}$, $R_Z^6$, $R_Z^7$, $V_Z$, W, W1, W2, W3, A, $R_A^1$, $R_A^2$, $R_A^3$, $R_A^4$, B, $R_w^1$, $R_w^2$, $R_w^3$, D, E, Q, $X^1$, $X^2$, $X^3$, $X^4$, $X^5$, $R_Q^1$, $R_Q^2$, $R_Q^3$, $R_Q^4$, $R_Q^5$, $R_Q^6$, $R_Q^7$, and $R_Q^8$, unless described otherwise below, have the same meaning as defined above, is provided for the treatment and/or prevention of, or for producing a medicament for the treatment and/or prevention of, diseases which are modulated by 5-$HT_5$ receptor activity, and in which the treatment and/or prevention is based on selectivity for the 5-$HT_{5A}$ receptor with a binding affinity (Ki) of less than or equal to 10 μM (Ki), and the modulation of the 5-$HT_{5A}$ receptor activity is selected from the group comprising antagonization (antagonist), agonization (agonist), partial agonization (partial agonist), inverse agonization (inverse agonist), and partial inverse agonization (partial inverse agonist). Preferred are substances having an antagonistic effect on the 5-$HT_{5A}$ receptor, i.e., antagonists or partial agonists or inverse agonists. Antagonists of the 5-$HT_{5A}$ receptor are very particularly preferred.

Within the context of the invention, the term "agonist" means a substance which produces an effect on the receptor (in this case, the 5-$HT_5$ receptor) that is similar to the physiological ligand; "antagonist" means a substance which reduces or eliminates the biological effect of an agonist; "partial agonist" means a substance which produces a submaximal effect on the receptor, whereby in the absence of an agonist the partial agonist may have an agonistic effect, and in the presence of an agonist the partial agonist may have an antagonistic effect; "inverse agonist" means a substance which produces a negative effect; "competitive antagonist" means a substance which has affinity for the receptor, reversible binding to the receptor (competition for the agonist), and no intrinsic activity at the receptor (relative efficacy: ability of a substance to initiate an effect for the same receptor loading); and "noncompetitive antagonist" is a substance which has allosteric binding at the receptor and which influences the efficacy (and possibly the agonist binding) by means of a change in the receptor conformation.

According to one preferred embodiment, the term "additional binding affinity for the 5-$HT_{5A}$ receptor" is understood to mean that, for the use according to the invention of at least one compound of general formula I as described above, the activity of one, two, or more 5-$HT_5$ receptors is modulated, where the term "modulation" or "modulate" in the context of use according to the invention may mean, for example, the effect of an antagonist, partial antagonist, partial agonist, and/or agonist, in each case independently with reference to one, two, or more or 5-$HT_5$ receptors, and a binding affinity for the 5-$HT_{5A}$ receptor may be present simultaneously with or in addition to the modulation of one, two, or more 5-$HT_5$ receptors.

The treatment of neuropathological, neuropsychiatric, and neurodegenerative disorders, symptoms and dysfunctions is preferred, in particular the treatment of migraine and brain damage. Named as examples of brain damage and/or disorders are cerebral ischemia, stroke, epilepsy, and attacks in general, psychoses, schizophrenia, autism, OCD syndrome, cognitive disorders, attention disorders, depression, bipolar and/or unipolar depression, anxiety, dementia, senile dementia, Alzheimer's dementia, demyelinating diseases, multiple sclerosis, and brain tumors. Also preferred is the treatment of cerebrovascular disorders, pain, pain-related disorders, dependency, drug-related disorders, amnesia, alcohol abuse, drug abuse, circadian rhythm disorders, and Cushing's syndrome.

DETAILED DESCRIPTION OF THE INVENTION

The radicals of formula I have the following meanings in preferred embodiments:

In the present invention the terms used have the meanings given below:

"Alkyl" is an unsubstituted or optionally substituted straight-chain or branched saturated hydrocarbon chain containing the respective stated number of carbon atoms, preferably 1, 2, 3, 4, 5, 6, 7, 8, 9, or 10 carbon atoms, particularly preferably 1, 2, 3, 4, 5, or 6, more preferably 1, 2, 3, or 4 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, n-hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, or 1-ethyl-2-methylpropyl, preferably methyl, ethyl, propyl, n-butyl, or isobutyl. The term "alkyl" is also intended to include halogen-substituted alkyl ("haloalkyl"). Analogously, "$C_5$-$C_{18}$ alkyl" or "$C_1$-$C_8$ alkyl" means an unsubstituted or optionally substituted straight-chain or branched saturated hydrocarbon chain containing the respective stated number of carbon atoms, i.e., 1, 2, 3, 4, 5, 6, 7, 8, 9, 10, 11, 12, 13, 14, 15, 16, 17, or 18 carbon atoms or 1, 2, 3, 4, 5, 6, 7, or 8 carbon atoms.

"Alkylene" is an unsubstituted or optionally substituted straight-chain or branched alkyl group as defined above, in which a hydrogen atom is replaced by a bond. Named in particular are methylene, 1,2-ethylene, 1,2-propylene, 1,3-propylene, 1,2-butylene, 1,3-butylene, 2,3-butylene, 1,4-butylene, 2-methyl-1,3-propylene, 1,2-pentylene, 1,3-pentylene, 1,4-pentylene, 1,5-pentylene, 2,3-pentylene, 2,4- pentylene, 1-methyl-1,4-butylene, 2-methyl-1,4-butylene, 2-methyl-1,3-butylene, 2-ethyl-1,3-propylene, 3,4-hexylene, 3-methyl-2,4-pentylene, 3,5-heptylene, 2-ethyl-1,3-pentylene, 3-ethyl-3,5-heptylene, etc., preferably methylene, 1,2-ethylene, and 1,2-propylene. The term "alkylene" is also intended to include halogen-substituted alkylene ("haloalkylene").

"Cycloalkyl" is an unsubstituted or optionally substituted branched or unbranched saturated hydrocarbon ring containing 3, 4, 5, 6, or 7, preferably 3, 4, 5, or 6, carbon atoms, such as cyclopropyl, cyclobutyl, cyclopentyl, cyclohexyl, or cycloheptyl. The term "cycloalkyl" is also intended to include halogen-substituted cycloalkyl ("halocycloalkyl").

"Alkylene-O-alkyl" is a straight-chain or branched saturated alkyl ether chain which is unsubstituted or optionally substituted in the alkylene and/or alkyl radical, containing a total of 2 to 12 carbon atoms and one oxygen atom, wherein the alkylene radical and the alkyl radical independently contain 1, 2, 3, 4, 5, or 6, more preferably 1, 2, 3, or 4, most preferably 1 or 2, carbon atoms, both radicals being defined as above. Preferred examples of alkylene-O-alkyl include methoxymethylene, ethoxymethylene, t-butoxymethylene, methoxyethylene, or ethoxyethylene. The term "alkylene-O-alkyl" is also intended to include halogen-substituted alkylene-O-alkyl in the sense of "haloalkylene-O-alkyl" or "alkylene-O-haloalkyl" or "haloalkylene-O-haloalkyl."

"Thioalkyl" is an unsubstituted or optionally substituted straight-chain or branched alkylene sulfanyl chain containing 1, 2, 3, 4, 5, or 6 carbon atoms and one sulfur atom. The alkylene radical preferably contains 1, 2, 3, or 4, more preferably 1 or 2, carbon atoms, where alkylene is defined as above. Examples of thioalkyl include thiomethyl or thio-tert-butyl. The term "thioalkyl" is also intended to include halogen-substituted thioalkyl ("halothioalkyl").

"Alkenyl" is an unsubstituted or optionally substituted branched or unbranched hydrocarbon chain having at least one double bond and containing 2, 3, 4, 5, or 6, preferably 2, 3, or 4, carbon atoms. The alkenyl preferably has one or two double bonds, most preferably one double bond. Examples of alkenyl groups include those stated above for alkyl, wherein these groups have one or two double bonds, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-entenyl, [sic; 3-methyl-4-pentenyl], 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl, and 1-ethyl-2-methyl-2-propenyl, in particular 2-propenyl, 2-butenyl, 3-methyl-2-butenyl, or 3-methyl-2-pentenyl. The term "alkenyl" is also intended to include halogen-substituted alkenyl ("haloalkenyl").

"Alkynyl" is an unsubstituted or optionally substituted branched or unbranched hydrocarbon chain having at least one triple bond and containing 2, 3, 4, 5, or 6, preferably 2, 3, or 4, carbon atoms. The alkynyl preferably has one or two triple bonds, most preferably one triple bond. Examples of alkynyl groups include those stated above for alkyl, wherein these groups have one or two triple bonds, for example ethynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl, and 1-ethyl-1-methyl-2-propynyl, preferably ethynyl, 2-propynyl, 2-butynyl, 1-methyl-2-propynyl, or 1-methyl-2-butynyl. The term "alkynyl" is also intended to include halogen-substituted alkynyl ("haloalkynyl").

"Heterocycloalkyl" is an unsubstituted or optionally substituted saturated alkyl ring, or an alkyl ring to which a further unsubstituted or optionally substituted saturated alkyl ring is anellated, preferably containing a total of 3, 4, 5, 6, 7, 8, 9, or 10 ring atoms, more preferably 3, 4, 5, or 6 ring atoms, most preferably 5 or 6 ring atoms, wherein this heterocycloalkyl contains at least one heteroatom, preferably 1, 2, or 3 heteroatoms, which may be the same or different, selected from the group comprising O, N, and S, and containing 1, 2, 3, 4, 5, or 6, preferably 1, 2, 3, 4, or 5, carbon atoms. The heterocycloalkyl preferably contains 1 or 2 heteroatoms, which may be the same or different, preferably selected from the group comprising N and O. Examples of a heterocycloalkyl group include N-pyrrolidinyl, N-piperidinyl, N-hexahydroazepinyl, N-morpholinyl, or N-piperazinyl, wherein for heterocycles which contain amino groups, for example N-piperazinyl, these amino groups may be substituted with common radicals, for example methyl, benzyl, Boc (tert-butoxycarbonyl), benzyloxycarbonyl, tosyl(p-toluenesulfonyl), —$SO_2$—$C_1$-$C_4$ alkyl, —$SO_2$-phenyl, or —$SO_2$-benzyl. The term "heterocycloalkyl" is also intended to include halogen-substituted heterocycloalkyl ("haloheterocycloalkyl").

"Aryl" is an unsubstituted or optionally substituted aromatic mono-, bi-, or polycyclic radical preferably containing 6, 7, 8, 9, 10, 11, 12, 13, 14, 15, 16, 17, 18, 19, or 20 carbon atoms, more preferably 6, 7, 8, 9, or 10 carbon atoms, and is preferably selected from phenyl, biphenyl, naphthyl, tetrahydronaphthyl, fluorenyl, indenyl, and phenanthrenyl, more preferably from phenyl and naphthyl, such as 1-naphthyl or 2-naphthyl. Phenyl is most preferred.

"Alkylenearyl" is an optionally substituted aryl which is bonded by $C_1$-$C_6$ alkylene, more preferably $C_1$-$C_4$ alkylene, in the aryl and/or alkylene radical, whereby alkylene and aryl are defined as above. Alkylenearyl in particular is an optionally substituted benzyl or phenethyl in the aryl radical. The term "alkenylaryl" is also intended to include halogen-substituted alkenylaryl ("haloalkenylaryl").

"Aryloxy" or "—O-aryl" is an unsubstituted or optionally substituted aryl, defined as above, in particular —O-phenyl, which is bonded by oxygen.

"Hetaryl" (or also "heteroaryl") is an unsubstituted or optionally substituted mono-, bi-, or tricyclic aromatic ring containing at least one heteroatom, preferably 1, 2, or 3 heteroatoms which may be the same or different, more preferably 1 or 2 heteroatoms which may be the same or different, selected from the group comprising O, N, and S, and preferably containing 1, 2, 3, 4, 5, 6, 7, 8, 9, 10, 11, or 12, more preferably 1, 2, 3, 4, 5, or 6, carbon atoms. The aromatic ring is preferably a 5- or 6-membered ring. Hetaryl also includes the derivatives thereof anellated with aryl, namely, an aromatic radical preferably containing 6, 7, 8, 9, 10, 11, 12, 13, 14, 15, 16, 17, 18, 19, or 20 carbon atoms, more preferably 6, 7, 8, 9, or 10 carbon atoms, most preferably phenyl, which is anellated with this aromatic ring, which contains at least one heteroatom. Hetaryl may also be selected from an aromatic radical preferably containing 6, 7, 8, 9, 10, 11, 12, 13, 14, 15, 16, 17, 18, 19, or 20, more preferably 6, 7, 8, 9, or 10, carbon atoms, most preferably phenyl, having a heterocycloalkyl group anellated thereto. The heterocycloalkyl group is defined as above. Hetaryl is preferably selected from 2-furyl, 3-furyl, 2-pyrrolyl, 3-pyrrolyl, 2-thienyl, 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl, triazinyl, indolinyl, benzothienyl, naphthothienyl, benzofuranyl, chromenyl, indolyl, isoindolyl, indazolyl, quinolyl, isoquinolyl, phthalazinyl, quinoxalinyl, benzimidazolyl, and benzoxazolyl, 2,3-dihydro-1,4-benzodioxinyl, 1,3-benzodioxolyl, and 2,1,3-benzothiadiazolyl.

In the context of the present invention, the terms "pyridyl" and "pyridinyl" refer to the same radical. The same applies for "pyrimidyl" and "pyrimidinyl."

"Alkylenehetaryl" is an optionally substituted hetaryl which is bonded by $C_1$-$C_6$ alkylene, more preferably $C_1$-$C_4$ alkylene, in the alkenyl and/or hetaryl radical, wherein alkylene and hetaryl are as defined herein. Alkylenehetaryl is preferably optionally substituted —$CH_2$-2-pyridyl, —$CH_2$-3-pyridyl, —$CH_2$-4-pyridyl, —$CH_2$-2-thienyl, —$CH_2$-3-thienyl, —$CH_2$-2-thiazolyl, —$CH_2$-4-thiazolyl, $CH_2$-5-thiazolyl, —$CH_2$—$CH_2$-2-pyridyl, —$CH_2$—$CH_2$-3-pyridyl, —$CH_2$—$CH_2$-4-pyridyl, —$CH_2$—$CH_2$-2-thienyl, —$CH_2$—$CH_2$-3-thienyl, —$CH_2$—$CH_2$-2-thiazolyl, —$CH_2$—$CH_2$-4-thiazolyl, or —$CH_2$—$CH_2$-5-thiazolyl. The term "alkenylhetaryl" is also intended to include halogen-substituted alkenylhetaryl ("haloalkenylhetaryl").

A "bi- or tricyclic, saturated hydrocarbon radical" is an unsubstituted or optionally substituted bicycloalkyl or tricycloalkyl radical, and contains 5, 6, 7, 8, 9, 10, 11, 12, 13, 14, 15, 16, 17, or 18 carbon atoms. For a bicycloalkyl radical the ring system preferably contains 5, 6, 7, 8, 9, 10, 11, or 12, more preferably 6, 7, 8, 9, or 10, carbon atoms. For a tricycloalkyl radical the ring system preferably contains 6, 7, 8, 9, 10, 11, 12, 13, 14, 15, or 16, more preferably 6, 7, 8, 9, 10, 11, or 12, carbon atoms. Examples of a bicycloalkyl radical include indanyl, camphyl, and norbornyl. Examples of a tricycloalkyl radical include adamantyl.

"Halogen" is a halogen atom selected from fluorine, chlorine, bromine, or iodine, preferably fluorine, chlorine, or bromine, more preferably fluorine or chlorine, most preferably fluorine.

"Halogen-substituted alkyl" ("haloalkyl") refers to an alkyl radical as defined above which is partially or completed substituted by fluorine, chlorine, bromine, and/or iodine, for example $CH_2F$, $CHF_2$, $CF_3$, $CH_2Cl$, 2-fluoroethyl, 2-chloroethyl, 2,2,2-trifluoroethyl. This applies analogously to the terms "haloalkylene," "haloalkenyl," "haloalkynyl," "haloalkenylaryl," "haloalkenylhetaryl," "haloalkylene-O-alkyl," "alkylene-O-haloalkyl," or "haloalkylene-O-haloalkyl," and "halothioalkyl," and "halocycloalkyl."

When the term "optionally substituted" is used, the radicals and groups may preferably be substituted one, two, three, four, or five times, more preferably singly, doubly, or triply, most preferably singly or doubly. The term "in each case optionally substituted" is intended to clarify that not only the radical directly following, but also all of the radicals named in the particular group may be substituted the same or differently.

Examples of suitable substituents for the terms "optionally substituted" or "in each case optionally substituted" include the following: halogen, CN, $CF_3$, $CHF_2$, $OCF_3$, $OCHF_2$, $NO_2$, $NH_2$, OH, COOH, in each case branched or unbranched, optionally substituted $C_1$-$C_6$ alkyl, $C_3$-$C_7$-cycloalkyl, $C_1$-$C_6$ alkylene-O—$C_1$-$C_6$ alkyl, or $C_1$-$C_6$ thioalkyl, O—$C_1$-$C_6$ alkyl, N($C_1$-$C_6$ alkyl)($C_1$-$C_6$ alkyl), NH($C_1$-$C_6$ alkyl), aryl, —O-aryl, $C_1$-$C_6$ alkylene-O-aryl, NHCO—$C_1$-$C_4$ alkyl, NH—$SO_2$—$C_1$-$C_4$ alkyl, CO—$C_1$-$C_6$ alkyl, $SO_2$—$C_1$-$C_6$ alkyl, and NHCO-aryl, $NHSO_2$-aryl, $CONH_2$, $SO_2NH_2$, $SO_2$-aryl, SO—$C_1$-$C_6$ alkyl, $SO_2$—$C_1$-$C_6$ alkyl, SO-aryl, N-pyrrolidinyl, N-piperidinyl, and N-morpholinyl optionally substituted in the aryl radical. Preferred substituents are F, Cl, $CF_3$, $OCF_3$, $NH_2$, $NO_2$, OH, COOH, $C_1$-$C_4$ alkyl, methoxy, acetyl, NH-acetyl, and $SO_2NH_2$.

The prefix "$C_1$-$C_6$" means that the subsequently named radical, for example the radical "alkyl" in "$C_1$-$C_6$ alkyl," may contain 1, 2, 3, 4, 5, or 6 carbon atoms. The same analogously applies to the meaning of the other prefixes used in the present patent specification and the claims, for example "$C_3$-$C_7$" (3, 4, 5, 6, or 7 carbon atoms), "$C_1$-$C_4$" (1, 2, 3, or 4 carbon atoms), "$C_2$-$C_6$" (2, 3, 4, 5, or 6 carbon atoms), etc.

The term "3- to 7-membered" carbocycle, heterocycle, or ring refers to the total number of ring members, i.e., to a ring containing a total of 3, 4, 5, 6, or 7 ring members. In the case of ring systems anellated to one another, whereby "anellated" may mean neighboring (vicinal) as well as geminal (spriro-bridged ring systems), the term "3- to 7-membered" means the total number of ring members, including the ring members which are part of the neighboring anellated ring system. The same analogously applies for the terms "5- to 7-membered," "5- or 6-membered," "4- to 7-membered," etc.

In general, a radical placed in parentheses, for example the radical "($C_1$-$C_6$ alkyl)" in the term "N($C_1$-$C_6$ alkyl)$_2$," together with a numerical value associated with the expression in parentheses refers to the multiple occurrence, corresponding to the numerical value, of the particular radical, i.e., in the case of the above-referenced example stands for a radical "N($C_1$-$C_6$ alkyl)($C_1$-$C_6$ alkyl)," wherein the multiply occurring radicals in each case may independently have the same or different meanings. The same analogously applies for all expressions according to the scheme "(radical)$_x$," where x is an integer equal to or greater than two.

Optical Isomers-Diastereomers-Geometric Isomers-Tautomers

The compounds of general formula I according to the invention or the salts thereof may have at least one asymmetrical center, and may be present as racemates and racemic mixtures, individual enantiomers, diastereomeric mixtures, and individual diastereomers. The present invention encompasses all of these stereoisomeric forms of the compounds of general formula I according to the invention.

The compounds of general formula I according to the invention may be split into their individual stereoisomers by use of customary methods, for example fractional crystallization from a suitable solvent such as methanol or ethyl acetate or a mixture thereof, or by chiral chromatography, using an optically active stationary phase. The absolute configuration may be determined by X-ray crystallography of the crystalline products or crystalline intermediate products which, if necessary, may be derivatized using a reactant containing an asymmetrical center having a known absolute configuration.

Alternatively, any given stereoisomer of a compound of general formula I according to the invention may be obtained by stereospecific synthesis, using optically pure starting materials or reactants having a known absolute configuration, or by use of asymmetrical synthesis methods.

Use of an enantiomerically or diastereomerically pure compound is preferred.

In particular, the compounds of general formula I according to the invention may also be present in the form of various tautomers, it being obvious to one skilled in the art that the type of tautomerism depends on the nature of the radicals. Other tautomers such as keto enol tautomers may also be present. All of the individually possible tautomers as well as mixtures thereof are encompassed by the compounds of general formula I according to the invention.

Salts

The term "pharmaceutically acceptable salts" refers to salts that are prepared from pharmaceutically acceptable, physiologically tolerable bases or acids, including inorganic or organic bases and inorganic or organic acids.

Salts that are derived from inorganic bases contain aluminum, ammonium, calcium, copper, iron(II), iron(III), lithium, magnesium, manganese, potassium, sodium, zinc, and the like. Particularly preferred are the ammonium, calcium, lithium, magnesium, potassium, and sodium salts derived from pharmaceutically acceptable organic, nontoxic bases, and include salts of primary, secondary, and tertiary amines, substituted amines, including naturally occurring substituted amines, cyclic amines, and basic ion exchange resins such as arginine, betaine, caffeine, choline, N,N'-dibenzylethylenediamine, diethylamine, 2-diethylaminomethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purine, theobromine, triethylamine, trimethylamine, tripropylamine, tromethamine, and the like.

When the compounds of general formula I according to the invention are basic, salts of pharmaceutically acceptable, physiologically tolerable acids, including inorganic and organic acids, may be prepared. Such acids include, among others, acetic acid (acetate), benzenesulfonic acid, benzoic acid, camphorsulfonic acid, citric acid, ethanesulfonic acid, formic acid, fumaric acid, gluconic acid, glutaminic acid, hydrobromic acid, hydrochloric acid, lactic acid, malic acid, maleic acid, mandelic acid, methanesulfonic acid, malonic acid, nitric acid, pantothenic acid, phosphoric acid, propionic acid, succinic acid, sulfuric acid, tartaric acid, p-toluenesulfonic acid, trifluoroacetic acid, and the like. Acetic acid, citric acid, fumaric acid, hydrobromic acid, hydrochloric acid, maleic acid, phosphoric acid, sulfuric acid, and malic acid are particularly preferred.

When reference is made to the compounds of general formula I according to the invention, this is intended to mean that the pharmaceutically acceptable salts thereof are also included.

When reference is made to the compounds of general formula I according to the invention, this is intended to mean that the active substance precursors ("prodrugs") thereof are also included. "Prodrugs" are understood to mean derivatives of the compounds of general formula I according to the invention which under the physiological, including the physical, thermal, chemical, or enzymatic, conditions are converted to the compounds of general formula I according to the invention after administration to a patient, preferably a human or nonhuman mammal.

Use, Fields of Application, and Effects

The subject matter of the invention also concerns the use of the compounds of general formula I according to the invention for the treatment of:

Depression and/or bipolar disorders, for example dysthymic disorders, seasonally related disorders, and/or psychotic disorders Anxiety and/or stress-related disorders, for example general anxiety disorders, panic attacks, compulsive disorders, post-traumatic stress disorders, acute stress disorders, and/or social phobias Memory disorders and/or Alzheimer's disease Schizophrenia, psychoses, psychotic disorders, and/or psychosis-related disorders Cerebrovascular disorders Pain and/or pain-related disorders, dependency and drug-related disorders, including medication-related disorders Amnesia Alcohol and/or drug abuse, including medication abuse Circadian rhythm disorders and/or Cushing's syndrome.

The term "disorder" in the context of the invention refers to anomalies which are generally regarded as medical conditions and which may be identified by virtue of specific signs, symptoms and/or dysfunctions. The treatment may be directed to individual disorders, i.e., anomalies or medical conditions, or multiple anomalies which may be etiologically associated can also be combined into patterns, i.e., syndromes, which may be treated according to the invention. This state may be transient, progressive, or persistent.

Compounds of the present invention may be used for the treatment or prevention of various diseases for which $5\text{-HT}_5$ receptors are involved in the origin and/or progression thereof, i.e., diseases which are modulated by $5\text{-HT}_5$ receptor activity, such as mental disorders. Examples of such mental disorders include those [classified] in the American Psychiatric Association DSM-IV, Diagnostic and Statistical Manual of Mental Disorders, 4th edition, 1994: Attention disorders and socially disruptive behavior; learning disabilities, delirium, dementia, and amnesiac and other cognitive disorders; disorders relating to various substances, for example disorders relating to alcohol consumption and alcohol-induced disorders, withdrawal symptoms; schizophrenia and other psychotic disorders, for example schizoid disorders, schizoaffective disorder, and delusional disorder; substance-induced psychoses; paranoid disorders; disorders induced by neuroleptic agents; affective disorders, for example depressive disorders (major depression, dysthymic disorder, seasonally related disorders, depressive disorders not further classified), bipolar disorders (bipolar I disorder, bipolar II disorder, cyclothymic disorder, bipolar disorders not further classified, substance-induced affective disorder (amphetamine or amphetamine-like substances), affective disorders not further classified); stress-related disorders, for example acute traumatic stress; anxiety disorders, for example panic attacks without agoraphobia, attacks with agoraphobia, agoraphobia without a previous history of panic attacks, specific phobias, social phobias, compulsive disorder, post-traumatic stress disorder, acute traumatic stress disorder, generalized anxiety, substance-induced anxiety; somatoform disorders, for example somatic disorder, somatic disorders not further classified, conversion disorder, pain disorder, eating disorders; sleep disorders, for example primary sleep disorders (dyssomnia, parasomnia), sleep disorders in conjunction with another mental disorder.

The subject matter of the invention in particular also concerns the use of the compounds of general formula I according to the invention for the treatment of neuropathological, neuropsychiatric, and neurodegenerative disorders.

Neuropathological disorders are understood to be disorders that are accompanied by neurological deficits, i.e., a condition characterized by neurological symptoms.

The treatment of neurodegenerative and/or neuropsychiatric disorders is preferred according to the invention. These disorders occur in particular in neuropathological medical conditions which as a rule cause brain damage, for example cerebral ischemia, stroke, epilepsy, and attacks in general, chronic schizophrenia, other psychotic conditions, depression, anxiety, bipolar disorders, dementia, in particular Alzheimer's dementia, demyelinating diseases, in particular multiple sclerosis, brain tumors, and general inflammatory processes. Migraine and its associated signs, symptoms and dysfunctions represent a further neuropathological disorder.

According to a further aspect of the present invention, neuropathological disorders which are accompanied by a glial reaction are treated. The use according to the invention relates in particular to the modulation of a glial reaction. One advantageous effect of the binding partners is shown for the preventative or acute treatment of neurological deficits, which are observed in patients with psychiatric conditions such as epilepsy, psychosis, for example psychoses of the acute exogenous reaction type, or accompanying psychoses of organic or exogenous origin, such as those following trauma, primarily brain lesions and diffuse brain damage, for metabolic disorders, infections, and endocrinopathy; endogenous psychoses such as schizophrenia and schizoid and delusional disorders; affective disorders, such as depressive, manic, or manic-depressive states; and mixed forms of the previously described psychoses; senile dementia and Alzheimer's-type senile dementia, and in the treatment or prevention of demyelination processes.

The compounds according to the invention are particularly effective for the treatment of ischemic conditions, for example as the result of brain and spinal cord trauma, as well as vascular occlusion or heart failure. Noted in particular is stroke (synonyms: apoplexia cerebri, cerebral or apoplectic stroke, cerebrovascular accident). Conditions which may be treated according to the invention include transitory ischemic attacks, reversible ischemic neurological deficits, prolonged reversible ischemic neurological deficits, partially reversible ischemic neurological symptoms, and persistent complete cerebral infarctions. The treatment of acute forms according to the invention is particularly advantageous.

The forms of neuropathological disorders preferably treated according to the invention are based on one or more of the following listed changes in the nerve tissues: Degeneration or death of neurons, in particular of gangliocytes, for example tigrolysis, nuclear membrane blurring, cell shrinkage, cytoplasmic vacuolation and encrustation, cerebral parenchymal necroses, cerebral edemas, neuronal changes caused by oxygen deficiency, atrophy, morphological changes such as demyelination, in particular myelin sheath degeneration, perivascular infiltrates, glial proliferation and/or glial scars; degeneration of the substantia nigra.

The indication to be treated according to the invention is frequently characterized by a progressive development; i.e., the above-described states change over time, generally with increased severity, it being possible for states to intermerge, or for states to occur in addition to the existing states. As the result of treatment according to the invention of neuropathological, neuropsychiatric, or neurodegenerative disorders or their underlying conditions, a number of additional signs, symptoms, and/or dysfunctions may be treated which are associated with these disorders, i.e., which in particular accompany the above-described medical conditions. These include, for example, shock lung; cranial nerve deficits, for example retrobulbar neuritis, paralysis of the ocular muscles, staccato speech, spastic paralyses, cerebellar symptoms, sensitivity disorders, bladder and rectal disorders, euphoria, dementia; hypokinesis and akinesis, absence of synkinesis, shuffling gait, bent posture of trunk and limbs, pro-, retro-, and lateropulsion, tremors, lack of facial expression, monotonous speech, depression, apathy, labile or rigid affectivity, deficient spontaneity and resolution, slowing of thought, reduced association ability; muscular atrophy.

Treatment in the context of the invention encompasses not only the treatment of acute or chronic signs, symptoms, and/or dysfunctions, but also preventative treatment (prophylaxis), in particular as recidivism or phase prophylaxis. The treatment may be directed to symptoms, for example as symptom suppression. The treatment may be oriented toward short- or medium-term measures, or it may also be a long-term treatment, for example within the scope of maintenance therapy.

The term "binding partner for $5-HT_5$ receptors" describes substances which bind to $5-HT_5$ receptors, and which therefore may also be referred to as $5-HT_5$ receptor ligands.

"Binding" is understood as the molecular interaction between the binding partner and the receptor, in particular under physiological conditions. These are generally classical interactions which include electrostatic attraction, hydrogen bridge bonding, hydrophobic bonds, van der Waals forces, or metal complex-like coordinative bonds. In addition to the above-referenced reversible molecular interactions, irreversible interactions between binding partner and receptor are also possible, such as covalent bonds.

The compounds of general formula I according to the invention are able to competitively inhibit the binding of comparison binding partners such as 5-HT (5-hydroxytryptamine) or 5-CT (5-carboxamidotryptamine) to $5-HT_5$ receptors. Competitive inhibition is understood to mean that the compounds of general formula I according to the invention compete with a comparison binding partner, in the present case 5-HT or 5-CT, for example, for the binding to the receptor.

According to a further embodiment, the compounds of general formula I according to the invention noncompetitively inhibit the binding of comparison binding partners, such as 5-HT (5-hydroxytryptamine) or 5-CT (5-carboxamidotryptamine), to $5-HT_5$ receptors. Noncompetitive inhibition is understood to mean that the compounds of general formula I according to the invention by means of their binding to the receptor modulate the binding of a comparison binding partner, in the present case 5-HT or 5-CT, for example, and in particular reduce its binding affinity.

At least for the case of competitive inhibition, i.e., reversible binding, the principle applies that the displacement of one binding partner by another increases with decreasing binding affinity of the one binding partner, i.e., increasing binding affinity of the other binding partner with respect to the receptor. Therefore, it is practical for the compounds of general formula I according to the invention to have a high binding affinity for $5-HT_5$ receptors. Such a binding affinity on the one hand allows an effective displacement of naturally occurring binding partners for $5-HT_5$ receptors, for example serotonin (5-hydroxytryptamine, 5-HT) itself, whereby the concentration of the compound of general formula I according to the invention necessary for binding a given quantity of this binding partner to $5-HT_5$ receptors decreases with increasing binding affinity. With respect to medical use, guanidine compounds of general formula I are therefore preferred whose binding affinity is so great that these may be administered in justifiable quantities as an active substance within the scope of an effective medical treatment.

The competition experiments referenced above, according to which the concentration of guanidine compounds according to the invention which suppresses 50% of the other comparison binding partner from the receptor binding site ($IC_{50}$-values) is determined in vitro, offers one possibility for expressing the binding affinity. Thus, the competitive inhibition of the binding of 5-CT to 5-$HT_5$ receptors is evaluated in such a way that preferred guanidine compounds according to the invention have half-maximal $IC_{50}$ inhibition constants of less than $10^{-5}$ M, preferably less than $10^{-6}$ M, and in particular less than $10^{-7}$ M. The binding affinity of guanidine compounds according to the invention may also be expressed by means of the inhibition constant Ki, which generally is likewise determined in vitro by means of competition experiments. For binding to 5-$HT_5$ receptors, guanidine compounds according to the invention preferably have Ki values of less than $10^{-6}$ M, advantageously less than $10^{-7}$ M, and particularly preferably less than $10^{-8}$ M.

Binding partners which may be used are able to bind to 5-$HT_5$ with an affinity that is less than, essentially the same as, or greater than that for a given receptor other than 5-$HT_5$. Thus, binding partners for 5-$HT_5$ receptors with regard to use according to the invention are in particular those whose binding affinity for 5-$HT_5$ receptors compared to the affinity for 5-HT receptors is so high that they are advantageously suited for use according to the invention. This does not necessarily assume a comparatively more selective binding to 5-$HT_5$ receptors, although selective binding partners for 5-$HT_5$ receptors are a preferred embodiment of the present invention.

For example, binding partners may be used which have high affinity for 5-$HT_5$ as well as for other 5-HT receptors. In this context, "high affinity" means Ki values which generally range from $1 \cdot 10^{-10}$ M to $1 \cdot 10^{-8}$ M. According to one particular embodiment, the guanidine compounds according to the invention have a binding profile in the high-affinity range for 5-HT receptors which is characterized by a binding affinity for 5-$HT_5$ which in comparison to other binding affinities in this range is essentially the same or only slightly lower. Factors of 10 or less may be advantageous.

The guanidine compounds according to the invention preferably have binding affinities for 5-$HT_5$ receptors which are greater than those for one or more 5-HT receptors other than 5-$HT_5$, i.e., in particular receptors associated with the above-mentioned 5-HT receptor classes 5-$HT_2$, 5-$HT_3$, 5-$HT_4$, 5-$HT_6$, and 5-$HT_7$. If the binding affinity of a binding partner for 5-$HT_5$ receptors is greater than that for a 5-HT receptor other than 5-$HT_5$, the binding of this binding partner to 5-$HT_5$ receptors is referred to as selective binding with respect to a 5-HT receptor other than 5-$HT_5$. Special binding partners are those whose binding affinity for 5-$HT_5$ receptors is greater than that for at least one 5-HT receptor. Guanidine compounds whose binding affinity for 5-$HT_5$ receptors is greater than that for all 5-HT receptors other than 5-$HT_5$ represent a further special class of guanidine compounds according to the invention.

Selectivity is understood as the property of a binding partner to preferentially bind to 5-$HT_5$ receptors. For the selectivity described above, it is crucial that there is an adequate difference between the binding affinities for 5-$HT_5$ receptors and the binding affinities for one or more 5-HT receptors other than 5-$HT_5$. Affinity differences are preferred for which the binding affinity ratio is at least 2, advantageously at least 5, particularly advantageously at least 10, preferably at least 20, particularly preferably at least 50, and most particularly preferably at least 100.

According to a further embodiment, guanidine compounds according to the invention bind preferably selectively to 5-$HT_5$ receptors having the above-described advantageous binding affinities with respect to one or more 5-HT receptors other than 5-$HT_5$.

According to a further embodiment, guanidine compounds according to the invention preferably bind selectively to 5-$HT_5$ receptors having the above-described advantageous binding affinities with respect to all 5-HT receptors other than 5-$HT_5$.

Particularly advantageous are guanidine compounds of general formula I which bind with the above-described affinities and selectivities to 5-$HT_5$ receptors which are expressed by glia cells and in particular by astrocytes. According to the invention, the human receptor variant is a preferred target for the guanidine compounds according to the invention.

The binding of guanidine compounds of general formula I to 5-$HT_5$ receptors is coupled to an effector function. Binding partners may act agonistically or antagonistically, as well as partially agonistically and/or partially antagonistically. Compounds according to the invention which completely or partially mimic the activity of 5-HT on 5-$HT_5$ receptors are referred to as agonists. Guanidine compounds according to the invention which are able to block the agonistic activity of 5-HT on 5-$HT_5$ receptors are referred to as antagonists.

According to one preferred embodiment of the present invention, guanidine compounds of general formula I are used whose binding at least to 5-$HT_5$ receptors of h5-$HT_5$-transfected CHO, HEK 293, or SHSY-5Y cells brings about a change in the agonist-induced stimulation of GTP binding to membrane-bound G proteins, a change in intracellular calcium levels, a change in the agonist-induced induction of phospholipase C activity, and/or a change in cAMP production. With regard to the change in intracellular calcium levels, the use of guanidine compounds of general formula I which bring about an increase in intracellular calcium levels represents a preferred embodiment of the invention. This embodiment also includes guanidine compounds which are active in known animal models for neurodegenerative and neuropsychiatric processes.

Preferred are guanidine compounds of general formula I which are also selective for 5-$HT_5$ receptors with respect to their effector function in the sense described above.

Administration Forms and Formulation

On account of their pharmacological properties, the guanidine compounds according to the invention may be used as active substances for therapeutic purposes. The guanidine compounds according to the invention are preferably brought into a suitable administration form before administration. Therefore, the subject matter of the present invention is also concerned with compositions, in particular pharmaceutical compositions, containing at least one guanidine compound according to the invention and optionally a pharmaceutically acceptable carrier or diluent.

Carriers or adjuvants which are known for use in the field of pharmacy and related fields, in particular those listed in relevant pharmacopoeias (for example, DAB (Deutsches Arzneimittelbuch), Ph. Eur. (Pharmacopoeia Europaea), BP (Baccalaureus Pharmaciae), NF (National Formulary), USP (United States Pharmacopoeia), as well as other carriers having properties that are compatible with physiological use are pharmaceutically acceptable.

Suitable carriers and adjuvants may be the following: wetting agents; emulsifying and suspending agents; preservatives; antioxidants; anti-irritants; chelate-forming agents; dragee adjuvants; emulsion stabilizers; film-forming agents; gel-forming agents; odor masking agents, flavorants; resins; hydrocolloids; solvents; solubilizers; neutralizing agents; permeation accelerators; pigments; quaternary ammonium compounds; emollients and moisturizers; salve, creme, or oil bases; silicone derivatives; spreading agents; stabilizers; sterilizers; suppository bases; tabletting adjuvants such as binders, fillers, lubricants, disintegrants, or coatings; propellants; drying agents; opacifiers; thickeners; waxes; softeners; and white oils. This type of formulation is based on technical knowledge as described, for example, in Fiedler, H. P., Lexikon der Hilfsstoffe für Pharmazie, Kosmetik and angrenzende Gebiete [Lexicon of Adjuvants for Pharmacy, Cosmetics, and Related Fields], 4th Edition, Aulendorf: ECV-Editio-Kantor-Verlag, 1996.

Examples of suitable carriers and diluents include lactose, dextrose, sucrose, sorbitol, mannitol, starches, gum acacia, calcium phosphate, alginate, gum tragacanth, gelatin, calcium silicate, microcrystalline cellulose, polyvinyl pyrrolidone, cellulose, water syrup, methylcellulose, methyl- and propylhydroxybenzoates, talcum, magnesium stearate, and mineral oil.

The guanidine compounds according to the invention may be formulated to ensure immediate or delayed release of the active substance to the patient.

Examples of suitable pharmaceutical compositions include solid dosage forms such as meals, powders, granulates, tablets, in particular film tablets, lozenges, sachets, cachets, dragees, capsules such as hard and soft gelatin capsules, suppositories or vaginal dosage forms, semisolid dosage forms such as salves, cremes, hydrogels, pastes, or plasters, and liquid dosage forms such as solutions, emulsions, in particular oil-in-water emulsions, suspensions, for example lotions, injection and infusion preparations, and eye drops and ear drops. Implanted dispensing devices may also be used to administer the guanidine compounds according to the invention. Liposomes or microspheres may also be used.

The compositions according to the invention may be administered, for example, using customary methods.

In the preparation of the compositions according to the invention, the active substances are usually mixed or diluted with a suitable adjuvant, in this case also referred to as an excipient. Excipients may be solid, semisolid, or liquid materials which serve as a vehicle, carrier, or medium for the active substance. If necessary, further adjuvants are admixed in a manner known as such. Shaping steps, optionally in conjunction with mixing processes, may be carried out, such as granulation, compression, and the like.

The use according to the invention of the active substances according to the invention includes a process within the scope of treatment. The individual to be treated, preferably a mammal, in particular a human, or also a nonhuman mammal such as a domestic animal or house pet, is administered an effective quantity of at least one guanidine compound of general formula I, generally formulated according to pharmaceutical practice.

The invention further relates to the preparation of agents for treating an individual, preferably a mammal, in particular a human, domestic animal, or house pet.

The guanidine compounds of general formula I according to the invention or the corresponding pharmaceutical composition may be administered by oral, rectal, topical, parenteral, including subcutaneous, intravenous and intramuscular, and ocular, pulmonary, or nasal means. Oral administration is preferred.

Effective dosing of the active substance may depend on the type of guanidine compound of formula I, the mode of administration, the condition to be treated, and the severity of the condition to be treated. Such an effective dosing of the active substance may be easily determined by one skilled in the art in the field.

The dosage depends on the age, condition, and weight of the patient, as well as the mode of administration. As a rule, the daily dose of active substance is between approximately 0.5 and 100 mg/kg body weight for oral administration, and between approximately 0.1 and 10 mg/kg body weight for parenteral administration.

Preparation of the Guanidine Compounds

The guanidine compounds according to the invention may be prepared analogously to methods known from the literature, which are familiar to one skilled in the art. The synthesis of guanidines in general is description in *J. Org. Chem.* 1997, 9, 1053; *Tetrahedron* 1999, 55 (10), 713; *Tetrahedron Letters* 1999, 40, 53; *J. Org. Chem.* 2000, 65, 8080, and the literature references cited therein. The guanidine compounds according to the invention may be synthesized under customary reaction conditions according to diagram 1, as described, for example, in *Journal of Medicinal Chemistry* 1997, 40, 2462-2465; *Journal of Medicinal Chemistry* 1999, 42, 2920-2926; *Bioorganic & Medicinal Chemistry Letters* 2001, 11, 523-528; *Journal of Medicinal Chemistry* 2000, 43, 3315-3321; *Journal of Organic Chemistry* 1991, 56, 2139-2143, or *Bioorganic and Medicinal Chemistry* 2003, 11, 1319-1341.

Diagram 1:

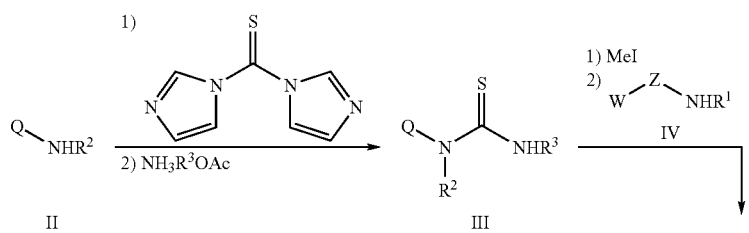

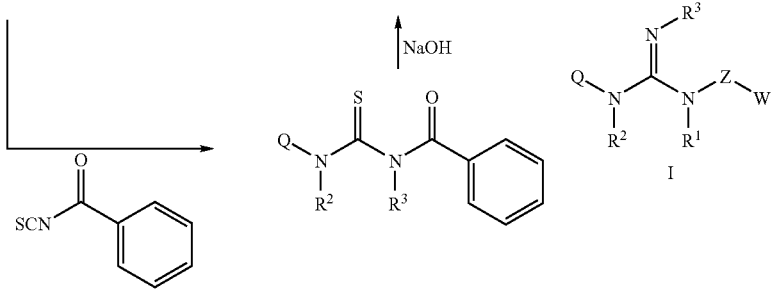

Hetarylamines II are commercially available, or may be prepared according to methods known from the literature (for example, Houben-Weyl, *Methoden der organischen Chemie* [Methods of Organic Chemistry], Volumes E8b and E8c, Stuttgart, 1994; M. B. Smith, J. March, *March's Advanced Organic Chemistry*, New York, 2001). The amines IV used in the synthesis path illustrated in diagram 1 are likewise commercially available, or may be prepared according to known procedures (e.g., Houben-Weyl, *Methods of Organic Chemistry*, 4th Edition, Volume XI/1, Stuttgart, 1957).

For the case that the radical Q may also be substituted with the radicals $R^4$, $R^5$, $R^6$, $R^7$, and $R^8$ analogously to general formula Q, functionalization to produce Q may be performed in an earlier stage of the hetarylamines by use of methods, known to one skilled in the art, for preparing functionalized hetarylamines (for example Houben-Weyl, *Methods of Organic Chemistry*, Additional and Supplementary Volumes to the 4th Edition, Volume E7b, *Hetarene* [Hetarenes], Thieme-Verlag, Stuttgart 1992; Houben-Weyl, *Methods of Organic Chemistry*, Additional and Supplementary Volumes to the 4th Edition, Volume E9a, *Hetarenes*, Thieme-Verlag, Stuttgart 1997; Houben-Weyl, *Methods of Organic Chemistry*, Additional and Supplementary Volumes to the 4th Edition, Volume E9b, *Hetarenes*, Thieme-Verlag, Stuttgart 1998; Houben-Weyl, *Methods of Organic Chemistry*, Additional and Supplementary Volumes to the 4th Edition, Volume E9c, *Hetarenes*, Thieme-Verlag, Stuttgart 1998). The functionalization of the hetarylamines may also be carried out at the stage of the guanidine compounds of general formula I by use of methods, known to one skilled in the art, for derivatization of the hetaryl radical Q (for example, the cyanation according to D. M. Tschaen, R. Desmond et al., *Synth. Commun.* 1994, 24, 887-890; or benzylations with zinc organyls according to A: Rosowsky, H. Chen, *J. Org. Chem.* 2001, 66, 7522-7526; or the methods of Suzuki analogous to the literature citation of F. Mongin, A. S. Rebstock, F. Trecourt, G. Queguiner, F. Marsais, *J. Org. Chem.* 2004, 69, 6766, or also M. Schlosser (Editor), *Organometallics in Synthesis*, A Manual, Wiley & Sons, Chichester 2002; M. Beller, C. Bolm (Editors), *Transition Metals for Organic Synthesis*, Wiley-VCH, Weinheim, 2003; T. Eicher, S. Hauptmann, *The Chemistry of Heterocycles*, 2nd Edition, Wiley-VCH, Weinheim, 2003; Houben-Weyl, *Methods of Organic Chemistry*, Additional and Supplementary Volumes to the 4th Edition, Volume E7b, *Hetarenes*, Thieme-Verlag, Stuttgart 1992; Houben-Weyl, *Methods of Organic Chemistry*, Additional and Supplementary Volumes to the 4th Edition, Volume E9a, *Hetarenes*, Thieme-Verlag, Stuttgart 1997; Houben-Weyl, *Methods of Organic Chemistry*, Additional and Supplementary Volumes to the 4th Edition, Volume E9b, *Hetarenes*, Thieme-Verlag, Stuttgart 1998; Houben-Weyl, *Methods of Organic Chemistry*, Additional and Supplementary Volumes to the 4th Edition, Volume E9c, *Hetarenes*, Thieme-Verlag, Stuttgart 1998). The necessary reagents and starting materials are either commercially available (for example, boric acid derivatives, metal organyls, nucleophiles, etc.), or may be prepared by methods known to one skilled in the art (for example, G. Hall, *Boronic Acids*, Wiley-VCH, Weinheim, 2005; M. Schlosser (Editor), *Organometallics in Synthesis*, A Manual, Wiley & Sons, Chichester 2002; M. Beller, C. Bolm (Editors), *Transition Metals for Organic Synthesis*, Wiley-VCH, Weinheim, 2003; T. Eicher, S. Hauptmann, *The Chemistry of Heterocycles*, 2nd Edition, Wiley-VCH, Weinheim, 2003; Houben-Weyl, *Methods of Organic Chemistry*, Additional and Supplementary Volumes to the 4th Edition, Volume E7b, *Hetarenes*, Thieme-Verlag, Stuttgart 1992; Houben-Weyl, *Methods of Organic Chemistry*, Additional and Supplementary Volumes to the 4th Edition, Volume E9a, *Hetarenes*, Thieme-Verlag, Stuttgart 1997; Houben-Weyl, *Methods of Organic Chemistry*, Additional and Supplementary Volumes to the 4th Edition, Volume E9b, *Hetarenes*, Thieme-Verlag, Stuttgart 1998; Houben-Weyl, *Methods of Organic Chemistry*, Additional and Supplementary Volumes to the 4th Edition, Volume E9c, *Hetarenes*, Thieme-Verlag, Stuttgart 1998).

The guanidine compounds of general formula I according to the invention as well as any intermediate products may be obtained and, if necessary, purified by conventional means, for example by recrystallization from common organic solvents, preferably a short-chain alcohol such as methanol or ethanol, or also acetonitrile, water, or acetoacetic ester, or in low-volatile solvents such as diethyl ether, pentane, or dichloromethane, or by using chromatographic techniques.

Depending on the starting materials, the guanidine compounds of formula I according to the invention occur in the free form or as acid addition salts. The compounds in free form as well as the salts of said compounds resulting from the method may be converted to the desired acid addition salts or to the free form in a manner known as such.

The following examples illustrate the invention without limiting same. It is noted that the designation and formulaic representation of salts containing protonated nitrogen reflect only one of the many possibilities with regard to the charge distribution. This applies for tautomeric forms as well. The term "acetate" refers to an addition salt with acetic acid.

PRODUCTION EXAMPLES

The named starting materials and reactants such as N-pyridin-2-yl-thiourea, N-phenylthiourea, N-(5-iodopyridin-2-yl)thiourea, N-[3-chloro-5-(trifluoromethyl)pyridin-2-yl] thiourea, phenylboric acid, 2-thienylboric acid, zinc(II) cyanide, (4-fluorophenyl)boric acid, [4-(trifluoromethyl)phenyl]boric acid, benzyl zinc bromide, [4-(trifluoromethoxy)phenyl]boric acid, 2-methoxybenzylamine 2,6-dimethoxybenzylamine, 6-bromopyridine-2-amine, 3-bromopyridine-2-amine, 4-bromopyridine-2-amine, 2-chloro-6-methoxybenzylamine, 2-chloro-6-methoxybenzylamine hydrochloride, 2-methoxy-6-methylbenzylamine, 2-methoxy-6-methylbenzylamine hydrochloride, 2-fluoro-6-methoxybenzylamine, 2-ethoxybenzylamine, 2-chlorobenzylamine, 1-(2-isopropoxyphenyl)methanamine, 2-(trifluoromethoxy)benzylamine, 2-ethylbenzylamine hydrochloride, 2-difluoromethoxybenzylamine, 2-chloro-6-phenoxybenzylamine, isoquinoline-3-amine, 2-aminoquinoline, N,N'-thiocarbonyldiimidazole, benzoyl isothiocyanate, N-(3-methylpyridin-2-yl)thiourea, N-(4-methylpyridin-2-yl)thiourea, N-(5-methylpyridin-2-yl)thiourea, N-(6-methylpyridin-2-yl)thiourea, N-[3-chloro-5-(trifluoromethyl)-pyridin-2-yl]thiourea, N-pyrimidin-2-yl-thiourea, N-pyridin-3-yl-thiourea, N-[4-(2-thienyl)pyrimidin-2-yl]thiourea, N-quinolin-3-yl-thiourea, and 1-phenyl-2-thiourea are commercially available.

Example 1

N-(2-methoxybenzyl)-N'-pyridin-2-yl-guanidine acetate 0.800 g (5.117 mmol) N-pyridin-2-yl-thiourea was dissolved in 10 mL methanol, 0.45 mL (7.164 mmol) methyl iodide in 5 mL methanol was added dropwise, and the mixture was heated for 1 hr at 70° C. (oil bath temperature) and subsequently stirred at room temperature. The solvent was removed under vacuum and the intermediate product, methyl N-(pyridin-2-yl)imidothiocarbamate hydroiodide, was redissolved in 15 mL ethanol. 1.36 mL (10.235 mmol) 2-methoxybenzylamine was added dropwise, and the mixture was heated for 2.75 hr at 85° C. (oil bath temperature) and subsequently stirred at room temperature. The solvent was then evaporated under vacuum. The crude product was redissolved with dichloromethane and extracted with water (2×30 mL). After drying over magnesium sulfate and removal of the solvent, purification was carried out via preparative HPLC (Merck Chromolith RP-18 100×25 mm, eluent: water/acetonitrile/0.1 M acetic acid). For complete ion exchange with the ion exchanger (Fluka, acetate on 1.5 mmol $CH_3COO/g/resign$ polymer substrate), the purified N-(2-methoxybenzyl)-N'-pyridin-2-yl-guanidine was converted to the acetate salt in a yield of 0.357 g (1.128 mmol).
ESI-MS [M+H$^+$]=257.25 Calculated for $C_{14}H_{16}N_4O$=256.31

Example 3

N-(2,6-dimethoxybenzyl)-N'-(5-iodopyridin-2-yl) guanidine 2.019 g (7.233 mmol) N-(5-iodopyridin-2-yl)thiourea was dissolved in 50 mL methanol, 0.60 mL (9.553 mmol) methyl iodide in 2 mL methanol was added dropwise, and the mixture was heated for 2.7 hr at 75° C. (oil bath temperature). The solvent was removed under vacuum, and the intermediate product was redissolved in 50 mL ethanol. 1.870 g (0.736 mmol) 2,6-dimethoxybenzylamine was added to the reaction mixture and heated for 2.25 hr at 90° C. (oil bath temperature). The solvent was then evaporated under vacuum. The crude product was dissolved in acetonitrile, and the product crystallized out with addition of water. The solid was suctioned off and washed with water. 2.698 g (6.152 mmol, 85%) N-(2,6-dimethoxybenzyl)-N'-(5-iodopyridin-2-yl)guanidine was isolated and used for further reaction.

For additional purification, a portion of the first crystallizate was again recrystallized from dichloromethane/methanol.
ESI-MS [M+H$^+$]=413.05 Calculated for $C_{15}H_{17}IN_4O_2$=412.23

Example 4

N-(5-Iodopyridin-2-yl)-N'''-(2-methoxybenzyl)guanidine 0.970 g (3.475 mmol) N-(5-iodopyridin-2-yl)thiourea was dissolved in 30 mL methanol, 0.30 mL (4.777 mmol) methyl iodide in 2 mL methanol was added dropwise, and the mixture was heated at 60° C. (oil bath temperature) for 20 min and subsequently stirred at room temperature for 18 hr. The solvent was removed under vacuum, and the intermediate product was redissolved in 30 mL ethanol. 1.50 mL (11.262 mmol) 2-methoxybenzylamine was added dropwise and heated for 1.5 hr at 85° C. (oil bath temperature). The solvent was then evaporated under vacuum. The crude product was redissolved in dichloromethane and extracted with water (2×50 mL). The organic phase was then extracted again with 2 N sodium hydroxide solution (1×50 mL) and washed with water (1×50 mL) to remove iodide salt from the product. After drying over magnesium sulfate and overlayering with pentane the product was crystallized. 1.252 g (3.080 mmol, 89%) N-(5-iodopyridin-2-yl)-N'-(2-methoxybenzyl)guanidine was obtained. For additional purification, a portion of the first crystallizate was again recrystallized from dichloromethane/water.
ESI-MS [M+H$^+$]=383.05 Calculated for $C_{14}H_{15}IN_4O$=382.21

Example 5

N-(2,6-dimethoxybenzyl)-N'-pyridin-2-yl-guanidine acetate 0.800 g (5.117 mmol) N-pyridin-2-yl-thiourea was dissolved in 20 mL methanol and combined with 0.45 mL (10.235 mmol) methyl iodide. The mixture was heated under reflux for 15 min and subsequently stirred at room temperature. After reaction was complete the solvent was removed under vacuum, and the residue was used for the subsequent reaction without further purification. For this purpose the solid was dissolved in 20 mL ethanol, and 0.946 g (5.658 mmol) 2,6-dimethoxybenzylamine was added. After addition of 1.80 mL (10.235 mmol) diisopropylethylamine the mixture was heated under reflux for a total of 7 hr. After reaction was complete the solvent was removed under vacuum. The residue was taken up in dichloromethane and extracted with water (2×30 mL). The organic phase was dried over magnesium sulfate, and the solvent was evaporated under vacuum. 0.402 g of the desired product N-(2,6-dimethoxybenzyl)-N'-pyridin-2-yl-guanidine crystallized from acetonitrile/water (1:1), and by use of ion exchanger (Fluka, acetate on 1.5 mmol $CH_3COO/g/resign$ polymer substrate) was converted to the acetate salt. The residual mother liquor of the crystallizate was separated from impurities via preparative HPLC (Merck Chromolith RP-18 100×25 mm, eluent: water/acetonitrile/0.1 M acetic acid), resulting in isolation of a total of 0.516 g (1.489 mmol) N-(2,6-dimethoxybenzyl)-N'-pyridin-2-yl-guanidine acetate as a pure substance.

ESI-MS [M+H$^+$]=288.1 Calculated for C$_{15}$H$_{18}$N$_4$O$_2$=287.34

Example 6

N-(2-methoxybenzyl)-N'-(5-methylpyridin-2-yl) guanidine acetate

6.1 Methyl N-(5-methylpyridin-2-yl)imidothiocarbamate 0.700 g (4.19 mmol) N-(5-methylpyridin-2-yl)thiourea was suspended in 20 mL methanol, and 0.315 mL (5.02 mmol) iodomethane was added. The mixture was heated under reflux for 2 hr, whereupon the reaction mixture turned into a clear yellowish solution. The course of the reaction was tracked by thin-layer chromatography (eluent dichloromethane/methanol (9:1)) and by mass spectrometry. The solvent was evaporated under vacuum, and the residue was dissolved in dichloromethane. After extraction with 1 N sodium hydroxide solution (1×10 mL) to release the iodide salt formed in an intermediate step, washing of the organic phase with water (1×50 mL), drying with magnesium sulfate, and removal of the solvent under vacuum, 0.680 g (3.75 mmol, 90%) of the methyl N-(5-methylpyridin-2-yl)imidothiocarbamate was isolated.

ESI-MS [M+H$^+$]=182.05 Calculated for C$_8$H$_{11}$N$_3$S=181.26

6.2 N-(2-methoxybenzyl)-N'-(5-methylpyridin-2-yl) guanidine acetate 0.334 g (2.44 mmol) 2-methoxybenzylamine was added to 0.340 g (1.88 mmol) methyl N-(5-methylpyridin-2-yl)imidothiocarbamate dissolved in 3 mL ethanol, and the mixture was heated for 25 min at 85° C. in a CEM microwave (150 watts). After reaction was complete the solvent was removed under vacuum. The residue was then dissolved in acetonitrile/water (1:1), and the mixture was purified via preparative HPLC (Merck Chromolith RP-18 100×25 mm, eluent: water/acetonitrile/0.1 M acetic acid). 0.220 g (0.67 mmol, 36%) of pure N-(2-methoxybenzyl)-N'-(5-methylpyridin-2-yl)guanidine acetate was obtained in the form of the acetate salt (base/acetate in a 1:1 ratio).

ESI-MS [M+H$^+$]=271.15 Calculated for C$_{15}$H$_{18}$N$_4$O=270.34

Compounds 7, 8, 9, 10, 11, 12, 13, 14, 15, 16, and 17 were prepared analogously to Example 6 by the reaction of suitable starting materials of formulas III and IV.

Example 7

N-(2,6-dimethoxybenzyl)-N'-(5-methylpyridin-2-yl) guanidine

According to the above-referenced procedure of Example 6, 0.340 g (1.880 mmol) methyl N-(5-methylpyridin-2-yl)imidothiocarbamate was reacted with 0.408 g (2.44 mmol) 2,6-dimethoxybenzylamine, with ethanol as solvent, for 25 min at 85° C. in a CEM 5 microwave (150 watts). Instead of preparative HPLC it was possible to crystallize the product N-(2,6-dimethoxybenzyl)-N'-(5-methylpyridin-2-yl)guanidine directly from ethanol, resulting in the isolation of 0.176 g (0.59 mmol, 31%).

ESI-MS [M+H$^+$]=301.15 Calculated for C$_{16}$H$_{20}$N$_4$O$_2$=300.36

Example 8

N-(2-Methoxybenzyl)-N'-(6-methylpyridin-2-yl) guanidine

The methylated intermediate product methyl N-(6-methylpyridin-2-yl)imidothiocarbamate was obtained from N-(6-methylpyridin-2-yl)thiourea analogously to the above-described procedure of Example 6. For the subsequent reaction, 0.300 g (1.660 mmol) methyl N-(6-methylpyridin-2-yl)imidothiocarbamate was correspondingly reacted with 0.272 g (1.99 mmol) 2-methoxybenzylamine for 30 min at 90° C. in a CEM microwave (100 watts). The product precipitated directly as a crystallizate from the ethanolic solution and was suctioned off. The crude product was dissolved in dichloromethane and extracted with 2 N sodium hydroxide solution to completely remove the hydroiodide. Instead of preparative HPLC it was possible to crystallize the product N-(2-methoxybenzyl)-N'-(6-methylpyridin-2-yl)guanidine directly from isopropanol, resulting in the isolation of 0.190 g (0.70 mmol, 43%).

ESI-MS [M+H$^+$]=271.15 Calculated for C$_{15}$H$_{18}$N$_4$O=270.34

Example 9

N-(2,6-dimethoxybenzyl)-N'-(6-methylpyridin-2-yl) guanidine

The methylated intermediate product methyl N-(6-methylpyridin-2-yl)imidothiocarbamate was obtained from N-(6-methylpyridin-2-yl)thiourea analogously to the above-described procedure of Example 6. For the subsequent reaction, 0.300 g (1.660 mmol) methyl N-(6-methylpyridin-2-yl)imidothiocarbamate was correspondingly reacted with 0.332 g (1.99 mmol) 2,6-dimethoxybenzylamine for 30 min at 90° C. in a CEM microwave (100 watts). The product precipitated directly as a crystallizate from the ethanolic solution and was suctioned off. The crude product was dissolved in dichloromethane and extracted with 2 N sodium hydroxide solution to completely remove the hydroiodide. Instead of preparative HPLC it was possible to crystallize the product N-(2,6-dimethoxybenzyl)-N'-(6-methylpyridin-2-yl)guanidine directly from dichloromethane/diethyl ether, resulting in the isolation of 0.300 g (1.02 mmol, 61%).

ESI-MS [M+H$^+$]=301.15 Calculated for C$_{16}$H$_{20}$N$_4$O$_2$=300.36

Example 10

N-[3-Chloro-5-(trifluoromethyl)pyridin-2-yl]-N'-(2-methoxybenzyl)guanidine acetate The methylated intermediate product methyl N-[3-chloro-5-(trifluoromethyl)pyridin-2-yl]imidothiocarbamate was obtained from N-[3-chloro-5-(trifluoromethyl)pyridin-2-yl]thiourea analogously to the above-described procedure of Example 6. For the subsequent reaction, 0.270 g (1.000 mmol) methyl N-[3-chloro-5-(trifluoromethyl)pyridin-2-yl]imidothiocarbamate was correspondingly reacted with 0.179 g (1.300 mmol) 2-methoxybenzylamine, with ethanol as solvent, for 30 min at 90° C. in a CEM microwave (100 watts), and then for an additional 30 min at 100° C. (100 watts) with "heating by cooling." Preparative HPLC was used to obtain 0.112 g N-[3-chloro-5-(trifluoromethyl)pyridin-2-yl]-N'-(2-methoxybenzyl)guanidine in the form of the acetate salt (base/acetate in a 1:0.6 ratio).

ESI-MS [M+H$^+$]=359.05 Calculated for C$_{15}$H$_{14}$ClF$_3$N$_4$O=358.75

Example 11

N-[3-Chloro-5-(trifluoromethyl)pyridin-2-yl]-N'-(2,6-dimethoxybenzyl)guanidine acetate The methylated intermediate product methyl N-[3-chloro-5-(trifluoromethyl)pyridin-2-yl]imidothiocarbamate was obtained from N-[3-chloro-5-(trifluoromethyl)pyridin-2-yl]thiourea analogously to the above-described procedure of Example 6. For the subsequent reaction, 0.270 g (1.000 mmol) methyl N-[3-chloro-5-(trifluoromethyl)pyridin-2-yl]imidothiocarbamate was correspondingly reacted with 0.218 g (1.300 mmol) 2,6-dimethoxybenzylamine, with ethanol as solvent, for 30 min at 90° C. in a CEM microwave (100 watts), and then for an additional 30 min at 100° C. (100 watts) with "heating by cooling." Preparative HPLC was used to obtain 0.080 g N-[3-chloro-5-(trifluoromethyl)pyridin-2-yl]-N'-(2,6-dimethoxybenzyl)guanidine in the form of the acetate salt (base/acetate in a 1:0.75 ratio).

ESI-MS [M+H$^+$]=389.05 Calculated for C$_{16}$H$_{16}$ClF$_3$N$_4$=388.78

Example 12

N-(2-Methoxybenzyl)-N'-(3-methylpyridin-2-yl)guanidine acetate

The methylated intermediate product methyl N-(3-methylpyridin-2-yl)imidothiocarbamate was obtained from N-(3-methylpyridin-2-yl)thiourea analogously to the above-described procedure of Example 6. For the subsequent reaction, 0.250 g (1.380 mmol) methyl N-(3-methylpyridin-2-yl)imidothiocarbamate was correspondingly reacted to completion with 0.227 g (1.660 mmol) 2-methoxybenzylamine, with ethanol as solvent, for 50 min at 130° C. in a CEM microwave (200 watts) with "heating by cooling." After removal of the ethanol the crude product was dissolved in dichloromethane and extracted with 2 N sodium hydroxide solution, the organic phase was dried over magnesium sulfate, and the solvent was removed under vacuum. Preparative HPLC was used to obtain 0.120 g N-(2-methoxybenzyl)-N'-(3-methylpyridin-2-yl)guanidine in the form of the acetate salt (base/acetate in a 1:1 ratio).

ESI-MS [M+H$^+$]=271.15 Calculated for C$_{15}$H$_{18}$N$_4$O=270.34

Example 13

N-(2,6-Dimethoxybenzyl)-N'-(3-methylpyridin-2-yl)guanidine acetate

The methylated intermediate product methyl N-(3-methylpyridin-2-yl)imidothiocarbamate was obtained from N-(3-methylpyridin-2-yl)thiourea analogously to the above-described procedure of Example 6. For the subsequent reaction, 0.250 g (1.380 mmol) methyl N-(3-methylpyridin-2-yl)imidothiocarbamate was correspondingly reacted to completion with 0.277 g (1.660 mmol) 2,6-dimethoxybenzylamine, with ethanol as solvent, for 25 min at 130° C. in a CEM microwave (200 watts) with "heating by cooling." After removal of the ethanol the crude product was dissolved in dichloromethane and extracted with 2 N sodium hydroxide solution, the organic phase was dried over magnesium sulfate, and the solvent was removed under vacuum. Preparative HPLC was used to obtain 0.167 g N-(2,6-dimethoxybenzyl)-N'-(3-methylpyridin-2-yl)guanidine in the form of the acetate salt (base/acetate in a 1:1 ratio).

ESI-MS [M+H$^+$]=301.15 Calculated for C$_{16}$H$_{20}$N$_4$O$_2$=300.36

Example 14

N-(2-Methoxybenzyl)-N'-(4-(2-thienyl)pyrimidin-2-yl]guanidine acetate

The methylated intermediate product methyl N-[4-(2-thienyl)pyrimidin-2-yl]imidothiocarbamate was obtained from N-[4-(2-thienyl)pyrimidin-2-yl]thiourea analogously to the above-described procedure of Example 6. For the subsequent reaction, 0.250 g (1.00 mmol) methyl N-[4-(2-thienyl)pyrimidin-2-yl]imidothiocarbamate was correspondingly reacted to completion with 0.178 g (1.30 mmol) 2-methoxybenzylamine, with ethanol as solvent, for 45 min at 90° C. in a CEM microwave (100 watts). Preparative HPLC was used to obtain 0.260 g (0.64 mmol, 64%) N-(2-methoxybenzyl)-N'-[4-(2-thienyl)pyrimidin-2-yl]guanidine in the form of the acetate salt (base/acetate in a 1:1 ratio).

20 ESI-MS [M+H$^+$]=340.05 Calculated for C$_{17}$H$_{17}$N$_5$OS=339.42

Example 15

N-(2,6-Dimethoxybenzyl)-N'-[4-(2-thienyl)pyrimidin-2-yl]guanidine acetate

The methylated intermediate product methyl N-[4-(2-thienyl)pyrimidin-2-yl]imidothiocarbamate was obtained from N-[4-(2-thienyl)pyrimidin-2-yl]thiourea analogously to the above-described procedure of Example 6. For the subsequent reaction, 0.500 g (2.00 mmol) methyl N-[4-(2-thienyl)pyrimidin-2-yl]imidothiocarbamate was correspondingly reacted with 0.434 g (2.60 mmol) 2,6-dimethoxybenzylamine, with ethanol as solvent, for 45 min at 90° C. in a CEM microwave (100 watts). Preparative HPLC was used to obtain 40 mg pure N-(2,6-dimethoxybenzyl)-N'-[4-(2-thienyl)pyrimidin-2-yl]guanidine in the form of the acetate salt (base/acetate in a 1:0.8 ratio). The severe drop in yield was probably due to the purification, since it was possible to isolate an unpurified fraction of 168 mg.

ESI-MS [M+H$^+$]=370.15 Calculated for C$_{18}$H$_{19}$N$_5$O$_2$S=369.45

Example 16

N-(2-Methoxybenzyl)-N'-quinolin-3-yl-guanidine acetate

The methylated intermediate product methyl N-quinolin-3-yl-imidothiocarbamate was obtained from N-quinolin-3-yl-thiourea analogously to the above-described procedure of Example 6. For the subsequent reaction, 0.250 g (1.15 mmol) methyl N-quinolin-3-yl-imidothiocarbamate was correspondingly reacted with 0.205 g (1.50 mmol) 2-methoxybenzylamine, with ethanol as solvent for 45 min, at 90° C. in a CEM microwave (100 watts). After two preparative HPLC procedures, 0.134 g (0.368 mmol, 32%) N-(2-methoxybenzyl)-N'-quinoline-3-yl-guanidine was obtained in the form of the acetate salt (base/acetate in a 1:1 ratio).

ESI-MS [M+H$^+$]=307.15 Calculated for C$_{18}$H$_{18}$N$_4$O=306.37

Example 17

N-(2,6-Dimethoxybenzyl)-N'-quinolin-3-yl-guanidine acetate

The methylated intermediate product methyl N-quinolin-3-yl-imidothiocarbamate was obtained from N-quinolin-3-yl-thiourea analogously to the above-described procedure of Example 6. For the subsequent reaction, 0.500 g (2.30 mmol) methyl N-quinolin-3-yl-imidothiocarbamate was correspondingly reacted with 0.500 g (2.99 mmol) 2,6-dimethoxybenzylamine, with ethanol as solvent, at 90° C. in a CEM microwave (100 watts). After two preparative HPLC procedures, 86 mg (0.218 mmol, 9%) N-(2,6-dimethoxybenzyl)-N'-quinolin-3-yl-guanidine was obtained in the form of the acetate salt (base/acetate in a 1:1 ratio). The severe drop in yield was probably due to the purification.

ESI-MS [M+H$^+$]=337.15 Calculated for $C_{19}H_{20}N_4O_2$=336.40

Example 18

N-(2-Chloro-6-methoxybenzyl)-N'-(5-methylpyridin-2-yl)guanidine acetate

18.1 Methyl N-(5-methylpyridin-2-yl)imidothiocarbamate hydroiodide 0.700 g (4.19 mmol) N-(5-methylpyridin-2-yl)thiourea was suspended in 20 mL methanol, and 0.315 mL (5.02 mmol) iodomethane was added. The mixture was heated under reflux for 30 min, whereupon the reaction mixture turned into a clear yellowish solution. After stirring overnight at room temperature, the solvent was evaporated under vacuum and the residue was codistilled twice with dichloromethane to remove the excess iodomethane. 1.229 g (3.977 mmol, 95%) methyl N-(5-methylpyridin-2-yl)imidothiocarbamate in the form of its hydroiodide was isolated, and was used directly for the subsequent reaction without liberation from the salt.

18.2 N-(2-Chloro-6-methoxybenzyl)-N'-(5-methylpyridin-2-yl)guanidine 0.150 g (0.49 mmol) methyl N-(5-methylpyridin-2-yl)imidothiocarbamate hydroiodide and 2-chloro-6-methoxybenzylamine hydrochloride were combined and dissolved in 6 mL acetonitrile, then combined with 0.25 mL (1.46 mmol) diisopropylethylamine. The reaction mixture was heated for 45 min at 90° C. in a CEM microwave (100 watts). After reaction was complete the solvent was removed under vacuum, and the residue was dissolved in 30 mL dichloromethane, then extracted with water (1×50 mL) and then with 2 N sodium hydroxide solution (2×50 mL), and finally washed with water (1×50 mL). The organic phase was dried over magnesium sulfate, and the solvent was removed under vacuum. The crude product was then dissolved in acetonitrile/water and purified via preparative HPLC (Merck Chromolith RP-18 100×25 mm, eluent: water/acetonitrile/0.1 M acetic acid, with a flow rate of 20 mL/min and with gradients of 10% to 30% of the acetonitrile fraction in 15 min). After purification of the clean fractions, 0.100 g N-(2-chloro-6-methoxybenzyl)-N'-(5-methylpyridin-2-yl)guanidine was obtained in the form of the acetate salt (base/acetate in a 1:0.5 ratio).

ESI-MS [M+H$^+$]=305.05/307.05 Calculated for $C_{15}H_{17}ClN_4$=304.78

Compounds 19, 20, 21, 22, 23, 24, 25, 26, 27, 29, 30, 71, 72, 73, 74, 75, 91, 92, 93, and 94 were prepared analogously to Example 18 by the reaction of suitable starting materials of formulas III and IV.

Example 19

N-(2-Methoxy-6-methylbenzyl)-N'-(5-methylpyridin-2-yl)guanidine

In an analogous manner, 0.150 g (0.490 mmol) methyl N-(5-methylpyridin-2-yl)imidothiocarbamate hydroiodide was reacted with 0.100 g (0.530 mmol) 2-methoxy-6-methylbenzylamine hydrochloride, with the addition of 0.25 mL (1.46 mmol) diisopropylethylamine and acetonitrile as solvent, for 45 min at 90° C. in a CEM microwave (100 watts), and after workup and purification 53.5 mg of pure N-(2-methoxy-6-methylbenzyl)-N'-(5-methylpyridin-2-yl)guanidine was obtained in the form of the acetate salt (base/acetate in a 1:0.3 ratio).

ESI-MS [M+H$^+$]=285.15 Calculated for $C_{16}H_{20}N_4O$=284.36

Example 20

N-(2-Fluoro-6-methoxybenzyl)-N'-(5-methylpyridin-2-yl)guanidine acetate

In an analogous manner, 0.550 g (1.78 mmol) methyl N-(5-methylpyridin-2-yl)imidothiocarbamate hydroiodide was reacted with 0.304 g (0.1.96 mmol) 2-fluoro-6-methoxybenzylamine, with the addition of 0.62 mL (3.56 mmol) diisopropylethylamine and acetonitrile as solvent, for 50 min at 90-100° C. in a CEM microwave (150 watts), and after workup and purification, instead of preparative HPLC, crystallization from acetonitrile/water (1:1) and addition of acetic acid resulted in 0.560 g (1.60 mmol, 90%) pure N-(2-fluoro-6-methoxybenzyl)-N'-(5-methylpyridin-2-yl)guanidine in the form of the acetate salt (base/acetate in a 1:1 ratio).

ESI-MS [M+H$^+$]=289.05 Calculated for $C_{15}H_{17}FN_4O$=288.33

Example 21

N-(2-Chlorobenzyl)-N'-(5-methylpyridin-2-yl)guanidine

In an analogous manner, 0.550 g (1.779 mmol) methyl N-(5-methylpyridin-2-yl)imidothiocarbamate hydroiodide was reacted with 0.302 g (2.135 mmol) 2-chlorobenzylamine, with the addition of 0.62 mL (3.558 mmol) diisopropylethylamine and acetonitrile as solvent, for 60 min at 80° C. in a CEM microwave (100 watts), and after workup and purification 0.483 g pure N-(2-chlorobenzyl)-N'-(5-methylpyridin-2-yl)guanidine was obtained in the form of the acetate salt (base/acetate in a 1:0.3 ratio).

ESI-MS [M+H$^+$]=275.05/277.05 Calculated for $C_{14}H_{15}ClN_4$=274.76

Example 22

N-(2-Ethoxybenzyl)-N'-(5-methylpyridin-2-yl)guanidine acetate

In an analogous manner, 0.200 g (0.647 mmol) methyl N-(5-methylpyridin-2-yl)imidothiocarbamate hydroiodide was reacted with 0.117 g (0.776 mmol) 2-ethoxybenzylamine, with the addition of 0.23 mL (1.294 mmol) diisopropylethylamine and acetonitrile as solvent, by conventional means by heating for 5 hr at 80° C. (oil bath temperature), and after workup and purification 0.103 g pure N-(2-ethoxybenzyl)-N'-(5-methylpyridin-2-yl)guanidine was obtained in the form of the acetate salt (base/acetate in a 1:1 ratio).

ESI-MS [M+H$^+$]=285.15 Calculated for $C_{16}H_{20}N_4O$=284.36

Example 23

N-(2-Isopropoxybenzyl)-N'-(5-methylpyridin-2-yl) guanidine acetate

In an analogous manner, 0.200 g (0.647 mmol) methyl N-(5-methylpyridin-2-yl)imidothiocarbamate hydroiodide was reacted with 0.117 g (0.710 mmol) 1-(2-isopropoxyphenyl)methanamine, with the addition of 0.23 mL (1.294 mmol) diisopropylethylamine and acetonitrile as solvent, by conventional means by heating for 5 hr at 80° C. (oil bath temperature), and after workup and purification 0.089 g pure N-(2-isopropoxybenzyl)-N'-(5-methylpyridin-2-yl)guanidine was obtained in the form of the acetate salt (base/acetate in a 1:1 ratio).

ESI-MS [M+H$^+$]=299.15 Calculated for $C_{17}H_{22}N_4O$=298.39

Example 24

N-(5-Methylpyridin-2-yl)-N'-[2-(trifluoromethoxy) benzyl]guanidine

In an analogous manner, 0.200 g (0.647 mmol) methyl N-(5-methylpyridin-2-yl)imidothiocarbamate hydroiodide was reacted with 0.187 g (0.950 mmol) 2-(trifluoromethoxy)benzylamine, with the addition of 0.22 mL (1.290 mmol) diisopropylethylamine and acetonitrile as solvent, for 30 min at 90° C. in a CEM microwave (150 watts), and after workup and purification 0.147 g pure N-(5-methylpyridin-2-yl)-N'-[2-(trifluoromethoxy)benzyl]guanidine was obtained in the form of the acetate salt (base/acetate in a 1:0.3 ratio).

ESI-MS [M+H$^+$]=325.15 Calculated for $C_{15}H_{15}F_3N_4O$=324.31

Example 25

N-(2-Ethylbenzyl)-N'-(5-methylpyridin-2-yl)guanidine

In an analogous manner, 0.300 g (0.970 mmol) methyl N-(5-methylpyridin-2-yl)imidothiocarbamate hydroiodide was reacted with 0.183 g (1.070 mmol) 2-ethylbenzylamine hydrochloride, with the addition of 0.44 mL (1.94 mmol) diisopropylethylamine and acetonitrile as solvent, for 30 min at 90° C. in a CEM microwave (150 watts), and after workup and purification 0.147 g pure N-(2-ethylbenzyl)-N'-(5-methylpyridin-2-yl)guanidine was obtained in the form of the acetate salt (base/acetate in a 1:0.3 ratio).

ESI-MS [M+H$^+$]=269.15 Calculated for $C_{16}H_{20}N_4$=268.36

Example 26

N-[2-(Difluoromethoxy)benzyl]-N'-(5-methylpyridin-2-yl)guanidine

In an analogous manner, 0.350 g (1.130 mmol) methyl N-(5-methylpyridin-2-yl)imidothiocarbamate hydroiodide was reacted with 0.240 g (1.360 mmol) 2-difluoromethoxybenzylamine, with the addition of 0.39 mL (2.26 mmol) diisopropylethylamine and acetonitrile as solvent, for 40 min at 90-100° C. in a CEM microwave (150 watts), and after workup and purification 0.321 g pure N-[2-(difluoromethoxy)benzyl]-N'-(5-methylpyridin-2-yl)guanidine was obtained in the form of the acetate salt (base/acetate in a 1:0.3 ratio).

ESI-MS [M+H$^+$]=307.15 Calculated for $C_{15}H_{16}F_2N_4O$=306.32

Example 27

N-(2-Chloro-6-phenoxybenzyl)-N'-(5-methylpyridin-2-yl)guanidine acetate

In an analogous manner, 0.200 g (0.647 mmol) methyl N-(5-methylpyridin-2-yl)imidothiocarbamate hydroiodide was reacted with 0.181 g (0.776 mmol) 2-chloro-6-phenoxybenzylamine, with the addition of 0.22 mL (1.29 mmol) diisopropylethylamine and acetonitrile as solvent, by conventional means by heating for 5 hr at 80° C. (oil bath temperature), and after workup and purification) 0.150 g pure N-(2-chloro-6-phenoxybenzyl)-N'-(5-methylpyridin-2-yl)guanidine was obtained in the form of the acetate salt (base/acetate in a 1:1 ratio).

ESI-MS [M+H$^+$]=367.15/369.15 Calculated for $C_{20}H_{19}ClN_4O$=366.85

Example 28

N-(5-Methylpyridin-2-yl)-N'-(2-phenoxybenzyl) guanidine hydrochloride 0.111 g (0.261 mmol) N-(2-chloro-6-phenoxybenzyl)-N'-(5-methylpyridin-2-yl)guanidine acetate was dissolved in 10 mL methanol, and 10 mg Pearlman's catalyst (palladium hydroxide, 20% by weight Pd on C) was added. After evacuation and flushing of the reaction vessel with nitrogen, the reaction flask was re-evacuated and then filled with hydrogen. The reaction mixture was hydrogenated for 12 hr at room temperature. The catalyst was then separated via a membrane filter, and the resulting solution was removed from the solvent under vacuum. The viscous, clear residue was combined with diethyl ether, and after 2 hr crystallization 0.071 mg (0.192 mmol, 73%) purified N-(5-methylpyridin-2-yl)-N-(2-phenoxybenzyl) guanidine hydrochloride was isolated.

ESI-MS [M+H$^+$]=333.15 Calculated for $C_{20}H_{20}N_4O$=332.41

Example 29

N-(2-Methoxybenzyl)-N'-(4-methylpyridin-2-yl) guanidine acetate

The methylated intermediate product methyl N-(4-methylpyridin-2-yl)imidothiocarbamate hydroiodide was obtained from N-(4-methylpyridin-2-yl)thiourea by stirring at room temperature for 12 hr in methanol, analogously to the above-described procedure of Example 18. For the subsequent reaction, 0.900 g (2.911 mmol) methyl N-(4-methylpyridin-2-yl)imidothiocarbamate hydroiodide was correspondingly reacted with 0.439 g (3.202 mmol) 2-methoxybenzylamine, with the addition of 0.76 mL (4.366 mmol) diisopropylethylamine and ethanol as solvent, for 25 min at 90° C. in a CEM microwave (150 watts) under a nitrogen atmosphere. The crude product crystallized from the reaction mixture, and was suctioned off and washed with ethanol/pentane. For further purification the product was precipitated in acetonitrile/water (1:1) with addition of acetic acid, resulting in 0.511 g (1.547 mmol, 53%) pure N-(2-methoxybenzyl)-N'-(4-methylpyridin-2-yl)guanidine in the form of the acetate salt (base/acetate in a 1:1 ratio).

ESI-MS [M+H$^+$]=271.15 Calculated for $C_{15}H_{18}N_4O$=270.34

Example 30

N-(2,6-Dimethoxybenzyl)-N'-(4-methylpyridin-2-yl) guanidine acetate

The methylated intermediate product methyl N-(4-methylpyridin-2-yl)imidothiocarbamate hydroiodide was obtained from N-(4-methylpyridin-2-yl)thiourea by stirring at room temperature for 12 hr in methanol, analogously to the above-described procedure of Example 18. For the subsequent reaction, 0.900 g (2.911 mmol) methyl N-(4-methylpyridin-2-yl)imidothiocarbamate hydroiodide was correspondingly reacted with 0.535 g (3.202 mmol) 2,6-dimethoxybenzylamine, with the addition of 0.76 mL (4.366 mmol) diisopropylethylamine and ethanol as solvent, for 25 min at 90° C. in a CEM microwave (150 watts) under a nitrogen atmosphere, and after workup and purification preparative HPLC was used to obtain 0.272 g pure N-(2,6-dimethoxybenzyl)-N'-(4-methylpyridin-2-yl)guanidine in the form of the acetate salt (base/acetate in a 1:1 ratio).

ESI-MS [M+H$^+$]=301.15 Calculated for $C_{16}H_{20}N_4O_2$=300.36

Example 31

N-(2-Chloro-6-methoxybenzyl)-N'-(3-methylpyridin-2-yl)guanidine

31.1 Methyl N-(3-methylpyridin-2-yl)imidothiocarbamate 0.420 g (2.51 mmol) N-(3-methylpyridin-2-yl)thiourea was dissolved in 20 mL methanol, and 0.428 mL (3.01 mmol) iodomethane was added thereto. The mixture was heated for 1 hr under reflux, then stirred for 12 hr at room temperature. The solvent was evaporated under vacuum, and the residue was dissolved in dichloromethane. After addition of 50 mL water, the solution was adjusted to pH~10 with 1 N NaOH and extracted. The organic phase was separated, and the aqueous phase was extracted again with dichloromethane (1×50 mL). After combination of the organic phases, drying over magnesium sulfate, and removal of the solvents under vacuum, 0.710 g (2.30 mmol, 92%) methyl N-(3-methylpyridin-2-yl)imidothiocarbamate was isolated, which despite extraction with NaOH was present in the form of the hydroiodide.

ESI-MS [M+H$^+$]=182.05 Calculated for $C_8H_{11}N_3S$=181.26

31.2 N-(2-Chloro-6-methoxybenzyl)-N'-(3-methylpyridin-2-yl)guanidine 0.230 g (0.74 mmol) methyl N-(3-methylpyridin-2-yl)imidothiocarbamate hydroiodide and 2-chloro-6-methoxybenzylamine hydrochloride were combined and dissolved in 6 mL acetonitrile, then combined with 0.26 mL (1.49 mmol) diisopropylethylamine. The reaction mixture was heated for 30 min at 90° C. in a CEM microwave (150 watts). The solvent was removed under vacuum, and the residue was dissolved in 30 mL dichloromethane and extracted with water (3×50 mL). The organic phase was dried over magnesium sulfate, and the solvent was removed under vacuum. The crude product was then dissolved in acetonitrile/water and purified via preparative HPLC (Merck Chromolith RP-18 100×25 mm, eluent: water/acetonitrile/0.1 M acetic acid, with a flow rate of 20 mL/min and with gradients of 5% to 30% of the acetonitrile fraction in 15 min). After purification of the clean fractions and lyophilization under vacuum, 0.165 g N-(2-chloro-6-methoxybenzyl)-N'-(3-methylpyridin-2-yl)guanidine was obtained in the form of the acetate salt (base/acetate in a 1:0.2 ratio).

ESI-MS [M+H$^+$]=305.05/307.05 Calculated for $C_{15}H_{17}ClN_4O$=304.78

Example 32

N-(2-Fluoro-6-methoxybenzyl)-N'-(3-methylpyridin-2-yl)guanidine

In an analogous manner, 0.230 g (0.74 mmol) methyl N-(3-methylpyridin-2-yl)imidothiocarbamate hydroiodide was reacted with 0.127 g (0.820 mmol) 2-fluoro-6-methoxybenzylamine, with the addition of 0.26 mL (1.49 mmol) diisopropylethylamine and acetonitrile as solvent, for 30 min at 90° C. in a CEM microwave (150 watts), and after workup and purification 0.200 g pure N-(2-fluoro-6-methoxybenzyl)-N'-(3-methylpyridin-2-yl)guanidine was obtained in the form of the acetate salt (base/acetate in a 1:0.3 ratio).

ESI-MS [M+$^+$]=289.15 Calculated for $C_{15}H_{17}FN_4O$=288.33

Example 33

N-(2-Methoxy-6-methylbenzyl)-N'-(3-methylpyridin-2-yl)guanidine

In an analogous manner, 0.230 g (0.74 mmol) methyl N-(3-methylpyridin-2-yl)imidothiocarbamate hydroiodide was reacted with 0.154 g (0.820 mmol) 2-methoxy-6-methylbenzylamine hydrochloride, with the addition of 0.26 mL (1.49 mmol) diisopropylethylamine and acetonitrile as solvent, for 30 min at 90° C. in a CEM microwave (150 watts), and after workup and purification 0.111 g pure N-(2-methoxy-6-methylbenzyl)-N'-(3-methylpyridin-2-yl)guanidine was obtained in the form of the acetate salt (base/acetate in a 1:0.2 ratio).

ESI-MS [M+H$^+$]=285.15 Calculated for $C_{16}H_{20}N_4O$=284.36

Example 34

N-(2-Methoxybenzyl)-N'-pyridin-3-yl-guanidine acetate

Example 35

3-({Imino[(2-methoxybenzyl)amino]methyl}amino)-1-methylpyridinium acetate

34+35.1 Methyl N-pyridin-3-yl-imidothiocarbamate hydroiodide and 3-{[imino(methylthio)methyl]amino}-1-methylpyridinium iodide 1.20 g (7.83 mmol) N-pyridin-3-yl-thiourea was dissolved in 10 mL methanol with heating, and reacted with 0.98 mL (15.67 mmol) methyl iodide by stirring at room temperature for 48 hr. The precipitate which formed was filtered off and washed with pentane. It was possible to isolate a second crystallizate from the mother liquor, resulting in a total quantity of 1.32 g (4.361 mmol, 56%) as a mixture (1:1) of methyl N-pyridin-3-yl-imidothiocarbamate hydroiodide and 3-{[imino(methylthio)methyl]amino}-1-methylpyridinium iodide, which was used directly for the subsequent reaction without liberation from the iodide salt.

ESI-MS [M+H$^+$]=168.05 ESI-MS [M+H$^+$]=182.0
Calculated for $C_7H_9N_3S$=167.23 Calculated for $C_8H_{12}N_3S$=182.27

34+35.2 N-(2-Methoxybenzyl)-N'-pyridin-3-yl-guanidine acetate and 3-({imino[(2-methoxybenzyl)amino]methyl}amino)-1-methylpyridinium acetate For the subsequent reaction the mixture of 0.600 g (1.982 mmol) methyl N-pyridin-3-yl-imidothiocarbamate hydroiodide and 3-{[imino(methylthio)methyl]amino}-1-methylpyridinium iodide was combined with 0.335 g (2.44 mmol) 2-methoxybenzylamine, and 3 mL ethanol was added as solvent. The mixture was heated for 45 min at 90° C. in a CEM microwave (150 watts). The solvent was evaporated under vacuum, and the residue was dissolved in dichloromethane and combined with water. The phases were separated, and the aqueous phase was [extracted] with dichloromethane (2×50 mL). Lastly, the combined organic phases were washed with saturated sodium chloride solution (1×50 mL). This was followed by drying over magnesium sulfate and evaporation of the solvent, and purification via preparative HPLC (Merck Chromolith RP-18 100×25 mm, eluent: water/acetonitrile/0.1 M acetic acid, with a flow rate of 20 mL/min and with gradients of 10% to 30% of the acetonitrile fraction in 15 min), resulted in 12 mg pure N-(2-methoxybenzyl)-N'-pyridin-3-yl-guanidine acetate in the form of the acetate salt (base/acetate in a 1:1 ratio), in addition to 35 mg pure 3-({imino[(2-methoxybenzyl)amino]methyl}amino)-1-methylpyridinium acetate (base/acetate in a 1:1 ratio).

ESI-MS [M+H$^+$]=257.15 ESI-MS [M+H$^+$]=272.15
Calculated for $C_{14}H_{16}N_4O$=256.31 Calculated for $C_{15}H_{19}N_4O$=271.34

Example 36

N-(2-Methoxybenzyl)-N'-pyrimidin-2-yl-guanidine acetate 36.1 Methyl N-pyrimidin-2-yl-imidothiocarbamate 1.234 g (8.00 mmol) N-pyrimidin-2-yl-thiourea was dissolved in 30 mL dimethyl sulfoxide with heating, and 0.60 mL (9.60 mmol) iodomethane was added, resulting in the gradual formation of a clear yellowish solution. Stirring was performed for 36 hr. The solvent was removed under vacuum, and the remaining residue was diluted with water. To remove the secondary components the mixture was extracted with dichloromethane (2×100 mL), and the desired product remained in the aqueous phase. The aqueous phase was then purified by adsorptive filtration over an RP-18 column filled with silica gel. The aqueous phase was lyophilized and redissolved in a small amount of water, saturated with a sodium chloride solution, and adjusted to pH~10 with 1 N sodium hydroxide solution. The basic solution was extracted with acetic ester (5×70 mL), the combined organic phase was dried with magnesium sulfate, and the solvent was evaporated under vacuum. The desired product methyl N-pyrimidin-2-yl-imidothiocarbamate was obtained in a yield of 0.760 g (4.52 mmol, 57%).

ESI-MS [M+H$^+$]=169.05 Calculated for $C_6H_8N_4S$=168.22

36.2 N-(2-Methoxybenzyl)-N'-pyrimidin-2-yl-guanidine acetate 0.350 g (2.08 mmol) methyl N-pyrimidin-2-yl-imidothiocarbamate was dissolved in 4 mL ethanol, and 0.428 g (3.12 mmol) 2-methoxybenzylamine was added. The reaction mixture was heated for 30 min at 90° C. in a CEM microwave (100 watts). The solvent was removed under vacuum, and the crude product was then dissolved in acetonitrile/water and purified via preparative HPLC (Merck RP-18 Chromolith 100×25 mm, eluent: water/acetonitrile/0.1 M acetic acid, with a flow rate of 20 mL/min and with gradients of 10% to 50% of the acetonitrile fraction in 30 min). After purification of the clean fractions and lyophilization under vacuum, 0.21 g (0.666 mmol, 32%) N-(2-methoxybenzyl)-N'-pyrimidin-2-yl-guanidine was obtained in the form of the acetate salt (base/acetate in a ratio of 1:1).

ESI-MS [M+H$^+$]=258.15 Calculated for $C_{13}H_{15}N_5O$=257.30

Compound 37 was prepared analogously to Example 36 by the reaction of suitable starting materials.

Example 37

N-(2,6-Dimethoxybenzyl)-N'-pyrimidin-2-ylguanidine

Analogously to Example 36, 0.360 g (2.14 mmol) methyl N-pyrimidin-2-yl-imidothiocarbamate was reacted with 0.428 g (2.56 mmol) 2,6-dimethoxybenzylamine in 4 mL ethanol as solvent for 30 min at 90° C. in a CEM microwave (100 watts), whereupon the product began to crystallize from the reaction mixture. The solid was filtered off and washed with diethyl ether. The substance was purified by crystallizing again from ethanol, resulting in 0.377 g (1.38 mmol, 65%) pure N-(2,6-dimethoxybenzyl)-N'-pyrimidin-2-yl-guanidine.

ESI-MS [M+H$^+$]=288.15 Calculated for $C_{14}H_{17}N_5O_2$=287.32

Example 38

N-Isoquinolin-3-yl-N'-(2-methoxybenzyl)guanidine

38.1 N-Isoquinolin-3-yl-thiourea 0.618 g (3.47 mmol) N,N'-thiocarbonyldiimidazole was dissolved in 20 mL acetonitrile, and 0.500 g (3.47 mmol) isoquinoline-3-amine in the form of a suspension in 15 mL acetonitrile was added dropwise in portions. The clear orange solution which formed was stirred for 12 hr, whereupon a reddish precipitate formed. The intermediate product was directly reacted, without workup, with 0.535 g (6.940 mmol) ammonium acetate for 25 min at 85° C. in a CEM microwave (100 watts). The solvent was removed under vacuum. The residue was stirred in water, and the resulting precipitate was suctioned off and washed with water. For further purification the solid was taken up in 5 mL acetonitrile and combined with 50 mL diisopropyl ether. The precipitate was filtered again and dried in a vacuum drying oven at 40° C., resulting in the isolation of 0.540 g (2.647 mmol, 76%) purified N-isoquinolin-3-yl-thiourea.

ESI-MS [M+H$^+$]=204.15 Calculated for C$_{10}$H$_9$N$_3$S=203.27

38.2 Methy-N-isoquinolin-3-yl-imidothiocarbamate hydroiodide 0.400 g (1.160 mmol) N-isoquinolin-3-yl-thiourea was dissolved in 10 mL methanol and reacted with 0.197 mL (3.13 mmol) methyl iodide by stirring at room temperature for 12 hr. The solvent was removed under vacuum, and the residue was codistilled twice with dichloromethane. 0.86 g (2.48 mmol, 95%) methyl N-isoquinolin-3-yl-imidothiocarbamate hydroiodide was isolated and used directly for the subsequent reaction without liberation from the salt.

ESI-MS [M+H$^+$]=218.15 Calculated for C$_{11}$H$_{11}$N$_3$S=217.29

38.3 N-isoquinolin-3-yl-N'-(2-methoxybenzyl)guanidine acetate

For the subsequent reaction, 0.400 g (1.160 mmol) methyl N-isoquinolin-3-yl-imidothiocarbamate hydroiodide was combined with 0.175 g (1.270 mmol) 2-methoxybenzylamine, and 0.30 mL (1.74 mmol) diisopropylethylamine as auxiliary base and 5 mL ethanol as solvent were added. The mixture was heated for 20 min at 80° C. in a CEM microwave (100 watts). The solvent was evaporated under vacuum, and the residue was dissolved in dichloromethane, extracted with water (1×50 mL) and adjusted to neutral pH with 1 N sodium hydroxide solution (1×50 mL), and finally washed with water (1×50 mL). After drying over magnesium sulfate and removal of the solvent under vacuum, purification was performed via preparative HPLC (Merck Chromolith RP-18 100×25 mm, eluent: water/acetonitrile/0.1 M acetic acid, with a flow rate of 20 mL/min and with gradients of 10% to 30% of the acetonitrile fraction in 15 min), resulting in 0.111 g pure N-isoquinolin-3-yl-N'-(2-methoxybenzyl)guanidine in the form of the acetate salt (base/acetate in a ratio of 1:0.6).

ESI-MS [M+H$^+$]=307.15 Calculated for C$_{18}$H$_{18}$N$_4$O=306.37

Compound 39 was prepared analogously to Example 38 by the reaction of suitable starting materials.

Example 39

N-(2,6-Dimethoxybenzyl)-N'-isoquinolin-3-ylguanidine

Analogously to Example 38, 0.400 g (1.160 mmol) methyl N-isoquinolin-3-yl-imidothiocarbamate hydroiodide was reacted with 0.213 g (1.270 mmol) 2,6-dimethoxybenzylamine, with the addition of 0.30 mL (1.74 mmol) diisopropylethylamine and ethanol as solvent, for 20 min at 85° C. in a CEM microwave (100 watts) under a nitrogen atmosphere, and after workup and purification 0.070 g pure N-(2,6-dimethoxybenzyl)-N'-isoquinolin-3-yl-guanidine was obtained via preparative HPLC.

ESI-MS [M+H$^+$]=337.15 Calculated for C$_{19}$H$_{20}$N$_4$O$_2$=336.40

Example 40

N-(2-Methoxybenzyl)-N'-quinolin-2-yl-guanidine acetate

40.1 N-Quinolin-2-yl-thiourea 1.496 g (8.394 mmol) N,N'-thiocarbonyldiimidazole was dissolved in 30 mL acetonitrile, and 1.210 g (8.394 mmol) 2-amino-quinoline dissolved in 15 mL acetonitrile was added dropwise at room temperature. After 1 hr a precipitate deposited, and stirring was performed for an additional 12 hr. The solid was filtered off, and without further purification was reacted directly with 1.294 g (16.789 mmol) ammonium acetate in 50 mL methanol for 5 hr at 40° C. After mass spectrometric analysis the solvent was removed under vacuum, and the batch was dissolved in dichloromethane and shaken out with water (1×50 mL). The organic phase was dried over magnesium sulfate and filtered, and the solvent was removed under vacuum. The crude product was purified by column chromatography on silica gel (column Ø=3 cm, h=15 cm), first with dichloromethane as eluent, then with methanol to increase the polarity, and finally with pure methanol. The clean fraction was purified and the solvent was removed under vacuum, resulting in a total of 0.70 g (3.445 mmol, 41%) N-quinolin-2-yl-thiourea.

ESI-MS [M+H$^+$]=204.15 Calculated for C$_{10}$H$_9$N$_3$S=203.27

40.2 Methyl N-quinolin-2-yl-imidothiocarbamate hydroiodide 0.700 g (3.445 mmol) N-quinolin-2-yl-thiourea was dissolved in 15 mL methanol and reacted with 0.260 mL (4.130 mmol) methyl iodide by stirring at room temperature for 12 hr. The solvent was removed under vacuum, and 1.00 g (2.90 mmol, 84%) methyl N-quinolin-2-yl-imidothiocarbamate hydroiodide was isolated and used directly for the subsequent reaction without liberation from the salt.

ESI-MS [M+H$^+$]=218.05 Calculated for C$_{11}$H$_{11}$N$_3$S=217.29

40.3 N-(2-methoxybenzyl)-N'-quinolin-2-yl-guanidine acetate

For the subsequent reaction, 0.333 g (0.96 mmol) methyl N-quinolin-2-yl-imidothiocarbamate hydroiodide was correspondingly suspended in 5 mL ethanol and then combined with 0.33 mL (1.93 mmol) diisopropylethylamine as auxiliary base and with 0.154 mL (1.16 mmol) 2-methoxybenzylamine. The mixture was heated for 30 min at 90° C. in a CEM microwave (150 watts). The solvent was evaporated under vacuum, and the residue was dissolved in dichloromethane, adjusted to neutral pH with 1 N sodium hydroxide solution (1×50 mL), and finally washed with water (1×50 mL). After drying over magnesium sulfate and removal of the solvent under vacuum, purification was performed via preparative HPLC (Merck Chromolith RP-18 100×25 mm, eluent: water/acetonitrile/0.1 M acetic acid, with a flow rate of 20 mL/min and with gradients of 5% to 30% of the acetonitrile fraction in 15 min), resulting in 0.181 g pure N-(2-methoxybenzyl)-N-quinolin-2-yl-guanidine in the form of the acetate salt (base/acetate in a ratio of 1:1.1).

10 ESI-MS [M+H$^+$]=307.15 Calculated for C$_{18}$H$_{18}$N$_4$O=306.37

Compound 41 was prepared analogously to Example 40 by the reaction of suitable starting materials.

Example 41

N-(2,6-Dimethoxybenzyl)-N'-quinolin-2-yl-guanidine acetate

Analogously to Example 40, 0.333 g (0.96 mmol) methyl N-quinolin-2-yl-imidothiocarbamate hydroiodide was correspondingly reacted with 0.197 g (1.16 mmol) 2,6-dimethoxybenzylamine, with the addition of 0.33 mL (1.93 mmol) diisopropylethylamine and ethanol as solvent, for 30 min at 90° C. in a CEM microwave (150 watts), and after workup and purification preparative HPLC was used to obtain 0.178 g pure N-(2,6-dimethoxybenzyl)-N-quinolin-2-yl-guanidine in the form of the acetate salt (base/acetate in a ratio of 1:1.1).

ESI-MS [M+H$^+$]=337.15 Calculated for $C_{19}H_{20}N_4O_2$=336.40

Example 42

N-(6-Bromopyridin-2-yl)-N'-(2-methoxybenzyl) guanidine

42.1 N-{[(6-Bromopyridin-2-yl)amino] carbonothioyl}benzamide 2.604 g (14.75 mmol) 2-amino-6-bromopyridine was dissolved in 20 mL acetone, and 2.02 mL (14.75 mmol) undiluted benzoyl isothiocyanate was then added dropwise. The solution turned a brown color. The reaction mixture was then heated for 2 hr at 65° C. (oil bath temperature) with stirring. The light yellow solid which formed was filtered under vacuum and washed with pentane. The solvent of the mother liquor was also removed under vacuum. The resulting solids from the crystallizate (1.338 g) and from the mother liquor (3.595 g) were identical according to thin-layer chromatography (silica gel, eluents: dichloromethane/methanol (9:1)). A total of 4.933 g (14.67 mmol, 99.5%) N-{[(6-bromopyridin-2-yl)amino]carbonothioyl}benzamide was isolated.

ESI-MS [M+H$^+$]=335.05/337.05 Calculated for $C_{13}H_{10}BrN_3OS$=336.21

42.2 N-(6-Bromopyridin-2-yl)thiourea 4.933 g (14.67 mmol) N-{[(6-bromopyridin-2-yl)amino]carbonothioyl}benzamide was suspended in 40 mL methanol and additionally combined with 7 mL acetone. After addition of 1 N sodium hydroxide solution (40.0 mmol) the reaction mixture became completely clear with a light brown color. The mixture was heated for 40 min at 65° C. (oil bath temperature) and then stirred for 1 hr at room temperature. A solid crystallized out. The organic solvent was removed under vacuum, and after cooling on an ice bath the solid was filtered off and washed with water. The solid was dried over phosphorus pentoxide in a dessicator under high vacuum (4×10 mbar). The desired product N-(6-bromopyridin-2-yl)thiourea was obtained in the form of colorless needles in a yield of 3.158 g (13.61 mmol, 93%).

ESI-MS [M+H$^+$]=231.95/233.9 Calculated for $C_6H_6BrN_3S$=232.10

42.3 N-(6-Bromopyridin-2-yl)-N'-(2-methoxybenzyl)guanidine 0.87 mL (1384 mmol) methyl iodide diluted in 2 mL methanol was added dropwise to 2.00 g (8.65 mmol) N-(6-bromopyridin-2-yl)thiourea suspended in 30 mL methanol, and the mixture was heated for 1.45 hr under reflux. The reaction mixture was in solution. The methylated intermediate product, consisting of methyl N-(6-bromopyridin-2-yl)imidothiocarbamate hydroiodide (ESI-MS [M+H$^+$]=247.85 calculated for $C_7H_8BrN_3S$=246), was freed of solvent under vacuum. The intermediate product was then suspended in 25 mL ethanol, and after addition of 2.37 mL (18.168 mmol) 2-methoxybenzylamine was heated for 3 hr under reflux, whereupon the solid completely dissolved. For workup the solvent was removed under vacuum, and the crude mixture was taken up in dichloromethane. Extraction was performed with water (2×100 mL) and with 2 N sodium hydroxide solution (1×100 mL) to liberate the iodide salt. Subsequent washing of the organic phase with water (1×100 mL), drying over magnesium sulfate, and evaporation of the solvent under vacuum resulted in a light brown-yellow oil, from which a colorless crystallizate was isolated from dichloromethane/pentane in a refrigerator at 5° C. Further fractionated crystallization in acetonitrile/water resulted in a total of 2.18 g (6.50 mmol, 75%) N-(6-bromopyridin-2-yl)-N'-(2-methoxybenzyl)guanidine.

ESI-MS [M+H$^+$]=337.05/335.05 Calculated for $C_{14}H_{15}BrN_4O$=335.21

Example 43

N-(6-Bromopyridin-2-yl)-N'-(2,6-dimethoxybenzyl) guanidine 0.37 mL (5.89 mmol) methyl iodide diluted in 2 mL methanol was added dropwise to 1.032 g (4.46 mmol) N-(6-bromopyridin-2-yl)thiourea suspended in 30 mL methanol, and the mixture was heated for 2 hr under reflux. The reaction mixture was in solution. The methylated intermediate product, consisting of methyl N-(6-bromopyridin-2-yl)imidothiocarbamate hydroiodide (ESI-MS [M+H$^+$]=247.85 calculated for $C_7H_8BrN_3S$=246), was freed of solvent under vacuum. The intermediate product was then suspended in 30 mL ethanol, and 1.122 g (6.442 mmol) 2,6-dimethoxybenzylamine was added, whereupon the solid completely dissolved. The mixture was then heated for 2.25 hr under reflux. The colorless solid which precipitated was suctioned off and washed with ethanol. 1.197 g N-(6-bromopyridin-2-yl)-N'-(2,6-dimethoxybenzyl)guanidine was obtained as crude product. Repeated crystallization from acetonitrile/water resulted in the isolation of 1.311 g (3.589 mmol, 81%) N-(6-bromopyridin-2-yl)-N-(2,6-dimethoxybenzyl)guanidine, which was also used for the subsequent reaction and derivatizations.

ESI-MS [M+H$^+$]=337.05/335.05 Calculated for $C_{15}H_{17}BrN_4O_2$=365.23

Example 44

N-(4-Bromopyridin-2-yl)-N'-(2,6-dimethoxybenzyl) guanidine

44.1 N-{[(4-Bromopyridin-2-yl)amino] carbonothioyl}benzamide 2.500 g (14.01 mmol) 4-bromopyridine-2-amine was dissolved in 20 mL acetone, and 1.92 mL (14.01 mmol) undiluted benzoyl isothiocyanate was added dropwise. The solution turned an orange color. The reaction mixture was then heated for 1 hr under reflux with stirring. Half of the added quantity of acetone was removed under vacuum, and the precipitated solid was filtered under vacuum and washed with diethyl ether. After drying of the crystallizate, 3.500 g (10.410 mmol, 74%) pure N-{[(4-bromopyridin-2-yl)amino]carbonothioyl}benzamide was obtained which was directly used for further reaction.

ESI-MS [M+H$^+$]=335.95/337.95 Calculated for $C_{13}H_{10}BrN_3OS$=336.21

44.2 N-(4-Bromopyridin-2-yl)thiourea 3.500 g (10.41 mmol) N-{[(4-bromopyridin-2-yl)amino]carbonothioyl}benzamide was suspended in 30 mL methanol. After addition of 1 N sodium hydroxide solution (11.55 mmol) the reaction became completely clear. The mixture was heated under reflux for 60 min. Most of the methanol was removed under vacuum and the residue was taken up in water, whereupon a solid crystallized out. The solid was filtered and washed with water. The solid was dried in a vacuum drying oven at 20 mbar. 1.960 g (8.445 mmol, 81%) of the desired product N-(4-bromopyridin-2-yl)thiourea was isolated.

ESI-MS [M+H$^+$]=231.85/233.95 Calculated for $C_6H_6BrN_3S$=232.10

44.3 Methyl N-(4-bromopyridin-2-yl)imidothiocarbamate hydroiodide 0.64 mL (10.133 mmol) methyl iodide diluted in 5 mL methanol was added dropwise to 1.960 g (8.445 mmol) N-(4-bromopyridin-2-yl)thiourea in 30 mL methanol. The mixture was then heated under reflux for 90 min, and the reaction solution became completely clear. The course of the reaction was tracked by mass spectrometry. The solvent was removed under vacuum, and the methylated intermediate product consisting of 2.920 (7.807 mmol, 93%) methyl N-(4-bromopyridin-2-yl)imidothiocarbamate hydroiodide was directly reacted without purification.

ESI-MS [M+H$^+$]=245.95/247.95 Calculated for $C_7H_8BrN_3S$=246.13

44.4 N-(4-Bromopyridin-2-yl)-N'-(2,6-dimethoxybenzyl)guanidine 1.460 g (3.903 mmol) methyl N-(4-bromopyridin-2-yl)imidothiocarbamate hydroiodide was placed in 25 mL ethanol, and after addition of 0.830 g (4.765 mmol) 2,6-dimethoxybenzylamine was heated for 3.5 hr at 90° C. (oil bath temperature). Completion of the reaction was determined by mass spectrometry, and the ethanol was then removed under vacuum. The crude mixture was taken up in dichloromethane and extracted with water (1×100 mL) and with 1 N sodium hydroxide solution (1×100 mL) to free the product from hydroiodide possibly present. Extraction with water (1×100 mL) was performed again, followed by drying over magnesium sulfate and evaporation of the solvent under vacuum. For purification the crude mixture was suspended again in a small amount of dichloromethane and overlayered with diethyl ether and pentane to crystallize the product once again. The crystallizate was filtered off and washed with pentane. A total of 0.799 g (2.190 mmol, 56%) N-(4-bromopyridin-2-yl)-N-(2,6-dimethoxybenzyl) guanidine was obtained.

ESI-MS [M+H$^+$]=365.05/367.05 Calculated for $C_{15}H_{17}BrN_4O_2$=365.23

Compounds 45, 46, and 47 were prepared analogously to Example 44 by the reaction of suitable starting materials of formulas II and IV.

Example 45

N-(4-Bromopyridin-2-yl)-N'-(2-methoxybenzyl)guanidine

Analogously to Example 44, 1.460 g (3.903 mmol) methyl N-(4-bromopyridin-2-yl)imidothiocarbamate hydroiodide was correspondingly reacted with 0.68 mL (5.074 mmol) 2-methoxybenzylamine in 25 mL ethanol as solvent by heating for 3.5 hr at 90° C. (oil bath temperature), and after workup and purification by fractionated crystallization 0.897 g (2.675 mmol, 69%) pure N-(4-bromopyridin-2-yl)-N'-(2-methoxybenzyl)guanidine was obtained from diethyl ether and pentane.

ESI-MS [M+H$^+$]=335.05/337.05 Calculated for $C_{14}H_{15}BrN_4O$=335.21

Example 46

N-(3-Bromopyridin-2-yl)-N'-(2,6-dimethoxybenzyl)guanidine acetate

Analogously to Example 44, 2.480 g (6.630 mmol) methyl N-(3-bromopyridin-2-yl)imidothiocarbamate hydroiodide was correspondingly reacted with 1.441 g (8.619 mmol) 2,6-dimethoxybenzylamine in 30 mL ethanol as solvent by heating for 3 hr at 90° C. (oil bath temperature), and after appropriate workup and purification 2.77 g (6.513 mmol, 98%) N-(3-bromopyridin-2-yl)-N'-(2,6-dimethoxybenzyl)guanidine was initially obtained by crystallization from dichloromethane, followed by purification via preparative HPLC (Waters, XTerra RP-18, eluent: water/acetonitrile/0.1 M acetic acid, with a flow rate of 30 mL/min and with gradients of 10% to 30% of the acetonitrile fraction in 20 min), resulting in 1.210 g (2.851 mmol, 43%) of N-(3-bromopyridin-2-yl)-N'-(2,6-dimethoxybenzyl)guanidine of high purity in the form of the acetate salt (base/acetate in a ratio of 1:0.6).

ESI-MS [M+H$^+$]=365.05/367.05 Calculated for $C_{15}H_{17}BrN_4O_2$=365.23

Example 47

N-(3-Bromopyridin-2-yl)-N'-(2-methoxybenzyl)guanidine acetate

Analogously to Example 44, 2.480 g (6.630 mmol) methyl N-(3-bromopyridin-2-yl)imidothiocarbamate hydroiodide was correspondingly reacted with 1.15 mL (8.620 mmol) 2-methoxybenzylamine in 30 mL ethanol as solvent by heating for 3 hr at 90° C. (oil bath temperature), and after appropriate workup the purification in this case was performed not by crystallization, but via preparative HPLC (Waters, XTerra RP-18, eluent: water/acetonitrile/0.1 M acetic acid, with a flow rate of 30 mL/min and with gradients of 10% to 30% of the acetonitrile fraction in 20 min), resulting in a total of 1.61 g (4.073 mmol, 61%) of N-(3-bromopyridin-2-yl)-N'-(2-methoxybenzyl)guanidine of high purity in the form of the acetate salt (base/acetate in a ratio of 1:1).

ESI-MS [M+H$^+$]=335.05/337.05 Calculated for $C_{14}H_{15}BrN_4O$=335.21

Example 48

N-(2-Methoxybenzyl)-N'-{6-[4-(trifluoromethoxy)phenyl]pyridin-2-yl}guanidine 0.202 g (0.604 mmol) N-(6-bromopyridin-2-yl)-N-(2-methoxybenzyl)guanidine, 0.161 g (0.781 mmol) [4-(trifluoromethoxy)phenyl]boric acid, 0.192 g (1.811 mmol) sodium carbonate, and 0.035 g (0.030 mmol) tetrakis-(triphenylphosphine)palladium(0) were combined and added to 7.0 mL of a solvent mixture of 1,2-dimethoxyethane/water/ethanol (7:3:2). The mixture was degassed under a strong nitrogen stream and completely reacted by heating for 60 min at 120° C. in a CEM microwave (230 watts). After the reaction mixture was completely placed in solution by addition of dichloromethane, methanol, and water it was filtered over a Millipore filter (Ø=25 mm, 0.45 µm), and the solvent was removed under vacuum. When the residue was redissolved in acetonitrile/water, the yellow solid which precipitated was suctioned off and washed with water. After drying, 0.211 g (0.504 mmol, 15 84%) of a yellow powder was obtained.

ESI-MS [M+H$^+$]=417.2 Calculated for $C_{21}H_{19}F_3N_4O_2$=416.41

Compounds 49 and 50 were prepared analogously to Example 48 by the reaction of suitable starting materials.

Example 49

N-(2-Methoxybenzyl)-N'-[6-(2-thienyl)pyridin-2-yl]guanidine

The preparation was carried out analogously to Example 48, using 0.202 g (0.604 mmol) N-(6-bromopyridin-2-yl)-N'-(2-methoxybenzyl)guanidine, 0.111 g (0.865 mmol) thiophene-2-boric acid, 0.192 g (1.811 mmol) sodium carbonate, and 0.035 g (0.030 mmol) tetrakis-(triphenylphosphine)palladium(0). The mixture was likewise heated for 60 min at 120° C. in a CEM microwave (230 watts). After filtration over a Millipore filter (Ø=25 mm, 0.45 µm) the light brown, viscous crude product was combined with 150 mL water and extracted with dichloromethane (2×100 mL), the combined organic phases were washed with water (1×150 mL) and dried over magnesium sulfate, and the solvent was removed under vacuum. Repeated dissolution, first in methanol and then in acetonitrile, filtration of insoluble residue in each case, and extraction from isopropyl ether resulted in 0.150 g (0.443 mmol, 74%) of a light yellow solid of N-(2-methoxybenzyl)-N'-[6-(2-thienyl)pyridin-2-yl]guanidine.

ESI-MS [M+H$^+$]=339.1 Calculated for $C_{18}H_{18}N_4OS$=338.43

Example 50

N-[6-(4-Fluorophenyl)pyridin-2-yl]-N'-(2-methoxybenzyl)guanidine

The preparation was carried out analogously to Example 48, using 0.202 g (0.604 mmol) N-(6-bromopyridin-2-yl)-N'-(2-methoxybenzyl)guanidine, 0.121 g (0.863 mmol) (4-fluorophenyl)boric acid, 0.192 g (1.811 mmol) sodium carbonate, and 0.035 g (0.030 mmol) tetrakis-(triphenylphosphine)palladium(0). The mixture was likewise heated for 60 min at 120° C. in a CEM microwave (230 watts). After filtration over a Millipore filter a beige solid precipitated, which was purified by fractionated crystallization from acetonitrile and water to obtain 0.115 g (0.295 mmol, 49%) of product N-[6-(4-fluorophenyl)pyridin-2-yl]-N'-(2-methoxybenzyl)guanidine.

ESI-MS [M+H$^+$]=351.2 Calculated for $C_{20}H_{19}FN_4O$=350.40

Example 51

N-(2-Methoxybenzyl)-N'-(6-phenylpyridin-2-yl)guanidine acetate 0.203 g (0.606 mmol) N-(6-bromopyridin-2-yl)-N'-(2-methoxybenzyl)guanidine, 0.105 g (0.835 mmol) phenylboric acid, 0.164 g (1.547 mmol) sodium carbonate, and 0.053 g (0.061 mmol) [1,1'-bis-(diphenylphosphino)ferrocene]palladium(II) chloride-methylene chloride were combined and added to 7.0 mL of a solvent mixture of 1,2-dimethoxyethane/water/ethanol (7:3:2). The mixture was degassed under a strong nitrogen stream and reacted by heating for 60 min at 120° C. in a CEM microwave (200 watts). The solvent was removed under vacuum. After an attempt was made to take up the residue in acetonitrile/water a brown-black mass flocculated, which was filtered off. The filtered solution was further diluted with 100 mL water and extracted with dichloromethane (2×100 mL). The combined organic phases were washed again with water and dried over magnesium sulfate, and the solvent was evaporated. The brown, oily residue was purified via preparative HPLC (Merck Chromolith RP-18 100×25 mm, eluent: water/acetonitrile/0.1 M acetic acid). The fractions containing pure product were combined and lyophilized with freeze drying, resulting in 0.051 g N-(2-methoxybenzyl)-N'-(6-phenylpyridin-2-yl)guanidine in the form of the acetate salt (base/acetate in a ratio of 1:1.4).

ESI-MS [M+H$^+$]=332.9 Calculated for $C_{20}H_{20}N_4O$=332.41

Example 52

N-(6-Cyanopyridin-2-yl)-N'-(2-methoxybenzyl)guanidine acetate 0.202 g (0.604 mmol) N-(6-bromopyridin-2-yl)-N'-(2-methoxybenzyl)guanidine, 0.034 g (0.030 mmol) tetrakis-(triphenylphosphine)palladium(0), 0.192 g (1.811 mmol) sodium carbonate, and 0.07 g (0.596 mmol) zinc(II) cyanide were combined and added to 7.0 mL tetrahydrofuran. The mixture was degassed under a strong nitrogen stream and heated for 90 min at 140° C. in a CEM microwave (300 watts), and then for 60 min at 140° C. (300 watts). Since completion of the reaction was not observed, the mixture was combined with 0.14 g zinc(II) cyanide (total quantity 0.21 g, 1.789 mmol) and heated for an additional 90 min at 140° C. in a CEM microwave (300 watts). The reaction mixture was diluted by adding dichloromethane, extracted with water (3×150 mL), and dried over magnesium sulfate. During an attempt to dilute in acetonitrile, the yellow oil isolated after removal of the solvent precipitated a solid, which was filtered off but contained no product. The mother liquor was purified via preparative HPLC (Merck Chromolith RP-18 100×25 mm, eluent: water/acetonitrile/0.1 M acetic acid), and the desired product 0.031 g N-(6-cyanopyridin-2-yl)-N'-(2-methoxybenzyl)guanidine of high purity was obtained in the form of the acetate salt (base/acetate in a ratio of 1:0.7).

ESI-MS [M+H$^+$]=281.9 Calculated for $C_{15}H_{15}N_5O$=281.32

Example 53

N-(2,6-Dimethoxybenzyl)-N'-(6-phenylpyridin-2-yl)guanidine acetate 0.251 g (0.688 mmol) N-(6-bromopyridin-2-yl)-N'-(2,6-dimethoxybenzyl)guanidine, 0.250 g (2.050 mmol) phenylboric acid, 0.567 g (5.357 mmol) sodium carbonate, and 0.082 g (0.071 mmol) tetrakis-(triphenylphosphine)palladium(0) were reacted in 1,2-dimethoxyethane/water/ethanol (7:3:2) in a CEM microwave. After filtration and removal of the solvent under vacuum the product was precipitated from acetonitrile/water with the addition of acetic acid. The triphenylphosphine oxide which formed was leached out by thoroughly stirring the solid in water. 17.7 mg N-(2,6-dimethoxybenzyl)-N'-(6-phenylpyridin-2-yl)guanidine was obtained as a yellow solid in the form of the acetate salt (base/acetate in a ratio of 1:1.6).

ESI-MS [M+H$^+$]=363.15 Calculated for C$_{21}$H$_{22}$N$_4$O$_2$=362.44

Example 54

N-(2,6-Dimethoxybenzyl)-N'-[6-(4-fluorophenyl)pyridin-2-yl]guanidine 0.254 g (0.695 mmol) N-(6-bromopyridin-2-yl)-N'-(2,6-dimethoxybenzyl)guanidine, 0.128 g (0.913 mmol) 4-fluorophenylboric acid, 0.239 g (2.258 mmol) sodium carbonate, and 0.055 g (0.047 mmol) tetrakis-(triphenylphosphine)palladium(0) were heated to 110° C. in 1,2-dimethoxyethane/water/ethanol (7:3:2) in a reaction block (Variomag, Telemodul 40 CT) at standard pressure. Upon cooling of the reaction mixture a yellow solid precipitated, which was suctioned off and washed with water. After the yellow solid was dissolved in methanol and dichloromethane the catalyst was separated via a Millipore filter (Ø=25 mm, 0.45 μm). The target product N-(2,6-dimethoxybenzyl)-N'-[6-(4-fluorophenyl)pyridin-2-yl]guanidine was in the pure form after the removal of solvent, and the yield was 0.214 g (0.563 mmol, 81%).

ESI-MS [M+H$^+$]=381.15 Calculated for C$_{21}$H$_{21}$FN$_4$O$_2$=380.43

Example 55

N-(6-Cyanopyridin-2-yl)-N'-(2,6-dimethoxybenzyl)guanidine acetate 0.257 g (0.703 mmol) N-(6-bromopyridin-2-yl)-N'-(2,6-dimethoxybenzyl)guanidine, 0.043 g (0.037 mmol) tetrakis-(triphenylphosphine)palladium(0), 0.254 g (2.394 mmol) sodium carbonate, and 0.083 g (0.707 mmol) zinc(II) cyanide were combined and added to 7.0 mL tetrahydrofuran. The mixture was degassed under a strong nitrogen stream and heated for 90 min at 120° C. in a CEM microwave (300 watts), and then for 90 min at 160° C. (300 watts) with "heating by cooling." Since completion of the reaction was not observed, the mixture was combined with 0.092 g zinc(II) cyanide (total quantity 0.175 g, 1.491 mmol) and heated for an additional 90 min at 150° C. in a CEM microwave (300 watts). Due to the slow reaction speed, it was necessary to perform conventional heating in the reaction block (Variomag, Telemodul 40 CT) for 20 hr under reflux. The reaction mixture was worked up by adding diluted dichloromethane and extracting with water (1×150 mL), combining the separated aqueous phase with 2 N sodium hydroxide solution, and shaking out again with dichloromethane (2×100 mL). The combined organic phases were then washed with water (1×150 mL) and dried over magnesium sulfate. The crude product was purified via preparative HPLC (Merck Chromolith RP-18 100×25 mm, eluent: water/acetonitrile/0.1 M acetic acid), and the desired product, 15 mg (0.048 mmol, 7%) N-(6-cyanopyridin-2-yl)-N'-(2,6-dimethoxybenzyl)guanidine, was obtained in high purity in the form of the acetate salt (base/acetate in a ratio of 1:1).

ESI-MS [M+H$^+$]=312.15 Calculated for C$_{16}$H$_{17}$N$_5$O$_2$=311.35

Example 56

N-(2,6-Dimethoxybenzyl)-N'-(4-phenylpyridin-2-yl)guanidine diacetate 0.160 g (0.438 mmol) N-(4-bromopyridin-2-yl)-N'-(2,6-dimethoxybenzyl)guanidine, 0.080 g (0.657 mmol) phenylboric acid, 0.139 g (1.314 mmol) sodium carbonate, and 0.035 g (0.031 mmol) tetrakis-(triphenylphosphine)palladium(0) were combined in this order and added to 15.0 mL of a solvent mixture of 1,2-dimethoxyethane/water/ethanol (7:3:2). The mixture was degassed under a strong nitrogen stream and conventionally heated in a reaction block (Variomag, Telemodul 40 CT) by heating for 18.5 hr at 110° C. According to mass spectrometric analysis, a completely new product and the triphenylphosphine oxide had been formed from the catalyst. The reaction mixture was diluted with dichloromethane and first extracted with water (1×50 mL). The separated aqueous phase was shaken with additional dichloromethane (1×30 mL), and the combined organic phases were extracted with 1 N sodium hydroxide solution (1×50 mL) and with water (2×50 mL). After drying over magnesium sulfate the solvent was evaporated under vacuum. The residue (264 mg) was dissolved in acetonitrile/water (1:1) and purified via preparative HPLC (Merck Chromolith RP-18 100×25 mm, eluent: water/acetonitrile/0.1 M acetic acid, with a flow rate of 20 mL/min and with gradients of 10% to 30% of the acetonitrile fraction in 20 min). The fractions containing pure product were combined and lyophilized with freeze drying, resulting in 0.086 g N-(2,6-dimethoxybenzyl)-N'-(4-phenylpyridin-2-yl)guanidine, with severe losses in yield because of the necessity for two HPLC purification procedures, in the form of the acetate salt (base/acetate in a ratio of 1:1.6).

ESI-MS [M+H$^+$]=363.15 Calculated for C$_{21}$H$_{22}$N$_4$O$_2$=362.44

Compounds 58, 57, 59, 60, 61, 62 and 63 were prepared analogously to Example 56 by the reaction of suitable starting materials.

Example 57

N-(2,6-Dimethoxybenzyl)-N'-[4-(4-fluorophenyl)pyridin-2-yl]guanidine acetate

The preparation was carried out analogously to Example 56, using 0.160 g (0.438 mmol) N-(4-bromopyridin-2-yl)-N'-(2,6-dimethoxybenzyl)guanidine, 0.091 g (0.657 mmol) (4-fluorophenyl)boric acid, 0.139 g (1.314 mmol) sodium carbonate, and 0.035 g (0.031 mmol) tetrakis-(triphenylphosphine)palladium(0). The mixture was likewise heated in a reaction block for 18.5 hr at 110° C. under a nitrogen atmosphere. After appropriate workup and purification via preparative HPLC, 106.5 mg (0.242 mmol, 55%) pure N-(2,6-dimethoxybenzyl)-N'-[4-(4-fluorophenyl)pyridin-2-yl]guanidine was obtained in the form of the acetate salt (base/acetate in a ratio of 1:1).

ESI-MS [M+H$^+$]=381.15 Calculated for C$_{21}$H$_{21}$FN$_4$O$_2$=380.43

Example 58

N-(2-Methoxybenzyl)-N'-(4-phenylpyridin-2-yl)guanidine acetate

The preparation was carried out analogously to Example 56, using 0.150 g (0.447 mmol) N-(4-bromopyridin-2-yl)-N'-(2-methoxybenzyl)guanidine, 0.081 g (0.651 mmol) phenylboric acid, 0.142 g (1.343 mmol) sodium carbonate, and 0.036 g (0.031 mmol) tetrakis-(triphenylphosphine)palladium(0). The mixture was likewise heated in a reaction block for 17.5 hr at 110° C. under a nitrogen atmosphere. After appropriate workup and purification via preparative HPLC, 52 mg pure N-(2-methoxybenzyl)-N'-(4-phenylpyridin-2-yl)guanidine was obtained in the form of the acetate salt (base/acetate in a ratio of 1:1.2).

ESI-MS [M+H$^+$]=333.15 Calculated for C$_{20}$H$_{20}$N$_4$O=332.41

Example 59

N-[4-(4-Fluorophenyl)pyridin-2-yl]-N'-(2-methoxybenzyl)guanidine acetate

The preparation was carried out analogously to Example 56, using 0.150 g (0.447 mmol) N-(4-bromopyridin-2-yl)-N'-(2-methoxybenzyl)guanidine, 0.093 g (0.671 mmol) (4-fluorophenyl)boric acid, 0.142 g (1.343 mmol) sodium carbonate, and 0.036 g (0.031 mmol) tetrakis-(triphenylphosphine)palladium(0). The mixture was likewise heated in a reaction block for 17.5 hr at 110° C. under a nitrogen atmosphere. After appropriate workup and purification via preparative HPLC, 50.9 mg (0.124 mmol, 27%) pure N-[4-(4-fluorophenyl)pyridin-2-yl]-N'-(2-methoxybenzyl)guanidine was obtained in the form of the acetate salt (base/acetate in a ratio of 1:1).

ESI-MS [M+H$^+$]=351.15 Calculated for C$_{20}$H$_{19}$FN$_4$O=350.40

Example 60

N-(2,6-Dimethoxybenzyl)-N'-(3-phenylpyridin-2-yl)guanidine acetate

The preparation was carried out analogously to Example 56, using 0.200 g (0.470 mmol) N-(3-bromopyridin-2-yl)-N'-(2,6-dimethoxybenzyl)guanidine acetate, 0.086 g (0.705 mmol) phenylboric acid, 0.149 g (1.411 mmol) sodium carbonate, and 0.038 g (0.033 mmol) tetrakis-(triphenylphosphine)palladium(0). The mixture was likewise heated in a reaction block for 20 hr at 110° C. under a nitrogen atmosphere. However, after this reaction time the starting material/product ratio was still 1:1. Therefore, further heating was performed for 16 hr, and then for an additional 25 hr. After a total reaction time of 61 hr the reaction was terminated due to increasing formation of by-products. After appropriate workup and purification via preparative HPLC, 41 mg pure N-(2,6-dimethoxybenzyl)-N'-(3-phenylpyridin-2-yl)guanidine was obtained in the form of the acetate salt (base/acetate in a ratio of 1:1.2).

ESI-MS [M+H$^+$]=363.15 Calculated for C$_{21}$H$_{22}$N$_4$O$_2$=362.44

Example 61

N-(2,6-Dimethoxybenzyl)-N'-(3-(4-fluorophenyl)pyridin-2-yl)guanidine acetate

The preparation was carried out analogously to Example 56, using 0.200 g (0.470 mmol) N-(3-bromopyridin-2-yl)-N'-(2,6-dimethoxybenzyl)guanidine acetate, 0.099 g (0.705 mmol) (4-fluorophenyl)boric acid, 0.149 g (1.411 mmol) sodium carbonate, and 0.038 g (0.033 mmol) tetrakis-(triphenylphosphine)palladium(0). The mixture was likewise heated in a reaction block for 24 hr at 110° C. under a nitrogen atmosphere. After appropriate workup and purification via preparative HPLC, 65 mg (0.147 mmol, 31%) pure N-(2,6-dimethoxybenzyl)-N'-[3-(4-fluorophenyl)pyridin-2-yl]guanidine was obtained in the form of the acetate salt (base/acetate in a ratio of 1:1).

ESI-MS [M+H$^+$]=381.15 Calculated for C$_{21}$H$_{21}$FN$_4$O$_2$=380.43

Example 62

N-(2-Methoxybenzyl)-N'-(3-phenylpyridin-2-yl)guanidine acetate

The preparation was carried out analogously to Example 56, using 0.200 g (0.506 mmol) N-(3-bromopyridin-2-yl)-N'-(2-methoxybenzyl)guanidine acetate, 0.092 g (0.759 mmol) phenylboric acid, 0.165 g (1.518 mmol) sodium carbonate, and 0.040 g (0.035 mmol) tetrakis-(triphenylphosphine)palladium(0). The mixture was likewise heated in a reaction block at 110° C., first for 21 hr and then for an additional 20 hr, for a total of 41 hr under a nitrogen atmosphere. After appropriate workup and purification via preparative HPLC, 32 mg pure N-(2-methoxybenzyl)-N'-(3-phenylpyridin-2-yl)guanidine was obtained in the form of the acetate salt (base/acetate in a ratio of 1:1.2).

ESI-MS [M+H$^+$]=333.15 Calculated for C$_{20}$H$_{20}$N$_4$O=332.41

Example 63

N-[3-(4-Fluorophenyl)pyridin-2-yl]-N'-(2-methoxybenzyl)guanidine acetate

The preparation was carried out analogously to Example 56, using 0.200 g (0.506 mmol) N-(3-bromopyridin-2-yl)-N'-(2-methoxybenzyl)guanidine acetate, 0.106 g (0.759 mmol) (4-fluorophenyl)boric acid, 0.160 g (1.518 mmol) sodium carbonate, and 0.038 g (0.033 mmol) tetrakis-(triphenylphosphine)palladium(0). The mixture was likewise heated in a reaction block for 19 hr at 110° C. under a nitrogen atmosphere. Despite prolonging the reaction time to a total of 6 days and renewed addition of the starting materials sodium carbonate, (4-fluorophenyl)boric acid, and catalyst, the reaction reached an end point at which the starting material/product-ratio of 1:1 had not changed. After termination of the reaction, appropriate workup, and purification via preparative HPLC, 20 mg (0.048 mmol, 9.4%) pure N-[3-(4-fluorophenyl)pyridin-2-yl]-N'-(2-methoxybenzyl)guanidine was obtained in the form of the acetate salt (base/acetate in a ratio of 1:1).

ESI-MS [M+H$^+$]=351.15 Calculated for C$_{20}$H$_{19}$FN$_4$O=350.40

Compounds 64, 65, and 66 were prepared analogously to Example 76 (see procedure below) by the reaction of suitable starting materials.

Example 64

N-(4-Cyanopyridin-2-yl)-N'-(2,6-dimethoxybenzyl)guanidine acetate

Analogously to the procedure of Example 76 (see below), 0.130 g (0.356 mmol) N-(4-bromopyridin-2-yl)-N'-(2,6-dimethoxybenzyl)guanidine dissolved in 5 mL tetrahydrofuran together with 0.050 g (0.427 mmol) zinc(II) cyanide, under catalysis with 4×0.033 g (4×0.028 mmol) tetrakis-(triphenylphosphine)palladium(0), was heated under a nitrogen atmosphere for 4×30 min at 90° C. in a CEM microwave (150 watts). After appropriate workup and purification via preparative HPLC, following freeze drying with a lyophilizing agent 36 mg of the desired product N-(4-cyanopyridin-2- yl)-N'-(2,6-dimethoxybenzyl)guanidine was isolated in the form of the acetate salt (base/acetate in a ratio of 1:0.6).

ESI-MS [M+H$^+$]=312.15 Calculated for $C_{16}H_{17}N_5O_2$=311.35

Example 65

N-(3-Cyanopyridin-2-yl)-N'-(2,6-dimethoxybenzyl) guanidine acetate

Analogously to the procedure of Example 76 (see below), 0.260 g (0.611 mmol) N-(3-bromopyridin-2-yl)-N'-(2,6-dimethoxybenzyl)guanidine acetate dissolved in 5 mL tetrahydrofuran together with 0.100 g (0.854 mmol) zinc(II) cyanide, under catalysis with 2×0.066 g (2×0.038 mmol) tetrakis-(triphenylphosphine)palladium(0), was heated under a nitrogen atmosphere for 2×30 min at 90° C. in a CEM microwave (150 watts). According to mass spectrometric analysis the starting materials were still identifiable, so that 2×0.066 g (0.038 mmol) tetrakis-(triphenylphosphine)palladium(0) was additional added, followed by heating for 2×30 min at 110° C. in a CEM microwave (150 watts) with "heating by cooling." The reaction could not be carried out with full conversion to product, resulting in massive losses in yield. After appropriate workup and purification via preparative HPLC, following freeze drying with a lyophilizing agent 22.2 mg of the desired product N-(3-cyanopyridin-2-yl)-N'-(2,6-dimethoxybenzyl)guanidine was isolated in the form of the acetate salt (base/acetate in a ratio of 1:0.5).

ESI-MS [M+H$^+$]=312.15 Calculated for $C_{16}H_{17}N_5O_2$=311.35

Example 66

N-(4-Cyanopyridin-2-yl)-N'-(2-methoxybenzyl) guanidine acetate

Analogously to the procedure of Example 76 (see below), 0.160 g (0.477 mmol) N-(4-bromopyridin-2-yl)-N'-(2-methoxybenzyl)guanidine dissolved in 5 mL tetrahydrofuran together with 0.067 g (0.573 mmol) zinc(II) cyanide, under catalysis with 4×0.044 g (4×0.038 mmol) tetrakis-(triphenylphosphine)palladium(0), was heated under a nitrogen atmosphere for 4×30 min at 90° C. in a CEM microwave (150 watts). After appropriate workup and purification via preparative HPLC, following freeze drying with a lyophilizing agent 50 mg of the desired product N-(4-cyanopyridin-2-yl)-N'-(2-methoxybenzyl)guanidine was isolated in the form of the acetate salt (base/acetate in a ratio of 1:0.8).

ESI-MS [M+H$^+$]=282.15 Calculated for $C_{15}H_{15}N_5O$=281.32

Example 67

N-(5-Benzylpyridin-2-yl)-N'-(2-methoxybenzyl) guanidine acetate 20 mg (0.055 mmol) [1,1'-bis-(diphenylphosphino)-ferrocene]palladium(II) chloride-methylene chloride was placed in 10 mL tetrahydrofuran, and the solution was deoxygenated with nitrogen. 0.200 g (0.523 mmol) N-(5-iodopyridin-2-yl)-N'-(2-methoxybenzyl)guanidine dissolved in 5 mL tetrahydrofuran was added dropwise through a septum (syringe technique), and the mixture was stirred for an additional 10 min. 4.19 mL (2.093 mmol) of a benzyl zinc bromide solution (0.5 M in tetrahydrofuran) was added dropwise under a nitrogen atmosphere. The reaction mixture was then heated under reflux for 4 hr. Since very little of the desired product was obtained, an additional 2.6 mL (1.308 mmol) of the benzyl zinc bromide solution was added. After additional heating under reflux for 4 hr the reaction went to completion. The reaction mixture was taken up in dichloromethane, and was extracted with saturated ammonium chloride solution (3×20 mL) and then with saturated sodium chloride solution (2×20 mL). The organic phase was dried over sodium sulfate and filtered, and the solvent was removed under vacuum. The residue was dissolved in acetonitrile/water (1:1) and 0.5 mL acetic acid, and purified via preparative HPLC (Waters, XTerra RP-18, eluent: water/acetonitrile/0.1 M acetic acid, with a flow rate of 30 mL/min and with gradients of 10% to 30% of the acetonitrile fraction in 20 min). The fractions containing pure product were combined and lyophilized with freeze drying, resulting in 0.072 g (1.771 mmol, 34%) N-(5-benzylpyridin-2-yl)-N'-(2-methoxybenzyl)guanidine in the form of the acetate salt (base/acetate in a ratio of 1:1).

ESI-MS [M+H$^+$]=347.15 Calculated for $C_{21}H_{22}N_4O$=346.44

Compounds 68, 69, and 70 were prepared analogously to Example 67 by the reaction of suitable starting materials.

Example 68

N-(5-Benzylpyridin-2-yl)-N'-(2,6-dimethoxybenzyl) guanidine acetate

The preparation was carried out analogously to Example 67, using 0.200 g (0.485 mmol) N-(2,6-dimethoxybenzyl)-N'-(5-iodopyridin-2-yl)guanidine and 2.43 mL (1.213 mmol) of the benzyl zinc bromide solution (0.5 M in tetrahydrofuran) under Pd catalysis with 20 mg (0.055 mmol) [1,1-bis-(diphenylphosphino)ferrocene]palladium(II) chloride-methylene chloride. The mixture was likewise heated under a nitrogen atmosphere, first under reflux for 6 hr, and then after repeated additions of 2×2.43 mL (1.213 mmol) of the 0.5 M benzyl zinc bromide solution and the same quantity of Pd catalyst for an additional 6 hr and 4 hr, respectively, for a total of 16 hr of heating. After appropriate workup and purification via preparative HPLC (Merck Chromolith RP-18 100×25 mm, eluent: water/acetonitrile/0.1 M acetic acid), 48 mg (0.109 mmol, 23%) pure N-(5-benzylpyridin-2-yl)-N'-(2,6-dimethoxybenzyl)guanidine was obtained in the form of the acetate salt (base/acetate in a ratio of 1:1).

ESI-MS [M+H$^+$]=377.15 Calculated for $C_{22}H_{24}N_4O_2$=376.46

Example 69

N-(6-Benzylpyridin-2-yl)-N'-(2-methoxybenzyl) guanidine acetate

The preparation was carried out analogously to Example 67, using 0.200 g (0.597 mmol) N-(6-bromopyridin-2-yl)-N'-(2-methoxybenzyl)guanidine and 2.98 mL (1.491 mmol) of the benzyl zinc bromide solution (0.5 M in tetrahydrofuran) under Pd catalysis with 20 mg (0.055 mmol) [1,1'-bis-(diphenylphosphino)ferrocene]palladium(II) chloride-methylene chloride. The mixture was likewise heated under a nitrogen atmosphere, first under reflux for 9 hr, and then after repeated additions of 2.98 mL (1.491 mmol) of the 0.5 M benzyl zinc bromide solution and 20 mg (0.055 mmol) Pd catalyst the mixture was heated for an additional 8 hr and stirred for an additional 8 hr. After appropriate workup and purification via two preparative HPLC procedures (1× via Waters, XTerra RP-18 and Merck, 1× Chromolith RP-18 100×25 mm, each eluent: water/acetonitrile/0.1 M acetic acid), 18 mg (0.044 mmol, 7%) N-(6-benzylpyridin-2-yl)-N'-(2-methoxybenzyl)guanidine was obtained in the form of the acetate salt (base/acetate in a ratio of 1:1).

ESI-MS [M+H$^+$]=347.25 Calculated for $C_{21}H_{22}N_4O$=346.44

Example 70

N-(6-Benzylpyridin-2-yl)-N'-(2,6-dimethoxybenzyl)guanidine acetate

The preparation was carried out analogously to Example 67, using 0.200 g (0.548 mmol) N-(6-bromopyridin-2-yl)-N'-(2,6-dimethoxybenzyl)guanidine and 2.74 mL (1.369 mmol) of the benzyl zinc bromide solution (0.5 M in tetrahydrofuran) under Pd catalysis with 20 mg (0.055 mmol) [1,1'-bis-(diphenylphosphino)ferrocene]palladium(II) chloride-methylene chloride. The mixture was likewise heated under reflux under a nitrogen atmosphere, first for 4 hr, and then after repeated additions of 2.43 mL (1.213 mmol) of the 0.5 M benzyl zinc bromide solution and 20 mg (0.055 mmol) Pd catalyst for an additional 8 hr, i.e., for a total of 12 hr of heating. After appropriate workup and purification via preparative HPLC (Merck Chromolith RP-18 100×25 mm, eluent: water/acetonitrile/0.1 M acetic acid), 95 mg (0.216 mmol, 40%) pure N-(6-benzylpyridin-2-yl)-N'-(2,6-dimethoxybenzyl)guanidine was obtained in the form of the acetate salt (base/acetate in a ratio of 1:1).

ESI-MS [M+H$^+$]=377.25 Calculated for $C_{22}H_{24}N_4O_2$=376.46

Example 71

N-(6-Bromopyridin-2-yl)-N'-(2-methoxy-6-methylbenzyl)guanidine

The methylated intermediate product methyl N-(6-bromopyridin-2-yl)imidothiocarbamate hydroiodide was obtained, analogously to the above-described procedure of Example 42, from N-(6-bromopyridin-2-yl)thiourea by stirring for 30 min at 50° C. and additional stirring in methanol for 12 hr at room temperature. The solid was crystallized from the alcoholic solution and then suctioned off. Corresponding to Example 18, for the subsequent reaction 0.300 g (0.800 mmol) methyl N-(6-bromopyridin-2-yl)imidothiocarbamate hydroiodide was reacted with 0.133 g (0.880 mmol) 2-methoxy-6-methylbenzylamine, with the addition of 0.27 mL (1.60 mmol) diisopropylethylamine and 5 mL acetonitrile as solvent, for 30 min at 90° C. in a CEM microwave (150 watts). After workup and purification via preparative HPLC, 0.149 g pure N-(6-bromopyridin-2-yl)-N'-(2-methoxy-6-methylbenzyl)guanidine was obtained in the form of the acetate salt (base/acetate in a ratio of 1:0.3).

ESI-MS [M+H$^+$]=349.05/351.05 Calculated for $C_{15}H_{17}BrN_4O$=349.23

Example 72

N-(6-Bromopyridin-2-yl)-N'-(2-fluoro-6-methoxybenzyl)guanidine

The methylated intermediate product methyl N-(6-bromopyridin-2-yl)imidothiocarbamate hydroiodide was obtained, analogously to the above-described procedure of Example 42, from N-(6-bromopyridin-2-yl)thiourea by stirring for 30 min at 50° C. and additional stirring in methanol for 12 hr at room temperature. The solid was crystallized from the alcoholic solution and then suctioned off. Corresponding to Example 18, for the subsequent reaction 0.300 g (0.800 mmol) methyl N-(6-bromopyridin-2-yl)imidothiocarbamate hydroiodide was reacted with 0.137 g (0.880 mmol) 2-fluoro-6-methoxybenzylamine, with the addition of 0.27 mL (1.60 mmol) diisopropylethylamine and 5 mL acetonitrile as solvent, for 60 min at 90° C. in a CEM microwave (150 watts). After workup and purification via preparative HPLC, 0.188 g pure N-(6-bromopyridin-2-yl)-N'-(2-fluoro-6-methoxybenzyl)guanidine was obtained in the form of the acetate salt (base/acetate in a ratio of 1:0.3).

ESI-MS [M+H$^+$]=353.05/355.0 Calculated for $C_{14}H_{14}BrFN_4O$=353.20

Example 73

N-(6-Bromopyridin-2-yl)-N'-[2-(trifluoromethoxy)benzyl]guanidine

The methylated intermediate product methyl N-(6-bromopyridin-2-yl)imidothiocarbamate hydroiodide was obtained, analogously to the above-described procedure of Example 42, from N-(6-bromopyridin-2-yl)thiourea by stirring for 30 min at 50° C. and stirring in methanol for an additional 12 hr at room temperature. The solid was crystallized from the alcoholic solution and then suctioned off. Corresponding to Example 18, for the subsequent reaction 0.300 g (0.800 mmol) methyl N-(6-bromopyridin-2-yl)imidothiocarbamate hydroiodide was completely reacted with 0.169 g (0.880 mmol) 2-(trifluoromethoxy)benzylamine, with the addition of 0.27 mL (1.60 mmol) diisopropylethylamine and 5 mL acetonitrile as solvent, in a CEM microwave, first for 30 min at 90° C. (150 watts), and finally for 30 min at 90° C. (150 watts) under "heating by cooling" conditions. After workup and purification via preparative HPLC, 0.150 g pure N-(6-bromopyridin-2-yl)-N'-[2-(trifluoromethoxy)benzyl]guanidine was obtained in the form of the acetate salt (base/acetate in a ratio of 1:0.4).

ESI-MS [M+H$^+$]=389.05/390.05 Calculated for $C_{14}H_{12}BrF_3N_4O$=389.18

Example 74

N-(6-Bromopyridin-2-yl)-N'-(2-isopropoxybenzyl)guanidine

The methylated intermediate product methyl N-(6-bromopyridin-2-yl)imidothiocarbamate hydroiodide was obtained, analogously to the above-described procedure of Example 42, from N-(6-bromopyridin-2-yl)thiourea by stirring for 30 min at 50° C. and stirring in methanol for an additional 12 hr at room temperature. The solid was crystallized from the alcoholic solution and then suctioned off. Corresponding to Example 18, for the subsequent reaction 0.300 g (0.800 mmol) methyl N-(6-bromopyridin-2-yl)imidothiocarbamate hydroiodide was completely reacted with 0.146 g (0.880 mmol) 1-(2-isopropoxyphenyl)methanamine, with the addition of 0.27 mL (1.60 mmol) diisopropylethylamine and 5 mL acetonitrile as solvent, under conventional conditions by heating for 5 hr at 80° C. (oil bath temperature). After workup and purification via preparative HPLC, 0.213 g pure N-(6-bromopyridin-2-yl)-N'-(2-isopropoxybenzyl)guanidine was obtained in the form of the acetate salt (base/acetate in a ratio of 1:0.23).

ESI-MS [M+H$^+$]=363.05/365.05 Calculated for C$_{16}$H$_{19}$BrN$_4$O=363.26

Example 75

N-(6-Bromopyridin-2-yl)-N'-(2-ethoxybenzyl)guanidine acetate

The methylated intermediate product methyl N-(6-bromopyridin-2-yl)imidothiocarbamate hydroiodide was obtained, analogously to the above-described procedure of Example 42, from N-(6-bromopyridin-2-yl)thiourea by stirring for 30 min at 50° C. and stirring in methanol for an additional 12 hr at room temperature. The solid was crystallized from the alcoholic solution and then suctioned off. Corresponding to Example 18, for the subsequent reaction 0.300 g (0.800 mmol) methyl N-(6-bromopyridin-2-yl)imidothiocarbamate hydroiodide was completely reacted with 0.133 g (0.880 mmol) 1-(2-ethoxyphenyl)methanamine, with the addition of 0.27 mL (1.60 mmol) diisopropylethylamine and 5 mL acetonitrile as solvent, under conventional conditions by heating for 5 hr at 80° C. (oil bath temperature). After workup and purification via preparative HPLC, 0.225 g pure N-(6-bromopyridin-2-yl)-N'-(2-ethoxybenzyl)guanidine was obtained in the form of the acetate salt (base/acetate in a ratio of 1:0.6).

ESI-MS [M+H$^+$]=349.05/351.05 Calculated for C$_{15}$H$_{17}$BrN$_4$O=349.23

Example 76

N-(2-Methoxy-6-methylbenzyl)-N'-(6-cyanopyridin-2-yl)guanidine acetate 0.119 g (0.340 mmol) N-(6-bromopyridin-2-yl)-N'-(2-methoxy-6-methylbenzyl)guanidine was placed in 5 mL tetrahydrofuran, and the solution was degassed under a strong nitrogen stream. 0.056 g (0.48 mmol) zinc(II) cyanide and 0.032 g (0.030 mmol) tetrakis-(triphenylphosphine)palladium(0) were then added. The mixture was heated for 30 min at 90° C. in a CEM microwave (150 watts). Since the reaction had not completely converted the product, an additional 0.032 g (0.030 mmol) tetrakis-(triphenylphosphine) palladium(0) was added, and the mixture was heated for 30 min at 90° C. in a CEM microwave (150 watts). The reaction mixture solvent was removed under vacuum, and the residue was taken up in dichloromethane and washed with water (1×50 mL) and with saturated sodium chloride solution (1×50 mL). After the organic phase was dried over magnesium sulfate, the solvent was evaporated under vacuum. By use of acetonitrile/water (1:1) and 0.5 mL acetic acid the triphenylphosphine oxide produced in the reaction was separated from the crude product by precipitation. The mother liquor was purified via preparative HPLC (Merck Chromolith RP-18 100×25 mm, eluent: water/acetonitrile/0.1 M acetic acid, with a flow rate of 20 mL/min and with gradients of 5% to 30% of the acetonitrile fraction in 15 min). Following freeze drying with a lyophilizing agent, 35 mg of the desired product N-(2-methoxy-6-methylbenzyl)-N'-(6-cyanopyridin-2-yl)guanidine was isolated in the form of the acetate salt (base/acetate in a ratio of 1:0.6).

ESI-MS [M+H$^+$]=296.15 Calculated for C$_{16}$H$_{17}$N$_5$O=295.35

Compounds 64 (from the 4-Br derivative), 65 (from the 3-Br derivative), and 66 (from the 4-Br derivative), as well as 77, 78.2, 81, and 82, and 85, 95, 96, 97, and 98 (from the I derivative, described below) were prepared analogously to Example 76 by the reaction of suitable starting materials.

Example 77

N-(6-Cyanopyridin-2-yl)-N'-(2-fluoro-6-methoxybenzyl)guanidine acetate

Analogously to the procedure of Example 76, 0.120 g (0.45 mmol) N-(6-bromopyridin-2-yl)-N'-(2-fluoro-6-methoxybenzyl)guanidine dissolved in 5 mL tetrahydrofuran together with 0.073 g (0.63 mmol) zinc(II) cyanide, under catalysis with 2×0.041 g (2×0.04 mmol) tetrakis-(triphenylphosphine) palladium(0), was heated under a nitrogen atmosphere for 2×30 min at 90° C. in a CEM microwave (150 watts). After appropriate workup and purification via preparative HPLC, following freeze drying with a lyophilizing agent 72 mg of the desired product N-(6-cyanopyridin-2-yl)-N'-(2-fluoro-6-methoxybenzyl)guanidine was isolated in the form of the acetate salt (base/acetate in a ratio of 1:0.8).

ESI-MS [M+H$^+$]=300.15 Calculated for C$_{15}$H$_{14}$FN$_5$O=299.31

Example 78

N-(2-Chloro-6-methoxybenzyl)-N'-(6-cyanopyridin-2-yl)guanidine acetate 78.1 N-(6-Bromopyridin-2-yl)-N'-(2-chloro-6-methoxybenzyl)guanidine The methylated intermediate product methyl N-(6-bromopyridin-2-yl)imidothiocarbamate hydroiodide was obtained, analogously to the above-described procedure of Example 42, from N-(6-bromopyridin-2-yl)thiourea by stirring at room temperature for 15 hr in methanol. Corresponding to Example 18, for the subsequent reaction 0.142 g (0.382 mmol) methyl N-(6-bromopyridin-2-yl)imidothiocarbamate hydroiodide was completely reacted with 0.171 g (0.459 mmol) 2-chloro-6-methoxybenzylamine, with the addition of 0.130 mL (0.765 mmol) diisopropylethylamine and 3 mL acetonitrile as solvent, by conventional heating for 5 hr at 85° C. (oil bath temperature). Following workup, 0.141 g N-(6-bromopyridin-2-yl)-N'-(2-chloro-6-methoxybenzyl)guanidine was obtained and directly used for further reaction.

ESI-MS [M+H$^+$]=369.05 Calculated for C$_{14}$H$_{14}$BrClN$_4$O=369.65

78.2 N-(2-Chloro-6-methoxybenzyl)-N'-(6-cyanopyridin-2-yl)guanidine acetate

Analogously to the procedure of Example 76, 0.141 g (0.45 mmol) N-(6-bromopyridin-2-yl)-N'-(2-chloro-6-methoxybenzyl)guanidine dissolved in 5 mL tetrahydrofuran together with 0.063 g (0.534 mmol) zinc(II) cyanide, under catalysis with 0.035 g (0.031 mmol) tetrakis-(triphenylphosphine)palladium(0), was heated under a nitrogen atmosphere for 30 min at 90° C. in a CEM microwave (150 watts). After appropriate workup and purification via preparative HPLC, following freeze drying with a lyophilizing agent 21 mg of the desired product N-(2-chloro-6-methoxybenzyl)-N'-(6-cyanopyridin-2-yl)guanidine was isolated in the form of the acetate salt (base/acetate in a ratio of 1:1).

ESI-MS [M+H$^+$]=316.15/318.15 Calculated for C$_{15}$H$_{14}$ClN$_5$O=315.76

Example 79

N-(6-Cyanopyridin-2-yl)-N'-[2-(trifluoromethoxy)benzyl]guanidine acetate

Analogously to the procedure of Example 76, 0.120 g (0.31 mmol) N-(6-bromopyridin-2-yl)-N'-[2-(trifluoromethoxy)benzyl]guanidine dissolved in 4 mL tetrahydrofuran together with 0.051 g (0.43 mmol) zinc(II) cyanide, under catalysis with 2×0.028 g (2×0.02 mmol) tetrakis-(triphenylphosphine)palladium(0), was heated under a nitrogen atmosphere for 2×30 min at 90° C. in a CEM microwave (150 watts). After appropriate workup and purification via preparative HPLC, following freeze drying with a lyophilizing agent 55 mg of the desired product N-(6-cyanopyridin-2-yl)-N'-[2-(trifluoromethoxy)benzyl]guanidine was isolated in the form of the acetate salt (base/acetate in a ratio of 1:0.6).

ESI-MS [M+H$^+$]=336.10 Calculated for $C_{15}H_{12}F_3N_5O$=335.29

Example 80

N-(6-Cyanopyridin-2-yl)-N'-(2-isopropoxybenzyl)guanidine acetate

Analogously to the procedure of Example 76, 0.180 g (0.50 mmol) N-(6-bromopyridin-2-yl)-N'-(2-isopropoxybenzyl)guanidine dissolved in 5 mL tetrahydrofuran together with 0.046 g (0.43 mmol) zinc(II) cyanide, under catalysis with 0.028 g (0.02 mmol) tetrakis-(triphenylphosphine)palladium (0), was stirred under conventional heating under a nitrogen atmosphere for 4 hr at 80° C. (oil bath temperature) 4 hr. According to spectrometric analysis predominantly the starting materials were identified, so that after further addition of 0.028 g (0.02 mmol) tetrakis-(triphenylphosphine)palladium (0) the mixture was heated for 30 min at 90° C. in a CEM microwave (150 watts). After appropriate workup and purification via preparative HPLC, following freeze drying with a lyophilizing agent 52 mg of the desired product N-(6-cyanopyridin-2-yl)-N'-(2-isopropoxybenzyl)guanidine was isolated in the form of the acetate salt (base/acetate in a ratio of 1:0.6).

ESI-MS [M+H$^+$]=310.15 Calculated for $C_{17}H_{19}N_5O$=309.37

Example 81

N-(6-Cyanopyridin-2-yl)-N'-(2-ethoxybenzyl)guanidine acetate

Analogously to the procedure of Example 76, 0.195 g (0.56 mmol) N-(6-bromopyridin-2-yl)-N'-(2-ethoxybenzyl)guanidine dissolved in 5 mL tetrahydrofuran together with 0.091 g (0.78 mmol) zinc(II) cyanide under catalysis with 0.052 g (0.04 mmol) tetrakis-(triphenylphosphine)palladium(0) under a nitrogen atmosphere was stirred under conventional heating for 4 hr at 80° C. (oil bath temperature). According to spectrometric analysis predominantly the starting materials were identified, so that after further addition of 0.052 g (0.04 mmol) tetrakis-(triphenylphosphine)palladium(0) the mixture was heated for 30 min at 90° C. in a CEM microwave (150 watts). After appropriate workup and purification via preparative HPLC, following freeze drying with a lyophilizing agent 63 mg of the desired product N-(6-cyanopyridin-2-yl)-N'-(2-ethoxybenzyl)guanidine was isolated in the form of the acetate salt (base/acetate in a ratio of 1:0.8).

ESI-MS [M+H$^+$]=296.15 Calculated for $C_{16}H_{17}N_5O$=295.35

Example 82

N-(2-Chloro-6-phenoxybenzyl)-N'-(6-cyanopyridin-2-yl)guanidine acetate

82.1 N-(6-Bromopyridin-2-yl)-N'-(2-chloro-6-phenoxybenzyl)guanidine

The methylated intermediate product methyl N-(6-bromopyridin-2-yl)imidothiocarbamate hydroiodide was obtained, analogously to the above-described procedure of Example 42, from N-(6-bromopyridin-2-yl)thiourea by stirring for 30 min at 50° C. and stirring in methanol for an additional 12 hr at room temperature. The solid was crystallized from the alcoholic solution and then suctioned off. Corresponding to Example 18, for the subsequent reaction 0.300 g (0.800 mmol) methyl N-(6-bromopyridin-2-yl)imidothiocarbamate hydroiodide was completely reacted with 0.207 g (0.880 mmol) 2-chloro-6-phenoxybenzylamine, with the addition of 0.27 mL (1.60 mmol) diisopropylethylamine and 5 mL acetonitrile as solvent, under conventional conditions by heating for 5 hr at 80° C. (oil bath temperature). After workup and purification via preparative HPLC, 0.110 g pure N-(6-bromopyridin-2-yl)-N'-(2-chloro-6-phenoxybenzyl)guanidine was obtained, which was directly used for further reaction.

ESI-MS [M+H$^+$]=430.95/432.95 Calculated for $C_{19}H_{16}BrClN_4O$=431.72

82.2 N-(2-Chloro-6-phenoxybenzyl)-N'-(6-cyanopyridin-2-yl)guanidine acetate Analogously to the procedure of Example 76, 0.100 g (0.23 mmol) N-(6-bromopyridin-2-yl)-N'-(2-chloro-6-phenoxybenzyl)guanidine dissolved in 5 mL tetrahydrofuran together with 0.038 g (0.32 mmol) zinc(II) cyanide, under catalysis with 0.021 g (0.02 mmol) tetrakis-(triphenylphosphine)palladium(0), was stirred with conventional heating under a nitrogen atmosphere for 4 hr at 80° C. (oil bath temperature). According to spectrometric analysis predominantly the starting materials were identified, so that after further addition of 0.021 g (0.02 mmol) tetrakis-(triphenylphosphine)palladium (0) the mixture was heated for 30 min at 90° C. in a CEM microwave (150 watts). After appropriate workup and purification via preparative HPLC, following freeze drying with a lyophilizing agent 52 mg of the desired product N-(2-chloro-6-phenoxybenzyl)-N'-(6-cyanopyridin-2-yl)guanidine was isolated in the form of the acetate salt (base/acetate in a ratio of 1:0.6).

ESI-MS [M+H$^+$]=378.15/380.15 Calculated for $C_{20}H_{16}ClN_5O$=377.84

Example 83

N-(2,6-Dimethoxybenzyl)-N'-(5-phenylpyridin-2-yl)guanidine acetate 0.251 g (0.609 mmol) N-(2,6-dimethoxybenzyl)-N'-(5-iodopyridin-2-yl)guanidine, 0.100 g (0.792 mmol) phenylboric acid, 0.194 g (1.829 mmol) sodium carbonate, and 0.035 g (0.030 mmol) tetrakis-(triphenylphosphine) palladium(0) were combined and added to 7.0 mL of a solvent mixture of 1,2-dimethoxyethane/water/ethanol (7:3:2). The mixture was degassed under a strong nitrogen stream and reacted by heating for 60 min at 120° C. in a CEM microwave (230 watts). To prevent precipitation of product, the reaction mixture was first diluted with dichloromethane and then shaken out with water. After separation of the phases the aqueous phase was repeatedly extracted with dichloromethane, and the combined organic phases were neutralized with 150 mL 2 N sodium hydroxide solution and then washed again with water (2×100 mL). After drying over magnesium sulfate and evaporation of the solvent, purification was performed via preparative HPLC (Merck Chromolith RP-18 100×25 mm, eluent: water/acetonitrile/0.1 M acetic acid), with a flow rate of 20 mL/min and with gradients of 10% to 40% of the acetonitrile fraction in 15 min. Following freeze drying with a lyophilizing agent, 16 mg of the desired product N-(2,6-dimethoxybenzyl)-N'-(5-phenylpyridin-2-yl)guanidine was isolated in the form of the acetate salt (base/acetate in a ratio of 1:1).

ESI-MS [M+H$^+$]=363.2 Calculated for $C_{21}H_{22}N_4O_2$=362.44

Compound 84 was prepared analogously to Example 83 by the reaction of suitable starting materials.

Example 84

N-(2,6-Dimethoxybenzyl)-N'-[5-(4-fluorophenyl)pyridin-2-yl]guanidine acetate

The preparation was carried out analogously to Example 83, using 0.255 g (0.619 mmol) N-(2,6-dimethoxybenzyl)-N'-(5-iodopyridin-2-yl)guanidine, 0.115 g (0.819 mmol) (4-fluorophenyl)boric acid, 0.211 g (1.988 mmol) sodium carbonate, and 0.037 g (0.032 mmol) tetrakis-(triphenylphosphine) palladium(0). The mixture was likewise heated for 60 min at 120° C. in a CEM microwave (230 watts). After appropriate workup and purification via preparative HPLC, 51 mg N-(2,6-dimethoxybenzyl)-N-[5-(4-fluorophenyl)pyridin-2-yl]guanidine was isolated in the form of the acetate salt (base/acetate in a ratio of 1:1).

ESI-MS [M+H$^+$]=381.2 Calculated for $C_{21}H_{21}FN_4O_2$=380.43

Example 85

N-(5-Cyanopyridin-2-yl)-N'-(2,6-dimethoxybenzyl)guanidine acetate

The preparation was carried out analogously to Example 76, using 0.256 g (0.621 mmol) N-(2,6-dimethoxybenzyl)-N'-(5-iodopyridin-2-yl)guanidine, 0.042 g (0.036 mmol) tetrakis-(triphenylphosphine)palladium(0), 0.197 g (1.863 mmol) sodium carbonate, and 0.070 g (0.596 mmol) zinc(II) cyanide in 7 mL tetrahydrofuran. The mixture was likewise heated for 90 min at 120° C. in a CEM microwave (300 watts). After appropriate workup and purification via preparative HPLC, 44 mg N-(5-cyanopyridin-2-yl)-N'-(2,6-dimethoxybenzyl)guanidine was isolated in the form of the acetate salt (base/acetate in a ratio of 1:0.75).

ESI-MS [M+H$^+$]=312.15 Calculated for $C_{16}H_{17}N_5O_2$=311.35

Example 86

N-(2-Methoxybenzyl)-N'-(5-phenylpyridin-2-yl)guanidine 0.102 g (0.251 mmol) N-(5-iodopyridin-2-yl)-N'-(2-methoxybenzyl)guanidine, 0.041 g (0.337 mmol) phenylboric acid, 0.075 g (0.708 mmol) sodium carbonate, and 0.015 g (0.013 mmol) tetrakis-(triphenylphosphine) palladium(0) were combined and added to 7.0 mL of a solvent mixture of 1,2-dimethoxyethane/water/ethanol (7:3:2). The mixture was degassed under a strong nitrogen stream and heated for 110 min at 120° C. in a CEM microwave (150 watts) and reacted. After filtration through a Millipore filter (Ø=25 mm, 0.45 µm) the solvent was removed under vacuum and the crude mixture was purified via preparative HPLC (Merck Chromolith RP-18 100×25 mm, eluent: water/acetonitrile/0.1 M acetic acid), with a flow rate of 20 mL/min and with gradients of 10% to 30% of the acetonitrile fraction in 10 min. Following freeze drying with a lyophilizing agent, 23 mg of the desired product N-(2-methoxybenzyl)-N'-(5-phenylpyridin-2-yl)guanidine was isolated.

ESI-MS [M+H$^+$]=333.15 Calculated for $C_{20}H_{20}N_4O$=332.41

Compounds 87, 88, and 89 were prepared analogously to Example 86 by the reaction of suitable starting materials.

Example 87

N-(2-Methoxybenzyl)-N'-[5-(2-thienyl)pyridin-2-yl]guanidine

The preparation was carried out analogously to Example 86, using 0.125 g (0.308 mmol) N-(5-iodopyridin-2-yl)-N'-(2-methoxybenzyl)guanidine, 0.055 g (0.431 mmol) 2-thienylboric acid, 0.098 g (0.925 mmol) sodium carbonate, and 0.018 g (0.015 mmol) tetrakis-(triphenylphosphine)-palladium(0). The mixture was likewise heated for 60 min at 120° C. in a CEM microwave (200 watts). After filtration and purification via preparative HPLC, 23 mg N-(2-methoxybenzyl)-N'-[5-(2-thienyl)pyridin-2-yl]guanidine was isolated, a small portion of which was present in the form of the acetate salt (base/acetate in a ratio of 1:0.3).

5 ESI-MS [M+H$^+$]=339.15 Calculated for $C_{18}H_{18}N_4OS$=338.43

Example 88

N-[5-(4-Fluorophenyl)pyridin-2-yl]-N'-(2-methoxybenzyl)guanidine acetate

The preparation was carried out analogously to Example 86, using 0.127 g (0.313 mmol) N-(5-iodopyridin-2-yl)-N'-(2-methoxybenzyl)guanidine, 0.063 g (0.448 mmol) (4-fluorophenyl)boric acid, 0.133 g (1.253 mmol) sodium carbonate, and 0.022 g (0.019 mmol) tetrakis-(triphenylphosphine)palladium(0). The mixture was likewise heated for 60 min at 120° C. in a CEM microwave (230 watts). After filtration and purification via preparative HPLC, 35 mg N-(2-methoxybenzyl)-N'-[5-(2-thienyl)pyridin-2-yl]guanidine was isolated, a portion of which was present in the form of the acetate salt (base/acetate in a ratio of 1:0.6).

ESI-MS [M+H$^+$]=351.15 Calculated for $C_{20}H_{19}FN_4O$=350.40

Example 89

N-(2-Methoxybenzyl)-N'-{5-[4-(trifluoromethyl)phenyl]pyridin-2-yl}guanidine acetate The preparation was carried out analogously to Example 86, using 0.128 g (0.316 mmol) N-(5-iodopyridin-2-yl)-N'-(2-methoxybenzyl)guanidine, 0.097 g (0.511 mmol) [4-(trifluoromethyl)phenyl]boric acid, 0.112 g (1.052 mmol) sodium carbonate, and 0.022 g (0.019 mmol) tetrakis-(triphenylphosphine) palladium(0). The mixture was likewise heated for 60 min at 120° C. in a CEM microwave (230 watts). After filtration and purification via preparative HPLC, 33 mg N-(2-methoxybenzyl)-N'-{5-[4-(trifluoromethyl)phenyl]pyridin-2-yl}guanidine was isolated, a portion of which was present in the form of the acetate salt (base/acetate in a ratio of 1:0.6).

ESI-MS [M+H$^+$]=401.15 Calculated for $C_{21}H_{19}F_3N_4O$=400.41

Example 90

N-(5-Cyanopyridin-2-yl)-N'-(2-methoxybenzyl)guanidine 0.124 g (0.304 mmol) N-(5-iodopyridin-2-yl)-N'(2-methoxybenzyl)guanidine, 0.036 g (0.304 mmol) zinc(II) cyanide, and 0.018 g (0.015 mmol) tetrakis-(triphenylphosphine)palladium(0) were suspended in 7 mL tetrahydrofuran. The mixture was degassed under a strong nitrogen stream and heated for 60 min at 120° C. in a CEM microwave (200 watts). To complete the reaction, 0.103 g (0.972 mmol) sodium carbonate was added and the mixture was reheated for 90 min at 120° C. in a CEM microwave (300 watts). For workup and purification the mixture was filtered through a Millipore filter (Ø=25 mm, 0.45 µm), the solvent was removed under vacuum, and the crude mixture was purified via preparative HPLC (Merck Chromolith RP-18 100×25 mm, eluent: water/acetonitrile/0.1 M acetic acid), with a flow rate of 20 mL/min and with gradients of 10% to 30% of the acetonitrile fraction in 10 min. Following freeze drying with a lyophilizing agent, 26 mg of the desired product N-(5-cyanopyridin-2-yl)-N'-(2-methoxybenzyl)guanidine was isolated, a small portion of which was present in the form of the acetate salt (base/acetate in a ratio of 1:0.1).

ESI-MS [M+H$^+$]=282.15 Calculated for $C_{15}H_{15}N_5O$=281.32

Example 91

N-(2-Chloro-6-methoxybenzyl)-N'-(5-iodopyridin-2-yl)guanidine acetate

The methylated intermediate product methyl N-(5-iodopyridin-2-yl)imidothiocarbamate hydroiodide was obtained, analogously to the above-described procedure of Example 42, from N-(5-iodopyridin-2-yl)thiourea by stirring in methanol for 12 hr at room temperature. After distillation of the solvent and two codistillation procedures using dichloromethane, the intermediate product methyl N-(5-iodopyridin-2-yl)imidothiocarbamate hydroiodide was used without purification for further reaction. Corresponding to Example 18, for the subsequent reaction 0.500 g (1.19 mmol) methyl N-(5-iodopyridin-2-yl)imidothiocarbamate hydroiodide together with 0.245 g (1.43 mmol) 2-chloro-6-methoxybenzylamine, with the addition of 0.41 mL (2.37 mmol) diisopropylethylamine and 4 mL acetonitrile as solvent, were reacted for 40 min at 100° C. in a CEM microwave (150 watts). After workup and purification via preparative HPLC, 0.220 g pure N-(2-chloro-6-methoxybenzyl)-N'-(5-iodopyridin-2-yl)guanidine was obtained in the form of the acetate salt (base/acetate in a ratio of 1:1).

ESI-MS [M+H$^+$]=417.15/419.15 Calculated for $C_{14}H_{14}ClIN_4O$=416.65

Example 92

N-(2-Fluoro-6-methoxybenzyl)-N'-(5-iodopyridin-2-yl)guanidine acetate

The methylated intermediate product methyl N-(5-iodopyridin-2-yl)imidothiocarbamate hydroiodide was obtained, analogously to the above-described procedure of Example 42, from N-(5-iodopyridin-2-yl)thiourea by stirring in methanol for 12 hr at room temperature. After distillation of the solvent and two codistillation procedures using dichloromethane, the intermediate product methyl N-(5-iodopyridin-2-yl)imidothiocarbamate hydroiodide was used without purification for further reaction. Corresponding to Example 18, for the subsequent reaction 0.500 g (1.188 mmol) methyl N-(5-iodopyridin-2-yl)imidothiocarbamate hydroiodide together with 0.221 g (1.425 mmol) 2-fluoro-6-methoxybenzylamine, with the addition of 0.41 mL (2.375 mmol) diisopropylethylamine and 4 mL acetonitrile as solvent, were reacted for 30 min at 90° C. in a CEM microwave (150 watts) with "heating by cooling." After workup and dissolution of the suitable residue in acetonitrile/water (1:1) and 5 drops of acetic acid a colorless solid precipitated, and after filtration and washing with water 0.342 g pure N-(2-fluoro-6-methoxybenzyl)-N'-(5-iodopyridin-2-yl)guanidine was obtained in the form of the acetate salt (base/acetate in a ratio of 1:1.6). Purification by preparative HPLC was not necessary.

ESI-MS [M+H$^+$]=401.05 Calculated for $C_{14}H_{14}FIN_4O$=400.20

Example 93

N-(5-Iodopyridin-2-yl)-N'-(2-methoxy-6-methylbenzyl)guanidine acetate

The methylated intermediate product methyl N-(5-iodopyridin-2-yl)imidothiocarbamate hydroiodide was obtained, analogously to the above-described procedure of Example 42, from N-(5-iodopyridin-2-yl)thiourea by stirring in methanol for 12 hr at room temperature. After distillation of the solvent and two codistillation procedures using dichloromethane, the intermediate product methyl N-(5-iodopyridin-2-yl)imidothiocarbamate hydroiodide was used without purification for further reaction. Corresponding to Example 18, for the subsequent reaction 0.700 g (1.66 mmol) methyl N-(5-iodopyridin-2-yl)imidothiocarbamate hydroiodide together with 0.302 g (2.00 mmol) 2-methoxy-6-methylbenzylamine, with the addition of 0.57 mL (3.32 mmol) diisopropylethylamine and 4 mL acetonitrile as solvent, were reacted for 30 min at 90° C. in a CEM microwave (150 watts). After workup and purification via preparative HPLC, 0.330 g pure N-(5-iodopyridin-2-yl)-N'-(2-methoxy-6-methylbenzyl)guanidine was obtained in the form of the acetate salt (base/acetate in a ratio of 1:0.6).

ESI-MS [M+H+]=397.05 Calculated for $C_{15}H_{17}IN_4O$=396.23

Example 94

N-(2-Chlorobenzyl)-N'-(5-iodopyridin-2-yl)guanidine acetate

The methylated intermediate product methyl N-(5-iodopyridin-2-yl)imidothiocarbamate hydroiodide was obtained, analogously to the above-described procedure of Example 42, from N-(5-iodopyridin-2-yl)thiourea by stirring in methanol for 12 hr at room temperature. After distillation of the solvent and two codistillation procedures using dichloromethane, the intermediate product methyl N-(5-iodopyridin-2-yl)imidothiocarbamate hydroiodide was used without purification for further reaction. Corresponding to Example 18, for the subsequent reaction 0.400 g (0.950 mmol) methyl N-(5-iodopyridin-2-yl)imidothiocarbamate hydroiodide together with 0.161 g (1.140 mmol) 2-chlorobenzylamine, with the addition of 0.33 mL (1.900 mmol) diisopropylethylamine and 4 mL acetonitrile as solvent, were reacted in a conventional manner by heating for 6 hr at 80° C. (oil bath temperature). After workup and purification via preparative HPLC, 0.242 g pure N-(2-chlorobenzyl)-N'-(5-iodopyridin-2-yl)guanidine was obtained in the form of the acetate salt (base/acetate in a ratio of 1:1).

ESI-MS [M+H+]=387.0/389.0 Calculated for $C_{13}H_{12}ClIN_4$=386.62

Example 95

N-(2-Chloro-6-methoxybenzyl)-N'-(5-cyanopyridin-2-yl)guanidine acetate

Analogously to the procedure of Example 76, 0.129 g (0.271 mmol) N-(2-chloro-6-methoxybenzyl)-N'-(5-iodopyridin-2-yl)guanidine acetate dissolved in 5 mL tetrahydrofuran together with 0.054 g (0.46 mmol) zinc(II) cyanide, under catalysis with 0.025 g (0.02 mmol) tetrakis-(triphenylphosphine) palladium(0), were heated under a nitrogen atmosphere for 30 min at 90° C. in a CEM microwave (150 watts). According to mass spectrometric analysis the starting materials reacted to completion, and were appropriately purified. In this case, after dissolution of the crude product in acetonitrile/water (1:1) no precipitate deposited, so that purification of the crude product directly followed via preparative HPLC, resulting in isolation of 26.6 mg of the desired product N-(2-chloro-6-methoxybenzyl)-N'-(5-cyanopyridin-2-yl)guanidine in the form of the acetate salt (base/acetate in a ratio of 1:0.8).

ESI-MS [M+H$^+$]=316.05/318.05 Calculated for $C_{15}H_{14}ClN_5O$=315.76

Example 96

N-(5-Cyanopyridin-2-yl)-N'-(2-fluoro-6-methoxybenzyl)guanidine acetate

Analogously to the procedure of Example 76, 0.280 g (0.61 mmol) N-(2-fluoro-6-methoxybenzyl)-N'-(5-iodopyridin-2-yl)guanidine acetate dissolved in 5 mL tetrahydrofuran together with 0.106 g (0.91 mmol) zinc(II) cyanide, under catalysis with 0.057 g (0.05 mmol) tetrakis-(triphenylphosphine)palladium(0), were heated under a nitrogen atmosphere for 30 min at 90° C. in a CEM microwave (150 watts) 30. According to mass spectrometric analysis the starting materials reacted to completion, and were appropriately purified. In this case, after dissolution of the crude product in acetonitrile/water (1:1) no precipitate deposited, so that purification of the crude product directly followed via preparative HPLC, resulting in isolation of 100 mg of the desired product N-(5-cyanopyridin-2-yl)-N'-(2-fluoro-6-methoxybenzyl)guanidine in the form of the acetate salt (base/acetate in a ratio of 1:0.8).

ESI-MS [M+H$^+$]=300.10 Calculated for $C_{15}H_{14}FN_5O$=299.31

Example 97

N-(5-Cyanopyridin-2-yl)-N'-(2-methoxy-6-methylbenzyl)guanidine acetate

Analogously to the procedure of Example 76, 0.266 g (0.583 mmol) N-(5-iodpyridin-2-yl)-N'-(2-methoxy-6-methylbenzyl)guanidine acetate dissolved in 5 mL tetrahydrofuran together with 0.095 g (0.816 mmol) zinc(II) cyanide, under catalysis with 0.054 g (0.047 mmol) tetrakis-(triphenylphosphine) palladium(0), were heated under a nitrogen atmosphere for 30 min at 90° C. in a CEM microwave (150 watts). According to mass spectrometric analysis the starting materials did not react to completion, and therefore after addition of 0.054 g (0.047 mmol) tetrakis-(triphenylphosphine)palladium(0) the mixture was reheated for 30 min at 90° C. in a CEM microwave (150 watts). After appropriate workup and purification via preparative HPLC, 7 mg pure N-(5-cyanopyridin-2-yl)-N'-(2-methoxy-6-methylbenzyl)guanidine was obtained in the form of the acetate salt (base/acetate in a ratio of 1:0.8). The severe drop in yield was probably due to the purification.

ESI-MS [M+H$^+$]=296.15 Calculated for $C_{16}H_{17}N_5O$=295.35

Example 98

N-(2-Chlorobenzyl)-N'-(5-cyanopyridin-2-yl)guanidine acetate

Analogously to the procedure of Example 76, 0.167 g (0.37 mmol) N-(2-chlorobenzyl)-N'-(5-iodopyridin-2-yl)guanidine acetate dissolved in 4 mL tetrahydrofuran together with 0.061 g (0.52 mmol) zinc(II) cyanide, under catalysis with 0.035 g (0.03 mmol) tetrakis-(triphenylphosphine)palladium (0), were heated under a nitrogen atmosphere for 30 min at 90° C. in a CEM microwave (150 watts). According to mass spectrometric analysis the starting materials did not react to completion, and therefore after addition of 0.035 g (0.03 mmol) tetrakis-(triphenylphosphine)palladium(0) the mixture was reheated for 30 min at 90° C. in a CEM microwave (150 watts). After appropriate workup and purification via preparative HPLC, 11 mg pure N-(2-chlorobenzyl)-N'-(5-cyanopyridin-2-yl)guanidine was obtained in the form of the acetate salt (base/acetate in a ratio of 1:0.6). The severe drop in yield was probably due to the purification.

ESI-MS [M+H$^+$]=286.05/288.05 Calculated for $C_{14}H_{12}ClN_5$=285.74

Biological Tests h5-HT$_{5A}$ [$^3$H]5-CT Binding Assay

Membranes of HEK293 cells which permanently express the h5-HT$_{5A}$ receptor gene were incubated in 100 mM tris-HCl buffer (pH 7.7) containing 1 mM EDTA, in the presence of 2.5 nM [$^3$H]5-CT (total volume 600 µL). The total binding is defined as the binding that is observed when the membranes are incubated in the presence of only the radioligand. The inhibition induced by the compound is determined by incubation of cell membranes in the presence of the radioligand and various concentrations of the compound of interest. Nonspecific binding is defined as the [$^3$H]5-CT binding obtained by incubation of the membranes, the same as for the total binding, but in the presence of 10 µM methiothepine. Following incubation for 75 min at 30° C., the membrane suspension was filtered through a GF/B-Filter coated with 0.03% PEI, using a Skatron® harvesting system. The residual radioactivity in the filter was quantified by liquid scintillation counting.

Functional Assay for Human 5-HT$_{5A}$ Receptor Ligands, Serotonin-Induced Increase in GTP-Europium Binding General Description:

Stimulation of G protein-coupled receptors by means of suitable agonists results in binding of GTP to the a subunit of trimeric G proteins, followed by dissociation of the GTP-bound a subunit of the βγ subunits and the activation of signal transduction. By use of a europium-labeled GTP analog GTP-Eu, the activation of a G protein-coupled receptor by an agonist may be tracked as an increase in the binding of GTP-Eu to the receptor-G protein complex.

After removal of unbound GTP-Eu, bound GTP-Eu may be quantified by measuring the time-resolved fluorescence emission in suitable detection devices.

Cell line: h5-HT$_{5A}$_18.2_SH-sy-5y, a human neuroblastoma cell line which stably expresses the human 5-HT$_{5A}$ receptor.

Membrane preparation: Cell membranes were prepared according to a standard operating procedure in the presence of protease inhibitors, and were partially purified in two successive centrifugation steps at 40000×g. Aliquots were stored at −80° C.

Assay:

The assay was carried out in 96-well filter plates (AcroWell-96, Pall Corp.). The receptor membranes diluted in assay buffer (2.5 μM GDP, 100 mM NaCl, 3 mM MgCl$_2$, 50 mM HEPES at pH 7.4) were added to the filter plate (5 μg receptor membrane/well). Test compounds were dissolved in 100% DMSO, and series dilutions were added to the receptor membranes (DMSO end concentration 0.5%). The reaction was initiated by adding serotonin (end concentration 1 μM, total assay volume 100 μL). After an initial incubation period of 30 min at 30° C. GTP-Eu (end concentration 10 nM) was added, followed by a second incubation period of 30 min at 30° C. The reaction was terminated by rapid vacuum filtration, and the wells were washed twice with chilled assay buffer. Bound GTP-Eu was measured in a VICTOR multilabel counter (PerkinElmer Corp.), using the time-resolved europium settings. The data were corrected for nonspecific binding, and IC$_{50}$ values were calculated by means of PRISM4.0. (GraphPad Inc.), using standard nonlinear curve-fitting algorithms. Kb values were calculated from IC$_{50}$ values, using the Cheng-Prusoff approximation.

Various concentrations of the test substances were used in both assays, and the K$_i$ or IC$_{50}$ values were determined. The affinities of selected compounds are presented in Table 1 below:

TABLE 1

Affinity of selected compounds for 5-HT$_{5A}$ (K$_i$)

| Example # | 5-HT$_{5A}$ (K$_i$) |
|---|---|
| 1 | +++ |
| 3 | +++ |
| 4 | +++ |
| 5 | +++ |
| 6 | +++ |
| 7 | +++ |
| 8 | +++ |
| 9 | +++ |
| 10 | + |
| 11 | + |
| 12 | +++ |
| 13 | +++ |
| 14 | + |
| 15 | +++ |
| 16 | + |
| 17 | +++ |
| 18 | +++ |
| 19 | +++ |
| 20 | +++ |
| 21 | ++ |
| 22 | +++ |
| 23 | +++ |
| 24 | +++ |
| 25 | ++ |
| 26 | +++ |
| 27 | +++ |
| 28 | +++ |
| 29 | +++ |
| 30 | +++ |
| 31 | +++ |
| 32 | +++ |
| 33 | +++ |
| 34 | + |
| 35 | + |
| 36 | + |
| 37 | +++ |
| 38 | +++ |
| 39 | +++ |
| 40 | +++ |
| 41 | +++ |
| 42 | +++ |
| 43 | +++ |
| 44 | +++ |
| 45 | +++ |
| 46 | +++ |
| 47 | + |
| 48 | + |
| 49 | +++ |
| 50 | ++ |
| 51 | +++ |
| 52 | +++ |
| 53 | +++ |
| 54 | +++ |
| 55 | +++ |
| 56 | +++ |
| 57 | +++ |
| 58 | +++ |
| 59 | ++ |
| 60 | ++ |
| 61 | ++ |
| 62 | +++ |
| 63 | + |
| 64 | +++ |
| 65 | + |
| 66 | +++ |
| 67 | +++ |
| 68 | +++ |
| 69 | +++ |
| 70 | +++ |
| 71 | +++ |
| 72 | +++ |
| 73 | +++ |
| 74 | +++ |
| 75 | +++ |
| 76 | +++ |
| 77 | +++ |
| 78 | +++ |
| 79 | +++ |
| 80 | +++ |
| 81 | +++ |
| 82 | +++ |
| 83 | +++ |
| 84 | +++ |
| 85 | +++ |
| 86 | +++ |
| 87 | +++ |
| 88 | +++ |
| 89 | ++ |
| 90 | +++ |
| 91 | +++ |
| 92 | +++ |
| 93 | +++ |

TABLE 1-continued

Affinity of selected compounds for 5-HT$_{5A}$ (K$_i$)

| Example # | 5-HT$_{5A}$ (K$_i$) |
|---|---|
| 94 | ++ |
| 95 | +++ |
| 96 | +++ |
| 97 | +++ |
| 98 | ++ |

+ stands for an affinity <10 μM
++ stands for an affinity <300 nM
+++ stands for an affinity <100 nM

The invention claimed is:
1. A guanidine compound of general formula I

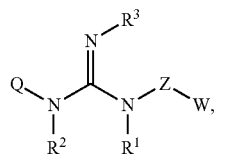

I an enantiomeric, diastereomeric, and/or tautomeric form thereof, and/or pharmaceutically acceptable salt thereof, wherein:
$R^1$, $R^2$ in each case independently stand for:
hydrogen or $C_1$-$C_6$ alkyl;
$R^3$ is hydrogen;
Z is —CH$_2$—;
W is a radical of general formula W1

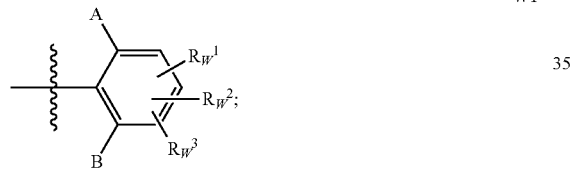

W1

A is OCF$_3$, OCHF$_2$, OCH$_2$F, halogen, O—C$_1$-$C_6$ alkyl, or
O—R$_A^1$;
$R_A^1$ independently of its respective occurrence stands for:
in each case optionally substituted $C_1$-$C_6$ alkyl, $C_1$-$C_6$ alkylene-O—$C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_2$-$C_6$ alkenylene-aryl, or in each case optionally substituted $C_1$-$C_4$ alkylene-hetaryl, —CO—$C_1$-$C_6$ alkyl, —CO—O—$C_1$-$C_6$ alkyl, —CO-aryl, —CO-hetaryl, —CO—O-aryl, —CO—O-hetaryl, —CO—$C_3$-$C_7$ cycloalkyl, —CO—O—$C_3$-$C_7$ cycloalkyl, —CO-heterocycloalkyl, —CO—O-heterocycloalkyl, $C_1$-$C_4$ alkylene-NR$_A^2$R$_A^3$, $C_1$-$C_4$ alkylene-CONR$_A^2$R$_A^3$, $C_1$-$C_4$ alkylene-SO$_2$—NR$_A^2$R$_A^3$, or $C_1$-$C_6$ alkylene-O—R$_A^2$;
$R_A^2$ independently of its respective occurrence stands for:
hydrogen, OH, CN, or
in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, SO$_2$—$C_1$-$C_6$ alkyl, SO$_2$-aryl, SO$_2$-hetaryl, SO$_2$—$C_1$-$C_4$ alkylene-aryl, or SO$_2$—$C_4$-$C_4$ alkylene-hetaryl;

$R_A^3$ independently of its respective occurrence stands for:
in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_4$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, SO$_2$—$C_1$-$C_6$ alkyl, SO$_2$-aryl, SO$_2$-hetaryl, SO$_2$—$C_1$-$C_4$ alkylene-aryl, or SO$_2$—$C_1$-$C_4$ alkylene-hetaryl;

or the radicals $R_A^2$ and $R_A^3$ together with the nitrogen atom to which they are bonded form a 3- to 7-membered optionally substituted, saturated or aromatic heterocycle which may contain one, two, or three further heteroatoms, which may be different or the same, selected from the group consisting of O, N, and S, wherein optionally two radicals substituted on this heterocycle together with the ring atom to which they are bonded may form a 3- to 7-membered optionally substituted, anellated, saturated, unsaturated, or aromatic carbocycle or heterocycle, wherein the heterocycle may contain one, two, or three heteroatoms, which may be different or the same, selected from the group consisting of O, N, and S, and wherein the cyclic compound formed may optionally be substituted;

B is a radical that is
hydrogen, or in each case optionally substituted aryl or hetaryl, or, independently of radical A, has the same meaning as for radical A;

$R_w^1$, $R_w^2$, and $R_w^3$ in each case independently stand for:
hydrogen;

Q: is a radical of general formula Q1, Q2, or Q3

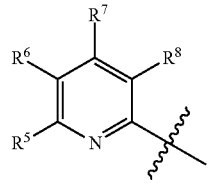

Q1

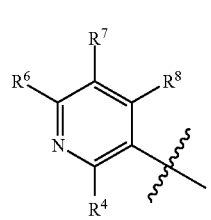

Q2

-continued

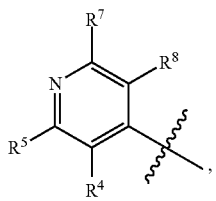
Q3 wherein $R^4$, $R^5$, $R^6$, $R^7$, and $R^8$ in each case independently stand for a radical selected from the group consisting of 1.), 2.), 3.), and 4.), which may be the same or different:

1.) Hydrogen, F, Cl, Br, I, CN, $CF_3$, $CHF_2$, $OCF_3$, $OCHF_2$, $NH_2$, $C_1$-$C_{10}$ alkyl or in each case optionally substituted $C_3$-$C_7$ cycloalkyl, or $C_1$-$C_6$ alkylene-$C_3$-$C_7$ cycloalkyl;

2.) In each case optionally substituted phenyl, 1-naphthyl, or 2-naphthyl, which in each case may be substituted with one, two, or three radicals selected from the group consisting of $R_Q^1$, $R_Q^2$, and $R_Q^3$, wherein $R_Q^1$, $R_Q^2$, and $R_Q^3$ in each case independently stand for a substituent, which may be the same or different, selected from the group consisting of:

Hydrogen, CN, $CF_3$, $CHF_2$, $OCF_3$, $OCHF_2$, and halogen;

3.) A 5- or 6-membered hetaryl radical which is unsubstituted, or optionally singly or doubly substituted the same or differently, selected from the group consisting of:

2-thienyl, 3-thienyl, 2-pyridyl, 3-pyridyl, 4-pyridyl, 2-thiazolyl, 4-thiazolyl, 5-thiazolyl, 2-pyrimidyl, 4-pyrimidyl, 5-pyrimidyl, and 6-pyrimidyl, wherein the substituents are selected from the group consisting of hydrogen, halogen, CN, $CF_3$, $OCF_3$, $C_1$-$C_6$ alkyl, and O—$C_1$-$C_6$ alkyl;

4.) Two adjacent radicals $R^4$ and $R^5$ in Q3; $R^5$ and $R^6$ in Q1; $R^6$ and $R^7$ in Q1 or Q2; or $R^7$ and $R^8$ in Q1, Q2, or Q3, together with the ring atom to which they are bonded form an optionally substituted quinolinyl or isoquinolinyl cyclic compound.

2. The guanidine compound of general formula I according to claim 1, an enantiomeric, diastereomeric, and/or tautomeric form thereof, and/or pharmaceutically acceptable salt thereof, wherein:

$R^1$, $R^2$ independently stand for:

hydrogen; and $R^3$ is hydrogen.

3. The guanidine compound of general formula I according to claim 1, an enantiomeric, diastereomeric, and/or tautomeric forms thereof, and/or pharmaceutically acceptable salt thereof, wherein:

W:

is a radical of general formula W1a

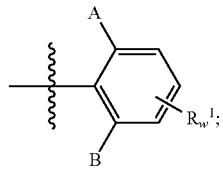
W1a

A:
is $OCF_3$, $OCHF_2$, $OCH_2F$, halogen, O—$C_1$-$C_6$ alkyl, or O—$R_A^1$;

$R_A^1$: independently of its respective occurrence stands for:
in each case optionally substituted $C_1$-$C_6$ alkyl, $C_3$-$C_7$ cycloalkyl, aryl, or hetaryl;

B:
is hydrogen, or in each case optionally substituted aryl or hetaryl, or independently of radical A stands for a radical selected from the radicals defined as for radical A; and $R_w^1$:
is hydrogen.

4. The guanidine compound of general formula I according to claim 1, an enantiomeric, diastereomeric, and/or tautomeric form thereof, and/or pharmaceutically acceptable salt thereof, wherein:

W:
is a radical of general formula W1a:

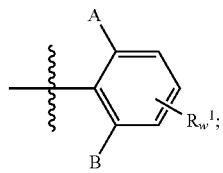
W1a

A:
is $OCF_3$, $OCHF_2$, F, Cl, Br, or O—$C_1$-$C_4$ alkyl;

B:
is hydrogen, optionally substituted phenyl, or independently of radical A stands for a radical selected from the radicals defined as for radical A; and $R_w^1$:
is hydrogen.

5. The guanidine compound of general formula I according to claim 1, an enantiomeric, diastereomeric, and/or tautomeric form thereof, and/or pharmaceutically acceptable salt thereof, wherein:

$R^1$, $R^2$, $R^3$: in each case stand for hydrogen;

W: is a radical of general formula W1a

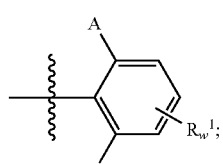
W1a

A:
  is OCF₃, OCHF₂, F, Cl, Br, or
  O—C₁-C₄ alkyl;
B:
  is hydrogen, optionally substituted phenyl, or independently of radical A stands for a radical selected from the radicals defined as for radical A;
$R_w^1$:
  is hydrogen;
Q is a radical of general formula Q1, Q2, or Q3

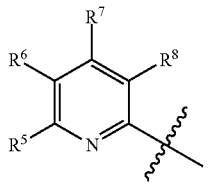
Q1

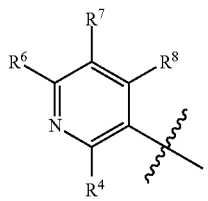
Q2

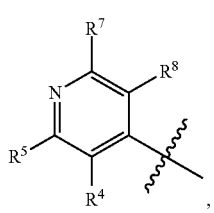
Q3 wherein $R^4$, $R^5$, $R^6$, $R^7$, and $R^8$ in each case independently stand for a radical selected from the group consisting of 1.), 2.), 3.), and 4.), which may be the same or different:

1.) Hydrogen, F, Cl, Br, I, CN, CF₃, CHF₂, OCF₃, OCHF₂, C₁-C₁₀ alkyl or in each case optionally substituted C₃-C₇ cycloalkyl, or C₁-C₆ alkylene-C₃-C₇ cycloalkyl;
2.) In each case optionally substituted phenyl, 1-naphthyl, or 2-naphthyl which may be substituted with one, two, or three radicals, which may be the same or different, independently selected from the group consisting of $R_Q^1$, $R_Q^2$, and $R_Q^3$, wherein
$R_Q^1$, $R_Q^2$, and $R_Q^3$ in each case independently stand for a substituent, which may be the same or different, from the following group: Hydrogen, CN, CF₃, CHF₂, OCF₃, OCHF₂, and halogen;
3.) A 5- or 6-membered hetaryl radical which is unsubstituted, or optionally singly or doubly substituted the same or differently, selected from the group consisting of:
2-thienyl, 3-thienyl, 2-pyridyl, 3-pyridyl, 4-pyridyl, 2-thiazolyl, 4-thiazolyl, 5-thiazolyl, 2-pyrimidyl, 4-pyrimidyl, 5-pyrimidyl, and 6-pyrimidyl, wherein the substituents are selected from the group consisting of hydrogen, halogen, CN, CF₃, OCF₃, or in each case optionally substituted C₁-C₆ alkyl, and O—C₁-C₆ alkyl;
4.) Two adjacent radicals $R^4$ and $R^5$ in Q3; $R^5$ and $R^6$ in Q1; $R^6$ and $R^7$ in Q1 or Q2; or $R^7$ and $R^8$ in Q1, Q2, or Q3, together with the ring atom to which they are bonded form an optionally substituted quinolinyl or isoquinolinyl cyclic compound.

6. The guanidine compound of general formula I according to claim 1, an enantiomeric, diastereomeric, and/or tautomeric form thereof, and/or pharmaceutically acceptable salt thereof,
wherein:
  A: is OCF₃, OCHF₂, OCH₃, O-ethyl, O-propyl, or O-isopropyl.

7. The guanidine compound of general formula I according to claim 1, an enantiomeric, diastereomeric, and/or tautomeric form thereof, and/or pharmaceutically acceptable salt thereof,
wherein:
  Q stands for a radical Q1

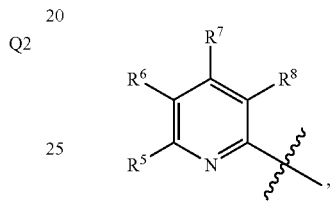
Q1 wherein the radicals $R^5$, $R^6$, $R^7$ are independently selected from the group consisting of H, CN, CH₃, F, Cl, Br, I, C₁-C₆alkyl, or
phenyl, 1-naphthyl, or 2-naphthyl, which in each case may be substituted with one, two, or three radicals selected from the group consisting of $R_Q^1$, $R_Q^2$, and $R_Q^3$; or
5- or 6-membered hetaryl which is unsubstituted, or optionally singly or double substituted the same or differently, selected from the group consisting of 2-thienyl, 3-thienyl, 2-pyridyl, 3-pyridyl, 4-pyridyl, 2-thiazolyl, 4-thiazolyl, 5-thiazolyl, 2-pyrimidyl, 4-pyrimidyl, 5-pyrimidyl, and 6-pyrimidyl, wherein the substituents are selected from the group consisting of hydrogen, halogen, CN, CF₃, OCF₃, C₁-C₆ alkyl, and O—C₁-C₆ alkyl.

8. The guanidine compound of general formula I according to claim 1, an enantiomeric, diastereomeric, and/or tautomeric form thereof, and/or pharmaceutically acceptable salt thereof,
wherein:
  A: is OCF₃, OCHF₂, OCH₃, or O-ethyl.

9. The guanidine compound of general formula I according to claim 1, an enantiomeric, diastereomeric, and/or tautomeric form thereof, and/or pharmaceutically acceptable salt thereof,
wherein:
  Q: is a radical of general formula Q1

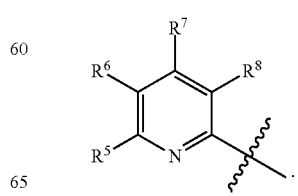
Q1

10. The guanidine compound of formula I according to claim 1, which is selected from the group consisting of:
N-(2-Methoxybenzyl)-N'-pyridin-2-ylguanidine;
N-(2,6-Dimethoxybenzyl)-N'-(5-iodpyridin-2-yl)guanidine;
N-(5-Iodopyridin-2-yl)-N'-(2-methoxybenzyl)guanidine;
N-(2,6-Dimethoxybenzyl)-N'-pyridin-2-ylguanidine;
N-(2-Methoxybenzyl)-N'-(5-methylpyridin-2-yl)guanidine;
N-(2,6-Dimethoxybenzyl)-N'-(5-methylpyridin-2-yl) guanidine;
N-(2-Methoxybenzyl)-N'-(6-methylpyridin-2-yl)guanidine;
N-(2,6-Dimethoxybenzyl)-N'-(6-methylpyridin-2-yl) guanidine;
N-[3-Chloro-5-(trifluoromethyl)pyridin-2-yl]-N'-(2-methoxybenzyl)guanidine;
N-[3-Chloro-5-(trifluoromethyl)pyridin-2-yl]-N'-(2,6-dimethoxybenzyl)guanidine;
N-(2-Methoxybenzyl)-N'-(3-methylpyridin-2-yl)guanidine;
N-(2,6-Dimethoxybenzyl)-N'-(3-methylpyridin-2-yl) guanidine;
N-(2-Methoxybenzyl)-N'-[4-(2-thienyl) pyrimidin-2-yl] guanidine;
N-(2,6-Dimethoxybenzyl)-N'-[4-(2-thienyl) pyrimidin-2-yl]guanidine;
N-(2-Methoxybenzyl)-N'-quinolin-3-ylguanidine;
N-(2,6-Dimethoxybenzyl)-N'-quinolin-3-ylguanidine;
N-(2-Chloro-6-methoxybenzyl)-N'-(5-methylpyridin-2-yl)guanidine;
N-(2-Methoxy-6-methylbenzyl)-N'-(5-methylpyridin-2-yl) guanidine;
N-(2-Fluoro-6-methoxybenzyl)-N'-(5-methylpyridin-2-yl)guanidine;
N-(2-Chlorbenzyl)-N'-(5-methylpyridin-2-yl) guanidine;
N-(2-Ethoxybenzyl)-N'-(5-methylpyridin-2-yl)guanidine;
N-(2-Isopropoxybenzyl)-N'-(5-methylpyridin-2-yl)guanidine;
N-(5-Methylpyridin-2-yl)-N'-[2-(trifluoromethoxy)benzyl]guanidine;
N-(2-Ethylbenzyl)-N'-(5-methylpyridin-2-yl)guanidine;
N-[2-(Difluoromethoxy)benzyl]-N'-(5-methylpyridin-2-yl)guanidine;
N-(2-Chloro-6-phenoxybenzyl)-N'-(5-methylpyridin-2-yl)guanidine;
N-(5-Methylpyridin-2-yl)-N'-(2-phenoxybenzyl)guanidine;
N-(2-Methoxybenzyl)-N'-(4-methylpyridin-2-yl)guanidine;
N-(2,6-Dimethoxybenzyl)-N'-(4-methylpyridin-2-yl) guanidine;
N-(2-Chloro-6-methoxybenzyl)-N'-(3-methylpyridin-2-yl)guanidine;
N-(2-Fluoro-6-methoxybenzyl)-N'-(3-methylpyridin-2-yl)guanidine;
N-(2-Methoxy-6-methylbenzyl)-N'-(3-methylpyridin-2-yl)guanidine;
N-(2-Methoxybenzyl)-N'-pyridin-3-ylguanidine;
3-({Imino[(2-methoxybenzyl)amino]methyl}amino)-1-methylpyridinium acetate;
N-(2-Methoxybenzyl)-N'-pyrimidin-2-ylguanidine;
N-(2,6-Dimethoxybenzyl)-N'-pyrimidin-2-ylguanidine;
N-Isoquinolin-3-yl-N'-(2-methoxybenzyl)guanidine;
N-(2,6-Dimethoxybenzyl)-N'-isoquinolin-3-ylguanidine;
N-(2-Methoxybenzyl)-N'-quinolin-2-ylguanidine;
N-(2,6-Dimethoxybenzyl)-N'-quinolin-2-ylguanidine;
N-(6-Brompyridin-2-yl)-N'-(2-methoxybenzyl)guanidine;
N-(6-Brompyridin-2-yl)-N'-(2,6-dimethoxybenzyl)guanidine;
N-(4-Brompyridin-2-yl)-N'-(2,6-dimethoxybenzyl)guanidine;
N-(4-Brompyridin-2-yl)-N'-(2-methoxybenzyl)guanidine;
N-(3-Brompyridin-2-yl)-N'-(2,6-dimethoxybenzyl)guanidine;
N-(3-Brompyridin-2-yl)-N'-(2-methoxybenzyl)guanidine;
N-(2-Methoxybenzyl)-N'-{6-[4-(trifluoromethoxy)phenyl]pyridin-2-yl}guanidine;
N-(2-Methoxybenzyl)-N'-[6-(2-thienyl)pyridin-2-yl] guanidine;
N-[6-(4-Fluorophenyl)pyridin-2-yl]-N'-(2-methoxybenzyl)guanidine;
N-(2-Methoxybenzyl)-N'-(6-phenylpyridin-2-yl)guanidine;
N-(6-Cyanopyridin-2-yl)-N'-(2-methoxybenzyl)guanidine;
N-(2,6-Dimethoxybenzyl)-N'-(6-phenylpyridin-2-yl) guanidine;
N-(2,6-Dimethoxybenzyl)-N'-[6-(4-fluorophenyl)pyridin-2-yl]guanidine;
N-(6-Cyanopyridin-2-yl)-N'-(2,6-dimethoxybenzyl) guanidine;
N-(2,6-Dimethoxybenzyl)-N'-(4-phenylpyridin-2-yl) guanidine;
N-(2,6-Dimethoxybenzyl)-N'-[4-(4-fluorophenyl)pyridin-2-yl]guanidine;
N-(2-Methoxybenzyl)-N'-(4-phenylpyridin-2-yl)guanidine;
N-[4-(4-Fluorophenyl)pyridin-2-yl]-N'-(2-methoxybenzyl)guanidine;
N-(2,6-Dimethoxybenzyl)-N'-(3-phenylpyridin-2-yl) guanidine;
N-(2,6-Dimethoxybenzyl)-N'-[3-(4-fluorophenyl)pyridin-2-yl]guanidine;
N-(2-Methoxybenzyl)-N'-(3-phenylpyridin-2-yl)guanidine;
N-[3-(4-Fluorophenyl)pyridin-2-yl]-N'-(2-methoxybenzyl)guanidine;
N-(4-Cyanopyridin-2-yl)-N'-(2,6-dimethoxybenzyl) guanidine;
N-(3-Cyanopyridin-2-yl)-N'-(2,6-dimethoxybenzyl) guanidine;
N-(4-Cyanopyridin-2-yl)-N'-(2-methoxybenzyl)guanidine;
N-(6-Bromopyridin-2-yl)-N'-(2-methoxy-6-methylbenzyl)guanidine;
N-(6-Bromopyridin-2-yl)-N'-(2-fluoro-6-methoxybenzyl) guanidine;
N-(6-Bromopyridin-2-yl)-N'-[2-(trifluoromethoxy)]benzyl)guanidine;
N-(6-Bromopyridin-2-yl)-N'-(2-isopropoxybenzyl)guanidine;
N-(6-Bromopyridin-2-yl)-N'-(2-ethoxybenzyl) guanidine;
N-(2-Methoxy-6-methylbenzyl)-N'-(6-cyanopyridin-2-yl)guanidine;
N-(6-Cyanopyridin-2-yl)-N'-(2-fluoro-6-methoxybenzyl) guanidine;
N-(2-Chloro-6-methoxybenzyl)-N'-(6-cyanopyridin-2-yl) guanidine;
N-(6-Cyanopyridin-2-yl)-N'-[2-(trifluoromethoxy)benzyl]guanidine;

N-(6-Cyanopyridin-2-yl)-N'-(2-isopropoxybenzyl)guanidine;
N-(6-Cyanopyridin-2-yl)-N'-(2-ethoxybenzyl)guanidine;
N-(2-Chloro-6-phenoxybenzyl)-N'-(6-cyanopyridin-2-yl) guanidine;
N-(2,6-Dimethoxybenzyl)-N'-(5-phenylpyridin-2-yl) guanidine;
N-(2,6-Dimethoxybenzyl)-N'-[5-(4-fluorophenyl)pyridin-2-yl]guanidine;
N-(5-Cyanopyridin-2-yl)-N'-(2,6-dimethoxybenzyl) guanidine;
N-(2-Methoxybenzyl)-N'-(5-phenylpyridin-2-yl)guanidine;
N-(2-Methoxybenzyl)-N'-[5-(2-thienyl)pyridin-2-yl] guanidine;
N-[5-(4-Fluorophenyl)pyridin-2-yl]-N'-(2-methoxybenzyl)guanidine;
N-(2-Methoxybenzyl)-N'-{5-[4-(trifluoromethyl)phenyl]pyridin-2-yl}guanidine;
N-(5-Cyanopyridin-2-yl)-N'-(2-methoxybenzyl)guanidine;
N-(2-Chloro-6-m ethoxybenzyl)-N'-(5-iodopyridin-2-yl) guanidine;
N-(2-Fluoro-6-methoxybenzyl)-N'-(5-iodopyridin-2-yl) guanidine;
N-(5-Iodopyridin-2-yl)-N'-(2-methoxy-6-methylbenzyl) guanidine;
N-(2-Chlorobenzyl)-N'-(5-iodpyridin-2-yl) guanidine;
N-(2-Chloro-6-methoxybenzyl)-N'-(5-cyanopyridin-2-yl) guanidine;
N-(5-Cyanopyridin-2-yl)-N'-(2-fluoro-6-methoxybenzyl) guanidine;
N-(5-Cyanopyridin-2-yl)-N'-(2-methoxy-6-methylbenzyl)guanidine; and
N-(2-Chlorobenzyl)-N'-(5-cyanopyridin-2-yl)guanidine;
or a pharmaceutically acceptable salt thereof.

11. A guanidine compound selected from the group consisting of:
N-(5-Benzylpyridin-2-yl)-N'-(2-methoxybenzyl)guanidine;
N-(5-Benzylpyridin-2-yl)-N'-(2,6-dimethoxybenzyl) guanidine;
N-(6-Benzylpyridin-2-yl)-N'-(2-methoxybenzyl)guanidine; and
N-(6-Benzylpyridin-2-yl)-N'-(2,6-dimethoxybenzyl) guanidine;
or a pharmaceutically acceptable salt thereof.

12. A pharmaceutical composition containing at least one guanidine compound of general formula I according to claim 1, together with at least one pharmaceutically acceptable carrier and/or diluent.

13. A method for the treatment of at least one disease which may be treated by modulation of the 5-HT$_5$ receptor activity in a patient suffering from said disease, comprising administering an effective amount of at least one guanidine compound of general formula I according to claim 1 to such patient.

14. A method for the treatment of at least one disease which may be treated by modulation of the 5-HT$_5$ receptor activity, with a simultaneous binding affinity for the 5-HT$_5$ receptor less than or equal to 10 µM (Ki), less than or equal to 300 nM (Ki), the Ki value in each case being determined according to a suitable test system, in a patient suffering from said disease, comprising administering an effective amount of at least one guanidine compound of general formula I according to claim 1 to such patient.

15. A method for the treatment of at least one disease selected from the group consisting of neuropathological, neuropsychiatric, and neurodegenerative disorders; neuropathological, neuropsychiatric, and neurodegenerative symptoms; and neuropathological, neuropsychiatric, and neurodegenerative dysfunctions, in a patient suffering from said disease, comprising administering an effective amount of at least one guanidine compound of general formula I according to claim 1 to such patient.

16. A method for the treatment of migraine and brain damage, in a patient suffering from migraine and brain damage, comprising administering an effective amount of at least one guanidine compound of general formula I according to claim 1 to such patient.

17. A method for the treatment of at least one neuropathological, neuropsychiatric, and/or neurodegenerative disease selected from the group consisting of cerebral ischemia, stroke, epilepsy, psychoses, schizophrenia, autism, OCD syndrome, cognitive disorders, attention disorders, depression, bipolar and/or unipolar depression, anxiety, dementia, senile dementia, Alzheimer's dementia, demyelinating diseases, multiple sclerosis, and brain tumors, in a patient suffering from said disease, comprising administering an effective amount of at least one guanidine compound of general formula I according to claim 1 to such patient.

18. A method for the treatment of at least one disease selected from the group consisting of cerebrovascular disorders, pain, amnesia, alcohol abuse, drug abuse, circadian rhythm disorders, and Cushing's syndrome, in a patient suffering from said disease, comprising administering an effective amount of at least one guanidine compound of general formula I according to claim 1 to such patient.

19. The method according to claim 13, characterized in that the treatment based on modulation of the 5-HT$_{5A}$ receptor activity in the patient.

20. The method according to claim 13, characterized in that the treatment is based on a binding affinity for the 5-HT$_{5A}$ receptor that is less than or equal to 10 µM (Ki), determined according to a suitable test model.

21. The method according to claim 13, characterized in that the treatment is based on a binding affinity for the 5-HT$_{5A}$ receptor that is less than or equal to 300 nM (Ki), determined according to a suitable test model.

22. The method according to claim 13, characterized in that the treatment is based on a binding affinity for the 5-HT$_{5A}$ receptor that is less than or equal to 100 nM (Ki), determined according to a suitable test model.

* * * * *